US011998610B2

(12) United States Patent
Peck et al.

(10) Patent No.: US 11,998,610 B2
(45) Date of Patent: Jun. 4, 2024

(54) CONJUGATES AND METHODS OF USING THE SAME

(71) Applicant: Flagship Pioneering Innovations V, Inc., Cambridge, MA (US)

(72) Inventors: Spencer Cory Peck, Watertown, MA (US); Steven John Taylor, Winchester, MA (US); Elijah Lane Bogart, Cambridge, MA (US); Devin Forest Reed Doud, Arlington, MA (US); Joo Hyun Im, Somerville, MA (US); Dervla Tamara Isaac, Boston, MA (US); Jenny Liu, Cambridge, MA (US); Ferdinand Edward Massari, Beverly, MA (US); Robert Walter Myers, Cresskill, NJ (US); John Robert Proudfoot, Newtown, CT (US); Cheri Ross, Winthrop, MA (US); John Patrick Casey, Jr., Boston, MA (US); David Arthur Berry, Newton, MA (US)

(73) Assignee: Flagship Pioneering Innovations V, Inc., Cambridge, MA (US)

( * ) Notice: Subject to any disclaimer, the term of this patent is extended or adjusted under 35 U.S.C. 154(b) by 0 days.

(21) Appl. No.: 17/173,498

(22) Filed: Feb. 11, 2021

(65) Prior Publication Data

US 2021/0162057 A1 Jun. 3, 2021

Related U.S. Application Data

(63) Continuation of application No. PCT/US2019/046428, filed on Aug. 13, 2019.

(60) Provisional application No. 62/776,395, filed on Dec. 6, 2018, provisional application No. 62/718,334, filed on Aug. 13, 2018.

(51) Int. Cl.
| | | |
|---|---|---|
| A61K 47/65 | (2017.01) | |
| A61K 47/54 | (2017.01) | |
| A61P 31/04 | (2006.01) | |
| A61P 35/00 | (2006.01) | |
| C07D 239/553 | (2006.01) | |
| C07D 311/16 | (2006.01) | |
| C07D 491/22 | (2006.01) | |
| C07H 19/06 | (2006.01) | |
| C07K 5/02 | (2006.01) | |
| C07K 5/062 | (2006.01) | |
| C07K 5/065 | (2006.01) | |
| C07K 5/068 | (2006.01) | |
| C07K 5/078 | (2006.01) | |

(52) U.S. Cl.
CPC ............ *A61K 47/65* (2017.08); *A61K 47/542* (2017.08); *A61P 31/04* (2018.01); *A61P 35/00* (2018.01); *C07D 239/553* (2013.01); *C07D 311/16* (2013.01); *C07D 491/22* (2013.01); *C07H 19/06* (2013.01); *C07K 5/0205* (2013.01); *C07K 5/06017* (2013.01); *C07K 5/06034* (2013.01); *C07K 5/06078* (2013.01); *C07K 5/06086* (2013.01); *C07K 5/06139* (2013.01)

(58) Field of Classification Search
None
See application file for complete search history.

(56) References Cited

U.S. PATENT DOCUMENTS

| | | | |
|---|---|---|---|
| 10,953,027 | B2 | 3/2021 | Taylor et al. |
| 2007/0154972 | A1 | 7/2007 | Salamone et al. |
| 2011/0275590 | A1 | 11/2011 | Gengrinovitch et al. |
| 2014/0135356 | A1* | 5/2014 | Sun ..................... C07D 491/22 514/283 |
| 2017/0022505 | A1 | 1/2017 | Hadwiger et al. |
| 2017/0173167 | A1 | 6/2017 | Goldenberg et al. |
| 2019/0031650 | A1 | 1/2019 | Herzon et al. |
| 2020/0055836 | A1 | 2/2020 | Volpe et al. |
| 2020/0101030 | A1 | 4/2020 | Casey, Jr. et al. |
| 2020/0188418 | A1 | 6/2020 | Taylor et al. |
| 2021/0085640 | A1 | 3/2021 | Taylor et al. |

FOREIGN PATENT DOCUMENTS

| | | |
|---|---|---|
| WO | WO-2017/109696 A1 | 6/2017 |
| WO | WO-2017/132459 A1 | 8/2017 |
| WO | WO-2017/219029 A2 | 12/2017 |

OTHER PUBLICATIONS

Duerre. Applied Microbiology, 1963, 1196), 467-471 (Year: 1963).*
Pitout. Antimicrobial Agents and Chemotherapy, 2015, 59(10), 5873-5884 (Year: 2015).*
Fan. Journal of the American Chemical Society, 1993, 115, 369-370 (Year: 1993).*
McMurry. Organic Chemistry, 2000, p. 659. (Year: 2000).*
Kummerer. Environmental Science and Pollution Research, 2016, 23, 14791-14804 (Year: 2016).*
Kates. Bioorganic & Medicinal Chemistry, 2013, 22, 505-512 (Year: 2013).*
Bosnajokovic et al., "Poly(amidoamine) dendrimer-erythromycin conjugates for drug delivery to macrophages involved in periprosthetic inflammation," Nanomedicine 7(3):284-94 (2011) (3 pages) (Abstract only).
Anttila et al., "Chlamydia pneumoniae infection and the risk of female early-onset lung cancer," Int J Cancer. 107(4): 681-682 (2003).

(Continued)

*Primary Examiner* — Noble E Jarrell
(74) *Attorney, Agent, or Firm* — Clark & Elbing LLP

(57) ABSTRACT

Disclosed are conjugates including a recognition element covalently bonded to or linked through a linker to a payload. The payload is a pharmaceutical agent (e.g., an antineoplastic agent, anti-infective agent, or anti-inflammatory agent) or a diagnostic agent. Also disclosed are methods of using the conjugates.

2 Claims, No Drawings

(56) References Cited

OTHER PUBLICATIONS

Volpe et al., "In Vitro Characterization of the Colibactin-Activating Peptidase ClbP Enables Development of a Fluorogenic Activity Probe," ACS Chem Biol. 14(6):1097-1101 (2019).
Brotherton et al., "A prodrug resistance mechanism is involved in colibactin biosynthesis and cytotoxicity," J Am Chem Soc. 135(9):3359-3362 (2013).
Extended European Search Report for European Application No. 19849936.0, dated May 24, 2022 (10 pages).
Fehri et al., "Prevalence of Propionibacterium acnes in diseased prostates and its inflammatory and transforming activity on prostate epithelial cells," Int J Med Microbiol. 301(1):69-78 (2010).
International Preliminary Report on Patentability for International Application No. PCT/US2019/046428, dated Feb. 16, 2021 (7 pages).
International Search Report and Written Opinion for International Application No. PCT/US2019/046428, dated Nov. 4, 2019 (19 pages).
Koshiol et al., "*Salmonella enterica* serovar Typhi and gallbladder cancer: a case-control study and meta-analysis," Cancer Med. 5(11):3310-25 (2016).
Lam et al., "Population genomics of hypervirulent Klebsiella pneumoniae clonal-group 23 reveals early emergence and rapid global dissemenation," Nat Commun. 9(1):2703 (2018) (10 pages).
Leu et al., "Benzyl ether-linked glucuronide derivative of 10-hydroxycamptothecin designed for selective camptothecin-based anticancer therapy," J Med Chem. 51(6):1740-6 (2008).
Li et al., "Preclinical Efficacy and Safety Assessment of Artemisinin-Chemotherapeutic Agent Conjugates for Ovarian Cancer," EBioMedicine 14:44-54 (2016).
Liu et al., "Synthesis and evaluation of anti-tumor activities of $N^4$ fatty acyl amino acid derivatives of 1-β-arabinofuranosylcytosine," Eur J Med Chem. 44(9):3596-600 (2009).
Madeleine et al., "Risk of cervical cancer associated with Chlamydia trachomatis antibodies by histology, HPV type and HPV cofactors," Int J Cancer. 120(3): 650-655 (2006).
Neumann et al., "Esterase-Catalyzed Siderophore Hydrolysis Activates an Enterobactin-Ciprofloxacin Conjugate and Confers Targeted Antibacterial Activity," J Am Chem Soc. 140(15):5193-201 (2018).
Reimer et al., "A natural prodrug activation mechanism in nonribosomal peptide synethesis," Nat Chem Biol. 7(12): 888-90 (2011).
Sears et al., "Perspective: Alpha-Bugs, Their Microbial Partners, and the Link to Colon Cancer," The Journal of Infectious Disease. 203(3): 306-311 (2011).
Xuan et al., "Microbial Dysbiosis Is Associated with Human Breast Cancer," PLoS One. 9(1):e83744 (2014) (7 pages).

\* cited by examiner

CONJUGATES AND METHODS OF USING THE SAME

FIELD OF THE INVENTION

The invention relates to compounds and methods of their medicinal use.

BACKGROUND

Chemotherapeutic treatment strategies are typically associated with numerous side effects. Many of the adverse events associated with the chemotherapeutic agents, which are typically cytotoxic, are believed to be caused by the lack of tissue selectivity of the chemotherapeutic agents. Lacking tissue selectivity, chemotherapeutic agents may affect non-cancerous tissue to cause side effects.

Agents to treat infections or infection-associated lesions can also be limited by toxicity, efficacy at the site of lesion, or both. Many of the toxicities associated with anti-infectives relate to their effects upon host cells and tissues when the agents are dosed at levels sufficient to effectively treat the infection or lesion. Lacking highly selective distribution, many anti-infectives may affect non-infected or non-lesional tissues to cause adverse effects.

There is a need for new therapeutic approaches to the treatment of cancer, pre-cancer, and infection-related lesions, in particular, for targeted approaches to the treatment of these conditions.

SUMMARY OF THE INVENTION

In general, the present invention provides conjugates, pharmaceutical compositions containing them, and methods of their use, e.g., for delivering a payload (e.g., an antineoplastic agent or an antibacterial agent) to a disease site (e.g., a cancer tissue (e.g., a colorectal cancer tissue)) in a subject in need thereof. The payload may be targeted to a microbiome populating a tumor, pre-cancerous tissue, or lesion.

In one aspect, the invention provides a conjugate, or a pharmaceutically acceptable salt thereof, including a recognition element covalently bonded to or linked through a linker to a payload. The payload is a pharmaceutical agent or diagnostic agent. Preferably, the payload is a pharmaceutical agent.

In some embodiments, the recognition element is recognizable by a microorganism or a protein produced thereby.

In certain embodiments, the recognition element is a group of formula $R^1$-L-, where $R^1$ is a fatty acid acyl optionally substituted with $N(R^N)_2$, methoxypolyethylene glycol acetic acid acyl, methoxypolyethylene glycol propionic acid acyl, an amino acid residue, a dipeptide, a tripeptide, β-N-acetylglucosamine, a β-1,4-glucan, an optionally substituted cinnamoyl, D-alanyl-meso-2,6-diamino-pimelyl amide, an optionally substituted alkyl, or an optionally substituted aryl alkyl; and L is an amino acid residue, —O—CO—, —NH—CO—, or —SO$_2$—; where each $R^N$ is independently $C_{1-6}$ alkyl. In some embodiments, $R^1$ is an optionally substituted $C_{1-22}$ alkanoyl, optionally substituted $C_{2-22}$ alkenoyl, optionally substituted $C_{2-22}$ alkynoyl, optionally substituted $C_{6-12}$ aroyl, optionally substituted $C_{1-22}$ alkoxycarbonyl, optionally substituted $C_{1-22}$ alkylaminocarbonyl, optionally substituted $C_{1-22}$ alkylureido, fatty acid acyl optionally substituted with —N($R^N$)$_2$, methoxypolyethylene glycol acetic acid acyl, methoxypolyethylene glycol propionic acid acyl, an amino acid residue, a dipeptide, a tripeptide, β-N-acetylglucosamine, a β-1,4-glucan, an optionally substituted cinnamoyl, D-alanyl-meso-2,6-diamino-pimelyl amide, an optionally substituted alkyl, or an optionally substituted aryl alkyl; and L is an amino acid residue, —O—CO-L$^1$-, —NH—CO-L$^1$-, or —SO$_2$-L$^1$-; wherein each $R^N$ is independently $C_{1-6}$ alkyl, and L$^1$ is an amino acid residue. In further embodiments, $R^1$ is optionally substituted $C_{1-14}$ alkanoyl, optionally substituted benzoyl, optionally substituted $C_{1-14}$ alkoxycarbonyl, or optionally substituted $C_{1-14}$ alkylureido. In yet further embodiments, $R^1$ is selected from the group consisting of optionally substituted propanoyl, optionally substituted benzoyl, optionally substituted phenylpropionyl, optionally substituted naphthyl propionyl, optionally substituted dihydroquinoline carbonyl, butanoyl, hexanoyl, octanoyl, dodecanoyl, tetradecanoyl, hexyloxycarbonyl, octyloxycarbonyl, dodecyloxycarbonyl, hexylureido, octylureido, and dodecyloxyureido. In still further embodiments, each optional substituent is independently hydroxyl, amino, $C_{1-6}$ alkoxy, $C_{1-6}$ alkyl, and phenyl optionally substituted with one to five groups independently selected from the group consisting of halogens, hydroxyl, amino, $C_{1-6}$ alkoxy, $C_{1-6}$ alkyl, 5-membered heterocycles, and 6-membered heterocycles. In other embodiments, each optional substituent is independently selected from the group consisting of hydroxyl, amino, $C_{1-6}$ alkoxy, $C_{1-6}$ alkyl, and phenyl optionally substituted with one, two, three, four, or five groups independently selected from the group consisting of hydroxyl, amino, $C_{1-6}$ alkoxy, and $C_{1-6}$ alkyl. In some embodiments, $R^1$ is a fatty acid acyl optionally substituted with —N($R^N$)$_2$, methoxypolyethylene glycol acetic acid acyl, methoxypolyethylene glycol propionic acid acyls, an amino acid residue, a dipeptide, a tripeptide, β-N-acetylglucosamine, a β-1,4-glucan, an optionally substituted cinnamoyl, D-alanyl-meso-2,6-diamino-pimelyl amide, an optionally substituted alkyl, or an optionally substituted aryl alkyl. In certain embodiments, L is an amino acid residue. In particular embodiments, L is an amino acid residue bonded to $R^1$ through its α-amino group. In further embodiments, $R^1$ is a $C_{1-14}$ fatty acid optionally substituted with phenyl. In yet further embodiments, L is a D-amino acid residue (e.g., an optionally substituted D-asparagine, optionally substituted D-arginine, optionally substituted D-glutamine, optionally substituted D-aspartic acid, or optionally substituted D-glutamic acid). In still further embodiments, the recognition element is an amino acid residue, a dipeptide, a tripeptide, β-N-acetylglucosamine, a β-1,4-glucan, an optionally substituted cinnamoyl, or D-alanyl-meso-2,6-diamino-pimelyl amide. In other embodiments, L is D-asparagine, D-arginine, D-glutamine, D-aspartic acid, D-histidine, or D-glutamic acid. In yet other embodiments, L is D-asparagine.

In yet other embodiments, the recognition element is selected from the group consisting of 3-(2-methoxyethoxy)propanoyl-D-asparaginyl, 2-(4-isobutylphenyl)propanoyl-D-asparaginyl, 6-methoxynaphthalen-2-yl)propanoyl-D-asparaginyl, (1-cyclopropyl-6-fluoro-4-oxo-7-(piperazin-1-yl)-1,4-dihydroquinoline-3-carbonyl, hexyloxycarbonyl-D-asparaginyl, dodecyloxycarbonyl-D-asparaginyl, hexylcarbamoyl-D-asparaginyl, dodecylcarbamoyl-D-asparaginyl, butanoyl-D-asparaginyl, hexanoyl-D-asparaginyl, octanoyl-D-asparaginyl, dodecanoyl-D-asparaginyl, tetradecanoyl-D-asparaginyl, benzoyl-D-asparaginyl, 2-hydroxybenzoyl-D-asparaginyl, 5-amino-2-hydroxybenzoyl-D-asparaginyl, 2-phenylacetyl-D-asparaginyl, butanoyl-D-argininyl, hexanoyl-D-argininyl, octanoyl-D-argininyl, dodecanoyl-D-argininyl, tetradecanoyl-D-argininyl, butanoyl-D-aspartyl, hexanoyl-D-aspartyl, octanoyl-D-aspartyl, dodecanoyl-D-aspartyl, tetradecanoyl-D-aspartyl, butanoyl-D-glutaminyl, hexanoyl-D-glutaminyl, octanoyl-D-glutaminyl, dodecanoyl-D-glutaminyl, tetradecanoyl-D-glutaminyl, butanoyl-D-glutamyl, hexanoyl-D-glutamyl, octanoyl-D-glutamyl, dodecanoyl-D-glutamyl, tetradecanoyl-D-glutamyl, butanoyl-D-histidinyl, hexanoyl-D-histidinyl, octanoyl-D-histidinyl, dodecanoyl-D-histidinyl, and tetradecanoyl-D-histidinyl. In some embodiments, the recognition element is not tetradecanoyl-D-asparaginyl.

In certain embodiments, the linker is a traceless linker. In particular embodiments, the linker is covalently bonded to the payload through an ester bond, an amide bond, a thioester bond, a glycosidic bond, a carbamate linker, a carbonate linker, or a urea linker. In particular embodiments, the linker is covalently bonded to the payload through an ester bond, an amide bond, a thioester bond, a glycosidic bond, a carbamate linker, or a urea linker. In some embodiments, the linker is of formula $R^A$—$(CO)_n$—NH-$L^1$-$(C(R^2)_2)_m$-$L^2$-$(R^B)_k$, where each of n and m is independently 0 or 1; k is 1, 2, or 3; $R^A$ is a bond to the recognition element; $R^B$ is a bond to the payload; $L^1$ is 1,4-phenylene, 1,2-phenylene, an optionally substituted styrene-diyl, an optionally substituted $C_{1-3}$ hydrocarbon chain, or -$L^A$-$NR^D$—CO—O-$L^B$-, where $L^A$ is optionally substituted $C_{2-6}$ alkylene, and $L^B$ is 1,4-phenylene, 1,2-phenylene, or an optionally substituted styrene-diyl; and $L^2$ combines with $(R^B)_k$ to form —$NR^D$—CO—$R^B$, —(CO)—$R^B$, —S—$R^B$, —OCO—$R^B$, —$N(R^B)_q(R^E)_{3-q}$,

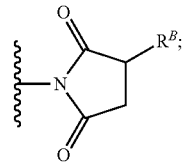

where $R^D$ is H or optionally substituted $C_{1-6}$ alkyl, q is 1, 2, or 3, and each $R^E$ is independently H or optionally substituted $C_{1-6}$ alkyl; and each $R^2$ is independently H or $C_{1-6}$ alkyl, or both $R^2$ combine with the atom to which each is attached to form a cycloalkylene. In certain embodiments, the linker is of formula $R^A$—$NR^3$-$L^1$-$(C(R^2)_2)_m$-$L^2$-$R^B$, wherein $R^A$ is a bond to the recognition element; $R^B$ is a bond to the payload; $L^1$ is 1,4-phenylene, or an optionally substituted $C_{1-3}$ alkylene; and $L^2$ combines with $R^B$ to form —$NR^D$—CO—$R^B$, —(CO)—$R^B$, or —COO—$R^B$; m is 0 or 1; wherein $R^D$ is H or optionally substituted $C_{1-6}$ alkyl; each $R^2$ is independently H or $C_{1-6}$ alkyl; and $R^3$ is H or $C_{1-6}$ alkyl.

In particular embodiments, the linker is of formula $R^A$—NH-$L^1$-$(C(R^2)_2)$-$L^2$-$R^B$, wherein $R^A$ is a bond to the recognition element; $R^B$ is a bond to the payload; $L^1$ is 1,4-phenylene, 1,2-phenylene, or an optionally substituted $C_{1-3}$ hydrocarbon chain; and $L^2$ combines with $R^B$ to form —$NR^D$—CO—$R^B$, —(CO)—$R^B$, —S—$R^B$, —OCO—$R^B$, —$N(R^B)_q(R^E)_{3-q}$, or

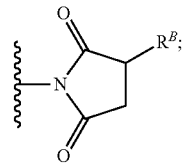

wherein $R^D$ is H or optionally substituted $C_{1-6}$ alkyl, q is 1, 2, or 3, and each $R^E$ is independently H or optionally substituted $C_{1-6}$ alkyl; and each $R^2$ is independently H or $C_{1-6}$ alkyl, or both $R^2$ combine with the atom to which each is attached to form a cycloalkylene.

In further embodiments, the linker is of formula $R^A$—NH-$L^1$-$(C(R^2)_2)$-$L^2$-$R^B$, where $R^A$ is a bond to the recognition element; $R^B$ is a bond to the payload; $L^1$ is 1,4-phenylene, 1,2-phenylene, or an optionally substituted $C_{1-3}$ hydrocarbon chain; and $L^2$ combines with $R^B$ to form —$NR^D$—CO—$R^B$, —(CO)—$R^B$, —S—$R^B$, —OCO—$R^B$, —$N(R^B)_q(R^E)_{3-q}$, or

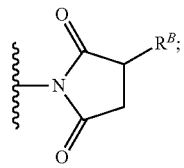

where $R^D$ is H or optionally substituted $C_{1-6}$ alkyl, q is 1, 2, or 3, and each $R^E$ is independently H or optionally substituted $C_{1-6}$ alkyl; and each $R^2$ is independently H or $C_{1-6}$ alkyl, or both $R^2$ combine with the atom to which each is attached to form a cycloalkylene.

In yet further embodiments, the linker is of formula $R^A$—$NR^3$-$L^1$-$(C(R^2)_2)_m$-$L^2$-$R^B$, wherein $R^A$ is a bond to the recognition element; $R^B$ is a bond to the payload; $L^1$ is 1,4-phenylene, or an optionally substituted $C_{1-3}$ alkylene; and $L^2$ combines with $R^B$ to form —$NR^D$—CO—$R^B$, —(CO)—$R^B$, or —COO—$R^B$; m is 0 or 1; wherein $R^D$ is H or optionally substituted $C_{1-6}$ alkyl; each $R^2$ is independently H or $C_{1-6}$ alkyl; and $R^3$ is H or $C_{1-6}$ alkyl.

In still further embodiments, the linker is of formula $R^A$—NH-$L^1$-$(C(R^2)_2)$-$L^2$-$R^B$, wherein $R^A$ is a bond to the recognition element; $R^B$ is a bond to the payload; $L^1$ is 1,4-phenylene, 1,2-phenylene, or an optionally substituted $C_{1-3}$ hydrocarbon chain; and $L^2$ combines with $R^B$ to form —$NR^D$—CO—$R^B$, —(CO)—$R^B$, —S—$R^B$, —OCO—$R^6$, —$N(R^B)_q(R^E)_{3-q}$, or

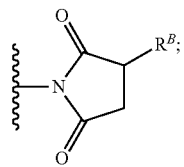

wherein $R^D$ is H or optionally substituted $C_{1-6}$ alkyl, q is 1, 2, or 3, and each $R^E$ is independently H or optionally substituted $C_{1-6}$ alkyl; each $R^2$ is independently H or $C_{1-6}$ alkyl, or both $R^2$ combine with the atom to which each is attached to form a cycloalkylene.

In other embodiments, the linker is selected from the group consisting of 2-aminobenzyl, 4-aminobenzyl, 4-aminobutanoyl, 4-aminopentanoyl, 2-amino-3-methylbutanoyl, 4-amino-2,2-dimethylbutanoyl, 2-aminopropanoyl, 2-amino-4-methylpentanoyl, 4-aminobutanoate carboxymethylene, 2-aminoethyl aminocarbonyl, 2-aminopropyl aminocarbonyl, 2-aminopropyl methylaminocarbonyl, 2-aminopropyl methylaminocarboxymethylene, 2-methylaminoethyl aminocarbonyl, and 2-aminoethyl methylaminocarbonyl. In yet other embodiments, the linker is selected from the group consisting of D-2-aminopropanoyl, L-2-aminopropanoyl, 2-aminoethyl aminocarbonyl, 4-aminopentanoyl, 4-aminobutanoate carboxymethylene, 2-aminopropyl methylaminocarbonyl, and 2-aminoethyl methylaminocarbonyl. In still other embodiments, the recognition element is covalently bonded to the payload.

In particular embodiments, the recognition element is covalently bonded to the payload. In further embodiments, the payload is an antineoplastic agent. In yet further embodiments, the antineoplastic agent is a cytotoxic antineoplastic agent. In still further embodiments, the antineoplastic agent is 7-ethyl-10-hydroxy-camptothecin (SN-38), irinotecan, monomethyl auristatin E, monomethyl auristatin F, paclitaxel, doxorubicin, daunorubicin, pyrrolobenzodiazepine, 10-hydroxycamptothecin, exatecan, cyclopamine, tacedinaline, 5-fluorouracil, calicheamicine, a maytansinoid, maytansine, methotrexate, duocarmycin, erlotinib, gefitinib, capecitabine, leucovorin, trifluridine, tipiracil, or CC-1065. In other embodiments, the antineoplastic agent is SN-38, monomethyl auristatin E, or 5-fluorouracil. In yet other embodiments, the payload is an anti-infective agent. In still other embodiments, the anti-infective agent is amikacin, kanamycin, neomycin, netilmicin, tobramycin, paromomycin, streptomycin, geldanamycin, herbimycin, rifaximin, loracarbef, ertapenem, doripenem, meropenem, cefadroxil, cefazolin, cefalexin, cefaclor, cefprozil, cefuroxime, cefixime, cefdinir, cefditoren, cefoperazone, cefotaxime, cefpodoxime, ceftibuten, ceftriaxone, cefepime, ceftaroline fosamil, ceftobiprole, vancomycin, teicoplanin, telavancin, dalbavancin, oritavancin, clindamycin, lincomycin, daptomycin, azithromycin, clarithromycin, erythromycin, roxithromycin, telithromycin, spiramycin, aztreonam, furazolidone, nitrofurantoin, linezolid, posizolid, radezolid, torezolid, amoxicillin, ampicillin, azlocillin, dicloxacillin, flucloxacillin, mezlocillin, methicillin, nafcillin, oxacillin, penicillin G, penicillin V, piperacillin, temocillin, ticarcillin, colistin, bacitracin, polymyxin B, ciprofloxacin, enoxacin, gatifloxacin, gemifloxacin, levofloxacin, lomefloxacin, moxifloxacin, nadifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfanilamide, sulfasalazine, sulfisoxazole, trimethoprim, sulfamethoxazole, sulfonamidochrysoidine, demeclocycline, doxycycline, metacycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalfopristin, thiamphenicol, tigecycline, tinidazole, teixobactin, malacidin, phenol, hydroxynaphthalene, quinine, hydroxychloroquine, ketoconazole, fluconazole, or amphotericin B.

In some embodiments, the conjugate is cleavable in vivo to release the payload from the conjugate. In certain embodiments, the payload is releasable upon cleavage in vivo of the covalent bond bonding the recognition element to the payload. In particular embodiments, the payload is releasable upon cleavage in vivo of the linker connecting the recognition element to the payload. In further embodiments, the conjugate is cleavable in vivo to release the recognition element from the conjugate. In yet further embodiments, the recognition element is recognizable by a protein produced by Fusobacteria, *P. acnes, C. pneumoniae, S. enterica* serovar *Typhi, M. radiotolerans, C. trachomatis, Escherichia coli* (*E. coli*), or *Klebsiella pneumoniae* (preferably, by *E. coli* or *Klebsiella pneumoniae* (e.g., clbP)). In still further embodiments, the conjugate is cleavable in vivo by the protein produced by Fusobacteria, *P. acnes, C. pneumoniae, S. enterica* serovar *Typhi, M. radiotolerans, C. trachomatis, E. coli*, or *Klebsiella pneumoniae* (preferably, by *E. coli* or *Klebsiella pneumoniae* (e.g., clbP)).

In particular embodiments, the conjugate is of the following structure:

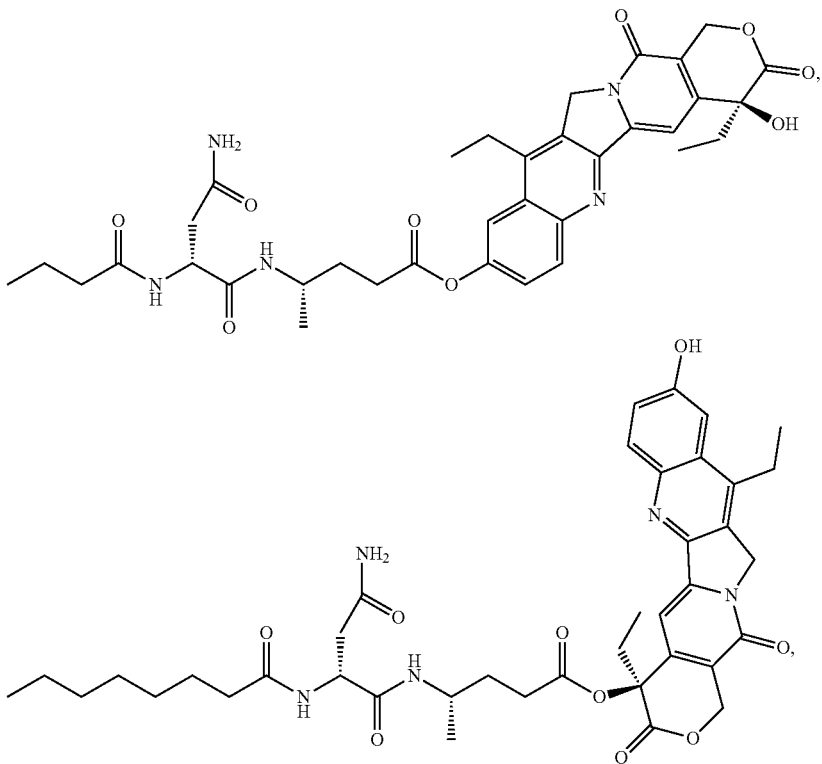

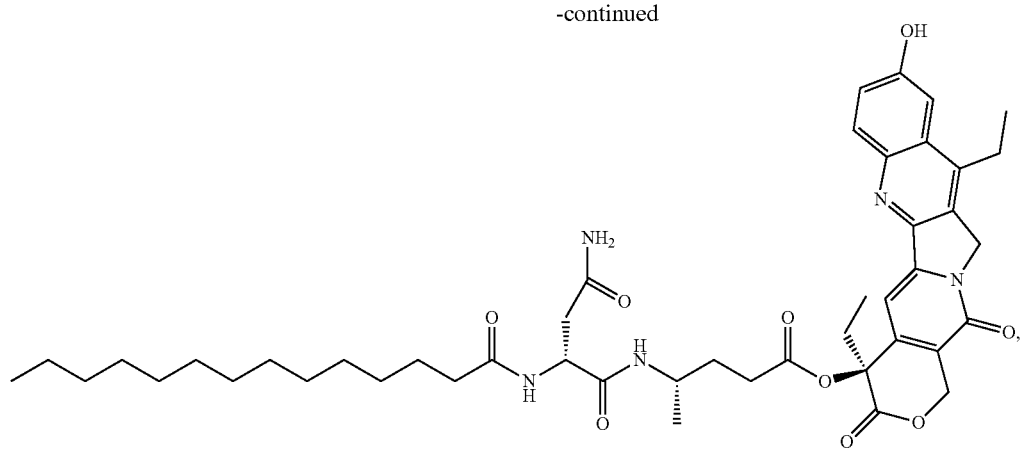
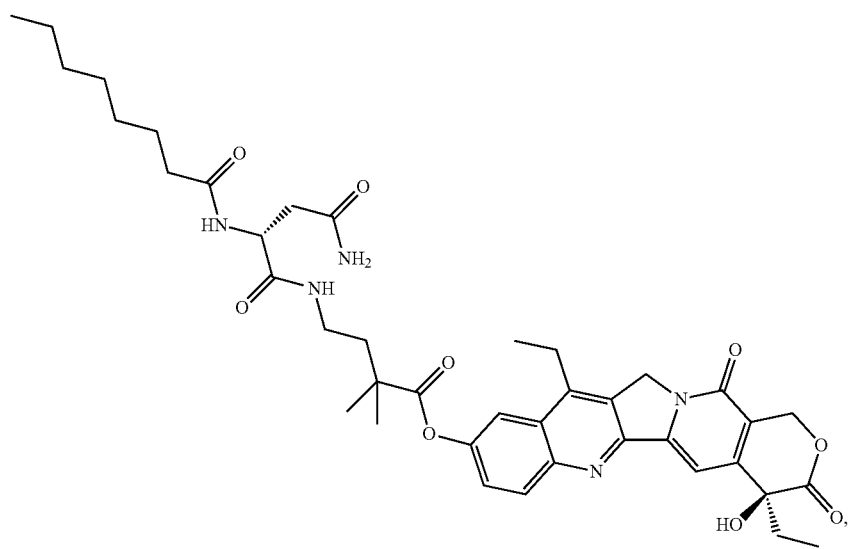
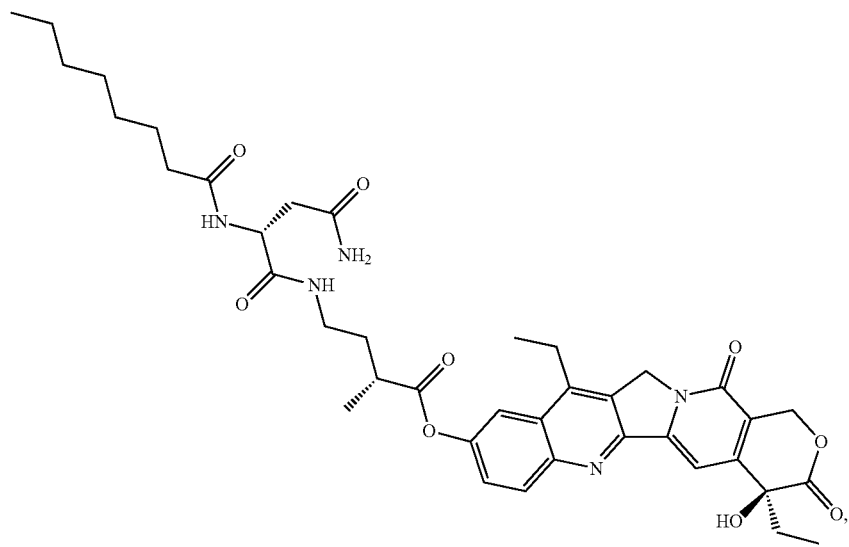

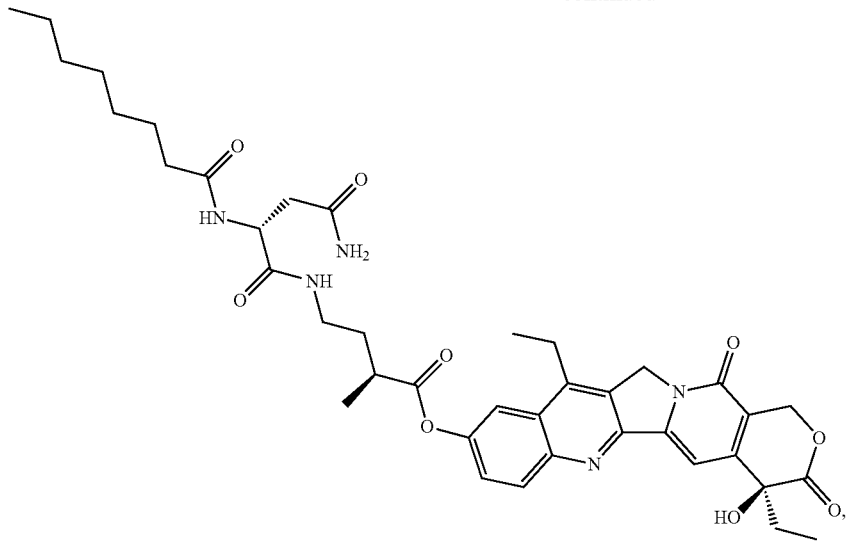
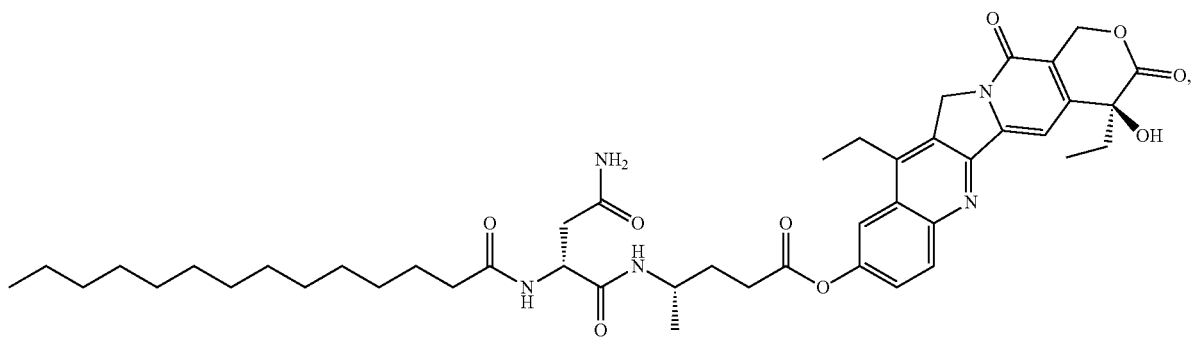
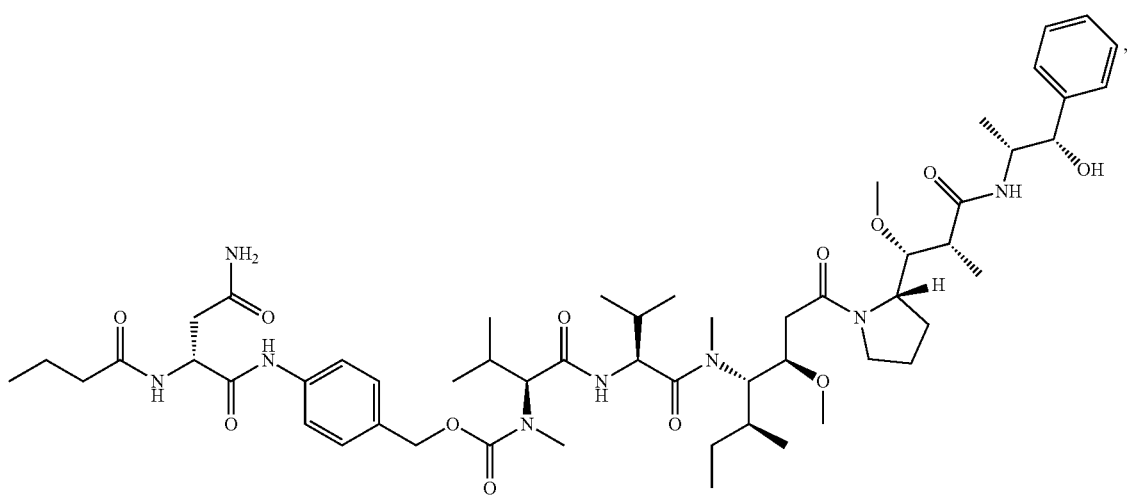

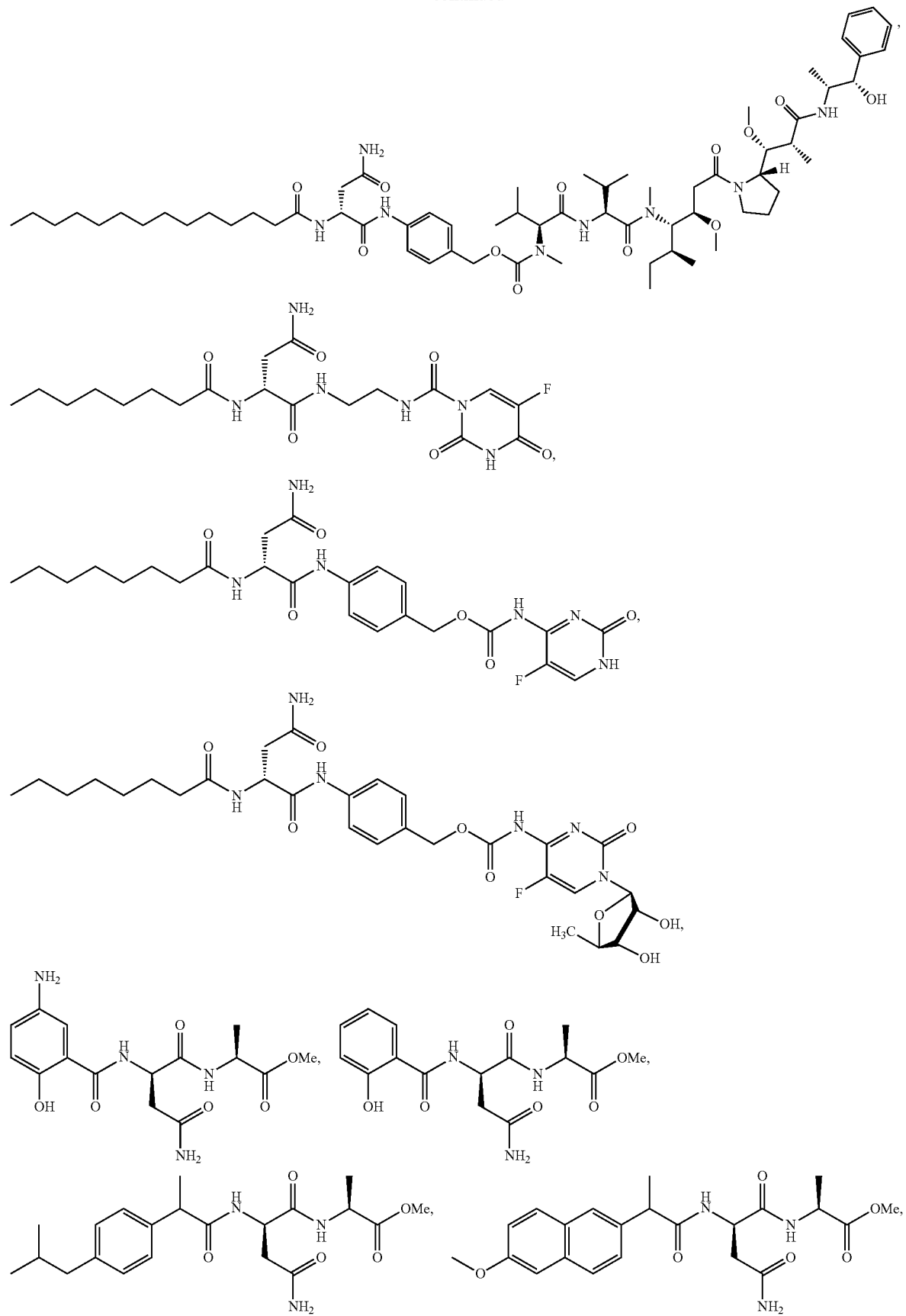

-continued
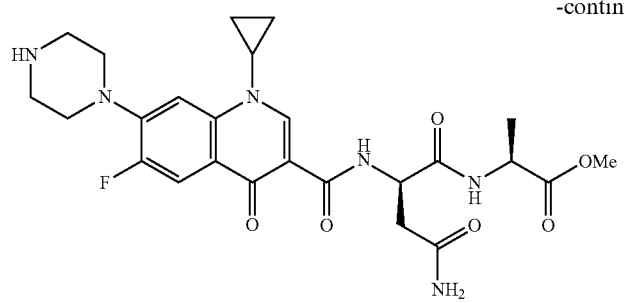
or a pharmaceutically acceptable salt thereof.
In certain embodiments, the conjugate is of the following structure:
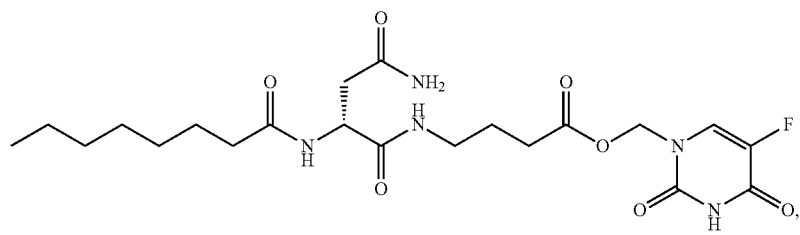
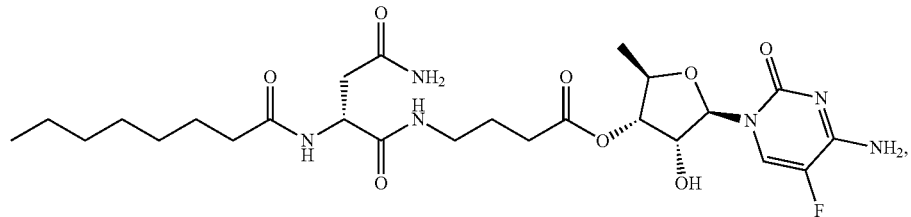
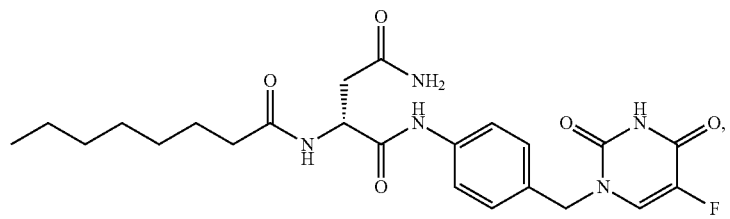
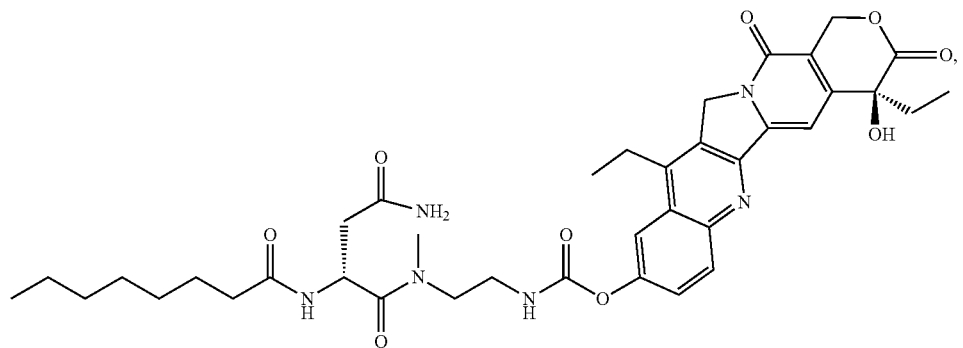

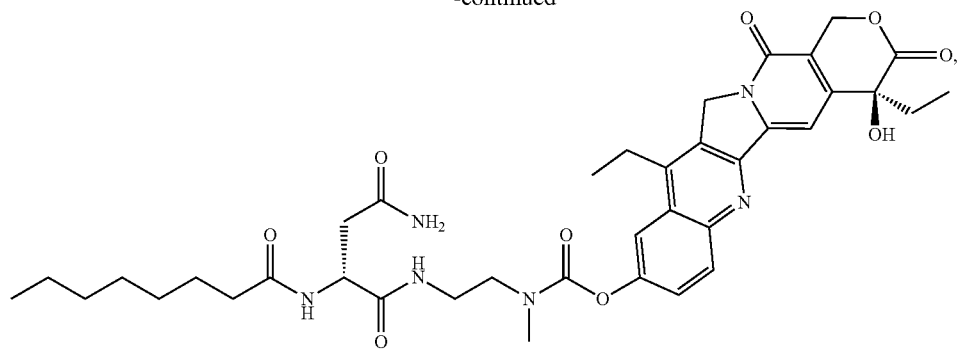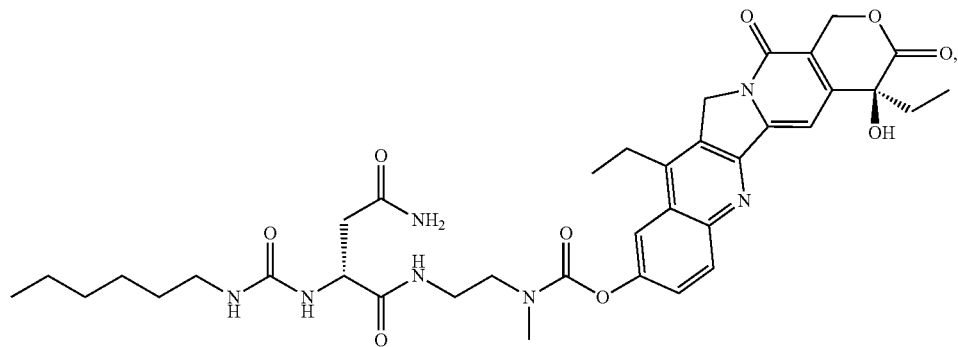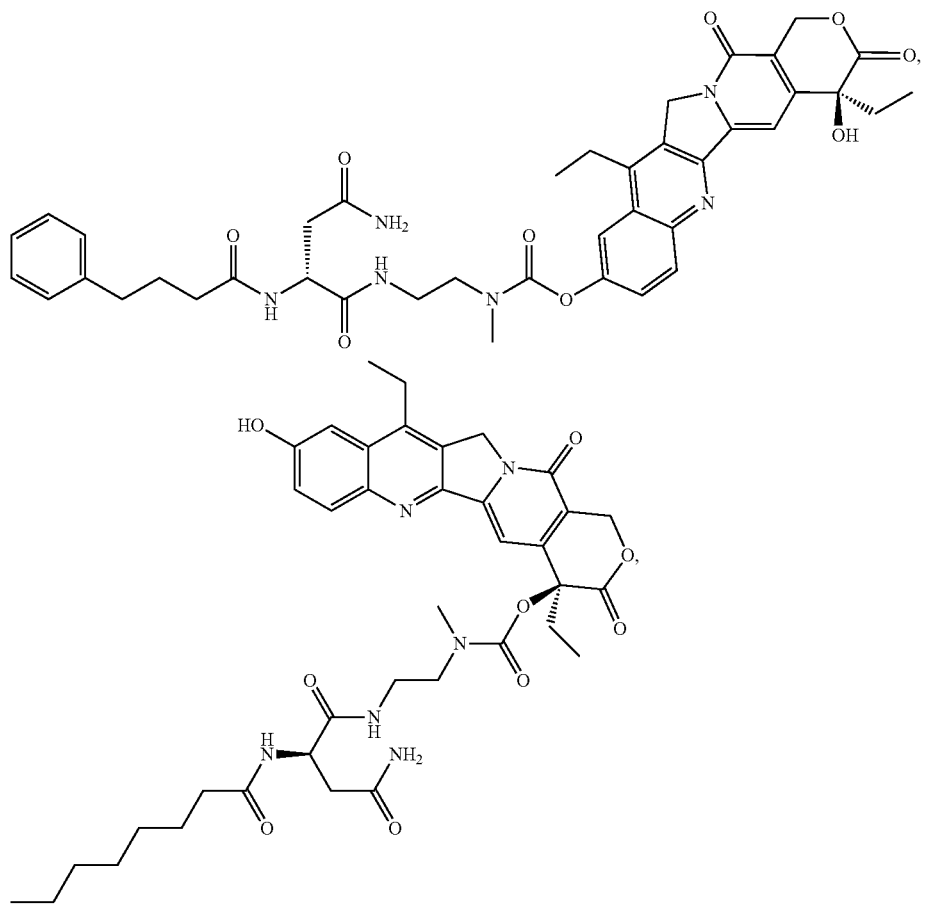

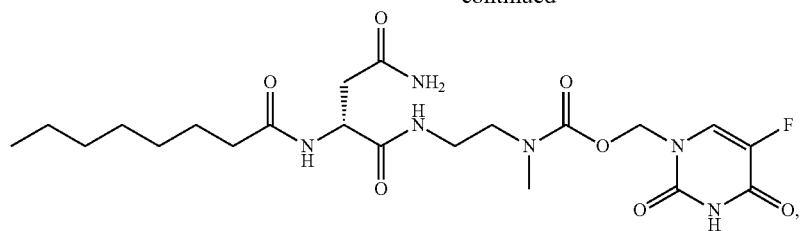
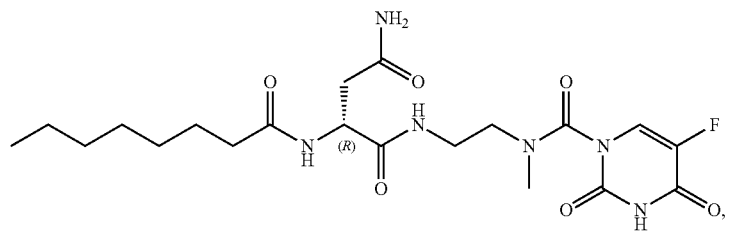
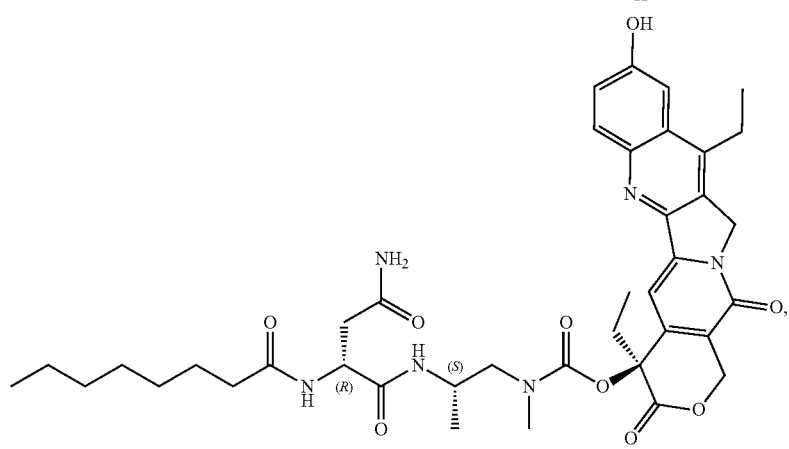
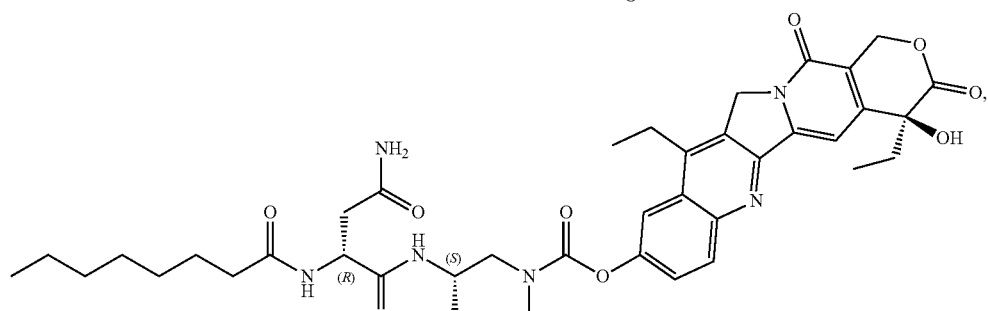
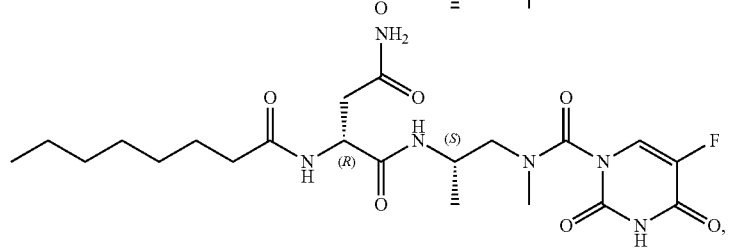
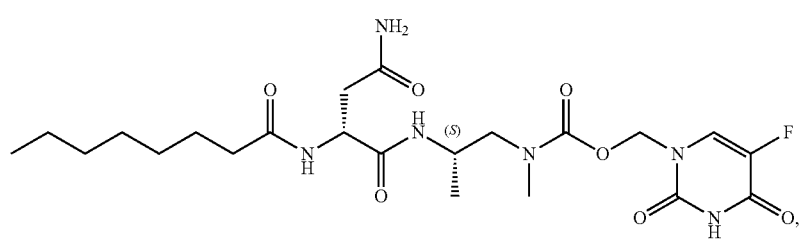

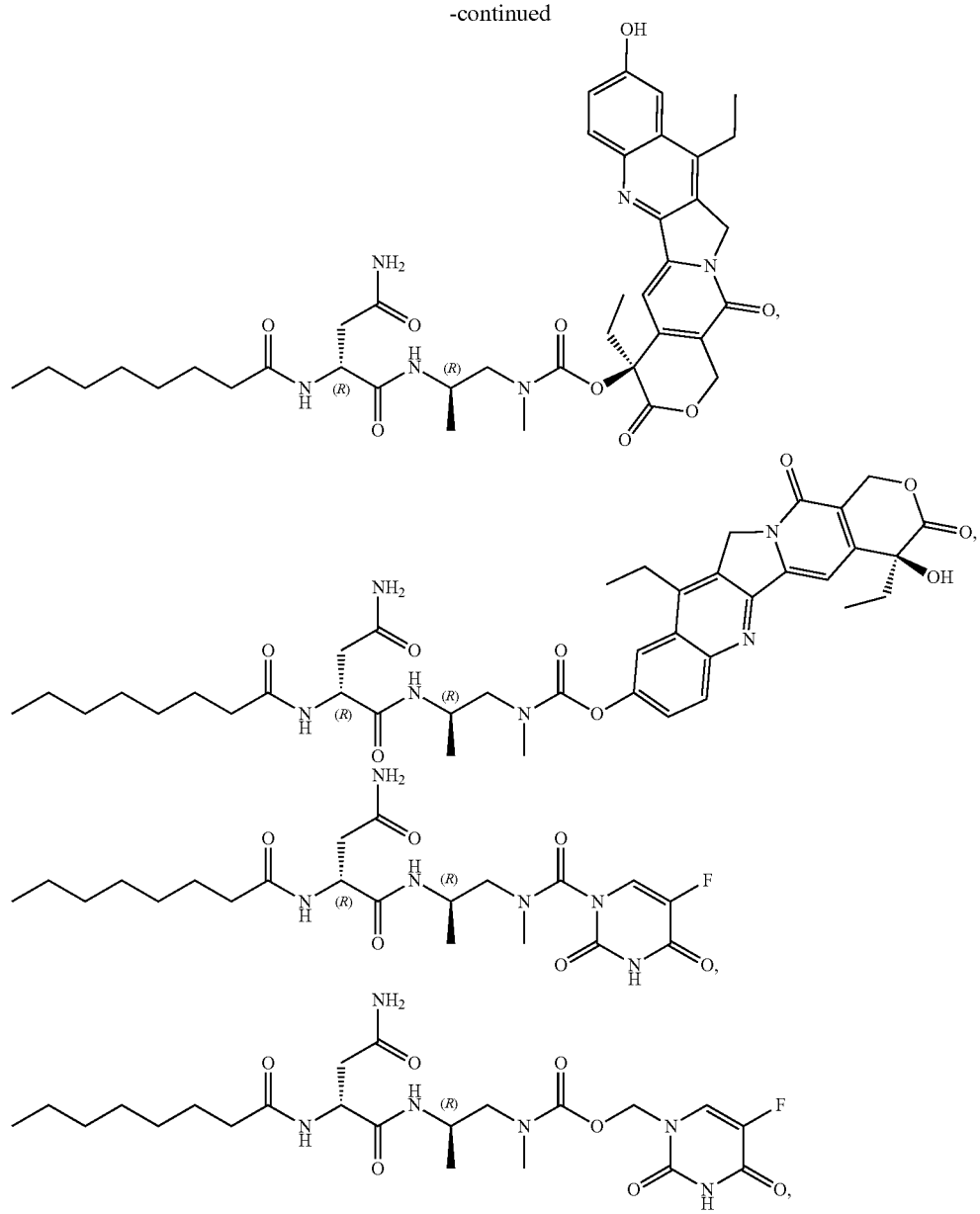

or a pharmaceutically acceptable salt thereof.

In another aspect, the invention provides a pharmaceutical composition including the conjugate of the invention and a pharmaceutically acceptable excipient (e.g., a pharmaceutical composition formulated for oral, rectal, intravenous, intratumoral, or intralesional administration).

In a yet another aspect, the invention provides a method of modulating a cancer marker in a subject in need thereof by administering to the subject a therapeutically effective amount of the conjugate of the invention or the pharmaceutical composition of the invention. In some embodiments, the cancer marker is for a cancer or pre-cancerous state selected from the group consisting of colorectal cancer, a colon polyp, lung cancer, gallbladder cancer, breast cancer, cervical cancer, non-small cell lung cancer, squamous cell carcinoma of the head and neck, classical Hodgkin's lymphoma, urothelial carcinoma, melanoma, renal cell carcinoma, hepatocellular carcinoma, Merkel cell carcinoma, and carcinomas with microsatellite instability. In certain embodiments, the cancer marker is a colorectal cancer marker selected from the group consisting of carbohydrate antigen 19-9 and carcinoembryonic antigen.

In particular embodiments, the subject suffers from cancer.

In a still another aspect, the invention provides a method of modulating an infection marker in a subject in need thereof by administering to the subject a therapeutically effective amount of the conjugate of the invention or the pharmaceutical composition of the invention.

In some embodiments, the infection marker is blood, urine or cerebrospinal white blood cell count; erythrocyte sedimentation rate; serum hepatic transaminase levels; serum blood alkaline phosphatase levels; or culture of sterile body fluid. In certain embodiments, the infection marker is a for an infection selected from the group consisting of pneumonia, lung abscess, liver abscess, meningitis, spinal infection, epidural abscess, brain abscess, bloodstream infection, urinary tract infection, and bacteremia.

In a further aspect, the invention provides a method of treating a disease in a subject in need thereof by administering to the subject a therapeutically effective amount of the conjugate of the invention or the pharmaceutical composition of the invention.

In a yet further aspect, the invention provides a method of delivering a payload to a disease site in a subject in need thereof by administering to the subject a therapeutically effective amount of the conjugate of the invention or the pharmaceutical composition of the invention.

In a still further aspect, the invention provides a method of modulating the microbiome of a subject having cancer, infection, or lesion, the method including administering to the subject a therapeutically effective amount of the conjugate of the invention or the pharmaceutical composition of the invention.

In a yet another aspect, the invention provides a method of treating a disease in a subject in need thereof by determining the presence or amount of a microorganism expressing a protein capable of cleaving the conjugate of the invention in the subject diagnosed with the disease, and administering to the subject a therapeutically effective amount of the conjugate of the invention or the pharmaceutical composition of the invention if the evaluation of the subject is positive for the presence of the microorganism.

In a still another aspect, the invention provides a method of treating a disease in a subject in need thereof by administering to the subject a therapeutically effective amount of the conjugate of the invention or the pharmaceutical composition of the invention, where the subject has a microorganism expressing a protein capable of cleaving the conjugate (e.g., the microorganism is a bacterium (e.g., Fusobacteria, P. acnes, C. pneumoniae, S. enterica serovar Typhi, M. radiotolerans, C. trachomatis, E. coli, or Klebsiella pneumoniae)). Preferably, the bacterium expresses clbP (e.g., the bacterium is E. coli or Klebsiella pneumoniae).

In certain embodiments, the determining step includes performing PCR, bacteriological culture analysis, fluorescent in situ hybridization, gas-liquid chromatography, and/or bacterial enzyme activity analysis. In some embodiments, the determining step is performed before, during, and/or after the administering step. In particular embodiments, the presence of the microorganism is determined in a sample from the subject. In further embodiments, the sample is a stool sample, a bodily fluid sample, or a biopsy sample.

In some embodiments, the disease is cancer or pre-cancerous state (e.g., colorectal cancer, a colon polyp, lung cancer, gallbladder cancer, breast cancer, cervical cancer, non-small cell lung cancer, squamous cell carcinoma of the head and neck, classical Hodgkin's lymphoma, urothelial carcinoma, melanoma, renal cell carcinoma, hepatocellular carcinoma, Merkel cell carcinoma, or carcinoma with microsatellite instability). In some embodiments, the cancer or pre-cancerous state is colorectal cancer, a colon polyp, lung cancer, gallbladder cancer, breast cancer, or cervical cancer.

In particular embodiments, the disease is an infection (e.g., pneumonia, lung abscess, liver abscess, meningitis, spinal infection, epidural abscess, brain abscess, bloodstream infection, urinary tract infection, or bacteremia).

In certain embodiments, the disease site is a tumor (e.g., a cancerous or pre-cancerous tissue) or lesion. In particular embodiments, the conjugate is cleavable in vivo to deliver the payload to the disease site (e.g., the tumor or lesion). In some embodiments, the tumor is a colorectal cancer tissue.

In particular embodiments, the conjugate is cleavable in vivo by a protein produced by bacteria (e.g., Fusobacteria, P. acnes, C. pneumoniae, S. enterica serovar Typhi, M. radiotolerans, C. trachomatis, or Klebsiella pneumoniae). Preferably, the bacteria are E. coli or Klebsiella pneumoniae.

In further embodiments, a CD4$^+$CD25$^+$ Treg cell count, cytotoxic T cell count, interferon γ (IFNγ) level, interleukin-17 (IL17) level, or intercellular adhesion molecule (ICAM) level is modulated following the administration of the conjugate or a pharmaceutically acceptable salt thereof. In yet further embodiments, an NFκB level, matrix metallopeptidase 9 (MMP9) level, 8-iso-prostaglandin $F_{2\alpha}$ (8-iso-PGF2α) level, or CXCL13 level is reduced following the administration of the conjugate or a pharmaceutically acceptable salt thereof. In still further embodiments, a $T_h1$ cell count, IgA level, or inducible nitric oxide synthase (iNOS) level is modulated following the administration of the conjugate or a pharmaceutically acceptable salt thereof.

In other embodiments, methods described herein further include determining the presence or amount of microorganisms, where the microorganisms are capable of cleaving an amide, ester, thioester, or glycosidic bond, or a carbamate or urea linker.

In some embodiments, the conjugate is administered as a pharmaceutical composition including the conjugate and a pharmaceutically acceptable excipient. In certain embodiments, the conjugate is administered orally, rectally, intravenously, intratumorally, or intralesionally.

The present invention is also partly described by the following enumerated items.

1. A conjugate, or a pharmaceutically acceptable salt thereof, comprising a recognition element covalently bonded to or linked through a linker to a payload, wherein the payload is a pharmaceutical agent.
2. The conjugate of item 1, or a pharmaceutically acceptable salt thereof, wherein the payload is an antineoplastic agent.
3. The conjugate of item 2, or a pharmaceutically acceptable salt thereof, wherein the antineoplastic agent is 7-ethyl-10-hydroxy-camptothecin (SN-38), irinotecan, monomethyl auristatin E, monomethyl auristatin F, paclitaxel, doxorubicin, daunorubicin, pyrrolobenzodiazepine, 10-hydroxycamptothecin, exatecan, cyclopamine, tacedinaline, 5'-deoxy-5-fluorouridine, 5-fluorouracil, calicheamicine, a maytansinoid, maytansine, methotrexate, duocarmycin, erlotinib, gefitinib, capecitabine, leucovorin, trifluridine, tipiracil, or CC-1065.
4. The conjugate of item 2, or a pharmaceutically acceptable salt thereof, wherein the antineoplastic agent is SN-38, monomethyl auristatin E, capecitabine, 5'-deoxy-5-fluorouridine, or 5-fluorouracil.
5. The conjugate of item 2, or a pharmaceutically acceptable salt thereof, wherein the antineoplastic agent is SN-38, monomethyl auristatin E, or 5-fluorouracil.
6. The conjugate of item 2, or a pharmaceutically acceptable salt thereof, wherein the antineoplastic agent is SN-38.
7. The conjugate of item 2, or a pharmaceutically acceptable salt thereof, wherein the antineoplastic agent is monomethyl auristatin E.
8. The conjugate of item 2, or a pharmaceutically acceptable salt thereof, wherein the antineoplastic agent is 5-fluorouracil.
9. The conjugate of item 2, or a pharmaceutically acceptable salt thereof, wherein the antineoplastic agent is 5'-deoxy-5-fluorouridine.

10. The conjugate of item 2, or a pharmaceutically acceptable salt thereof, wherein the antineoplastic agent is capecitabine.
11. The conjugate of item 1, or a pharmaceutically acceptable salt thereof, wherein the payload is an anti-infective agent.
12. The conjugate of item 11, or a pharmaceutically acceptable salt thereof, wherein the anti-infective agent is amikacin, kanamycin, neomycin, netilmicin, tobramycin, paromomycin, streptomycin, geldanamycin, herbimycin, rifaximin, loracarbef, ertapenem, doripenem, meropenem, cefadroxil, cefazolin, cefalexin, cefaclor, cefprozil, cefuroxime, cefixime, cefdinir, cefditoren, cefoperazone, cefotaxime, cefpodoxime, ceftibuten, ceftriaxone, cefepime, ceftaroline fosamil, ceftobiprole, vancomycin, teicoplanin, telavancin, dalbavancin, oritavancin, clindamycin, lincomycin, daptomycin, azithromycin, clarithromycin, erythromycin, roxithromycin, telithromycin, spiramycin, aztreonam, furazolidone, nitrofurantoin, linezolid, posizolid, radezolid, torezolid, amoxicillin, ampicillin, azlocillin, dicloxacillin, flucloxacillin, mezlocillin, methicillin, nafcillin, oxacillin, penicillin G, penicillin V, piperacillin, temocillin, ticarcillin, colistin, bacitracin, polymyxin B, ciprofloxacin, enoxacin, gatifloxacin, gemifloxacin, levofloxacin, lomefloxacin, moxifloxacin, nadifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfanilamide, sulfasalazine, sulfisoxazole, trimethoprim, sulfamethoxazole, sulfonamidochrysoidine, demeclocycline, doxycycline, metacycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalfopristin, thiamphenicol, tigecycline, tinidazole, teixobactin, malacidin, phenol, hydroxynaphthalene, quinine, hydroxychloroquine, ketoconazole, fluconazole, or amphotericin B.
12. A conjugate, or a pharmaceutically acceptable salt thereof, comprising a recognition element covalently bonded to or linked through a linker to a payload, wherein the payload is a diagnostic agent.
13. The conjugate of any one of items 1 to 12, or a pharmaceutically acceptable salt thereof, wherein the recognition element is recognizable by a microorganism or a protein produced thereby.
14. The conjugate of any one of items 1 to 13, or a pharmaceutically acceptable salt thereof, wherein the recognition element is a group of formula $R^1$-L-, wherein
$R^1$ is an optionally substituted $C_{1-22}$ alkanoyl, optionally substituted $C_{2-22}$ alkenoyl, optionally substituted $C_{2-22}$ alkynoyl, optionally substituted $C_{6-12}$ aroyl, optionally substituted $C_{1-22}$ alkoxycarbonyl, optionally substituted $C_{1-22}$ alkylaminocarbonyl, optionally substituted $C_{1-22}$ alkylureido, fatty acid acyl optionally substituted with —$N(R^N)_2$, methoxypolyethylene glycol acetic acid acyl, methoxypolyethylene glycol propionic acid acyl, an amino acid residue, a dipeptide, a tripeptide, β-N-acetylglucosamine, a β-1,4-glucan, an optionally substituted cinnamoyl, D-alanyl-meso-2,6-diamino-pimelyl amide, an optionally substituted alkyl, or an optionally substituted aryl alkyl; and
L is an amino acid residue, —O—CO-$L^1$-, —NH—CO-$L^1$-, or —$SO_2$-$L^1$-; wherein each $R^N$ is independently $C_{1-6}$ alkyl, and $L^1$ is an amino acid residue.
15. The conjugate of item 14, or a pharmaceutically acceptable salt thereof, wherein $R^1$ is optionally substituted $C_{1-14}$ alkanoyl, optionally substituted benzoyl, optionally substituted $C_{1-14}$ alkoxycarbonyl, or optionally substituted $C_{1-14}$ alkylureido.
16. The conjugate of item 14, or a pharmaceutically acceptable salt thereof, wherein $R^1$ is selected from the group consisting of optionally substituted propanoyl, optionally substituted benzoyl, optionally substituted phenylpropionyl, optionally substituted naphthyl propionyl, optionally substituted dihydroquinoline carbonyl, butanoyl, hexanoyl, octanoyl, dodecanoyl, tetradecanoyl, hexyloxycarbonyl, octyloxycarbonyl, dodecyloxycarbonyl, hexylureido, octylureido, and dodecyloxyureido.
17. The conjugate of any one of items 14 to 16, or a pharmaceutically acceptable salt thereof, wherein each optional substituent is independently hydroxyl, amino, $C_{1-6}$ alkoxy, $C_{1-6}$ alkyl, and phenyl optionally substituted with one to five groups independently selected from the group consisting of halogens, hydroxyl, amino, $C_{1-6}$ alkoxy, $C_{1-6}$ alkyl, 5-membered heterocycles, and 6-membered heterocycles.
18. The conjugate of item 17, or a pharmaceutically acceptable salt thereof, wherein each optional substituent is independently selected from the group consisting of hydroxyl, amino, $C_{1-6}$ alkoxy, $C_{1-6}$ alkyl, and phenyl optionally substituted with one, two, three, four, or five groups independently selected from the group consisting of hydroxyl, amino, $C_{1-6}$ alkoxy, and $C_{1-6}$ alkyl.
19. The conjugate of item 14, or a pharmaceutically acceptable salt thereof, wherein $R^1$ is a fatty acid acyl optionally substituted with —$N(R^N)_2$, methoxypolyethylene glycol acetic acid acyl, methoxypolyethylene glycol propionic acid acyls, an amino acid residue, a dipeptide, a tripeptide, β-N-acetylglucosamine, a β-1,4-glucan, an optionally substituted cinnamoyl, D-alanyl-meso-2,6-diamino-pimelyl amide, an optionally substituted alkyl, or an optionally substituted aryl alkyl.
20. The conjugate of any one of items 14 to 19, or a pharmaceutically acceptable salt thereof, wherein L is an amino acid residue.
21. The conjugate of any one of items 14 to 20, or a pharmaceutically acceptable salt thereof, wherein L is an amino acid residue bonded to $R^1$ through its α-amino group.
22. The conjugate of any one of items 14 to 21, or a pharmaceutically acceptable salt thereof, wherein $R^1$ is a $C_{1-14}$ fatty acid optionally substituted with phenyl.
23. The conjugate of any one of items 14 to 22, or a pharmaceutically acceptable salt thereof, wherein L is a D-amino acid residue.
24. The conjugate of item 23, or a pharmaceutically acceptable salt thereof, wherein L is D-asparagine, D-arginine, D-glutamine, D-aspartic acid, D-histidine, or D-glutamic acid.
25. The conjugate of item 23, or a pharmaceutically acceptable salt thereof, wherein L is an optionally substituted D-asparagine, optionally substituted D-arginine, optionally substituted D-glutamine, optionally substituted D-aspartic acid, or optionally substituted D-glutamic acid.

26. The conjugate of item 23, or a pharmaceutically acceptable salt thereof, wherein L is D-asparagine.

27. The conjugate of any one of items 1 to 13, or a pharmaceutically acceptable salt thereof, wherein the recognition element is selected from the group consisting of 3-(2-methoxyethoxy)propanoyl-D-asparaginyl, 2-(4-isobutylphenyl)propanoyl-D-asparaginyl, 6-methoxynaphthalen-2-yl)propanoyl-D-asparaginyl, (1-cyclopropyl-6-fluoro-4-oxo-7-(piperazin-1-yl)-1,4-dihydroquinoline-3-carbonyl, hexyloxycarbonyl-D-asparaginyl, dodecyloxycarbonyl-D-asparaginyl, hexylcarbamoyl-D-asparaginyl, dodecylcarbamoyl-D-asparaginyl, butanoyl-D-asparaginyl, hexanoyl-D-asparaginyl, octanoyl-D-asparaginyl, dodecanoyl-D-asparaginyl, tetradecanoyl-D-asparaginyl, benzoyl-D-asparaginyl, 2-hydroxybenzoyl-D-asparaginyl, 5-amino-2-hydroxybenzoyl-D-asparaginyl, 2-phenylacetyl-D-asparaginyl, butanoyl-D-argininyl, hexanoyl-D-argininyl, octanoyl-D-argininyl, dodecanoyl-D-argininyl, tetradecanoyl-D-argininyl, butanoyl-D-aspartyl, hexanoyl-D-aspartyl, octanoyl-D-aspartyl, dodecanoyl-D-aspartyl, tetradecanoyl-D-aspartyl, butanoyl-D-glutaminyl, hexanoyl-D-glutaminyl, octanoyl-D-glutaminyl, dodecanoyl-D-glutaminyl, tetradecanoyl-D-glutaminyl, butanoyl-D-glutamyl, hexanoyl-D-glutamyl, octanoyl-D-glutamyl, dodecanoyl-D-glutamyl, tetradecanoyl-D-glutamyl, butanoyl-D-histidinyl, hexanoyl-D-histidinyl, octanoyl-D-histidinyl, dodecanoyl-D-histidinyl, and tetradecanoyl-D-histidinyl.

28. The conjugate of any one of items 1 to 27, or a pharmaceutically acceptable salt thereof, wherein the recognition element is not tetradecanoyl-D-asparaginyl.

29. The conjugate of any one of items 1 to 14, or a pharmaceutically acceptable salt thereof, wherein the recognition element is an amino acid residue, a dipeptide, a tripeptide, β-N-acetylglucosamine, a β-1,4-glucan, an optionally substituted cinnamoyl, or D-alanyl-meso-2,6-diamino-pimelyl amide.

30. The conjugate of any one of items 1 to 29, or a pharmaceutically acceptable salt thereof, wherein the recognition element is covalently linked to the payload through a linker.

31. The conjugate of any one of items 1 to 30, or a pharmaceutically acceptable salt thereof, wherein the linker is covalently bonded to the payload through an ester bond, an amide bond, a thioester bond, a glycosidic bond, a carbonate linker, a carbamate linker, or a urea linker.

32. The conjugate of item 31, or a pharmaceutically acceptable salt thereof, wherein the linker is covalently bonded to the payload through an ester bond, an amide bond, a thioester bond, a glycosidic bond, a carbamate linker, or a urea linker.

33. The conjugate of any one of items 1 to 32, or a pharmaceutically acceptable salt thereof, wherein the linker is a traceless linker.

34. The conjugate of any one of items 30 to 33, or a pharmaceutically acceptable salt thereof, wherein the linker is of formula $R^A$—$(CO)_n$—$NR^3$-$L^1$-$(C(R^2)_2)_m$-$L^2$-$(R^B)_k$,
wherein each of n and m is independently 0 or 1; k is 1, 2, or 3; $R^A$ is a bond to the recognition element; $R^B$ is a bond to the payload; $L^1$ is 1,4-phenylene, 1,2-phenylene, an optionally substituted styrene-diyl, an optionally substituted $C_{1-3}$ hydrocarbon chain, or -$L^A$-$NR^D$—CO—O-$L^B$-, wherein $L^A$ is optionally substituted $C_{2-6}$ alkylene, and $L^B$ is 1,4-phenylene, 1,2-phenylene, or an optionally substituted styrene-diyl; and $L^2$ combines with $(R^B)_k$ to form —$NR^D$—CO—$R^B$, —(CO)—$R^B$, —S—$R^B$, —OCO—$R^B$, —$N(R^B)_q(R^E)_{3-q}$, or

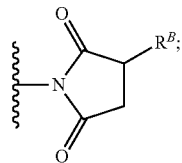

wherein $R^D$ is H or optionally substituted $C_{1-6}$ alkyl, q is 1, 2, or 3, and each $R^E$ is independently H or optionally substituted $C_{1-6}$ alkyl; each $R^2$ is independently H or $C_{1-6}$ alkyl, or both $R^2$ combine with the atom to which each is attached to form a cycloalkylene; and $R^3$ is H or $C_{1-6}$ alkyl.

35. The conjugate of any one of items 30 to 33, or a pharmaceutically acceptable salt thereof, wherein the linker is of formula $R^A$—$(CO)_n$—NH-$L^1$-$(C(R^2)_2)_m$-$L^2$-$(R^B)_k$,
wherein each of n and m is independently 0 or 1; k is 1, 2, or 3; $R^A$ is a bond to the recognition element; $R^B$ is a bond to the payload; $L^1$ is 1,4-phenylene, 1,2-phenylene, an optionally substituted styrene-diyl, an optionally substituted $C_{1-3}$ hydrocarbon chain, or -$L^A$-$NR^D$—CO—O-$L^B$-, wherein $L^A$ is optionally substituted $C_{2-6}$ alkylene, and $L^B$ is 1,4-phenylene, 1,2-phenylene, or an optionally substituted styrene-diyl; and $L^2$ combines with $(R^B)_k$ to form —$NR^D$—CO—$R^B$, —(CO)—$R^B$, —S—$R^B$, —OCO—$R^B$, —$N(R^B)_q(R^E)_{3-q}$, or

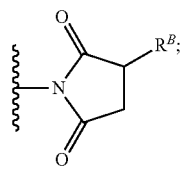

wherein $R^D$ is H or optionally substituted $C_{1-6}$ alkyl, q is 1, 2, or 3, and each $R^E$ is independently H or optionally substituted $C_{1-6}$ alkyl; and
each $R^2$ is independently H or $C_{1-6}$ alkyl, or both $R^2$ combine with the atom to which each is attached to form a cycloalkylene.

36. The conjugate of any one of items 30 to 33, or a pharmaceutically acceptable salt thereof, wherein the linker is of formula $R^A$—$NR^3$-$L^1$-$(C(R^2)_2)_m$-$L^2$-$R^B$,
wherein $R^A$ is a bond to the recognition element; $R^B$ is a bond to the payload; $L^1$ is 1,4-phenylene, or an optionally substituted $C_{1-3}$ alkylene; and $L^2$ combines with $R^B$ to form —$NR^D$—CO—$R^B$, —(CO)—$R^B$, or —COO—$R^B$; m is 0 or 1; wherein $R^D$ is H or optionally substituted $C_{1-6}$ alkyl; each $R^2$ is independently H or $C_{1-6}$ alkyl; and $R^3$ is H or $C_{1-6}$ alkyl.

37. The conjugate of any one of items 30 to 33, or a pharmaceutically acceptable salt thereof, wherein the linker is of formula $R^A$—NH-$L^1$-(C($R^2$)$_2$)-$L^2$-$R^B$, wherein $R^A$ is a bond to the recognition element; $R^B$ is a bond to the payload; $L^1$ is 1,4-phenylene, 1,2-phenylene, or an optionally substituted $C_{1-3}$ hydrocarbon chain; and $L^2$ combines with $R^B$ to form —$NR^D$—CO—$R^B$, —(CO)—$R^B$, —S—$R^B$, —OCO—$R^6$, —N($R^B$)$_q$($R^E$)$_{3-q}$, or O

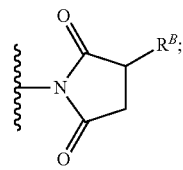

wherein $R^D$ is H or optionally substituted $C_{1-6}$ alkyl, q is 1, 2, or 3, and each $R^E$ is independently H or optionally substituted $C_{1-6}$ alkyl; each $R^2$ is independently H or $C_{1-6}$ alkyl, or both $R^2$ combine with the atom to which each is attached to form a cycloalkylene.

38. The conjugate of any one of items 30 to 33, or a pharmaceutically acceptable salt thereof, wherein the linker is selected from the group consisting of 2-aminobenzyl, 4-aminobenzyl, 4-aminobutanoyl, 4-aminopentanoyl, 2-amino-3-methylbutanoyl, 4-amino-2,2-dimethylbutanoyl, 2-aminopropanoyl, 2-amino-4-methylpentanoyl, 4-aminobutanoate carboxymethylene, 2-aminoethyl aminocarbonyl, 2-aminopropyl aminocarbonyl, 2-aminopropyl methylaminocarbonyl, 2-aminopropyl methylaminocarboxymethylene, 2-methylaminoethyl aminocarbonyl, and 2-aminoethyl methylaminocarbonyl.

39. The conjugate of any one of items 30 to 33, or a pharmaceutically acceptable salt thereof, wherein the linker is selected from the group consisting of D-2-aminopropanoyl, L-2-aminopropanoyl, 2-aminoethyl aminocarbonyl, 4-aminopentanoyl, 4-aminobutanoate carboxymethylene, 2-aminopropyl methylaminocarbonyl, and 2-aminoethyl methylaminocarbonyl.

40. The conjugate of any one of items 1 to 29, or a pharmaceutically acceptable salt thereof, wherein the recognition element is covalently bonded to the payload.

41. The conjugate of any one of items 1 to 40, or a pharmaceutically acceptable salt thereof, wherein the conjugate is cleavable in vivo to release the payload from the conjugate.

42. The conjugate of item 38, or a pharmaceutically acceptable salt thereof, wherein the payload is releasable upon cleavage in vivo of the covalent bond bonding the recognition element to the payload.

43. The conjugate of item 38, or a pharmaceutically acceptable salt thereof, wherein the payload is releasable upon cleavage in vivo of the linker connecting the recognition element to the payload.

44. The conjugate of any one of items 38 to 40, or a pharmaceutically acceptable salt thereof, wherein the conjugate is cleavable in vivo to release the recognition element from the conjugate.

45. The conjugate of any one of items 1 to 41, or a pharmaceutically acceptable salt thereof, wherein the recognition element is recognizable by an enzyme produced by *E. coli* or *Klebsiella pneumoniae*.

46. The conjugate of item 42, or a pharmaceutically acceptable salt thereof, wherein the conjugate is cleavable in vivo by the enzyme produced by *E. coli* or *Klebsiella pneumoniae*.

47. A conjugate of the following structure:

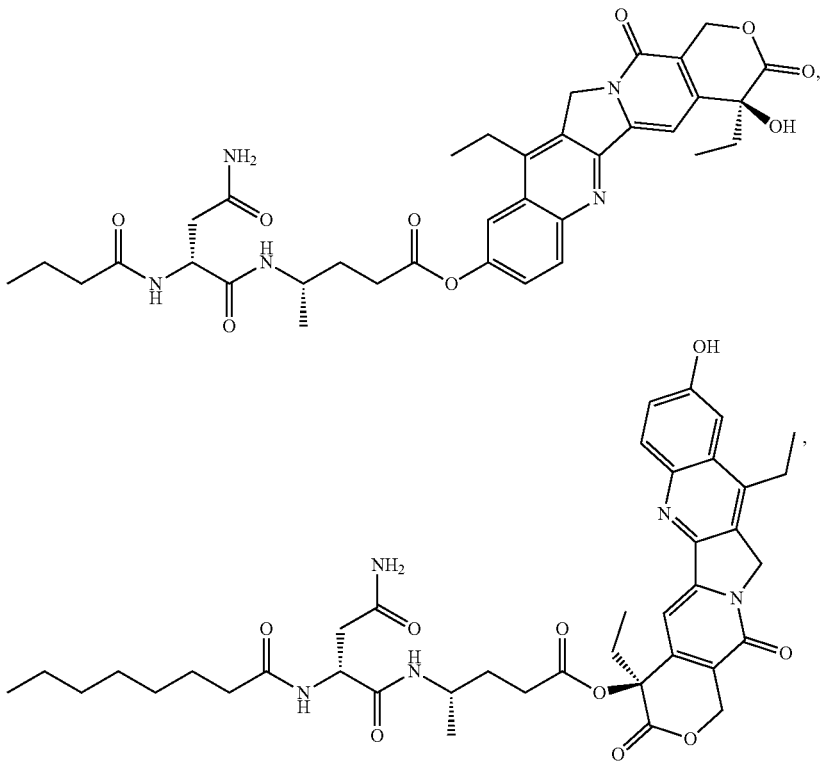

-continued
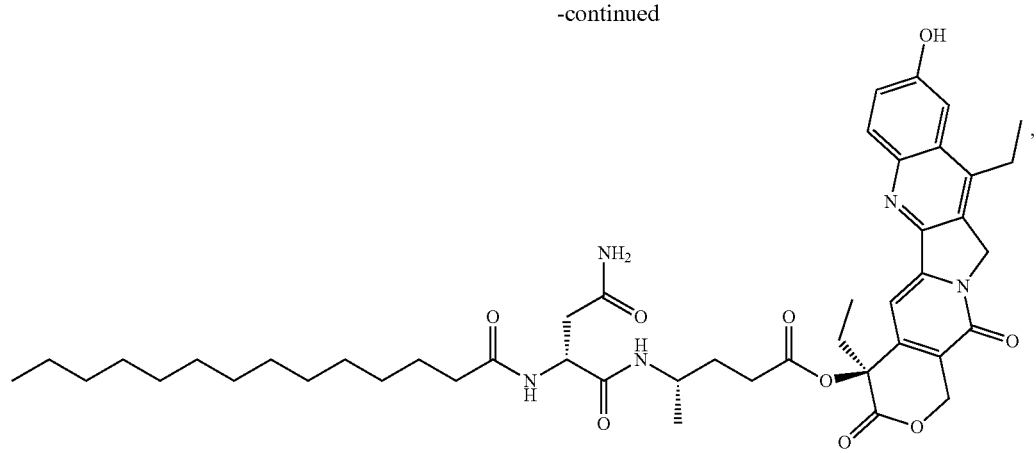
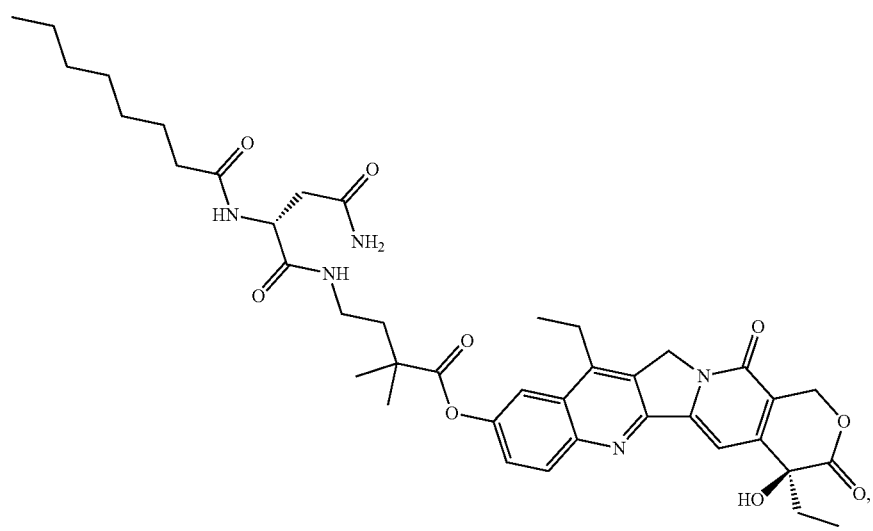
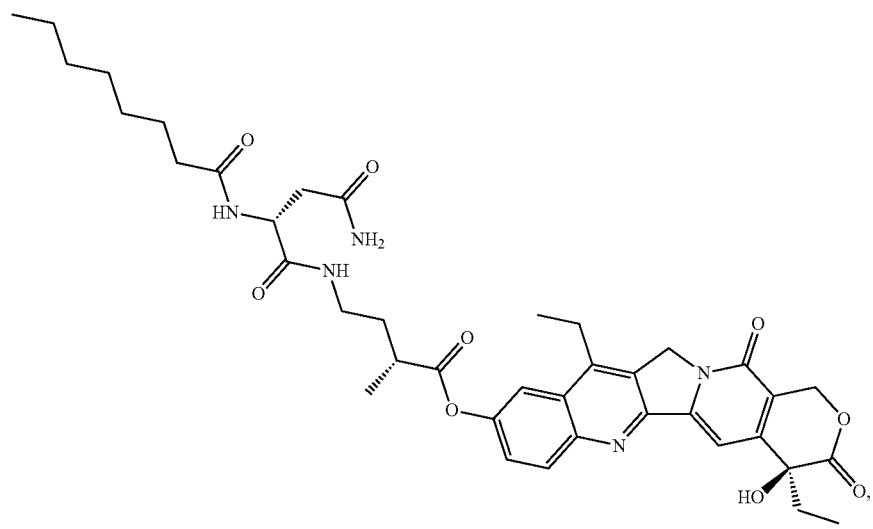

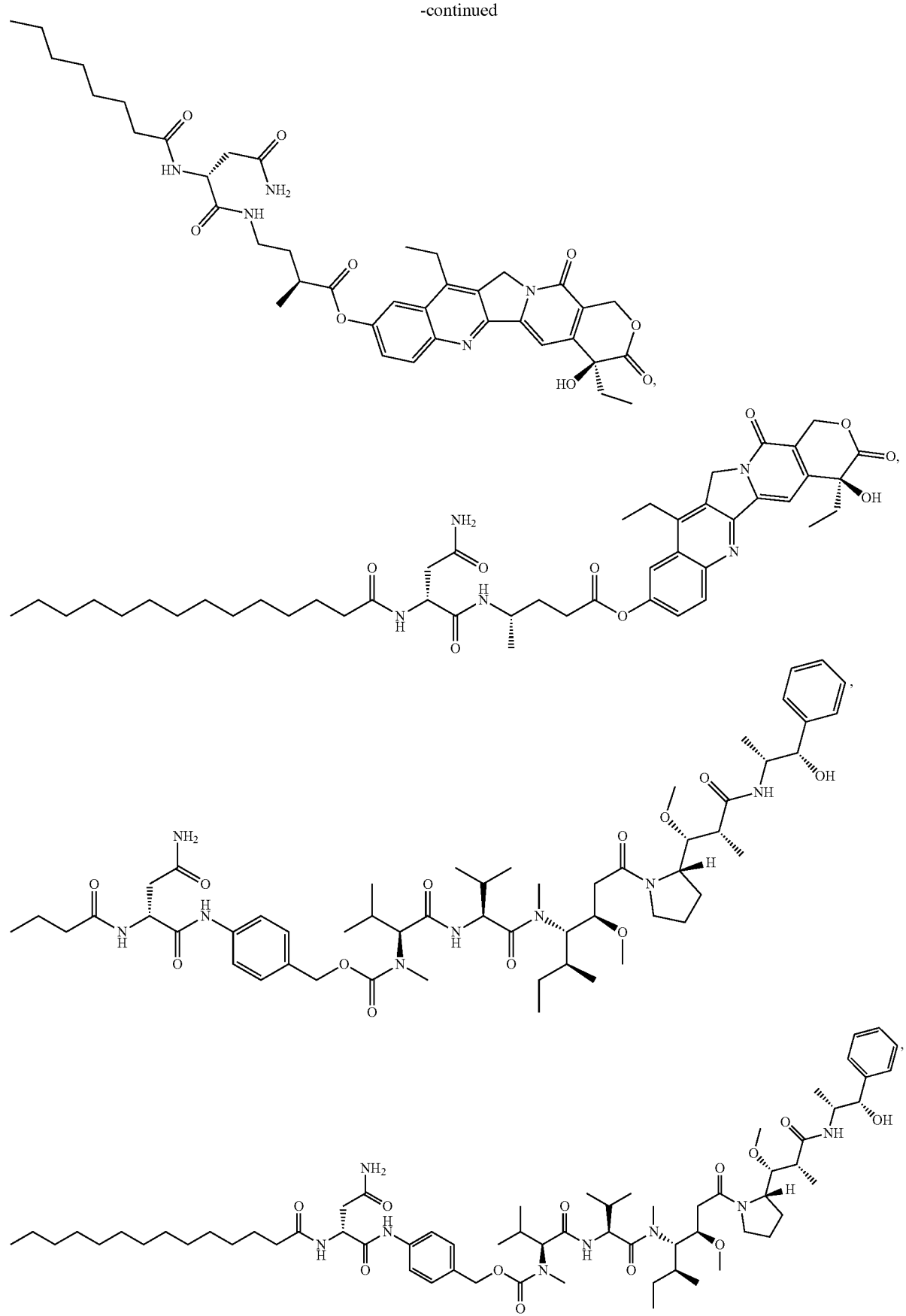

-continued
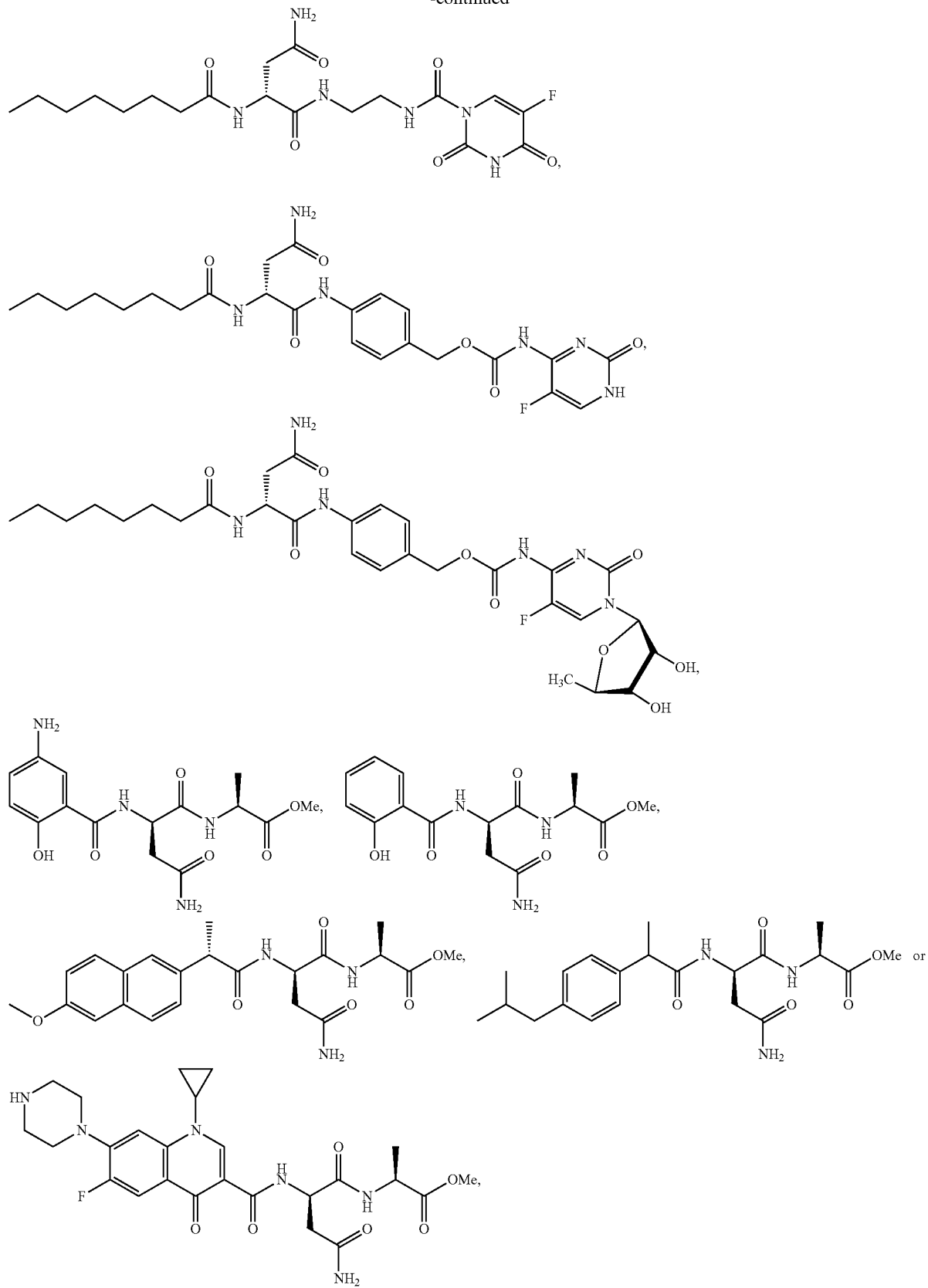
or a pharmaceutically acceptable salt thereof.

48. A compound of the following structure:
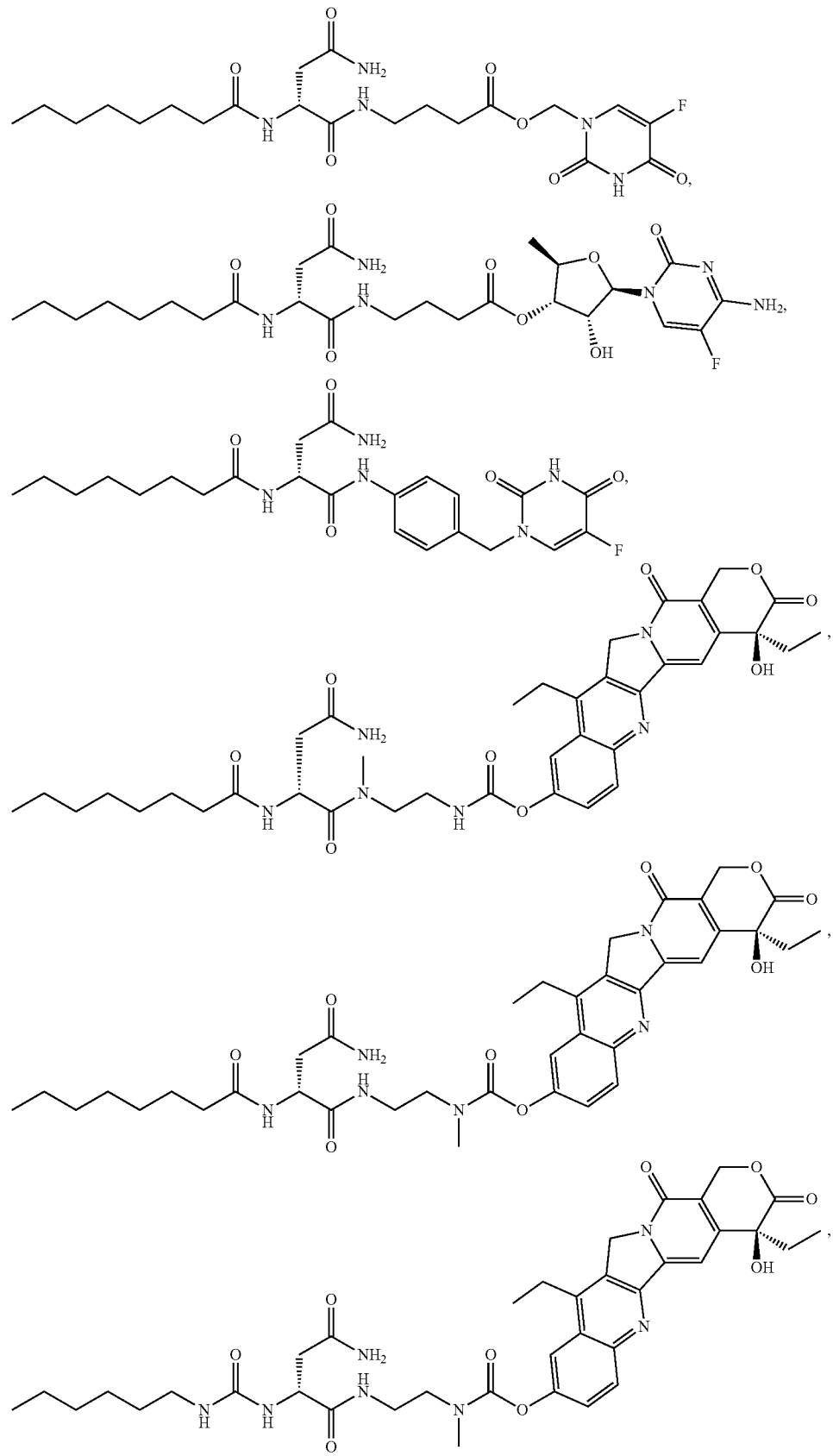

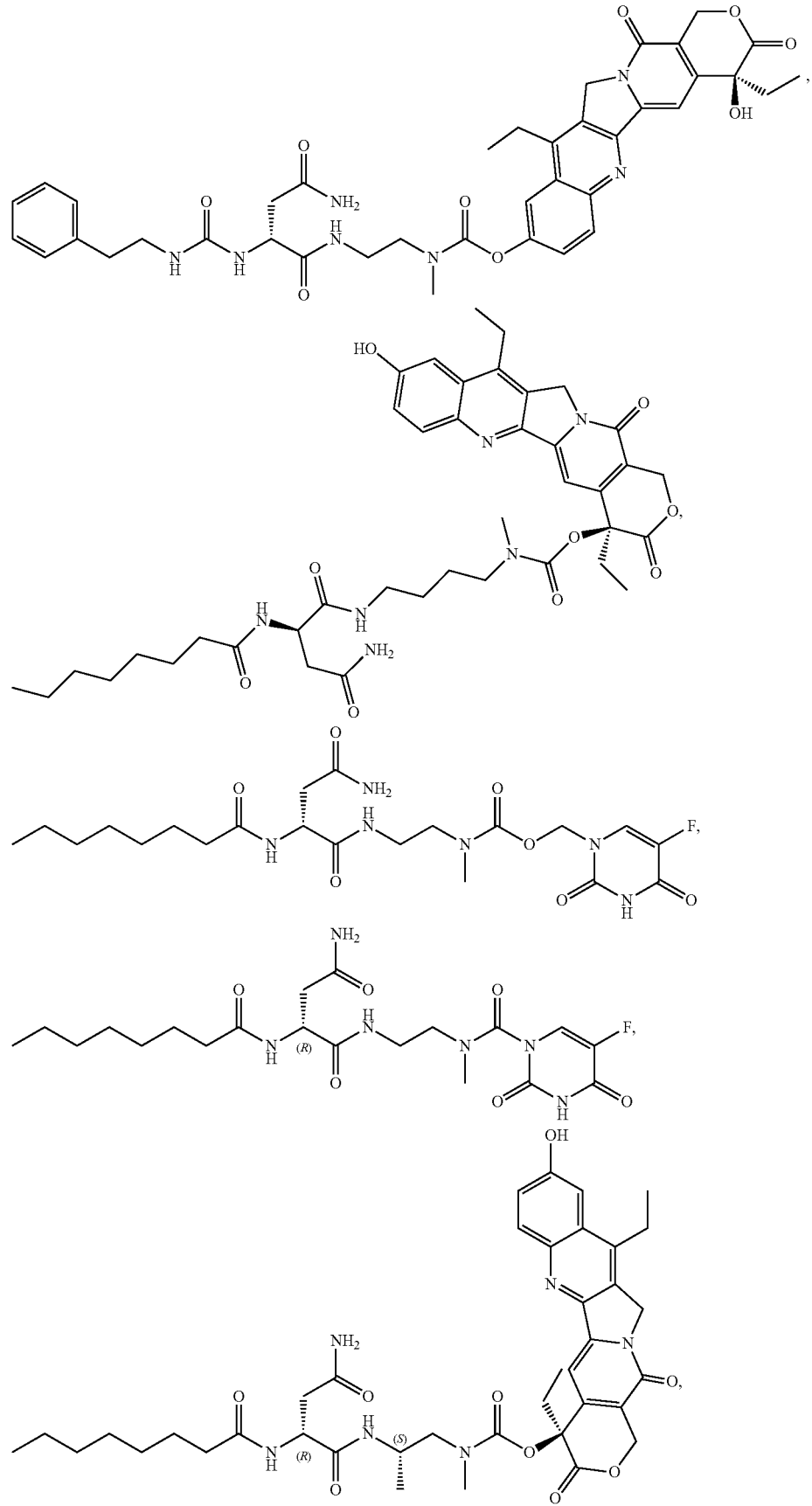

-continued
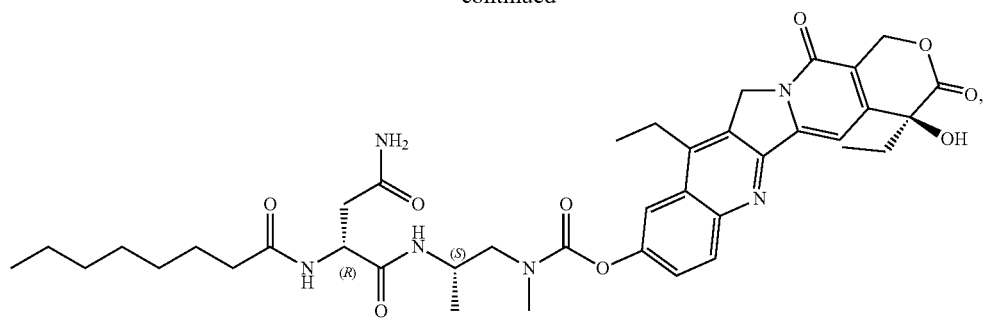
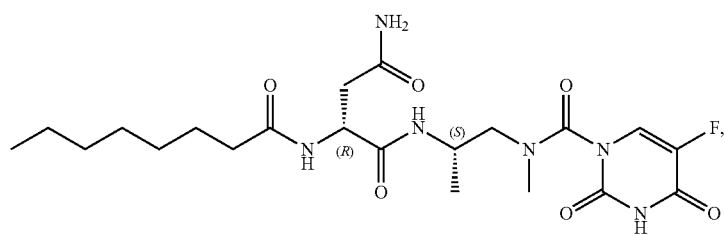
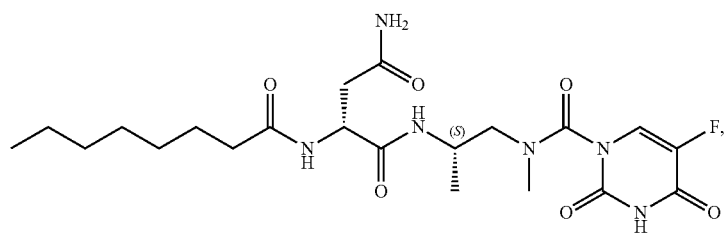
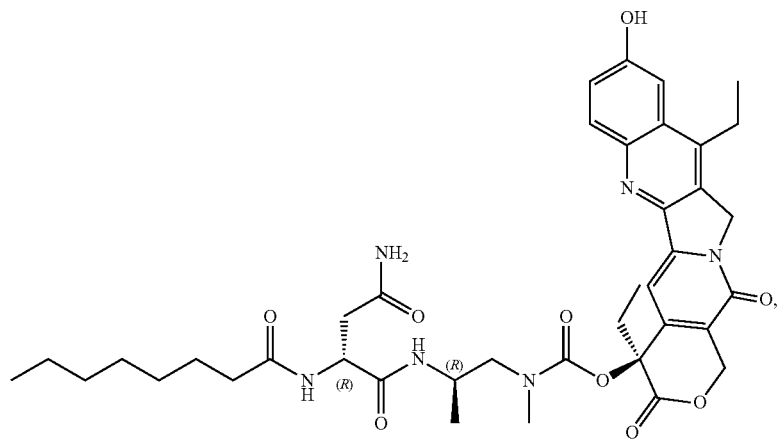
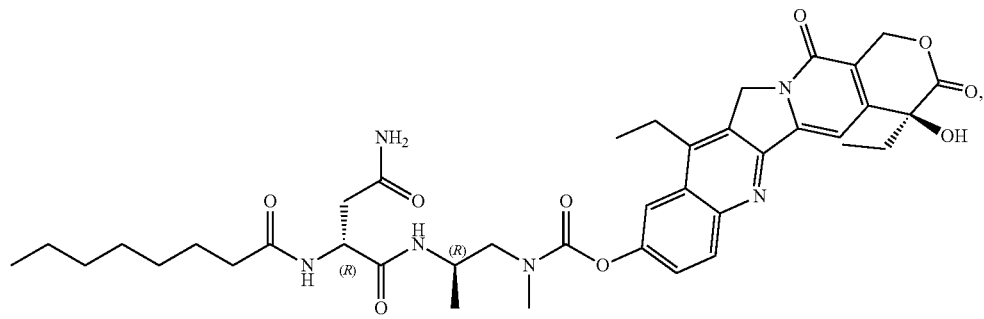

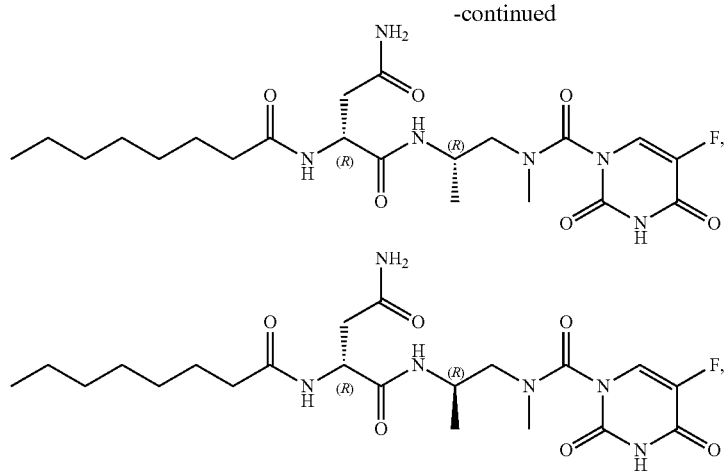

or a pharmaceutically acceptable salt thereof.
49. A pharmaceutical composition comprising the conjugate of any one of items 1 to 48 and a pharmaceutically acceptable excipient.
50. A method of modulating a cancer marker in a subject in need thereof, the method comprising administering to the subject a therapeutically effective amount of the conjugate of any one of items 1 to 48 or the pharmaceutical composition of 49.
51. The method of item 50, wherein the cancer marker is for a cancer or pre-cancerous state selected from the group consisting of colorectal cancer, a colon polyp, lung cancer, gallbladder cancer, breast cancer, cervical cancer, non-small cell lung cancer, squamous cell carcinoma of the head and neck, classical Hodgkin's lymphoma, urothelial carcinoma, melanoma, renal cell carcinoma, hepatocellular carcinoma, Merkel cell carcinoma, and carcinomas with microsatellite instability.
52. The method of item 50, wherein the cancer marker is a colorectal cancer marker selected from the group consisting of carbohydrate antigen 19-9 and carcinoembryonic antigen.
53. The method of any one of items 50 to 52, wherein the subject suffers from cancer.
54. A method of modulating an infection marker in a subject in need thereof, the method comprising administering to the subject a therapeutically effective amount of the conjugate of any one of items 1 to 48 or the pharmaceutical composition of item 49.
55. The method of item 54, wherein the infection marker is blood, urine or cerebrospinal white blood cell count; erythrocyte sedimentation rate; serum hepatic transaminase levels; serum blood alkaline phosphatase levels; or culture of sterile body fluid.
56. The method of item 54 or 55, wherein the infection marker is a for an infection selected from the group consisting of pneumonia, lung abscess, liver abscess, meningitis, spinal infection, epidural abscess, brain abscess, bloodstream infection, urinary tract infection, and bacteremia.
57. A method of treating a disease in a subject in need thereof, the method comprising administering to the subject a therapeutically effective amount of the conjugate of any one of items 1 to 48 or the pharmaceutical composition of item 49.
58. The method of item 57, wherein the disease is cancer or pre-cancerous state.
59. The method of item 58, wherein the cancer or pre-cancerous state is colorectal cancer, a colon polyp, lung cancer, gallbladder cancer, breast cancer, cervical cancer, non-small cell lung cancer, squamous cell carcinoma of the head and neck, classical Hodgkin's lymphoma, urothelial carcinoma, melanoma, renal cell carcinoma, hepatocellular carcinoma, Merkel cell carcinoma, or carcinoma with microsatellite instability.
60. The method of item 59, wherein the cancer or pre-cancerous state is colorectal cancer, a colon polyp, lung cancer, gallbladder cancer, breast cancer, or cervical cancer.
61. The method of item 57, wherein the disease is an infection.
62. The method of item 61, wherein the infection is pneumonia, lung abscess, liver abscess, meningitis, spinal infection, epidural abscess, brain abscess, bloodstream infection, urinary tract infection, or bacteremia.
63. A method of delivering a payload to a disease site in a subject in need thereof, the method comprising administering to the subject a therapeutically effective amount of the conjugate of any one of items 1 to 48 or the pharmaceutical composition of item 49.
64. The method of item 63, wherein the disease site is populated by a microorganism.
65. The method of item 64, wherein the microorganism is a bacterium.
66. The method of item 64 or 65, wherein the microorganism expresses ClbP.
67. The method of any one of items 64 to 66, wherein the disease site is populated by *E. coli, P. acnes, C. pneumoniae, S. enterica* serovar *Typhi, M. radiotolerans, C. trachomatis,* or *Klebsiella pneumoniae.*
68. The method of item any one of items 63 to 67, wherein the conjugate is cleavable in vivo to deliver the payload to the disease site.
69. A method of modulating the microbiome of a subject having cancer, infection, or lesion, the method comprising administering to the subject a therapeutically effective amount of the conjugate of any one of items 1 to 48 or the pharmaceutical composition of item 49.
70. The method of any one of items 68 to 69, wherein the conjugate is cleavable in vivo by a protein produced by a microorganism.

71. The method of item 70, wherein the conjugate is cleavable in vivo by a protein produced by bacteria.
72. The method of item 71, wherein the bacteria are *E. coli, P. acnes, C. pneumoniae, S. enterica* serovar *Typhi, M. radiotolerans, C. trachomatis,* or *Klebsiella pneumoniae.*
73. The method of item 71 or 72, wherein the bacterium expresses ClbP.
74. The method of any one of items 71 to 73, wherein the bacteria are *E. coli* or *Klebsiella pneumoniae*.
75. The method of any one of items 50 to 74, wherein a $CD4^+CD25^+$ Treg cell count, cytotoxic T cell count, interferon γ (IFNγ) level, interleukin-17 (IL17) level, or intercellular adhesion molecule (ICAM) level is modulated following the administration of the conjugate or a pharmaceutically acceptable salt thereof.
76. The method of any one of items 50 to 75, wherein an NFκB level, matrix metallopeptidase 9 (MMP9) level, 8-iso-prostaglandin $F_2$a (8-iso-PGF2α) level, or CXCL13 level is reduced following the administration of the conjugate or a pharmaceutically acceptable salt thereof.
77. The method of any one of items 50 to 76, wherein a $T_h1$ cell count, IgA level, or inducible nitric oxide synthase (iNOS) level is modulated following the administration of the conjugate or a pharmaceutically acceptable salt thereof.
78. The method of any one of items 50 to 77, further comprising determining the presence or amount of microorganisms, wherein the microorganisms are capable of cleaving an amide, ester, thioester, or glycosidic bond, or a carbamate or urea linker.
79. A method of treating a disease in a subject in need thereof, the method comprising:
    determining the presence or amount of a microorganism expressing a protein capable of cleaving the conjugate of any one of items 1 to 48 in the subject diagnosed with the disease, and
    administering to the subject a therapeutically effective amount of the conjugate of any one of items 1 to 48 or the pharmaceutical composition of item 49 if the evaluation of the subject is positive for the presence of the microorganism.
80. The method of item 78 or 79, wherein the determining step comprises performing PCR, bacteriological culture analysis, fluorescent in situ hybridization, gas-liquid chromatography, and/or bacterial enzyme activity analysis.
81. The method of any one of items 78 to 80, wherein the determining step is performed before, during, and/or after the administering step.
82. The method of any one of items 78 to 81, wherein the presence of the microorganism is determined in a sample from the subject.
83. The method of item 82, wherein the sample is a stool sample, a bodily fluid sample, or a biopsy sample.
84. The method of any one of items 78 to 83, wherein the microorganism is a bacterium.
85. The method of item 84, wherein the bacterium is *E. coli, P. acnes, C. pneumoniae, S. enterica* serovar *Typhi, M. radiotolerans, C. trachomatis,* or *Klebsiella pneumoniae.*
86. The method of item 84 or 85, wherein the bacterium expresses ClbP.
87. The method of any one of items 84 to 86, wherein the bacterium is *E. coli* or *Klebsiella pneumoniae*.
88. The method of any one of items 50 to 87, wherein the conjugate is administered as a pharmaceutical composition comprising the conjugate and a pharmaceutically acceptable excipient.
89. The method of any one of items 50 to 88, wherein the conjugate is administered orally, rectally, intravenously, intratumorally, or intralesionally.

Definitions

The term "acyl," as used herein, represents a chemical substituent of formula —C(O)—R, where R is alkyl, alkenyl, aryl, arylalkyl, cycloalkyl, heterocyclyl, heterocyclyl alkyl, heteroaryl, or heteroaryl alkyl. An optionally substituted acyl is an acyl that is optionally substituted as described herein for each group R. Non-limiting examples of acyl include fatty acid acyls (e.g., short chain fatty acid acyls (e.g., acetyl)) and benzoyl.

The term "acyloxy," as used herein, represents a chemical substituent of formula —OR, where R is acyl. An optionally substituted acyloxy is an acyloxy that is optionally substituted as described herein for acyl.

The term "alcohol oxygen atom," as used herein, refers to a divalent oxygen atom having at least one valency bonded to an $sp^3$-hybridized carbon atom.

The term "alkenoyl," as used herein, represents a chemical substituent of formula —C(O)—R, where R is alkenyl. An optionally substituted alkenoyl is an alkenoyl that is optionally substituted as described herein for alkyl.

The term "alkanoyl," as used herein, represents a chemical substituent of formula —C(O)—R, where R is alkyl. An optionally substituted alkanoyl is an alkanoyl that is optionally substituted as described herein for alkyl.

The term "alkynoyl," as used herein, represents a chemical substituent of formula —C(O)—R, where R is alkynyl. An optionally substituted alkynoyl is an alkynoyl that is optionally substituted as described herein for alkyl.

The term "alkoxy," as used herein, represents a chemical substituent of formula —OR, where R is a $C_{1-6}$ alkyl group, unless otherwise specified. An optionally substituted alkoxy is an alkoxy group that is optionally substituted as defined herein for alkyl.

The term "alkenyl," as used herein, represents acyclic monovalent straight or branched chain hydrocarbon groups containing one, two, or three carbon-carbon double bonds. Alkenyl, when unsubstituted, has from 2 to 22 carbons, unless otherwise specified. In certain preferred embodiments, alkenyl, when unsubstituted, has from 2 to 12 carbon atoms (e.g., 1 to 8 carbons). Non-limiting examples of the alkenyl groups include ethenyl, prop-1-enyl, prop-2-enyl, 1-methylethenyl, but-1-enyl, but-2-enyl, but-3-enyl, 1-methylprop-1-enyl, 2-methylprop-1-enyl, and 1-methylprop-2-enyl. Alkenyl groups may be optionally substituted as defined herein for alkyl.

The term "alkenylene," as used herein, refers to a straight or branched chain alkenyl group with one hydrogen removed, thereby rendering this group divalent. Non-limiting examples of the alkenylene groups include ethen-1,1-diyl; ethen-1,2-diyl; prop-1-en-1,1-diyl, prop-2-en-1,1-diyl; prop-1-en-1,2-diyl, prop-1-en-1,3-diyl; prop-2-en-1,1-diyl; prop-2-en-1,2-diyl; but-1-en-1,1-diyl; but-1-en-1,2-diyl; but-1-en-1,3-diyl; but-1-en-1,4-diyl; but-2-en-1,1-diyl; but-2-en-1,2-diyl; but-2-en-1,3-diyl; but-2-en-1,4-diyl; but-2-en-2,3-diyl; but-3-en-1,1-diyl; but-3-en-1,2-diyl; but-3-en-1,3-diyl; but-3-en-2,3-diyl; buta-1,2-dien-1,1-diyl; buta-1,2-dien-1,3-diyl; buta-1,2-dien-1,4-diyl; buta-1,3-dien-1,1-diyl; buta-1,3-dien-1,2-diyl; buta-1,3-dien-1,3-diyl; buta-1, 3-dien-1,4-diyl; buta-1,3-dien-2,3-diyl; buta-2,3-dien-1,1-diyl; and buta-2,3-dien-1,2-diyl. An optionally substituted alkenylene is an alkenylene that is optionally substituted as described herein for alkyl.

The term "alkoxycarbonyl," as used herein, represents a chemical substituent of formula —C(O)OR, where R is a $C_{1-6}$ alkyl group, unless otherwise specified. An optionally substituted alkoxycarbonyl is an alkoxycarbonyl group that is optionally substituted as defined herein for alkyl.

The term "alkyl," as used herein, refers to an acyclic straight or branched chain saturated hydrocarbon group, which, when unsubstituted, has from 1 to 22 carbons (e.g., 1 to 20 carbons), unless otherwise specified. In certain preferred embodiments, alkyl, when unsubstituted, has from 1 to 12 carbons (e.g., 1 to 8 carbons). Alkyl groups are exemplified by methyl; ethyl; n- and iso-propyl; n-, sec-, iso- and tert-butyl; neopentyl, and the like, and may be optionally substituted, valency permitting, with one, two, three, or, in the case of alkyl groups of two carbons or more, four or more substituents independently selected from the group consisting of: alkoxy; acyloxy; alkylsulfenyl; alkylsulfinyl; alkylsulfonyl; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thioalkyl; thioalkenyl; thioaryl; thiol; silyl; cyano; =O; =S; and =NR', where R' is H, alkyl, aryl, or heterocyclyl. Each of the substituents may itself be unsubstituted or, valency permitting, substituted with unsubstituted substituent(s) defined herein for each respective group.

The term "alkylaminocarbonyl," as used herein, represents a chemical substituent of formula —COR$^X$, where R$^X$ is amino as described herein. An optionally substituted alkylaminocarbonyl is an alkylaminocarbonyl that is optionally substituted as defined herein for alkyl.

The term "alkylene," as used herein, refers to a saturated divalent hydrocarbon group that is a straight or branched chain saturated hydrocarbon, in which two valencies replace two hydrogen atoms. Non-limiting examples of the alkylene group include methylene, ethane-1,2-diyl, ethane-1,1-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, and butane-2,2-diyl, butane-2,3-diyl. An optionally substituted alkylene is an alkylene that is optionally substituted as described herein for alkyl.

The term "alkylsulfenyl," as used herein, represents a group of formula —S-(alkyl). An optionally substituted alkylsulfenyl is an alkylsulfenyl that is optionally substituted as described herein for alkyl.

The term "alkylsulfinyl," as used herein, represents a group of formula —S(O)-(alkyl). An optionally substituted alkylsulfinyl is an alkylsulfinyl that is optionally substituted as described herein for alkyl.

The term "alkylsulfonyl," as used herein, represents a group of formula —S(O)$_2$-(alkyl). An optionally substituted alkylsulfonyl is an alkylsulfonyl that is optionally substituted as described herein for alkyl.

The term "alkylureido," as used herein, represents a group of formula —NR$^{N1}$—CO—NR$^{N2}$R$^{N3}$, where each of R$^{N1}$, R$^{N2}$, and R$^{N3}$ is independently H or alkyl, provided that at least one of R$^{N1}$, R$^{N2}$, and R$^{N3}$ is alkyl. Non-limiting examples include monomethylureido, monoethylureido, dimethylureido, diethylureido, N-methyl-N-ethylureido, hexylureido, octylureido, and dodecylureido. An optionally substituted alkylureido is an alkylureido that is optionally substituted as described herein for alkyl.

The term "amide bond," as used herein, refers to a covalent bond between a nitrogen atom and a carbon atom in a carbonyl group.

The term "amino," as used herein, unless otherwise specified, refers to a group of formula —NR$^{N1}$R$^{N2}$, where each of R$^{N1}$ and R$^{N2}$ is independently H or alkyl.

The term "amino acid," as used herein, represents proline, taurine, or a compound having an amino group and a carboxylate or sulfonate group separated by an optionally substituted alkylene or optionally substituted arylene. Amino acids are small molecules and have a molecular weight of <900 g/mol (preferably, <500 g/mol). Preferably, when the linker is alkylene, the linker may be optionally substituted as described herein for alkyl. In some embodiments, optionally substituted alkylene is an alkylene substituted with 1 or 2 groups that are independently hydroxyl, thiol, amino, guanidine, carbamoylamino, imidazolyl, indolyl, —SeH, oxo, 4-hydroxyphenyl, phenyl, or —SMe. Non-limiting examples of amino acids include alanine, arginine, asparagine, aspartic acid, cysteine, glutamic acid, glutamine, glycine, histidine, isoleucine, leucine, lysine, methionine, phenylalanine, proline, selenocysteine, serine, threonine, tyrosine, tryptophan, ornithine, citrulline, aminobenzoic acid, and taurine. Optionally substituted asparagine, arginine, glutamine, aspartic acid, and glutamic acid are asparagine, arginine, glutamine, aspartic acid, and glutamic acid having a side chain oxygen or nitrogen atom optionally substituted with an alkyl.

The term "ammonium nitrogen atom," as used herein, refers to the tetrasubstituted nitrogen atom in a quaternary ammonium salt.

The term "aproteinaceous," as used herein, refers to chemical substituents lacking within their structures three or more amino acids interconnected by peptidic bonds.

The term "aroyl," as used herein, represents a chemical substituent of formula —C(O)—R, where R is aryl. An optionally substituted aroyl is an aroyl that is optionally substituted as described herein for aryl.

The term "aryl," as used herein, represents a mono-, bicyclic, or multicyclic carbocyclic ring system having one or two aromatic rings. Aryl group may include from 6 to 10 carbon atoms. All atoms within an unsubstituted carbocyclic aryl group are carbon atoms. Non-limiting examples of carbocyclic aryl groups include phenyl, naphthyl, 1,2-dihydronaphthyl, 1,2,3,4-tetrahydronaphthyl, fluorenyl, indanyl, indenyl, etc. The aryl group may be unsubstituted or substituted with one, two, three, four, or five substituents independently selected from the group consisting of: alkyl; alkenyl; alkoxy; acyloxy; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thioalkyl; thioalkenyl; thioaryl; thiol; silyl; and cyano. Each of the substituents may itself be unsubstituted or substituted with unsubstituted substituent(s) defined herein for each respective group.

The term "arylene," as used herein, represents an aryl group, in which one hydrogen atom is replaced with a valency. An optionally substituted arylene is an arylene that is optionally substituted as described herein for aryl. In some embodiments, arylene is phenylene (e.g., 1,2-phenylene or 1,4-phenylene).

The term "aryl alkyl," as used herein, represents an alkyl group substituted with an aryl group. An optionally substituted aryl alkyl is an aryl alkyl, in which aryl and alkyl portions are each independently, optionally substituted as the individual groups as described herein.

The term "aryloxy," as used herein, represents a group —OR, where R is aryl. Aryloxy may be an optionally substituted aryloxy. An optionally substituted aryloxy is aryloxy that is optionally substituted as described herein for aryl.

The term "carboxylate," as used herein, represents group —COOH or a salt thereof.

The term "carboxylate oxygen atom," as used herein, refers to a divalent oxygen atom having at least one valency bonded to the carbon atom of a carbonyl group.

The term "cancer," as used herein, refers to a group of proliferative diseases characterized by uncontrolled division of abnormal cells in a subject. Non-limiting examples of cancers include non-small cell lung cancer, squamous cell carcinoma of the head and neck, classical Hodgkin's lymphoma, urothelial carcinoma, melanoma, renal cell carcinoma, hepatocellular carcinoma, Merkel cell carcinoma, carcinomas with microsatellite instability, colorectal cancer, small intestine cancer, acute lymphoblastic leukemia, acute myeloid leukemia, adrenocortical carcinoma, Kaposi sarcoma, primary CNS lymphoma, anal cancer, astrocytoma, glioblastoma, bladder cancer, Ewing sarcoma, osteosarcoma, non-Hodgkin lymphoma, breast cancer, brain tumor, cervical cancer, bile duct cancer, chronic lymphocytic leukemia, chronic myelogenous leukemia, gallbladder cancer, gastrointestinal stromal tumor, ovarian cancer, testicular cancer, multiple myeloma, neuroblastoma, pancreatic cancer, parathyroid cancer, prostate cancer, rectal cancer, and Wilms tumor.

The term "cancer marker," as used herein, is an observable indication of the presence, absence, or risk of a cancer (e.g., colorectal cancer, non-small cell lung cancer, squamous cell carcinoma of the head and neck, classical Hodgkin's lymphoma, urothelial carcinoma, melanoma, renal cell carcinoma, hepatocellular carcinoma, Merkel cell carcinoma, or a carcinoma with microsatellite instability) or pre-cancerous state. The level of a cancer marker may directly or inversely correlate with a cancer progression. A cancer marker that is inversely correlated to the cancer progression is an "inverse cancer marker." Non-limiting examples of the cancer markers are a $CD4^+CD25^+$ Treg cell (e.g., $CD4^+CD25^+Foxp3^+$ Treg cell) count, cytotoxic T cell count, $T_h1$ cell count, NFκB level, inducible nitric oxide synthase (iNOS) level, matrix metallopeptidase 9 (MMP9) level, interferon γ (IFNγ) level, interleukin-17 (IL17) level, intercellular adhesion molecule (ICAM) level, CXCL13 level, and 8-iso-prostaglandin $F_{2\alpha}$ (8-iso-PGF2α) level. The cancer markers may be measured using methods known in the art. For example, blood sample analyses may be performed to measure a $CD4^+CD25^+$ Treg cell (e.g., $CD4^+CD25^+Foxp3^+$ Treg cell) count, cytotoxic T cell count, $T_h1$ level, NFκB level, inducible nitric oxide synthase (iNOS) level, matrix metallopeptidase 9 (MMP9) level, interferon γ (IFNγ) level, interleukin-17 (IL17) level, intercellular adhesion molecule (ICAM) level, CXCL13 level, and 8-iso-prostaglandin $F_{2\alpha}$ (8-iso-PGF2α) level. Additional non-limiting examples of cancer markers include computerized tomography or magnetic resonance imagery for the presence of tumor and intensity of uptake of fludeoxyglucose signal on positron emission tomography. Additional non-limiting examples of cancer markers pertinent to specific cancer types include hormone receptors, human epidermal growth factor receptor 2 (HER-2), Ki67 antigen, tumor protein p53 and chemokine receptor type 4 (CXCR4) for breast cancer; human papilloma virus DNA (HPV DNA), squamous cell carcinoma antigen, serum fragments of cytokeratin (CYFRA), carcinoembryonic antigen (CEA) and soluble CD44 for cervical cancer; Cancer antigens (CA), alone or in combinations, 242, 199, 125, 15-3, CEA for gallbladder cancer; CYFRA 19, squamous cell carcinoma antigen, CEA, CA 125, tissue polypeptide specific antigen for lung cancer; and prostate-specific antigen, human kallikrein 2 (hK2), transforming growth factor beta-1, interleukin-6, fatty acid synthase (FAS), early prostate cancer antigen (EPCA), and prostate cancer antigen-3 (PCA-3) for prostate cancer, respectively. Cancer markers may be determined by biopsy of suspected tumor sites surgically, endoscopically or via transthoracic, transrectal or colposcopic means or with or without imaging guidance. Cancer markers may also be determined in the blood, plasma, serum, urine, cerebrospinal fluid, stool or other body fluids.

The term "carbamate linker," as used herein, refers to a group $R^1$—(CO)—$R^2$, where $R^1$ is a bond to an oxygen atom, and $R^2$ is a bond to a nitrogen atom.

The term "carbonate linker," as used herein, refers to a group $R^1$—(CO)—$R^2$, where $R^1$ is a bond to a first oxygen atom, and $R^2$ is a bond to a second oxygen atom.

The term "carbonyl," as used herein, refers to a divalent group of formula —(CO)—.

The term "cinnamoyl," as used herein, refers to a monovalent group of formula trans Ar—CH=CH—CO—, where Ar is phenyl optionally substituted with one or two substituents independently selected from the group consisting of hydroxy and alkoxy (e.g., methoxy). Non-limiting examples of the optionally substituted cinnamoyl groups include caffeic acid, ferulic acid, and 4-hydroxycinnamic acid.

The term "cleavable in vivo," as used herein, refers to a property of a compound or a bond within a compound that is broken down in vivo to produce at least two separate compounds. In some embodiments, the cleavage process is hydrolysis. Thus, a compound that is cleavable in vivo may be a compound hydrolyzable in vivo. Cleavage of a compound or bond can be mediated by an enzyme or may proceed spontaneously under conditions present in a given in vivo compartment (e.g., a portion of the gastrointestinal tract). In some embodiment, a cleavable in vivo bond or compound is cleavable substantially by an enzyme (e.g., a peptidase) produced by bacteria (e.g., bacteria present at the disease site (e.g., *E. coli* or *Klebsiella pneumoniae*)).

The term "colorectal cancer marker," as used herein, represents an observable indicative of the presence, absence, or risk of colorectal cancer. Colorectal cancer may be detected by colonoscopy, biopsy, biopsy and DNA microsatellite instability testing, complete blood count, carcinoembryonic antigen level measurement (e.g., in blood), imaging (e.g., computed tomography (CT), magnetic resonance imaging (MRI), ultrasound, X-ray, or positron emission tomography (PET)), or carbohydrate antigen 19-9 level.

The expression "$C_{x-y}$," as used herein, indicates that the group, the name of which immediately follows the expression, when unsubstituted, contains a total of from x to y carbon atoms. If the group is a composite group (e.g., aryl alkyl), $C_{x-y}$ indicates that the portion, the name of which immediately follows the expression, when unsubstituted, contains a total of from x to y carbon atoms. For example, ($C_{6-10}$-aryl)-$C_{1-6}$-alkyl is a group, in which the aryl portion, when unsubstituted, contains a total of from 6 to 10 carbon atoms, and the alkyl portion, when unsubstituted, contains a total of from 1 to 6 carbon atoms.

The term "cycloalkoxy," as used herein, represents a group —OR, where R is cycloalkyl. An optionally substituted cycloalkoxy is cycloalkoxy that is optionally substituted as described herein for cycloalkyl.

The term "cycloalkyl," as used herein, refers to a cyclic alkyl group having from three to ten carbons (e.g., a $C_3$-$C_{10}$ cycloalkyl), unless otherwise specified. Cycloalkyl groups may be monocyclic or bicyclic. Bicyclic cycloalkyl groups may be of bicyclo[p.q.0]alkyl type, in which each of p and q is, independently, 1, 2, 3, 4, 5, 6, or 7, provided that the sum of p and q is 2, 3, 4, 5, 6, 7, or 8. Alternatively, bicyclic cycloalkyl groups may include bridged cycloalkyl structures, e.g., bicyclo[p.q.r]alkyl, in which r is 1, 2, or 3, each of p and q is, independently, 1, 2, 3, 4, 5, or 6, provided that the sum of p, q, and r is 3, 4, 5, 6, 7, or 8. The cycloalkyl group may be a spirocyclic group, e.g., spiro[p.q]alkyl, in which each of p and q is, independently, 2, 3, 4, 5, 6, or 7, provided that the sum of p and q is 4, 5, 6, 7, 8, or 9. Non-limiting examples of cycloalkyl include cyclopropyl, cyclobutyl, cyclopentyl, cyclohexyl, cycloheptyl, 1-bicyclo[2.2.1.]heptyl, 2-bicyclo[2.2.1.]heptyl, 5-bicyclo[2.2.1.]heptyl, 7-bicyclo[2.2.1.]heptyl, and decalinyl. The cycloalkyl group may be unsubstituted or substituted (e.g., optionally substituted cycloalkyl) with one, two, three, four, or five substituents independently selected from the group consisting of: alkyl; alkenyl; alkoxy; acyloxy; alkylsulfenyl; alkylsulfinyl; alkylsulfonyl; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thioalkyl; thioalkenyl; thioaryl; thiol; silyl; cyano; =O; =S; =NR', where R' is H, alkyl, aryl, or heterocyclyl. Each of the substituents may itself be unsubstituted or substituted with unsubstituted substituent(s) defined herein for each respective group.

The term "cycloalkylene," as used herein, refers to a divalent group that is a cycloalkyl, in which one hydrogen atom is replaced with a valency. Cycloalkylene may be unsubstituted or substituted as described herein for cycloalkyl.

The term "ester bond," as used herein, refers to a covalent bond between an alcohol or phenolic oxygen atom and the carbon atom of carbonyl group that is further bonded to a carbon atom.

The term "fatty acid," as used herein, refers to a short-chain fatty acid, a medium chain fatty acid, a long chain fatty acid, a very long chain fatty acid, or an unsaturated analogue thereof, or a phenyl-substituted analogue thereof. Short chain fatty acids contain from 1 to 6 carbon atoms, medium chain fatty acids contain from 7 to 13 carbon atoms, long-chain fatty acids contain from 14 to 22 carbon atoms, and a very long-chain fatty acid contains 23 to 26 carbon atoms. A fatty acid may be saturated or unsaturated. An unsaturated fatty acid includes 1, 2, 3, 4, 5, or 6 carbon-carbon double bonds. Preferably, the carbon-carbon double bonds in unsaturated fatty acids have Z stereochemistry.

The term "fatty acid acyl," as used herein, refers to a fatty acid, in which the hydroxyl group is replaced with a valency.

The term "fatty acid acyloxy," as used herein, refers to group —OR, where R is a fatty acid acyl.

The term "glycosidic bond," as used herein, refers to a covalent bond between an oxygen atom and an anomeric carbon atom in a pyranose ring or furanose ring.

The term "halogen," as used herein, represents a halogen selected from bromine, chlorine, iodine, and fluorine. A halide, when used as a leaving group, is typically chloride, bromide, or iodide.

The term "heteroaryl," as used herein, represents a monocyclic 5-, 6-, 7-, or 8-membered ring system, or a fused or bridging bicyclic, tricyclic, or tetracyclic ring system; the ring system contains one, two, three, four heteroatoms independently selected from the group consisting of nitrogen, oxygen, and sulfur; and at least one of the rings is an aromatic ring. Non-limiting examples of heteroaryl groups include benzimidazolyl, benzofuryl, benzothiazolyl, benzothienyl, benzoxazolyl, furyl, imidazolyl, indolyl, isoindazolyl, isoquinolinyl, isothiazolyl, isothiazolyl, isoxazolyl, oxadiazolyl, oxazolyl, purinyl, pyrrolyl, pyridinyl, pyrazinyl, pyrimidinyl, quinazolinyl, quinolinyl, thiadiazolyl (e.g., 1,3,4-thiadiazole), thiazolyl, thienyl, triazolyl, tetrazolyl, dihydroindolyl, tetrahydroquinolyl, tetrahydroisoquinolyl, etc. The term bicyclic, tricyclic, and tetracyclic heteroaryls include at least one ring having at least one heteroatom as described above and at least one aromatic ring. For example, a ring having at least one heteroatom may be fused to one, two, or three carbocyclic rings, e.g., an aryl ring, a cyclohexane ring, a cyclohexene ring, a cyclopentane ring, a cyclopentene ring, or another monocyclic heterocyclic ring. Examples of fused heteroaryls include 1,2,3,5,8,8a-hexahydroindolizine; 2,3-dihydrobenzofuran; 2,3-dihydroindole; and 2,3-dihydrobenzothiophene. Heteroaryl may be optionally substituted with one, two, three, four, or five substituents independently selected from the group consisting of: alkyl; alkenyl; alkoxy; acyloxy; aryloxy; alkylsulfenyl; alkylsulfinyl; alkylsulfonyl; amino; arylalkoxy; cycloalkyl; cycloalkoxy; halogen; heterocyclyl; heterocyclyl alkyl; heteroaryl; heteroaryl alkyl; heterocyclyloxy; heteroaryloxy; hydroxyl; nitro; thioalkyl; thioalkenyl; thioaryl; thiol; cyano; =O; —$NR_2$, where each R is independently hydrogen, alkyl, acyl, aryl, arylalkyl, cycloalkyl, heterocyclyl, or heteroaryl; —$COOR^A$, where $R^A$ is hydrogen, alkyl, aryl, arylalkyl, cycloalkyl, heterocyclyl, or heteroaryl; and —$CON(R^B)_2$, where each $R^B$ is independently hydrogen, alkyl, aryl, arylalkyl, cycloalkyl, heterocyclyl, or heteroaryl. Each of the substituents may itself be unsubstituted or substituted with unsubstituted substituent(s) defined herein for each respective group.

The term "heteroaryloxy," as used herein, refers to a structure —OR, in which R is heteroaryl. Heteroaryloxy can be optionally substituted as defined for heteroaryl.

The term "heterocyclyl," as used herein, represents a monocyclic, bicyclic, tricyclic, or tetracyclic non-aromatic ring system having fused or bridging 4-, 5-, 6-, 7-, or 8-membered rings, unless otherwise specified, the ring system containing one, two, three, or four heteroatoms independently selected from the group consisting of nitrogen, oxygen, and sulfur. Non-aromatic 5-membered heterocyclyl has zero or one double bonds, non-aromatic 6- and 7-membered heterocyclyl groups have zero to two double bonds, and non-aromatic 8-membered heterocyclyl groups have zero to two double bonds and/or zero or one carbon-carbon triple bond. Heterocyclyl groups have a carbon count of 1 to 16 carbon atoms unless otherwise specified. Certain heterocyclyl groups may have a carbon count up to 9 carbon atoms. Non-aromatic heterocyclyl groups include pyrrolinyl, pyrrolidinyl, pyrazolinyl, pyrazolidinyl, imidazolinyl, imidazolidinyl, piperidinyl, homopiperidinyl, piperazinyl, pyridazinyl, oxazolidinyl, isoxazolidiniyl, morpholinyl, thiomorpholinyl, thiazolidinyl, isothiazolidinyl, thiazolidinyl, tetrahydrofuranyl, dihydrofuranyl, tetrahydrothienyl, dihydrothienyl, pyranyl, dihydropyranyl, dithiazolyl, etc. The term "heterocyclyl" also represents a heterocyclic compound having a bridged multicyclic structure in which one or more carbons and/or heteroatoms bridges two non-adjacent members of a monocyclic ring, e.g., quinuclidine, tropanes, or diaza-bicyclo[2.2.2]octane. The term "heterocyclyl" includes bicyclic, tricyclic, and tetracyclic groups in which any of the above heterocyclic rings is fused to one, two, or three carbocyclic rings, e.g., a cyclohexane ring, a cyclohexene ring, a cyclopentane ring, a cyclopentene ring, or another heterocyclic ring. Examples of fused heterocyclyls include 1,2,3,5,8,8a-hexahydroindolizine; 2,3-dihydrobenzofuran; 2,3-dihydroindole; and 2,3-dihydrobenzothiophene. The heterocyclyl group may be unsubstituted or substituted with one, two, three, four or five substituents independently selected from the group consisting of: alkyl; alkenyl; alkoxy; acyloxy; alkylsulfenyl; alkylsulfinyl; alkylsulfonyl; aryloxy; amino; arylalkoxy; cycloalkyl; cycloalkoxy; halogen; heterocyclyl; heterocyclyl alkyl; heteroaryl; heteroaryl alkyl; heterocyclyloxy; heteroaryloxy; hydroxyl; nitro; thioalkyl; thioalkenyl; thioaryl; thiol; cyano; =O; =S; $-NR_2$, where each R is independently hydrogen, alkyl, acyl, aryl, arylalkyl, cycloalkyl, heterocyclyl, or heteroaryl; $-COOR^A$, where $R^A$ is hydrogen, alkyl, aryl, arylalkyl, cycloalkyl, heterocyclyl, or heteroaryl; and $-CON(R^B)_2$, where each $R^B$ is independently hydrogen, alkyl, aryl, arylalkyl, cycloalkyl, heterocyclyl, or heteroaryl.

The term "heterocyclyl alkyl," as used herein, represents an alkyl group substituted with a heterocyclyl group. The heterocyclyl and alkyl portions of an optionally substituted heterocyclyl alkyl are optionally substituted as the described for heterocyclyl and alkyl, respectively.

The term "heterocyclyloxy," as used herein, refers to a structure —OR, in which R is heterocyclyl. Heterocyclyloxy can be optionally substituted as described for heterocyclyl.

The term "hydrocarbon chain," as used herein, refers to a structure of formula $-(C(R^X)_2)_n-$, where n is 1, 2, or 3; and each $R^X$ is independently H or $C_{1-3}$ alkyl, or both $R^X$ attached to the same carbon atom, together with the carbon atom to which they are attached, combine to form a $C_{3-8}$ cycloalkylene. A hydrocarbon chain may be unsubstituted (when each $R^X$ is H) or substituted (when at least one $R^X$ is not H).

The terms "hydroxyl" and "hydroxy," as used interchangeably herein, represent —OH.

The term "infection," as used herein, refers to a class of disease, disorder, or condition caused by a microorganism. Non-limiting examples of infections include pneumonia, lung abscess, liver abscess, meningitis, spinal infection, epidural abscess, brain abscess, bloodstream infection, urinary tract infection, and bacteremia.

The term "infection marker," as used herein, refers to a an observable indication of the presence, absence, or risk of an infection (e.g., pneumonia, lung abscess, liver abscess, meningitis, spinal infection, epidural abscess, brain abscess, bloodstream infection, urinary tract infection, or bacteremia). The level of an infection marker may directly or inversely correlate with the infection state. Non-limiting examples of infection markers include blood levels of IL1 or TNFα; blood, urine or cerebrospinal white blood cell count; erythrocyte sedimentation rate; serum hepatic transaminase levels; serum blood alkaline phosphatase levels; or culture of sterile body fluid, such as blood, pleural fluid, or cerebrospinal fluid. In some embodiments, following administration of a conjugate of the invention, cerebrospinal or urinary white blood cell counts, erythrocyte sedimentation rate, hepatic transaminases, serum alkaline phosphatase, or bacterial growth in sterile body fluid cultures decreases. Blood levels of white blood cells may be modulated towards normal levels, depending on whether these infection markers are above or below the normal range. An attendant health professional (e.g., physician or nurse practitioner) may determine the desired direction of the infection marker modulation.

The term "lesion," as used herein, tissue damage associated with a disease (e.g., tissue damage associated with pneumonia, lung abscess, liver abscess, meningitis, spinal infection, epidural abscess, brain abscess, bloodstream infection, urinary tract infection, bacteremia, or noncancerous tumors (e.g. polycystic kidney disease)).

The term "lesion marker" as used herein, is an observable indication of the presence, absence, or risk of a lesion (e.g. lesions found in pneumonia, lung abscess, liver abscess, meningitis, spinal infection, epidural abscess, brain abscess, bloodstream infection, urinary tract infection, bacteremia, or noncancerous tumors (e.g. polycystic kidney disease)). The level of a lesion marker may directly or inversely correlate with lesion progression. A lesion marker that is inversely correlated to lesion progression is an "inverse lesion marker." Non-limiting examples of lesion makers are fever, blood, urine or cerebrospinal white blood cell count; erythrocyte sedimentation rate; serum hepatic transaminase levels; serum blood alkaline phosphatase levels; or culture of sterile body fluid, such as blood, pleural fluid, or cerebrospinal fluid. The lesion markers may be measured using methods known in the art. For example, blood sample analyses may be performed to measure white blood cell count, erythrocyte sedimentation rate, blood cultures, serum alkaline phosphatase levels, serum hepatic transaminase levels. Additional non-limiting examples of lesion markers include visualization of masses by computerized tomography, magnetic resonance imaging or ultrasound examination, biopsy of suspected mass as well as cultures of presumed sterile body fluids such as blood, cerebrospinal fluid, urine, pleural fluid and peritoneal fluid. Lesion markers may be determined by biopsy of suspected lesion sites surgically, endoscopically or via transthoracic, transrectal, or colposcopic methods or with or without imaging guidance. Lesion markers may also be determined in the blood, plasma, serum, urine, cerebrospinal fluid, stool, or other body fluids.

The term "leucine-rich peptide," as used herein, refers to a polypeptide including a generally conserved leucine-rich repeat structure of xxLPxxLPxx (e.g., the motif xlxxGxxxxxxxxxLPxxxxLxxLxLGGxP, which may be used in targeting Chlamydiae), where each x is independently an amino acid (e.g., a proteinogenic amino acid). Non-limiting examples of leucine-rich peptides include peptides containing a leucine-rich repeat structure of xxLPxxLPxx (e.g., xlxxGxxxxxxxxxLPxxxxLxxLxLGGxP), where each x is independently an amino acid (e.g., a proteinogenic amino acid).

The term "microorganism," as used herein, refers to any entity that is not a mammalian-cell. Non-limiting examples of microorganisms include bacteria, archaea, viruses, and eukaryotes including but not limited to members of the kingdoms Protista and Fungi.

The term "modulating," as used herein, refers to an observable change in the level of a marker in a subject, as measured using techniques and methods known in the art for the measurement of the marker. Modulating the marker level in a subject may result in a change of at least 1% relative to prior to administration or a control (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration or a control; e.g., up to 100% relative to prior to administration or a control). In some embodiments, modulating is increasing the level of a marker in a subject. Increasing the marker level in a subject may result in an increase of at least 1% relative to prior to administration or a control (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration or a control; e.g., up to 100% relative to prior to administration or a control). In other embodiments, modulating is decreasing the level of a marker in a subject. Decreasing the marker level in a subject may result in a decrease of at least 1% relative to prior to administration or a control (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration or a control; e.g., up to 100% relative to prior to administration or a control). In embodiments in which a parameter is increased or decreased (or reduced) in a subject following a step of administering a composition described herein, the increase or decrease may take place and/or be detectable within a range of time following the administration (e.g., within six hours, 24 hours, 3 days, a week or longer), and may take place and/or be detectable after one or more administrations (e.g., after 2, 3, 4, 5, 6, 7, 8, 9, 10 or more administrations, e.g., as part of a dosing regimen for the subject).

The term "oxo," as used herein, represents a divalent oxygen atom (e.g., the structure of oxo may be shown as =O).

The term "payload," as used herein, represents a pharmaceutical or diagnostic agent to be delivered to a disease site (e.g., a cancer, pre-cancerous tissue, or lesion). Payloads used in the conjugates of the invention may be small molecule pharmaceutical agents. The payload (e.g., pharmaceutical agent) may be an antineoplastic agent, an anti-infective agent (e.g., an antibacterial, oxidizing, or biocidal agent), or an anti-inflammatory agent (e.g., a non-steroidal anti-inflammatory drug (NSAID) or mesalamine). Non-limiting examples of antineoplastic agents include 7-ethyl-10-hydroxy-camptothecin (SN-38), irinotecan, monomethyl auristatin E, monomethyl auristatin F, paclitaxel, doxorubicin, daunorubicin, pyrrolobenzodiazepine, 10-hydroxycamptothecin, exatecan, cyclopamine, tacedinaline, 5-fluorouracil, calicheamicine, a maytansinoid (e.g., mertansine or ravtansine), maytansine, methotrexate, duocarmycin, erlotinib, gefitinib, capecitabine, leucovorin, trifluridine, tipiracil, and CC-1065. Non-limiting examples of antibacterial agents include amikacin, kanamycin, neomycin, netilmicin, tobramycin, paromomycin, streptomycin, geldanamycin, herbimycin, rifaximin, loracarbef, ertapenem, doripenem, meropenem, cefadroxil, cefazolin, cefalexin, cefaclor, cefprozil, cefuroxime, cefixime, cefdinir, cefditoren, cefoperazone, cefotaxime, cefpodoxime, ceftibuten, ceftriaxone, cefepime, ceftaroline fosamil, ceftobiprole, vancomycin, teicoplanin, telavancin, dalbavancin, oritavancin, clindamycin, lincomycin, daptomycin, azithromycin, clarithromycin, erythromycin, roxithromycin, telithromycin, spiramycin, aztreonam, furazolidone, nitrofurantoin, linezolid, posizolid, radezolid, torezolid, amoxicillin, ampicillin, azlocillin, dicloxacillin, flucloxacillin, mezlocillin, methicillin, nafcillin, oxacillin, penicillin G, penicillin V, piperacillin, temocillin, ticarcillin, colistin, bacitracin, polymyxin B, ciprofloxacin, enoxacin, gatifloxacin, gemifloxacin, levofloxacin, lomefloxacin, moxifloxacin, nadifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfanilamide, sulfasalazine, sulfisoxazole, trimethoprim, sulfamethoxazole, sulfonamidochrysoidine, demeclocycline, doxycycline, metacycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalfopristin, thiamphenicol, tigecycline, tinidazole, teixobactin, malacidin, phenol, hydroxynaphthalene, quinine, hydroxychloroquine, ketoconazole, fluconazole, or amphotericin B. Non-limiting examples of NSAIDs include ibuprofen, ketoprofen, flurbiprofen, oxaprozin, ketorolac, naproxen, indomethacin, sulindac, etodolac, diclofenac, aceclofenac, piroxicam, meloxicam, tenoxicam, lornoxicam, mefenamic acid, or clonixin. Payloads used in the conjugates of the invention may be diagnostic agents (e.g., a fluorescent agent or radiolabeled contrast agent). A non-limiting example of a radiolabeled contrast agent includes $^{18}$F-fluorodeoxyglucose. A diagnostic agent may be used to determine the stage of a targeted tumor.

The term "pharmaceutically acceptable salt," as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium (e.g., quaternary ammonium) ammonium cations, including, but not limited to ammonium, tetramethylammonium, tetraethylammonium, methylammonium, dimethylammonium, trimethylammonium, triethylammonium, ethylammonium, and the like.

The term "phenolic oxygen atom," as used herein, refers to a divalent oxygen atom having at least one valency bonded to an sp$^2$-hybridized carbon atom within a carbocyclic, aromatic ring.

The term "pre-cancerous state," as used herein, represents a condition in which numerous growths or polyps form in a tissue or organ and start out benign, and, over the course of time, develop into cancer if left untreated. One example of a pre-cancerous state is familial adenomatous polyposis (FAP).

The term "protecting group," as used herein, represents a group intended to protect a hydroxy, an amino, or a carbonyl from participating in one or more undesirable reactions during chemical synthesis. The term "O-protecting group," as used herein, represents a group intended to protect a hydroxy or carbonyl group from participating in one or more undesirable reactions during chemical synthesis. The term "N-protecting group," as used herein, represents a group intended to protect a nitrogen containing (e.g., an amino or hydrazine) group from participating in one or more undesirable reactions during chemical synthesis. Commonly used O- and N-protecting groups are disclosed in Greene, "Protective Groups in Organic Synthesis," 3rd Edition (John Wiley & Sons, New York, 1999), which is incorporated herein by reference. Exemplary O- and N-protecting groups include alkanoyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, f-butyldimethylsilyl, tri-/so-propylsilyloxymethyl, 4,4'-dimethoxytrityl, isobutyryl, phenoxyacetyl, 4-isopropylpehenoxyacetyl, dimethylformamidino, and 4-nitrobenzoyl.

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and aryl-alkyl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected, L- or D-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Useful N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "pseudohalide," as used herein, refers to a leaving group of formula —OR, where R is optionally substituted aryl or alkylsulfonyl optionally substituted with one or more fluorine atoms. Non-limiting examples of pseudohalides are p-toluenesulfonyloxy, methanesulfonyloxy, and trifluoromethanesulfonyloxy.

The term "recognition element," as used herein, refers to a non-antibody group that is recognized by a protein produced by a microorganism populating or co-localized with a lesion, neoplastic cell, or pre-cancerous cell. Preferably, the recognition element is aproteinaceous.

The term "styrene-diyl," as used herein, refers to a divalent group formed by replacing two hydrogen atoms in styrene with valencies. An optionally substituted styrene-diyl is a styrene-diyl that is optionally substituted as described herein for aryl.

The term "subject," as used herein, represents a human or non-human animal (e.g., a mammal) that is suffering from, or is at risk of, a disease, as determined by a qualified professional (e.g., a doctor or a nurse practitioner) with or without known in the art laboratory test(s) of sample(s) from the subject. A non-limiting example of a disease is cancer (e.g., colorectal cancer).

The term "sulfide atom," as used herein, refers to a divalent group —S—.

The term "therapeutically effective amount," as used herein, is meant the amount of a conjugate or an unconjugated payload capable of providing a health benefit to (e.g., to treat a tumor, to modulate a cancer marker, and/or to modulate microbiome in) a subject in need thereof. The therapeutically effective amount of a conjugate or an unconjugated payload may vary depending on the subject and may be determined in accordance with a reasonable benefit/risk ratio. Ultimately, the attending physician, pharmacist, or nurse practitioner may determine the therapeutically effective amount for a given subject.

The term "thioalkenyl," as used herein, represents a group —SR, where R is alkenyl. An optionally substituted thioalkenyl is thioalkenyl that is optionally substituted as described herein for alkenyl.

The term "thioalkyl," as used herein, represents a group —SR, where R is alkyl. An optionally substituted thioalkyl is thioalkyl that is optionally substituted as described herein for alkyl.

The term "thioaryl," as used herein, represents a group —SR, where R is aryl. An optionally substituted thioaryl is thioaryl that is optionally substituted as described herein for aryl.

The term "thioester bond," as used herein, refers to a covalent bond between a sulfur atom and the carbon atom of a carbonyl group.

The term "traceless linker," as used herein, represents a multivalent (e.g., divalent) group covalently linking a recognition element to a payload, such that cleavage of a bond in the multivalent group, recognition element, or therebetween causes the cleavage of a bond between the multivalent group and the payload. A traceless linker may be a group of formula $R^A$—NH-$L^1$-$(C(R^2)_2)$-$L^2$-$R^B$, where $R^A$ is a bond to the recognition element; $R^B$ is a bond to the payload; $L^1$ is 1,4-phenylene, 1,2-phenylene, or an optionally substituted $C_{1-3}$ hydrocarbon chain; $L^2$ combines with $R^B$ to form —NHCO—$R^B$, —(CO)—$R^B$, or —OCO—$R^B$; and each $R^2$ is independently H or $C_{1-6}$ alkyl, or both $R^2$ combine with the atom to which each is attached to form a cycloalkylene. Non-limiting examples of traceless linkers include the following groups:

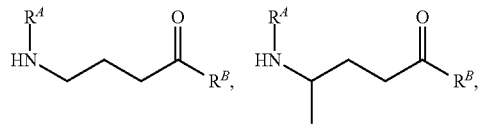

-continued

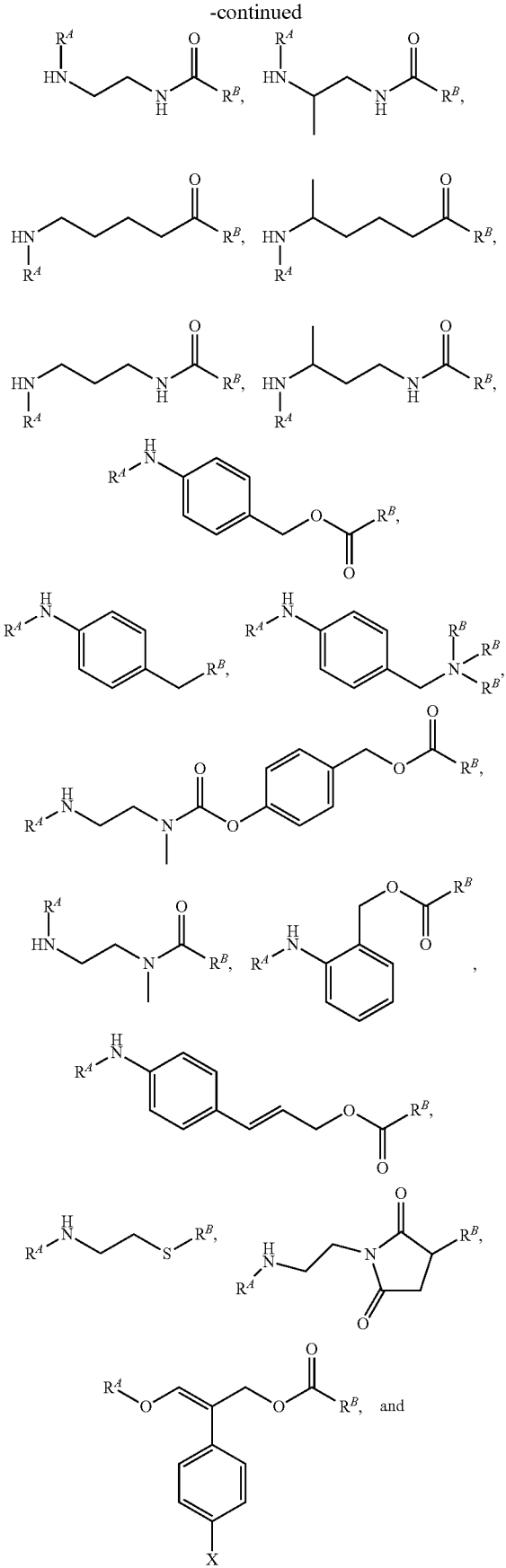

where $R^A$ is a bond to a recognition element, $R^B$ is a bond to a payload (e.g., an antineoplastic agent or an antibacterial agent); X is H, halogen, optionally substituted alkyl (e.g., haloalkyl (e.g., —$CF_3$)), alkylsulfonyl (e.g., —$SO_2Me$), or cyano; $R^C$ is H or methyl; and n is 1 or 2. $R^A$ may be a bond to the carbon of a carbonyl group in a recognition element (e.g., a carbonyl group of an amino acid residue). $R^B$ may be a bond to the oxygen (e.g., phenolic oxygen atom or carboxylate oxygen atom), nitrogen atom (e.g., ammonium nitrogen atom), or sulfur atom (e.g., sulfide atom) in the payload.

"Treatment" and "treating," as used herein, refer to the medical management of a subject with the intent to improve, ameliorate, stabilize, prevent or cure a disease. This term includes active treatment (treatment directed to improve the disease); causal treatment (treatment directed to the cause of the associated disease); palliative treatment (treatment designed for the relief of symptoms of the disease); preventative treatment (treatment directed to minimizing or partially or completely inhibiting the development of the associated disease); and supportive treatment (treatment employed to supplement another therapy).

The term "tumor," as used herein, refers to a tissue characterized as having an abnormal and excessive growth. A tumor may be malignant (e.g., cancerous tissue), precancerous (e.g., precancerous tissue) or benign.

The term "urea linker," as used herein, refers to a group $R^1$—(CO)—$R^2$, where $R^1$ is a bond to a nitrogen atom, and $R^2$ is a bond to another nitrogen atom.

The conjugates described herein, unless otherwise noted, encompass isotopically enriched compounds (e.g., deuterated compounds), tautomers, and stereoisomers and conformers (e.g. enantiomers, diastereomers, E/Z isomers, atropisomers, etc.), as well as racemates thereof and mixtures of different proportions of enantiomers or diastereomers, or mixtures of the foregoing forms as well as salts (e.g., pharmaceutically acceptable salts), or solvates.

DETAILED DESCRIPTION

The invention provides conjugates and pharmaceutically acceptable salts thereof, compositions containing them, and methods of using the same. The conjugate of the invention, or a pharmaceutically acceptable salt thereof, typically includes a recognition element covalently bonded to or linked through a linker to a payload. The payload may be a pharmaceutical agent (e.g., an antineoplastic agent, anti-infective agent, or anti-inflammatory agent) or a diagnostic agent.

Conjugates of the invention may be used to target a payload (e.g., an antineoplastic agent, anti-infective agent, or anti-inflammatory agent) to disease sites (e.g., tumors or lesions) in a subject in need thereof. Without wishing to be bound by theory, targeting conjugates of the invention to the disease site (e.g., tumors or lesions) may take advantage of the targeted tissue environment (e.g., microorganisms inhabiting a tissue containing neoplastic cells or a lesion). For example, E. coli and Klebsiella pneumoniae are believed to thrive in colorectal cancer tissue. These bacteria may be used to target a payload to colorectal cancer tissue, as these bacteria produce one or more enzymes (e.g., colibactin-maturating enzyme ClbP) capable of hydrolyzing the conjugate of the invention to release the payload into the area of the colorectal cancer tissue. Accordingly, the gastrointestinal tract of the subject may include E. coli or Klebsiella pneumoniae for cleaving the conjugate. Lesions co-located with microorganisms may be found in liver, brain, heart, bones or other areas of a body. Targeting lesions in, for example, liver, may include targeting a payload to ClbP produced by Klebsiella pneumoniae.

Advantageously, the disease tissue-targeting strategy described herein may be superior relative to that of unconjugated pharmaceutical agents. Advantageously, the disease tissue-targeting strategy described herein may allow for administration of lower payload (e.g., a pharmaceutical agent (e.g., an antineoplastic agent, antibacterial agent, or anti-inflammatory agent)) doses, as a conjugate of the invention targeting a disease tissue (e.g., tumor) would be expected to provide a higher local concentration of the payload relative to the administration of an unconjugated payload. Alternatively and advantageously, the disease tissue-targeting strategy described herein may allow for administration of higher payload (e.g., a pharmaceutical agent (e.g., an antineoplastic agent, antibacterial agent, or anti-inflammatory agent)) doses, as a conjugate of the invention targeting a disease tissue (e.g., tumor) would be expected to reduce an off-target concentration of the payload relative to the administration of an unconjugated payload. Also advantageously, conjugates of the invention may produce lower incidence and/or severity of side effects upon administration to a subject than an unconjugated payload at the same molar dosage.

Table 1 below shows further examples of bacteria and that are associated with the disease sites of particular cancers, pre-cancerous states, and lesions.

cally cleave the peptide $(Ac)_2$-L-Lys-D-Ala-D-Ala and glycoside terminal non-reducing β-N-acetylglucosamine bonds, respectively. In peptide $(Ac)_2$-L-Lys-D-Ala-D-Ala, the peptide bond between D-Ala and D-Ala is cleaved. In β-N-acetylglucosamine, the glycosidic bond is cleaved. Utilizing the activity of these enzymes, certain conjugates of the invention can be used to target cancer colocalized with P. acnes in the prostate. Non-limiting examples of the recognition elements cleavable by P. acnes proteins include $(Ac)_2$-L-Lys-D-Ala-D-Ala and β-N-acetylglucosamine.

Chlamydiae pneumoniae has been found associated with an elevated risk of lung cancer (Table 1). C. pneumoniae encodes a number of secreted and extracellular-presenting proteins for the cleavage of external chemical bonds. Examples of these proteins from C. pneumoniae CWL029 include protease (gene NP_224809.1) and cinnamoyl esterase (gene NP_224360.1). These gene-products canonically cleave leucine-rich peptides and carboxylic ester bonds of cinnamic acid derivates, respectively. Utilizing the activity of these enzymes, certain conjugates of the invention can be used to target cancer colocalized with C. pneumoniae in the lungs. Non-limiting examples of the recognition elements cleavable by C. pneumoniae proteins include optionally substituted cinnamoyl (e.g., caffeic acid acyl, 4-hydroxycinnamic acid acyl, or ferulic acid acyl) and leucine-rich peptides (e.g., a peptide containing a leucine-rich repeat structure of xxLPxxLPxx (e.g., xlxxGxxxxxxxxxLPxxxx-LxxLxLGGxP), where each x is independently an amino acid (e.g., a proteinogenic amino acid)).

Bacteroides fragilis (e.g., enterotoxigenic Bacteroides fragilis) has been found to be associated with colon cancer (Table 1). Bacteroides fragilis secretes extracellular proteases that can cleave Arg-Arg and Leu-Arg bonds. A conjugate of the invention targeting Bacteroides fragilis for the treatment of colon cancer include a dipeptide (Arg-Arg or Leu-Arg) as a recognition element. The cleavage typically occurs between the two arginines or the Leu-Arg bonds.

Salmonella enterica serovar Typhi has a positive association with the occurrence of gallbladder cancer (Table 1). S. enterica serovar Typhi encodes a number of secreted and extracellular-presenting proteins for the cleavage of external

TABLE 1

| Bacteria | Disease | Reference(s) |
|---|---|---|
| Propionibacterium acnes | Prostate cancer | Fehri et al., Int J Med Microbiol 2011; 301: 69-78 |
| Chlamydia pneumoniae | Lung cancer | Anttila, T. Int J Cancer. 2003 Nov. 20; 107(4):681-2 |
| Salmonella enterica ssp enterica serovar Typhi strain | Gallbladder cancer | Koshiol, J. Cancer Med. 2016 November; 5(11):3310-3235 |
| Bacteroides fragilis | Colon cancer (especially, with ETBF) | Sears and Pardoll, J Infect Dis. 2011 Feb. 1; 203(3):306-11. |
| Escherichia coli (PKS+) | Colorectal cancer | |
| Methylobacterium radiotolerans | Breast cancer | Xuan et al., PLoS One. 2014 Jan. 8; 9(1) |
| Chlamydia trachomatis | Cervical cancer | Madeleine et al., Int J Cancer. 2007 Feb. 1; 120(3): 650-655 |
| Klebsiella pneumoniae | Liver lesions | Lam et. al. Nature Comm. 2018, 9(2703), 1-10 |

Propionibacterium acnes is frequently found in the tissue of prostate cancers and is absent from healthy prostates (Table 1). P. acnes encodes a number of secreted and extracellularly oriented proteins for the cleavage of external chemical bonds. Examples of these proteins from P. acnes strain KPA171202 include D-alanyl-D-alanine carboxypeptidase (gene WP_002531210.1) and β-N-acetylglucosaminidase (gene WP_041444232.1). These gene-products canonichemical bonds. Examples of these proteins from S. enterica ssp. enterica serovar Typhi strain CT18 include penicillin-insensitive murein endopeptidase (gene NP_456924.1) and endoglucanase (gene NP_458303.1). These gene-products canonically cleave the D-alanyl-meso-2,6-diamino-pimelyl amide bond and β-1,4-glucan bonds, respectively. Utilizing the activity of these enzymes, certain conjugates of the invention can be used to target cancer colocalized with S.

enterica serovar Typhi in the gallbladder. Non-limiting examples of the recognition elements cleavable by S. enterica serovar Typhi proteins include D-alanyl-meso-2,6-diamino-pimelyl and a β-1,4-glucan (e.g., a β-1,4-glucan having 2-10 glucose monomers; preferably, 2-4 glucose monomers).

Methylobacterium radiotolerans was found enriched in breast cancer tissue and depleted in normal breast tissue (Table 1). M. radiotolerans encodes a number of secreted and extracellular-presenting proteins for the cleavage of external chemical bonds. Examples of these proteins from M. radiotolerans JCM 2831 include D-alanyl-D-alanine carboxypeptidase (gene WP_041372295.1) and cellulase (WP_012317297.1). These gene-products canonically cleave the peptide $(Ac)_2$-L-Lys-D-Ala-D-Ala and β-1,4-glucan bonds, respectively. Utilizing the activity of these enzymes, certain conjugates of the invention can be used to target cancer colocalized with M. radiotolerans in the breast. Non-limiting examples of the recognition elements cleavable by M. radiotolerans proteins include $(Ac)_2$-L-Lys-D-Ala-D-Ala and a β-1,4-glucan (e.g., a β-1,4-glucan having 2-10 glucose monomers; preferably, 2-4 glucose monomers).

The presence of Chlamydia trachomatis has been implicated as an increased risk factor in cervical cancer (Table 1). C. trachomatis encodes a number of secreted and extracellular-presenting proteins for the cleavage of external chemical bonds. Examples of these proteins from C. trachomatis D/UW-3/CX include D-alanyl-D-alanine carboxypeptidase (gene NP_220066.1) and Cinnamoyl esterase (gene NP_219652.1). These gene-products canonically cleave the $(Ac)_2$-L-Lys-D-Ala-D-Ala and carboxylic ester bonds of cinnamic acid derivates, respectively. Utilizing the activity of these enzymes, certain conjugates of the invention can be used to target cancer colocalized with C. trachomatis in the cervix. Non-limiting examples of the recognition elements cleavable by C. trachomatis proteins include $(Ac)_2$-L-Lys-D-Ala-D-Ala and optionally substituted cinnamoyl (e.g., caffeic acid acyl, 4-hydroxycinnamic acid acyl, or ferulic acid acyl).

Targeting Klebsiella pneumoniae can be performed in a manner similar to the E. coli targeting, e.g., by targeting colibactin-maturating enzyme ClbP, which cleaves certain amide bonds. Non-limiting examples of recognition elements for targeting ClbP are $R^1$-L-, where $R^1$ is a fatty acid acyl (e.g., capryloyl), and L is an amino acid residue (e.g., optionally substituted D-asparagine, optionally substituted D-arginine, optionally substituted D-glutamine, optionally substituted D-aspartic acid, or optionally substituted D-glutamic acid).

Conjugates of the Invention

The conjugates of the invention, or pharmaceutically acceptable salts thereof, include a recognition element covalently bonded to or linked through a linker to a payload. The payload is a pharmaceutical agent (e.g., an antineoplastic agent or an antibacterial agent) or a diagnostic agent. Preferred antineoplastic agents are cytotoxic antineoplastic agents.

In the conjugates of the invention, the antineoplastic agent may be, e.g., 7-ethyl-10-hydroxy-camptothecin (SN-38), irinotecan, monomethyl auristatin E, monomethyl auristatin F, paclitaxel, doxorubicin, daunorubicin, pyrrolobenzodiazepine, 10-hydroxycamptothecin, exatecan, cyclopamine, tacedinaline, 5'-deoxy-5-fluorouridine, 5-fluorouracil, calicheamicine, a maytansinoid (e.g., mertansine or ravtansine), maytansine, methotrexate, duocarmycin, erlotinib, gefitinib, capecitabine, leucovorin, trifluridine, tipiracil, or CC-1065. Without wishing to be bound by theory, an antineoplastic agent, upon delivery to the targeted tumor (e.g., a tumor populated by the E. coli or Klebsiella pneumoniae, such as a colorectal cancer tissue or a colon polyp; a tumor populated by P. acnes, such as a prostate cancer tissue; a tumor populated by C. pneumoniae, such as a lung cancer tissue; a tumor populated by S. enterica serovar Typhi, such as a gallbladder cancer tissue; tumor populated by M. radiotolerans, such as a breast cancer tissue; or a tumor populated by C. trachomatis, such as a cervical cancer tissue), is released from the conjugate into the targeted tissue. Once released in the targeted cancer or pre-cancerous tissue (e.g., a colorectal cancer tissue, colon polyp, lung cancer tissue, gallbladder cancer tissue, breast cancer tissue, or cervical cancer tissue), the antineoplastic agent may treat cancer or pre-cancerous state (e.g., colorectal cancer, a colon polyp, lung cancer, gallbladder cancer, breast cancer, or cervical cancer). In some embodiments, the antineoplastic agent is monomethyl auristatin E. In certain embodiments, the antineoplastic agent is 7-ethyl-10-hydroxy-camptothecin (SN-38).

In the conjugates of the invention, the antibacterial agent may be, e.g., amikacin, kanamycin, neomycin, netilmicin, tobramycin, paromomycin, streptomycin, geldanamycin, herbimycin, rifaximin, loracarbef, ertapenem, doripenem, meropenem, cefadroxil, cefazolin, cefalexin, cefaclor, cefprozil, cefuroxime, cefixime, cefdinir, cefditoren, cefoperazone, cefotaxime, cefpodoxime, ceftibuten, ceftriaxone, cefepime, ceftaroline fosamil, ceftobiprole, vancomycin, teicoplanin, telavancin, dalbavancin, oritavancin, clindamycin, lincomycin, daptomycin, azithromycin, clarithromycin, erythromycin, roxithromycin, telithromycin, spiramycin, aztreonam, furazolidone, nitrofurantoin, linezolid, posizolid, radezolid, torezolid, amoxicillin, ampicillin, azlocillin, dicloxacillin, flucloxacillin, mezlocillin, methicillin, nafcillin, oxacillin, penicillin G, penicillin V, piperacillin, temocillin, ticarcillin, colistin, bacitracin, polymyxin B, ciprofloxacin, enoxacin, gatifloxacin, gemifloxacin, levofloxacin, lomefloxacin, moxifloxacin, nadifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfanilamide, sulfasalazine, sulfisoxazole, trimethoprim, sulfamethoxazole, sulfonamidochrysoidine, demeclocycline, doxycycline, metacycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalfopristin, thiamphenicol, tigecycline, tinidazole, teixobactin, malacidin, phenol, hydroxynaphthalene, quinine, hydroxychloroquine, ketoconazole, fluconazole, or amphotericin B. Without wishing to be bound by theory, an antibacterial agent, upon delivery to the targeted tumor (e.g., tumor populated by the E. coli or Klebsiella pneumoniae, such as the colorectal cancer tissue), is released from the conjugate into the targeted tumor. Once released in the targeted tumor (e.g., colorectal cancer tissue), the antibacterial agent may modulate the microbiome present in the targeted tumor.

In the conjugates of the invention, the recognition element is a non-antibody array of atoms connected by covalent bonds. The recognition element is capable of binding to a protein produced by a microorganism located substantially at the site of a disease. Non-limiting examples of recognition elements include a group of formula $R^1$-L-, where $R^1$ is a fatty acid acyl (e.g., capriloyl, acetyl, or valeryl), an amino acid residue (e.g., Ala $C_{1-6}$ alkyl ester), dipeptide (e.g., L-Lys-D-Ala- or D-Ala-D-Ala), tripeptide (Leu-Leu-Leu-), β-N-acetylglucosamine, β-1,4-glucan, optionally substituted cinnamoyl, D-alanyl-meso-2,6-diamino-pimelyl amide, optionally substituted with phenyl, optionally substituted alkyl, or optionally substituted aryl alkyl; and L is a bond, an amino acid residue (e.g., optionally substituted D-asparagine, optionally substituted D-arginine, optionally substituted D-glutamine, optionally substituted D-aspartic acid, or optionally substituted D-glutamic acid), —NH—CO—, —O—CO—, or —SO$_2$—. In some embodiments, L is bonded to $R^1$ through its α-amino group. Non-limiting examples of the recognition elements include fatty acid acyls (e.g., capriloyl, acetyl, or valeryl), L-Lys-D-Ala-, L-Ala-D-Asn, β-N-acetylglucosamine, Leu-Leu-Leu-, cinnamoyl, D-alanyl-meso-2,6-diamino-pimelyl amide, and β-D-1,4-glucan.

In the conjugates of the invention, the payload may be covalently bonded or linked through a linker to a recognition element. When the payload is covalently bonded to the recognition element, the covalent bond between the payload and the recognition element is an ester bond, amide bond, glycosidic bond, carbamate linker, or carbonate linker. When the payload is covalently linked through a linker to the recognition element, the covalent bond between the payload and the linker is typically cleaved directly or indirectly by the environment of the targeted tumor (e.g., by an enzyme produced by a microorganism populating the tumor). An indirect cleavage of the covalent bond between the linker and the payload may occur following the cleavage of a bond in or between the linker and/or the recognition element. For example, the linker may be a traceless linker. A traceless linker may be bonded to a recognition element, e.g., through an amide bond. A traceless linker may be bonded to a payload, e.g., through an amide bond, an ester bond, a thioester bond, a carbonate linker, a carbamate linker. A traceless linker may be a group of formula $R^A$—NH-$L^1$-(C($R^2$)$_2$)-$L^2$-$R^B$, where $R^A$ is a bond to the recognition element; $R^B$ is a bond to the payload; $L^1$ is 1,4-phenylene, 1,2-phenylene, or an optionally substituted $C_{1-3}$ hydrocarbon chain; $L^2$ combines with $R^B$ to form —NHCO—$R^B$, —(CO)—$R^B$, or —OCO—$R^B$; and each $R^2$ is independently H or $C_{1-6}$ alkyl, or both $R^2$ combine with the atom to which each is attached to form a cycloalkylene. Non-limiting examples of traceless linkers include the following groups:

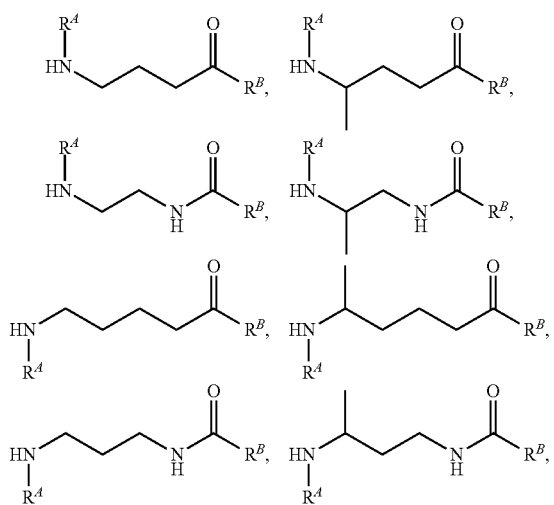

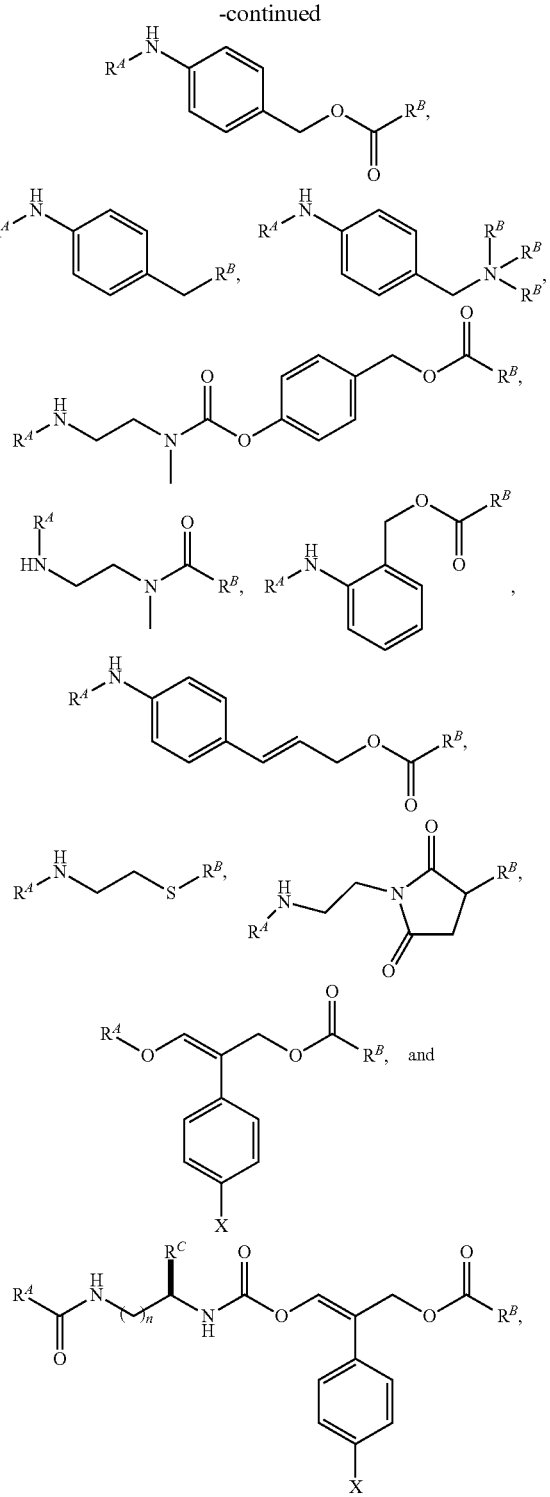

where $R^A$ is a bond to a recognition element; $R^B$ is a bond to a payload (e.g., an antineoplastic agent or an antibacterial agent); X is H, halogen, optionally substituted alkyl (e.g., haloalkyl (e.g., —CF$_3$)), alkylsulfonyl (e.g., —SO$_2$Me), or cyano; $R^C$ is H or methyl; and n is 1 or 2. $R^A$ may be a bond to the carbon of a carbonyl group in a recognition element (e.g., a carbonyl group of an amino acid residue). $R^B$ may be a bond to the oxygen atom (e.g., phenolic oxygen atom or carboxylate oxygen atom), nitrogen atom (e.g., ammonium nitrogen atom), or sulfur atom (e.g., sulfide atom) in the payload.
Non-limiting examples of the conjugates of the invention include:
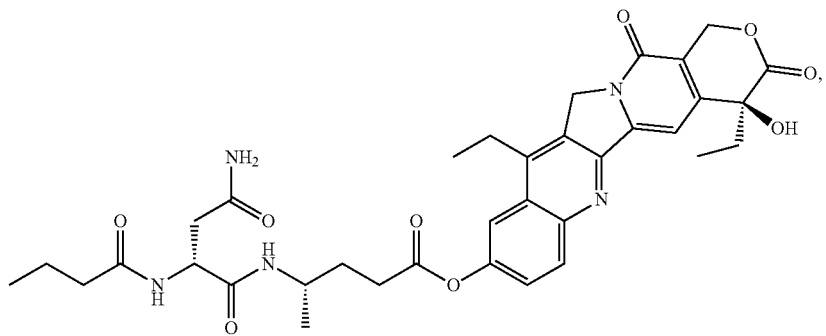
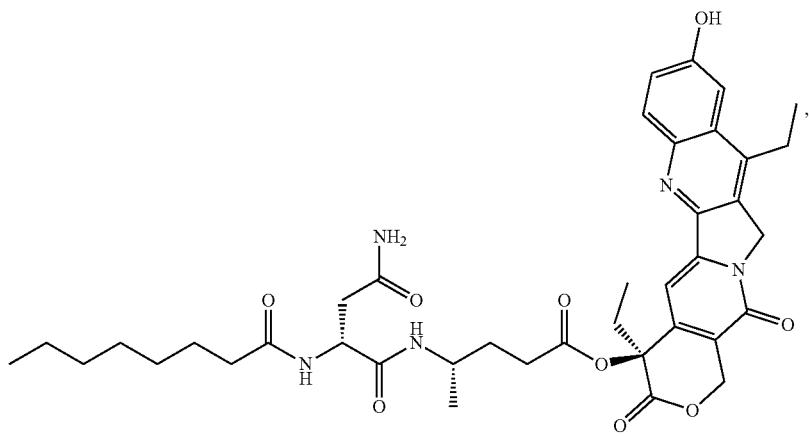
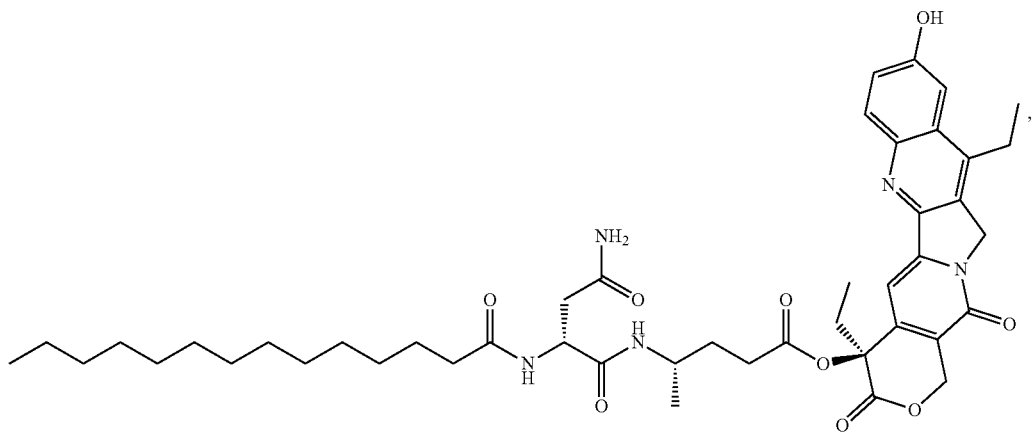

-continued
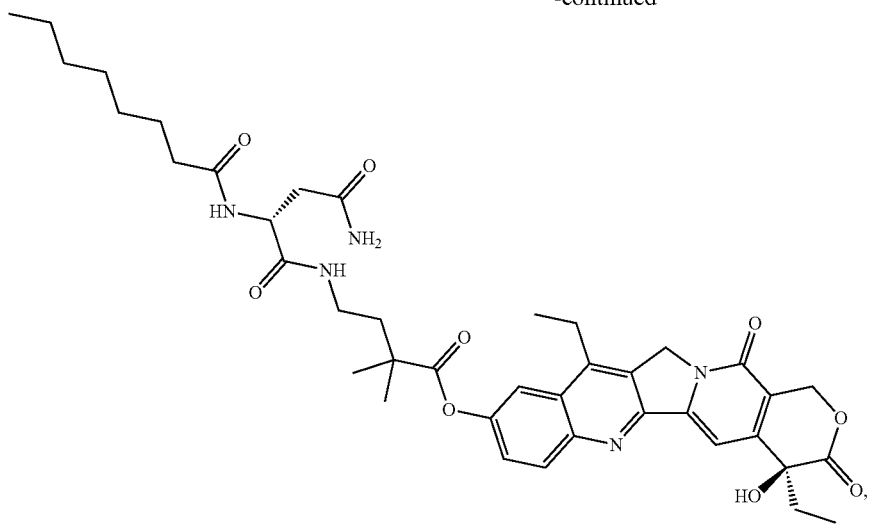
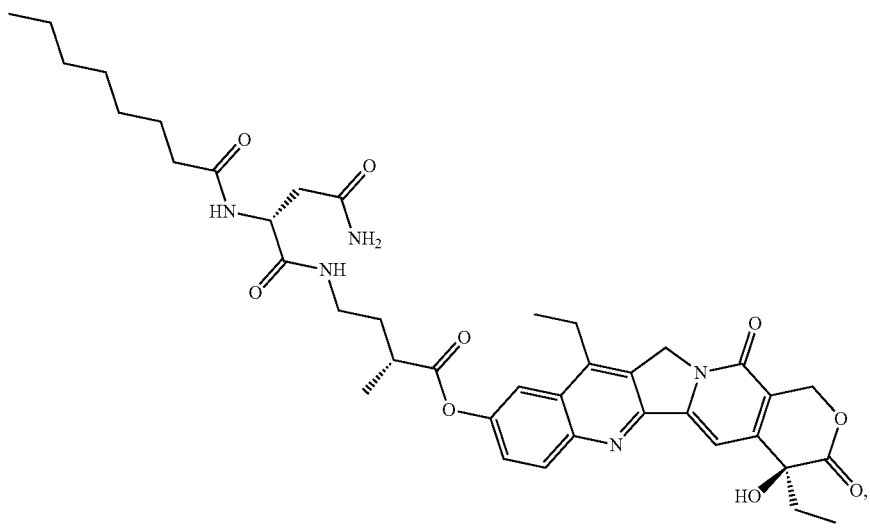
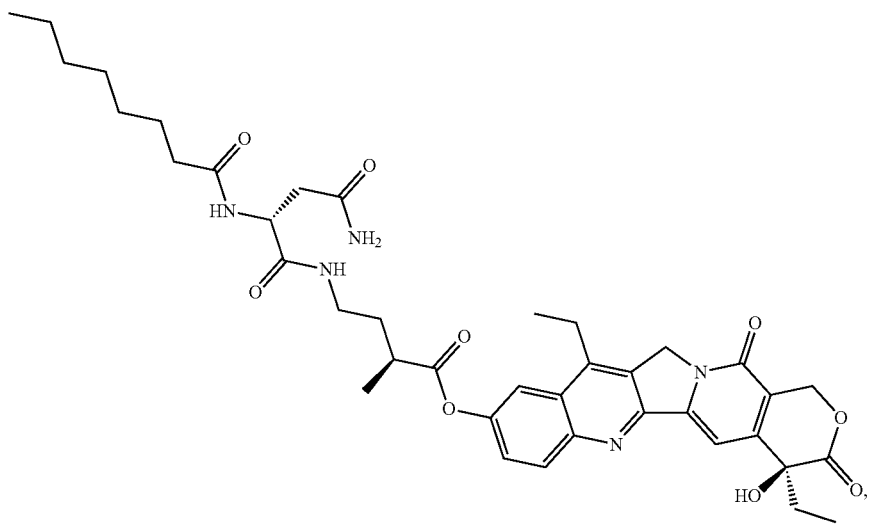

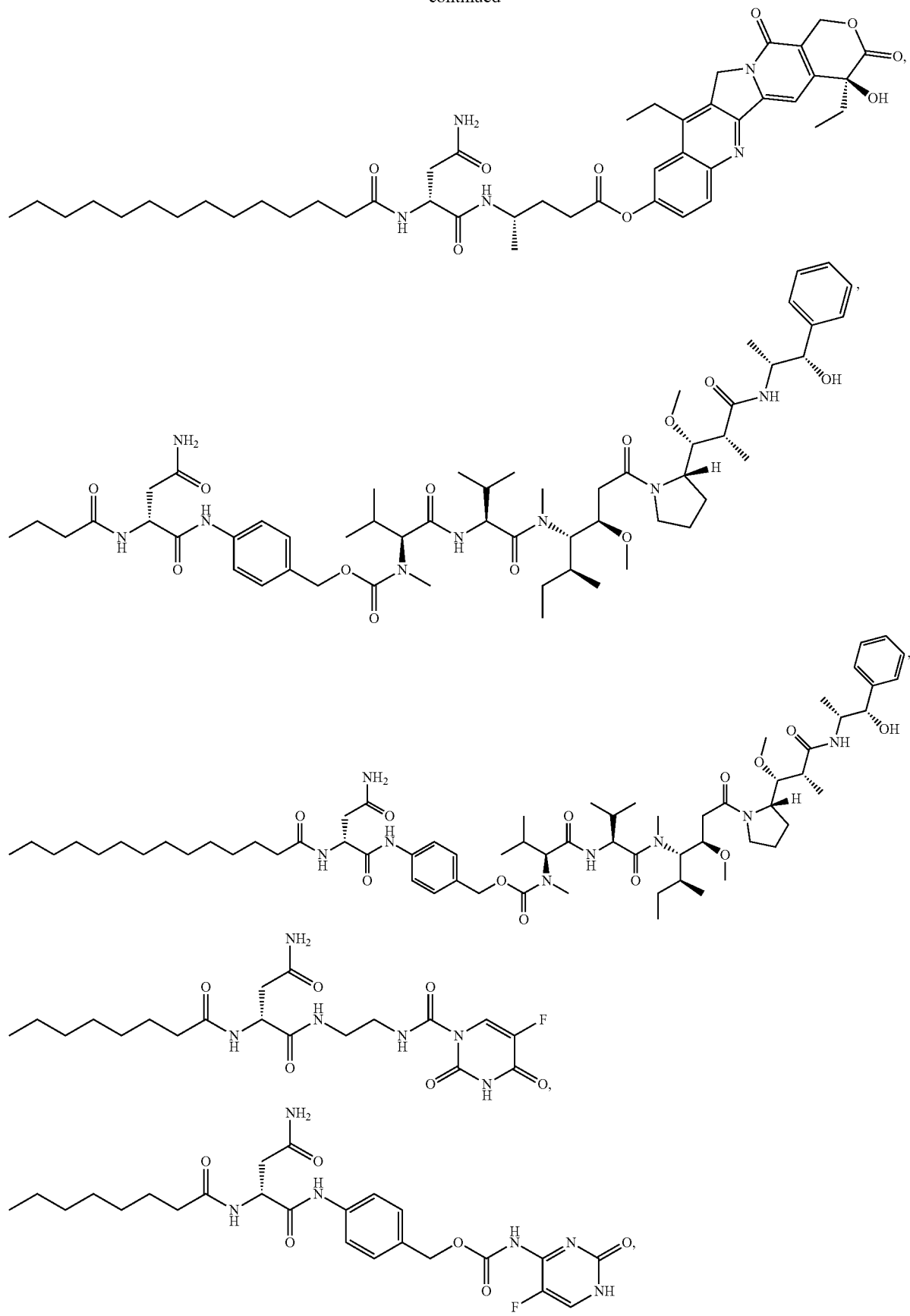

-continued
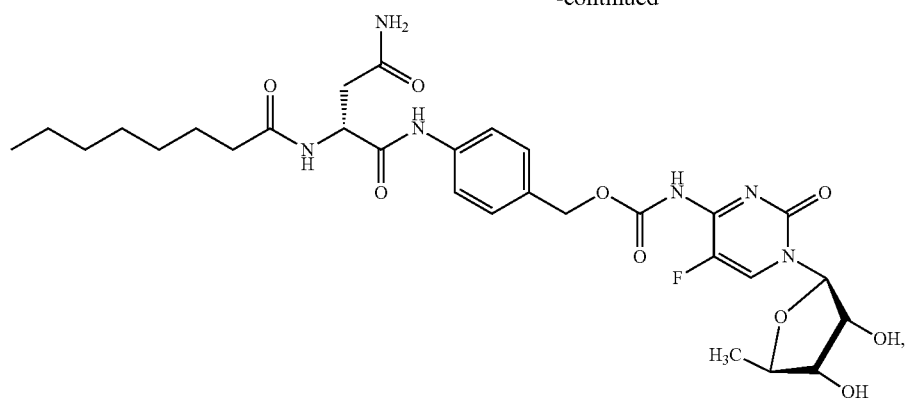
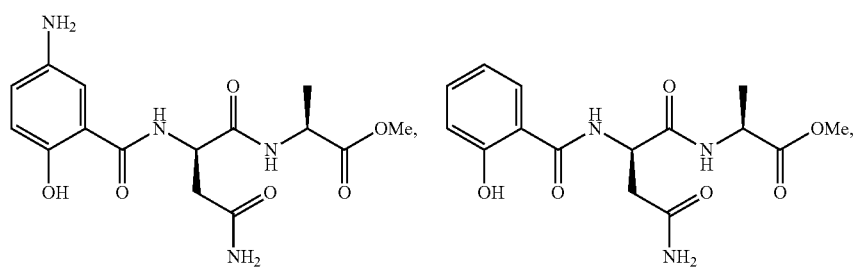
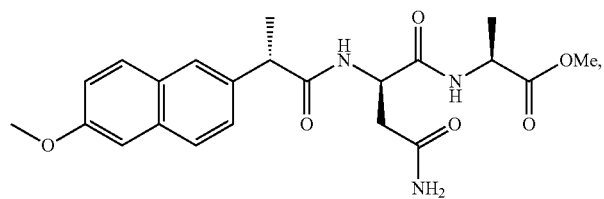
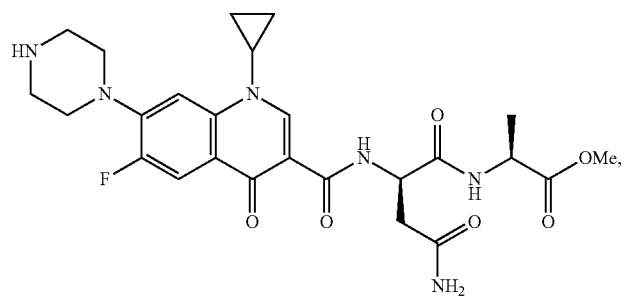 [SMILES: COC(=O)[C@H](C)NC(=O)[C@@H](CC(N)=O)NC(=O)c1cn(C2CC2)c2cc(N3CCNCC3)c(F)cc2c1=O]
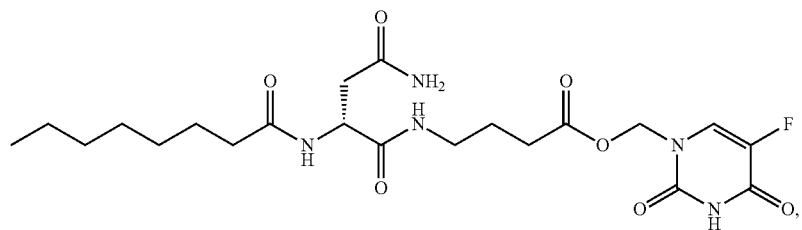
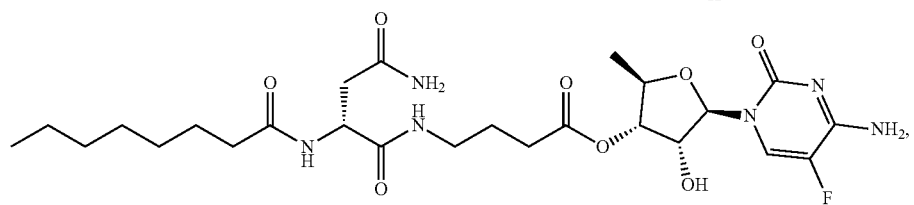

-continued
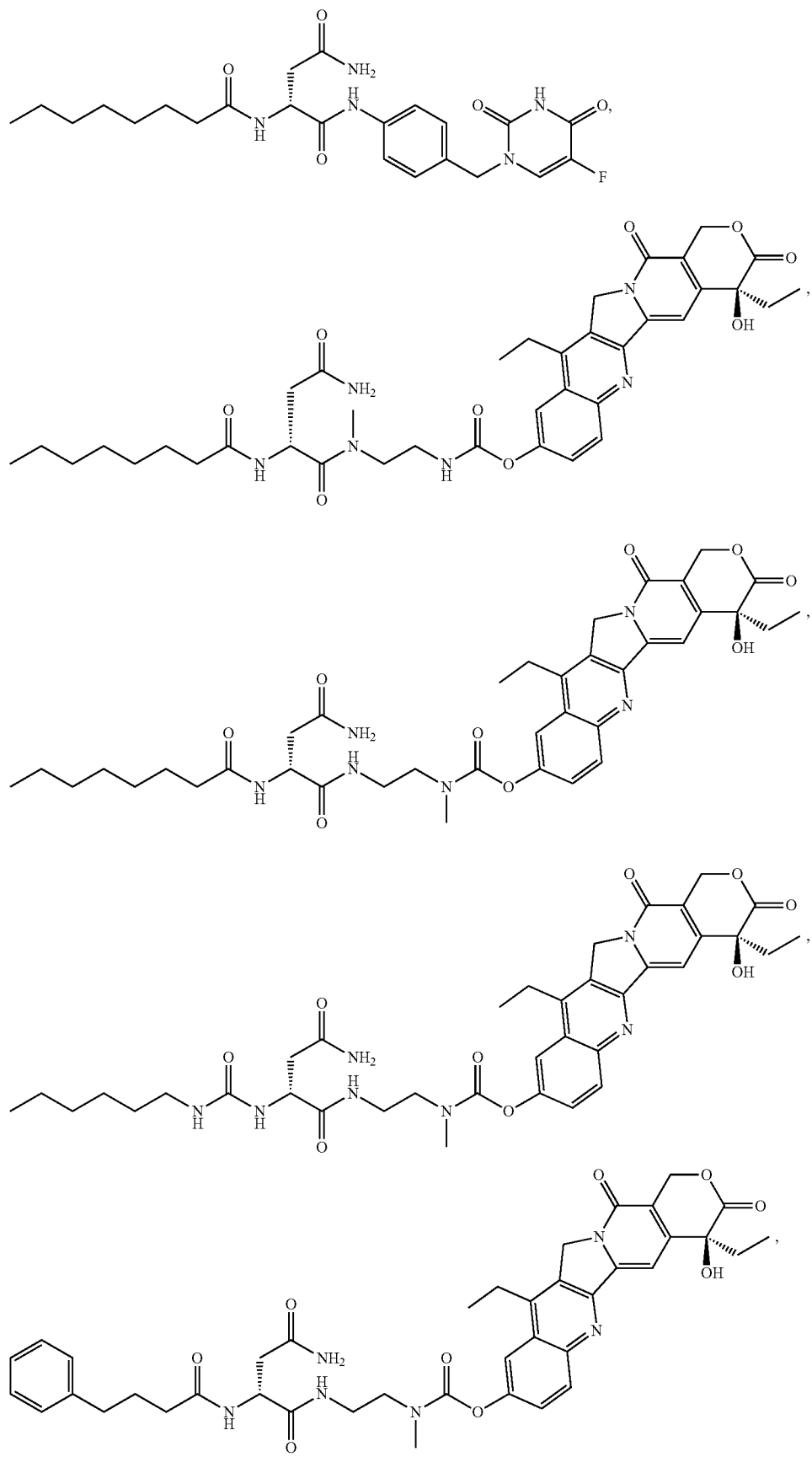

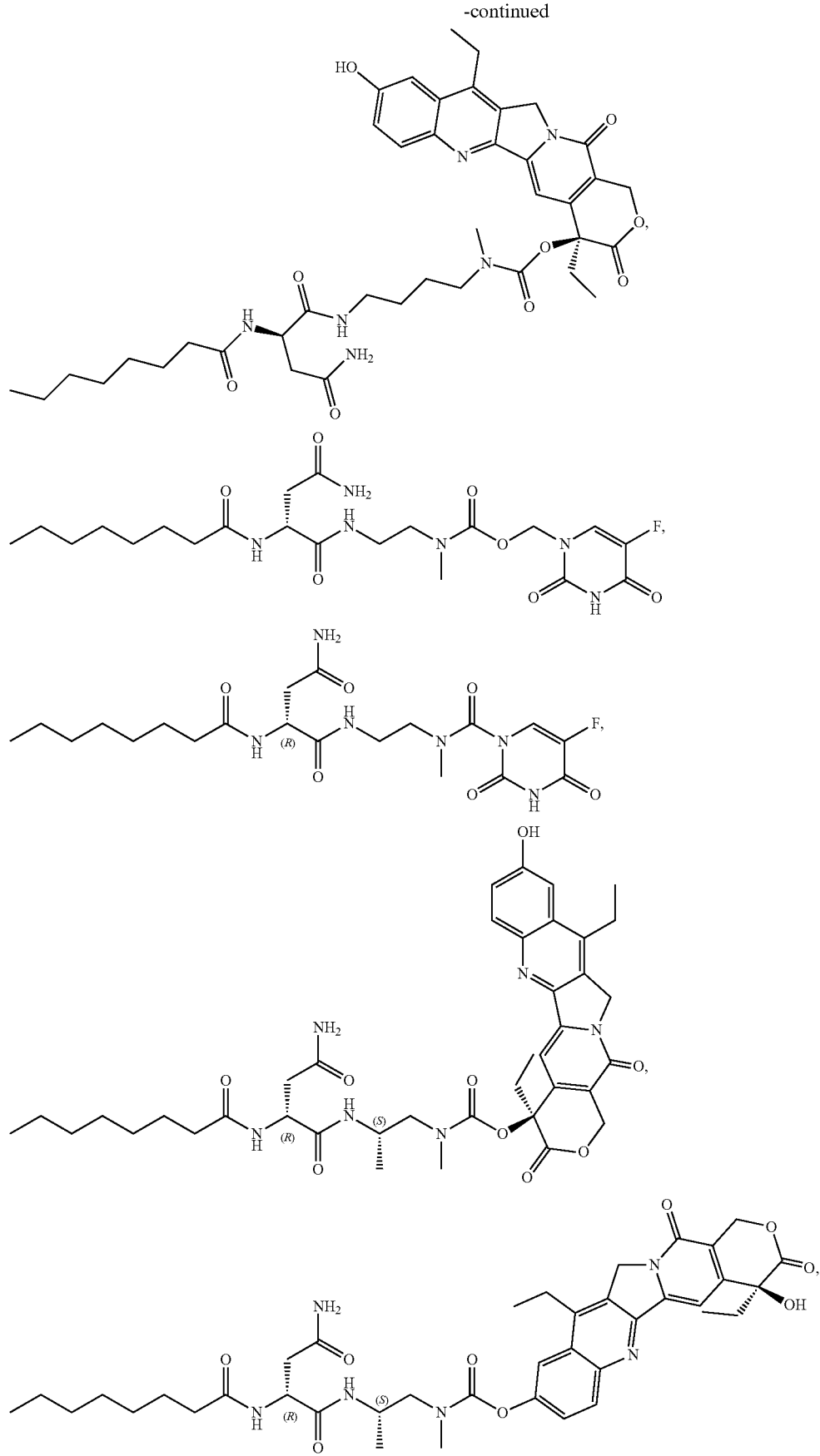

-continued
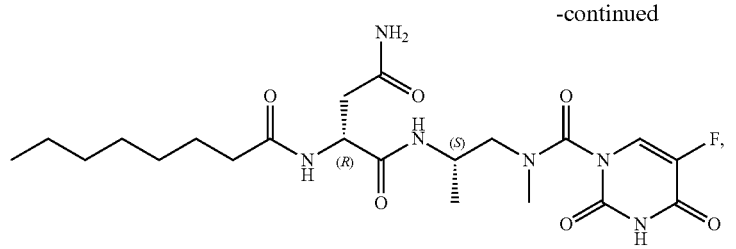
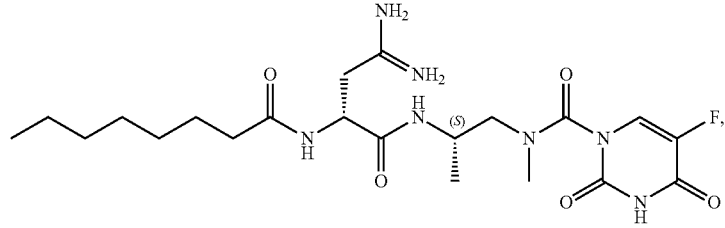
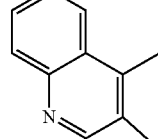
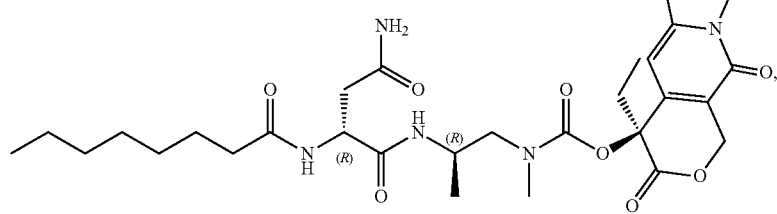
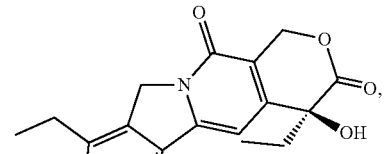
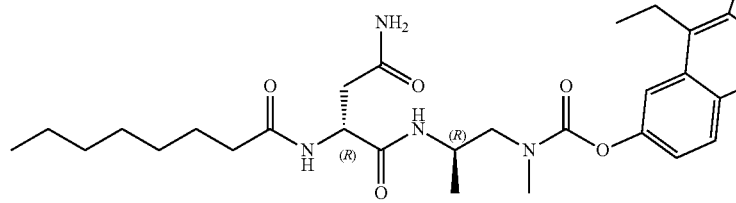
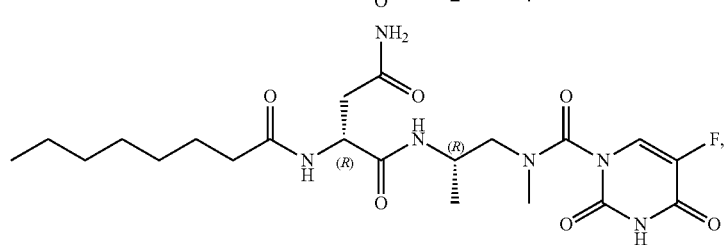
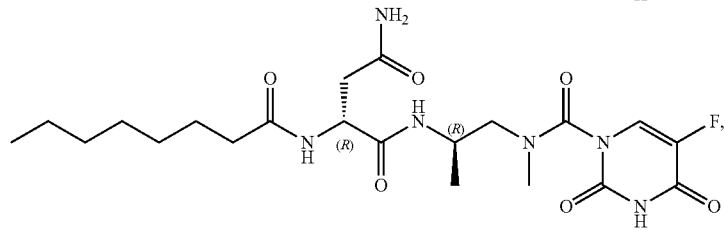
and pharmaceutically acceptable salts thereof.

Methods of Use

The conjugates of the invention may be used to deliver a payload (e.g., an antineoplastic agent, an anti-infective agent, or an anti-inflammatory agent) to the tissue in a subject. The delivered payload may be used to modulate a cancer marker (e.g., a colorectal cancer marker) in a subject in need thereof, to treat cancer (e.g., colorectal cancer) in a subject in need thereof, to treat an infection or an infection-related lesion, to modulate an infection marker, or to modulate the microbiome of the subject in need thereof (e.g., at the site of the payload delivery). Conjugates including an anti-inflammatory agent may be used to target inflammations secondary to cancers, infections, and lesions described herein.

The methods of the invention may be for modulating a cancer marker (e.g., a colorectal cancer marker) in a subject in need thereof. Modulating the cancer marker (e.g., colorectal cancer marker) level in a subject may result in a change of at least 1% relative to prior to administration or a control (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration or a control; e.g., up to 100% relative to prior to administration or a control). Some cancer markers may directly correlate with the cancer state or a risk thereof, while other cancer markers may inversely correlate with the cancer state or a risk thereof. Accordingly, in some embodiments, modulating is increasing the level of a cancer marker in a subject. Increasing the cancer marker level in a subject may result in an increase of at least 1% relative to prior to administration or a control (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration or a control; e.g., up to 100% relative to prior to administration or a control). In other embodiments, modulating is decreasing the cancer marker level in a subject. Decreasing the cancer marker level in a subject may result in a decrease of at least 1% relative to prior to administration or a control (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration or a control; e.g., up to 100% relative to prior to administration or a control).

The methods of the invention may be for modulating an infection marker (e.g. blood, urine or cerebrospinal white blood cell count, erythrocyte sedimentation rate, serum hepatic transaminase levels, serum blood alkaline phosphatase levels, or culture of sterile body fluid such as blood, pleural fluid or cerebrospinal fluid) in a subject in need thereof. Modulating the infection marker (e.g., blood or liver infection marker) level in a subject may result in a change of at least 1% relative to prior to administration or a control (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration or a control; e.g., up to 100% relative to prior to administration or a control). Some infection markers may directly correlate with the infectious state or a risk thereof, while other infectious markers may inversely correlate with the infectious state or a risk thereof. Accordingly, in some embodiments, modulating is increasing the level of an infection marker in a subject. Increasing the infection marker level in a subject may result in an increase of at least 1% relative to prior to administration or a control (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration or a control; e.g., up to 100% relative to prior to administration or a control). In other embodiments, modulating is decreasing the infection marker level in a subject. Decreasing the infection marker level in a subject may result in a decrease of at least 1% relative to prior to administration or a control (e.g., at least 5%, 10%, 15%, 20%, 25%, 30%, 35%, 40%, 45%, 50%, 55%, 60%, 65%, 70%, 75%, 80%, 85%, 90%, 95% or at least 98% or more relative to prior to administration or a control; e.g., up to 100% relative to prior to administration or a control). In some embodiments, following administration of a conjugate of the invention, cerebrospinal or urinary white blood cell counts, erythrocyte sedimentation rate, hepatic transaminases, serum alkaline phosphatase, or bacterial growth in sterile body fluid cultures decreases. Blood levels of white blood cells may be modulated towards normal levels, depending on whether these infection markers are above or below the normal range. An attendant health professional (e.g., physician or nurse practitioner) may determine the desired direction of the infection marker modulation.

In particular embodiments, a conjugate described herein (e.g., upon cleavage to release a payload (e.g., an antineoplastic agent)) reduces the viability of neoplastic cells in in vitro assays or decreases tumor burden in an animal model of cancer. In some embodiments, a conjugate described herein (e.g., upon cleavage to release a payload (e.g., an antineoplastic agent)) reduces the amount of pain and or supportive medication used by a patient, e.g., change in duration of opioid medication or decreases the need for recombinant human granulocyte colony-stimulating factor analogs in a subject (e.g., at least 5%, 10%, 15%, 20%, 25%, 30%, 35%, 40%, 45%, 50%, 55%, 60%, 65%, 70%, 75%, 80%, 85%, 90%, 95%, or 98% or more relative to a control group). In certain embodiments, a conjugate described herein (e.g., upon cleavage to release a payload (e.g., an antineoplastic agent)) reduces the incidence of adverse events in patients, e.g., change in a patient-reported outcome of CIPN, patients' pain intensity score, percentage of patients stopping chemotherapy due to sensory peripheral neuropathy, or percentage of patients requiring a decrease in chemotherapy dose intensity due to adverse events (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to a control group). In particular embodiments, a conjugate described herein (e.g., upon cleavage to release a payload (e.g., an antineoplastic agent)) improves composite outcome measures of disease progression in patients, e.g., objective response rate, progression free survival, overall survival, response rate in subjects (e.g., at least 5%, 10%, 15%, 20%, 25%, 30%, 35%, 40%, 45%, 50%, 55%, 60%, 65%, 70%, 75%, 80%, 85%, 90%, 95% or 98% or more relative to a control group). In some embodiments, a conjugate described herein (e.g., upon cleavage to release a payload (e.g., an antineoplastic agent)) increases a cancer marker level, e.g., cytotoxic T cell count, $T_h1$ cell count, interferon γ (IFNγ) level, interleukin-17 (IL17) level, or intercellular adhesion molecule (ICAM) level in a subject (e.g., at least 5%, 10%, 15%, 20%, 25%, 30%, 35%, 40%, 45%, 50%, 55%, 60%, 65%, 70%, 75%, 80%, 85%, 90%, 95%, or 98% or more relative to a control group or to the level prior to administration or a control). In certain embodiments, a conjugate described herein (e.g., upon cleavage to release a payload (e.g., an antineoplastic agent)) reduces a cancer marker, e.g., NFκB level, MMP9 level, 8-iso-PGF2a level, or CXCL13 level in a subject (e.g., at least 5%, 10%, 15%, 20%, 25%, 30%, 35%, 40%, 45%, 50%, 55%, 60%, 65%, 70%, 75%, 80%, 85%, 90%, 95%, or 98% or more relative to a control group or to the level prior to administration or a control). In further embodiments, a conjugate described herein (e.g., upon cleavage to release a payload (e.g., an antineoplastic agent)) modulates (increases or decreases) a cancer marker, e.g., $T_h1$ cell count, IgA level, or iNOS level in a subject (e.g., at least 5%, 10%, 15%, 20%, 25%, 30%, 35%, 40%, 45%, 50%, 55%, 60%, 65%, 70%, 75%, 80%, 85%, 90%, 95%, or 98% or more relative to a control group or to the level prior to administration or a control). An attendant doctor or nurse practitioner can determine whether an increase or a decrease in the $T_h1$ cell count, IgA level, or iNOS level is desired.

The cancer markers may be measured using methods known in the art. For example, blood sample analyses may be performed to measure a $CD4^+CD25^+$ Treg cell (e.g., $CD4^+CD25^+Foxp3^+$ Treg cell) count, cytotoxic T cell count, $T_h1$ level, NFκB level, inducible nitric oxide synthase (iNOS) level, matrix metallopeptidase 9 (MMP9) level, interferon γ (IFNγ) level, interleukin-17 (IL17) level, intercellular adhesion molecule (ICAM) level, CXCL13 level, and 8-iso-prostaglandin $F_{2\alpha}$ (8-iso-PGF2α) level.

In particular embodiments, a conjugate described herein (e.g., upon cleavage to release a payload (e.g., an anti-infective agent)) reduces the viability of infectious cells in in vitro assays or decreases infection burden in an animal model of infection.

Additionally or alternatively, the method of the invention may be to treat an infection or lesion associated with the infection. In particular embodiments, a conjugate described herein (e.g., upon cleavage to release a payload (e.g., an anti-infective)) reduces the viability of infectious agent in in vitro assays or decreases infection burden in an animal model of infection. In particular embodiments, a conjugate described herein (e.g., upon cleavage to release a payload (e.g., an anti-infective) improves individual or composite outcome measures of disease progression or regression in patients, e.g., duration of fever, duration of elevated blood white blood cell count levels, duration of hospitalization, clinical cure rate, microbiological cure rate, time to extubation, time to intensive care unit discharge, incidence or duration of major organ failure.

Additionally or alternatively, the method of the invention may be for modulating the microbiome in a subject in need thereof. Modulating the microbiome in a subject in need thereof may result in the reduction of E. coli or Klebsiella pneumoniae.

Additionally or alternatively, the method of the invention may be for treating cancer (e.g., colorectal cancer) in a subject in need thereof. Without wishing to be bound by theory, it is believed that the conjugate of the invention upon administration may diffuse or be propelled through the subject's body The methods of the invention include administering a therapeutically effective amount of the conjugate of the invention to a subject in need thereof (e.g., a subject suffering from colorectal cancer). The therapeutically effective amount of the conjugate of the invention, when measured in moles, may be lower than the therapeutically effective amount of an unconjugated payload (e.g., an antineoplastic agent or an antibacterial agent). For example, the therapeutically effective amount of the conjugate of the invention may be at least 10% (e.g., at least 20%, at least 30%, at least 40%, or at least 50%; e.g., up to 90%, up to 80%, up to 70%, or up to 60%) lower than the therapeutically effective amount of the corresponding unconjugated payload (e.g., an antineoplastic agent or an antibacterial agent). Alternatively, the therapeutically effective amount of a conjugate of the invention may be equal to or even exceed the therapeutically effective amount of the corresponding unconjugated payload (e.g., an antineoplastic agent or an antibacterial agent). For example, the therapeutically effective amount of the conjugate of the invention may be higher by at least 10% (e.g., at least 20%, at least 30%, at least 40%, at least 50%, at least 100%, or at least 200%; e.g., up to 500%, up to 400%, up to 300%, or up to 200%) higher than the therapeutically effective amount of the corresponding unconjugated payload (e.g., an antineoplastic agent or an antibacterial agent).

Additionally, the methods described herein may include determining the presence or amount of E. coli or Klebsiella pneumoniae in the GI tract of the subject diagnosed with colorectal cancer. For example, the determining step may include performing an evaluation, providing an evaluation, or obtaining the result of an evaluation of the subject for the presence or amount of E. coli or Klebsiella pneumoniae in the GI tract of the subject diagnosed with colorectal cancer. Typically, presence or amount of E. coli or Klebsiella pneumoniae in the GI tract of the subject may be determined in a stool sample of the subject or in a sample from the oral cavity of the subject. The presence or amount of E. coli or Klebsiella pneumoniae in a sample from a subject may be measured using methods known in the art, e.g., using PCR, bacteriological culture analysis, fluorescent in situ hybridization, gas-liquid chromatography, and/or bacterial enzyme activity analysis.

The invention also provides a method of identifying a subject as a preferred candidate for a therapy using a conjugate of the invention by determining if the subject includes a neoplastic cell and bacteria capable of cleaving a conjugate of the invention. In some embodiments, the method is a method of treating a subject in need thereof, where the method further includes administering the conjugate of the invention to the subject. Prior to or after the identifying step, the subject may be diagnosed with cancer (e.g., colorectal cancer). To assess whether a subject may be a preferred candidate for a therapy using a conjugate of the invention, a diagnostic conjugate a protected and inactive fluorescent or colorimetric dye as a payload may be added to a portion of a sample (e.g., a biopsy sample) from a subject ex vivo. If the bacteria are present, the dye may be released and result in a signal emitted by the dye (a fluorophore/chromophore in the dye), thereby identifying the subject as a preferred candidate for a therapy using a conjugate of the invention.

In certain situations, a stool sample or bodily fluid is collected to screen for the presence of bacteria or protein produced by bacteria co-located with a tumor. For example, subjects suffering from a cancer (e.g., prostate cancer, gall bladder cancer, cervical cancer, colorectal cancer, or precancerous FAP) that are associated with bacteria described above, are appropriate candidates for such collection.

The presence of bacteria or bacterial proteins in tumor biopsies may be assessed to identify the appropriate subjects for therapy. To perform this assessment, biopsies may be collected and partitioned for histological analysis (to determine the presence of malignant cells), sequencing analysis (to determine the presence of bacteria or bacterial protein), and/or diagnostic activity analysis. For sequencing analysis, DNA and RNA may be extracted from neoplastic cells and probed using 16S rRNA sequencing to identify bacteria of interest. The presence of the bacterial protein itself may be determined using qPCR or whole genome DNA or RNA sequencing (i.e., RNA seq). A subject is a candidate for therapy if the tumor biopsy is both malignant and positive for bacteria/bacterial protein of interest.

In certain embodiments, the subject may be identified as having cancer based on the same sample as that which is used to identify the subject as having the bacteria capable of cleaving the conjugate of the invention. In the methods of the invention, a sample from the subject may be screened for the presence of neoplastic cells (e.g., gallbladder, colon, breast, or cervix) known to be located in the immediate vicinity of a bacteria (e.g., *Salmonella enterica* (e.g., *Salmonella enterica* ssp *enterica* serovar *Typhi* strain), *Bacteroides fragilis* (e.g., enterotoxigenic *Bacteroides fragilis*), *Escherichia coli* (e.g., PKS+*Escherichia coli*), *Methylobacterium radiotolerans*, or *Chlamydia trachomatis*). In the methods of the invention, the subject may be screened for the presence of bacteria or bacterial protein (e.g., *Salmonella enterica* (e.g., *Salmonella enterica* ssp *enterica* serovar *Typhi* strain), *Bacteroides fragilis* (e.g., enterotoxigenic *Bacteroides fragilis*), *Escherichia coli* (e.g., PKS+*Escherichia coli*), *Methylobacterium radiotolerans*, or *Chlamydia trachomatis*).

In the methods described herein, the conjugates of the invention may be administered in a pharmaceutical composition (e.g., those described herein).

Preparation of the Conjugates

The conjugates of the invention may be prepared using reaction classes and techniques known in the art. For example, a payload may be directly bonded to a recognition element by an amidation or esterification reaction. Alternatively, a payload may be covalently linked to a recognition element through a linker. Preparation of a conjugate having a covalent linker linking a payload to a recognition element may involve, first, a covalent bond formation between the linker moiety and the payload and, second, a covalent bond formation between the recognition element the linker moiety; or the order of the covalent bond forming steps may be reversed. The covalent bond formation steps may be performed under the amidation and/or esterification reaction conditions.

Amidation conditions are known in the art, for example, typical amidation conditions include the use of reagents, such as EDC/DMAP, EDC/HOBt, HATU/HOAt, or HBTU/HOAt. The esterification reaction conditions are known in the art. For example, esterification conditions may include Steglich esterification (e.g., EDC/DMAP) or treatment with iso-butyl chloroformate and N-methylmorpholine to prepare an intermediate mixed anhydride, which is then reacted with a nucleophile. In the amidation and esterification reactions, EDC may be provided, for example, as EDC-HCl or as EDCl.

One of skill in the art will recognize that certain transformations in the preparation of the conjugates of the invention may require the use of protecting groups. The protecting groups and methods of their use are described in detail in Greene, "Protective Groups in Organic Synthesis," 3rd Edition (John Wiley & Sons, New York, 1999).

Non-limiting examples of synthetic routes to the conjugates of the invention are provided in the schemes below.

Scheme 1 Conjugation of Payloads Having a Hydroxyl

Step 1

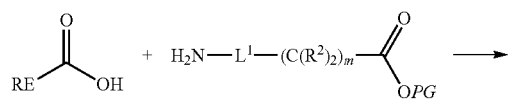

-continued

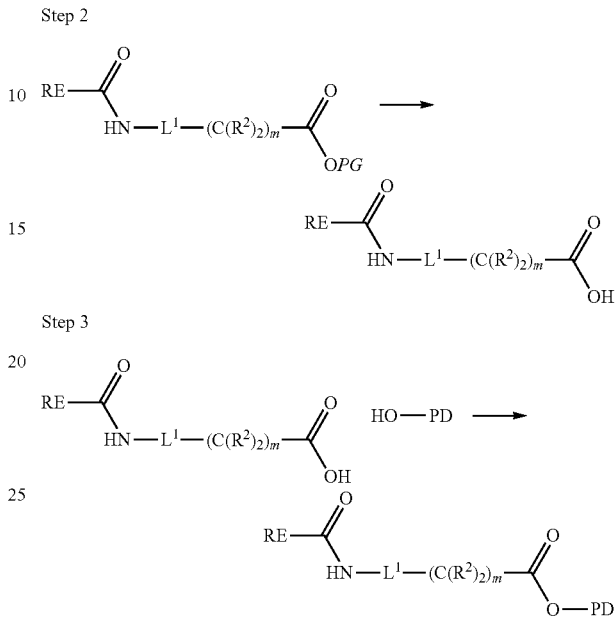

RE = Recognition element
PD = Payload
PG = O-protecting group
the remaining variables are as described herein Scheme 1 illustrates the preparation of a conjugate of the invention by (Step 1) amidation between an O-protected linker moiety and a recognition element, (Step 2) removal of the O-protecting group on the linker moiety to reveal —COOH, and (Step 3) esterification of the Step 2 product with a payload having a hydroxyl group to form an embodiment of a conjugate of the invention.

Scheme 2 Conjugation of Payloads Having an Amine

Step 1

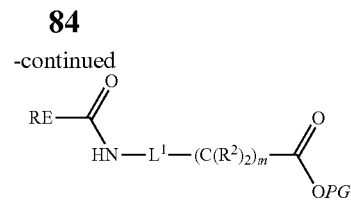

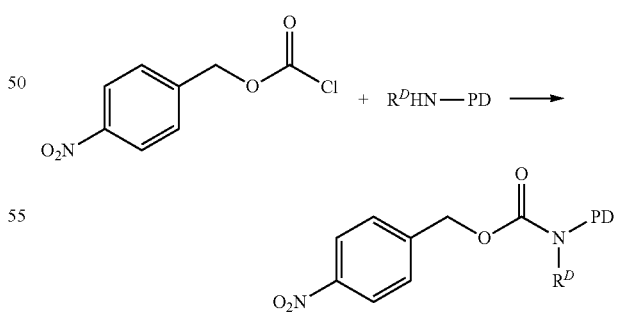

Step 2

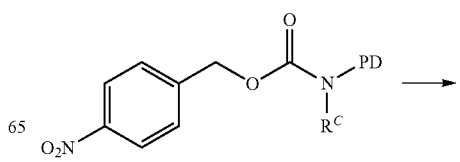

-continued

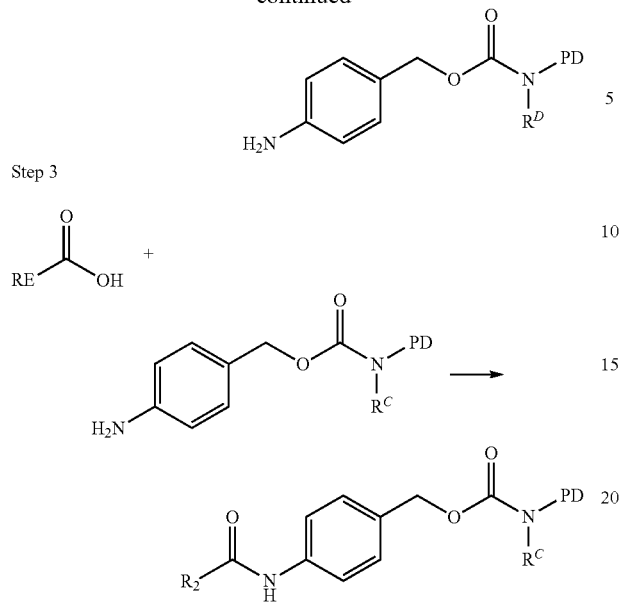

RE = recognition element
PD = payload
$R^D$ = H or optionally substituted $C_{1-6}$ alkyl Scheme 2 illustrates the preparation of a conjugate of the invention by (Step 1) the carbamate formation through the reaction between a payload having an amine and a p-nitrobenzyl chloroformate, (Step 2) reduction of the nitro group in the Step 1 product, and (Step 3) the amidation reaction between a recognition element and the Step 2 product to form an embodiment of a conjugate of the invention.

Scheme 3 Conjugation of Payloads to Form a Quaternary Ammonium Salt

Step 1

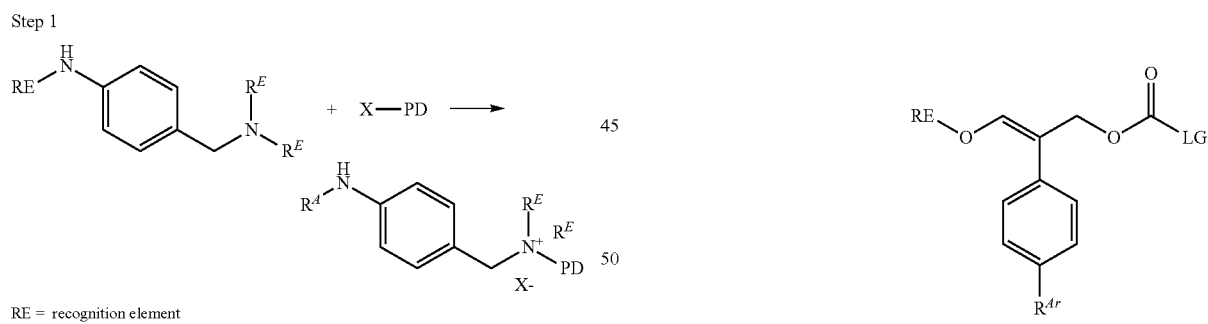

RE = recognition element
PD = payload
X = leaving group (e.g., halide or pseudohalide)
$R^E$ = H, optionally substituted $C_{1-6}$ alkyl, or payload Scheme 3 illustrates the preparation of quaternary ammonium salt-based conjugates of the invention by subjecting a recognition element bonded to a linker or a conjugate of the invention to a nucleophilic substitution reaction with a payload having a leaving group (e.g., halide or pseudohalide) to produce an embodiment of a conjugate of the invention. Nucleophilic substitution reaction conditions are known in the art. See, for example, Carey and Sundberg, "Advanced Organic Chemistry, Part B: Reactions and Synthesis," 4$^{th}$ Edition (Kluwer Academic/Plenum Publishers, New York, 2001).

Scheme 4 Conjugation of Payloads through Styrene-diyl Linkers

Step 1

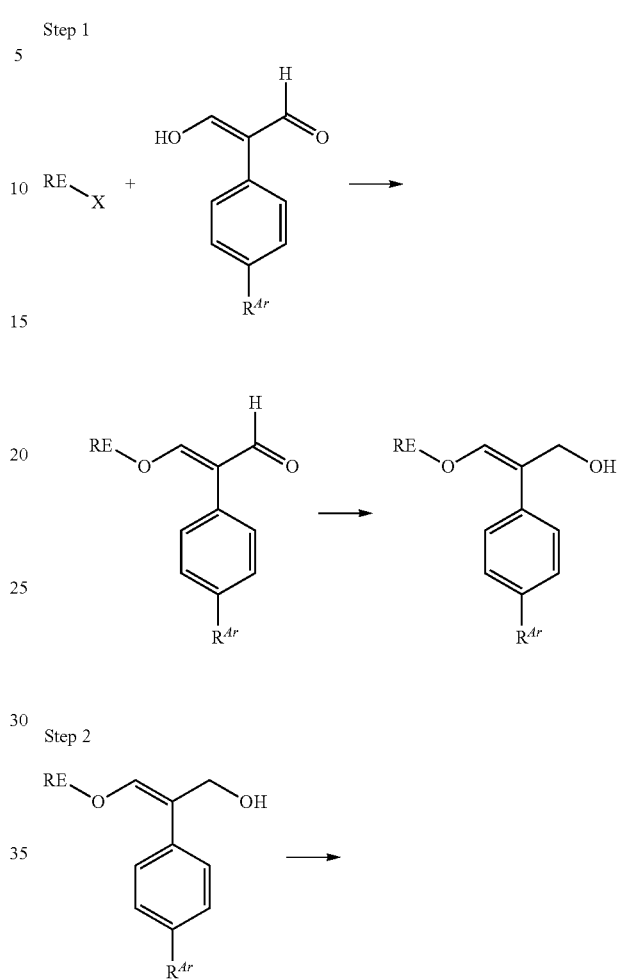

Step 2

Step 3

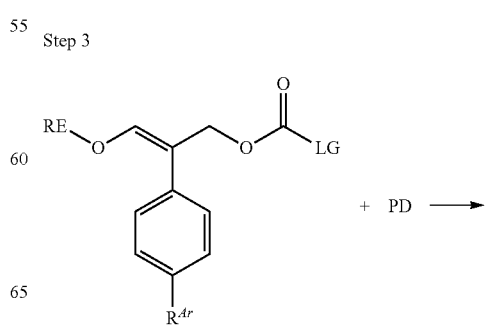

+ PD →

87

-continued

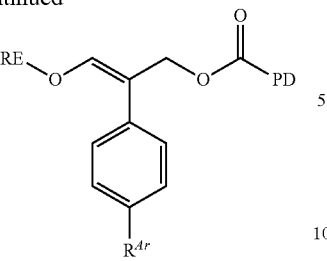

RE = recognition element
PD = payload
LG = leaving group (e.g., halide or pseudohalide)
X = leaving group (e.g., halide or pseudohalide)
$R^{AR}$ = H, halogen, optionally substituted alkyl (e.g., haloalkyl (e.g., —CF$_3$)), alkylsulfonyl (e.g., —SO$_2$Me), or cyano Scheme 4 illustrates the preparation of a conjugate of the invention by (Step 1) reacting a recognition element having a leaving group (e.g., a halide or pseudohalide) with an optionally substituted 2-phenyl-3-hydroxylacrolein under the nucleophilic substituted reaction conditions followed by a reduction of the aldehyde carbonyl, (Step 2) converting the Step 1 product to an electrophilic formate transfer agent, and (Step 3) reacting the Step 2 product with the payload (e.g., a payload having a hydroxyl or amino group) to form an embodiments of a conjugate of the invention (e.g., a conjugate of the invention, in which the payload is linked to the linker through a carbonate or carbamate group). Carbonyl reduction reaction conditions are known in the art. Typically, an aldehyde carbonyl may be reduced using a boron hydride compound (e.g., sodium borohydride, lithium borohydride, or lithium triethylborohydride).

Scheme 5 Conjugation of Payloads through Styrene-diyl/diamine-Linkers

Step 1

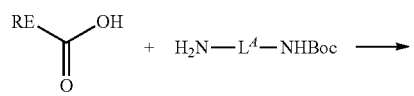

Step 2

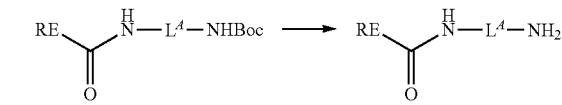

Step 3

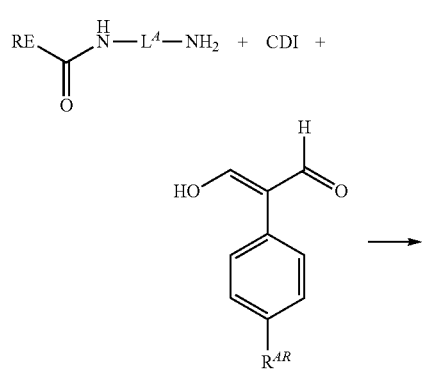

88

-continued

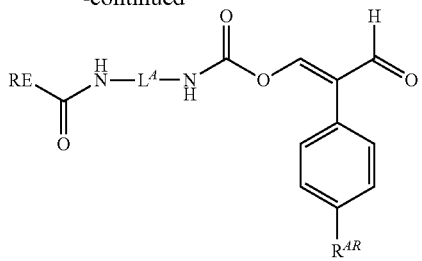

Step 4

Step 5

RE = recognition element
PD = payload
LG = leaving group (e.g., halide or pseudohalide)
X = leaving group (e.g., halide or pseudohalide)
$R^{AR}$ = H, halogen, optionally substituted alkyl (e.g., haloalkyl (e.g., —CF$_3$)), alkylsulfonyl (e.g., —SO$_2$Me), or cyano Scheme 5 illustrates the preparation of a conjugate of the invention by (Step 1) an amidation reaction between a recognition element having a carboxylate group and a linker moiety H$_2$N-L$^A$-NHBoc, (Step 2) removal of Boc-protecting group on the Step 1 product, (Step 3) reacting the Step 2 product with carbonyl diimidazole and optionally substituted 2-phenyl-3-hydroxyacrolein, (Step 4) reducing the aldehyde carbonyl and converting the resulting alcohol to an electrophilic formate transfer group, and (Step 5) reacting the Step 4 product with a payload under, e.g., esterification or amidation reaction conditions, to produce an embodiment of a conjugate of the invention.

Pharmaceutical Compositions

The conjugates disclosed herein may be formulated into pharmaceutical compositions for administration to human subjects in a biologically compatible form suitable for administration in vivo. Pharmaceutical compositions typically include a conjugate as described herein and a physiologically acceptable excipient (e.g., a pharmaceutically acceptable excipient).

The conjugates described herein can also be used in the form of the free acid/base, in the form of salts, zwitterions, or as solvates. All forms are within the scope of the invention. The conjugates, salts, zwitterions, solvates, or pharmaceutical compositions thereof, may be administered to a subject in a variety of forms depending on the selected route of administration, as will be understood by those skilled in the art. The conjugates described herein may be administered, for example, by oral, rectal, intravenous, intraperitoneal, subcutaneous, intramuscular, transepithelial, nasal, intrapulmonary, intrathecal, rectal, topical, intralesional, or intratumoral administration, and the pharmaceutical compositions formulated accordingly. The conjugates of the invention may be used in the methods described herein may be administered, for example, by oral, parenteral, buccal, sublingual, nasal, rectal, patch, pump, or transdermal administration, and the pharmaceutical compositions formulated accordingly. Parenteral administration may be by continuous infusion over a selected period of time.

For human use, a conjugate disclosed herein can be administered alone or in admixture with a pharmaceutical carrier selected regarding the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of conjugates disclosed herein into preparations which can be used pharmaceutically.

This disclosure also includes pharmaceutical compositions which can contain one or more physiologically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, e.g., preservatives.

The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, 21$^{st}$ Ed., Gennaro, Ed., Lippencott Williams & Wilkins (2005), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in *Handbook of Pharmaceutical Excipients*, 6$^{th}$ Edition, Rowe et al., Eds., Pharmaceutical Press (2009).

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in *Remington: The Science and Practice of Pharmacy*, 21$^{st}$ Ed., Gennaro, Ed., Lippincott Williams & Wilkins (2005), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, the conjugates can be milled to provide the appropriate particle size prior to combining with the other ingredients. If the conjugate is substantially insoluble, it can be milled to a particle size of less than 200 mesh. If the conjugate is substantially water soluble, the particle size can be adjusted by milling to provide a substantially uniform distribution in the formulation, e.g., about 40 mesh.

Dosages

The dosage of the conjugate used in the methods described herein, or pharmaceutically acceptable salts or prodrugs thereof, or pharmaceutical compositions thereof, can vary depending on many factors, e.g., the pharmacodynamic properties of the conjugate; the mode of administration; the age, health, and weight of the recipient; the nature and extent of the symptoms; the frequency of the treatment, and the type of concurrent treatment, if any; and the clearance rate of the conjugate in the subject to be treated. One of skill in the art can determine the appropriate dosage based on the above factors. The conjugates used in the methods described herein may be administered initially in a suitable dosage that may be adjusted as required, depending on the clinical response. In general, a suitable daily dose of a conjugate disclosed herein will be that amount of the conjugate that is the lowest dose effective to produce a therapeutic effect. Such an effective dose will generally depend upon the factors described above.

A conjugate disclosed herein may be administered to the subject in a single dose or in multiple doses. When multiple doses are administered, the doses may be separated from one another by, for example, 1-24 hours, 1-7 days, or 1-4 weeks. The conjugate may be administered according to a schedule, or the conjugate may be administered without a predetermined schedule. It is to be understood that, for any particular subject, specific dosage regimes should be adjusted over time according to the individual need and the professional judgment of the person administering or supervising the administration of the compositions.

The conjugates may be provided in a dosage form. In certain embodiments, the dosage form is designed for administration of at least one conjugate disclosed herein, where the total amount of an administered conjugate may be established by, for example, an attending physician or nurse practitioner.

In the methods of the invention, the time period during which multiple doses of a conjugate disclosed herein are administered to a subject can vary. For example, in some embodiments doses of the conjugates are administered to a subject over a time period that is 1-7 days; 1-12 weeks; or 1-3 months. In other embodiments, the conjugates are administered to the subject over a time period that is, for example, 4-11 months or 1-30 years. In yet other embodiments, the conjugates disclosed herein are administered to a subject at the onset of symptoms. In any of these embodiments, the amount of the conjugate that is administered may vary during the time period of administration. When a conjugate is administered daily, administration may occur, for example, 1, 2, 3, or 4 times per day.

Formulations

A conjugate described herein may be administered to a subject with a pharmaceutically acceptable diluent, carrier, or excipient, in unit dosage form. Conventional pharmaceutical practice may be employed to provide suitable formulations or compositions to administer the conjugate to subjects suffering from a disorder. Administration may begin before the subject is symptomatic.

Exemplary routes of administration of the conjugates disclosed herein or pharmaceutical compositions thereof, used in the present invention include oral, sublingual, buccal, transdermal, intradermal, intramuscular, parenteral, intravenous, intra-arterial, intrapulmonary, intracranial, subcutaneous, intraorbital, intraventricular, intraspinal, intrathecal, intralesional, intratumoral, intraperitoneal, intranasal, inhalation, and topical administration. The conjugates desirably are administered with a physiologically acceptable carrier (e.g., a pharmaceutically acceptable carrier). Pharmaceutical formulations of the conjugates described herein formulated for treatment of the disorders described herein are also part of the present invention. In some preferred embodiments, the conjugates disclosed herein are administered to a subject orally. In other preferred embodiments, the conjugates disclosed herein are administered to a subject topically.

Formulations for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with physiologically acceptable excipients (e.g., pharmaceutically acceptable excipients). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other physiologically acceptable excipients (e.g., pharmaceutically acceptable excipients) can be colorants, flavoring agents, plasticizers, humectants, buffering agents, and the like.

Formulations for oral administration may also be presented as chewable tablets, as hard gelatin capsules where the active ingredient is mixed with an inert solid diluent (e.g., potato starch, lactose, microcrystalline cellulose, calcium carbonate, calcium phosphate or kaolin), or as soft gelatin capsules where the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of conjugates, or by incorporating the conjugate into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the conjugates and compositions of the present invention can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical vehicles.

Formulations for Buccal Administration

Dosages for buccal or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but individual instances exist wherein higher or lower dosages are merited, and such are within the scope of this invention.

For buccal administration, the compositions may take the form of tablets, lozenges, etc. formulated in a conventional manner. Liquid drug formulations suitable for use with nebulizers and liquid spray devices and electrohydrodynamic (EHD) aerosol devices will typically include a conjugate of the invention with a pharmaceutically acceptable carrier. Preferably, the pharmaceutically acceptable carrier is a liquid, e.g., alcohol, water, polyethylene glycol, or a perfluorocarbon. Optionally, another material may be added to alter the aerosol properties of the solution or suspension of conjugates of the invention. Desirably, this material is liquid, e.g., an alcohol, glycol, polyglycol, or a fatty acid. Other methods of formulating liquid drug solutions or suspension suitable for use in aerosol devices are known to those of skill in the art (see, e.g., Biesalski, U.S. Pat. No. 5,112,598 and Biesalski, U.S. Pat. No. 5,556,611, each of which is herein incorporated by reference).

Formulations for Nasal or Inhalation Administration

The conjugates may also be formulated for nasal administration. Compositions for nasal administration also may conveniently be formulated as aerosols, drops, gels, and powders. The formulations may be provided in a single or multidose form. In the case of a dropper or pipette, dosing may be achieved by the patient administering an appropriate, predetermined volume of the solution or suspension. In the case of a spray, this may be achieved, for example, by means of a metering atomizing spray pump.

The conjugates may further be formulated for aerosol administration, particularly to the respiratory tract by inhalation and including intranasal administration. The conjugate will generally have a small particle size for example on the order of five (5) microns or less. Such a particle size may be obtained by means known in the art, for example by micronization. The active ingredient is provided in a pressurized pack with a suitable propellant, e.g., a chlorofluorocarbon (CFC), for example, dichlorodifluoromethane, trichlorofluoromethane, or dichlorotetrafluoroethane, or carbon dioxide, or other suitable gas. The aerosol may conveniently also contain a surfactant, e.g., lecithin. The dose of drug may be controlled by a metered valve. Alternatively, the active ingredients may be provided in a form of a dry powder, e.g., a powder mix of the conjugate in a suitable powder base, e.g., lactose, starch, and starch derivatives, e.g., hydroxypropylmethyl cellulose, and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, e.g., a single dose nasal inhaler or an aerosol dispenser fitted with a metering valve which is intended for disposal after use. Where the dosage form comprises an aerosol dispenser, it will contain a propellant, which can be a compressed gas, e.g., compressed air or an organic propellant, e.g., fluorochlorohydrocarbon. The aerosol dosage forms can also take the form of a pump-atomizer.

Formulations for Parenteral Administration

The conjugates described herein for use in the methods of the invention can be administered in a pharmaceutically acceptable parenteral (e.g., intravenous or intramuscular) formulation as described herein. The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. For example, to prepare such a composition, the conjugates of the invention may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate. Additional information regarding parenteral formulations can be found, for example, in the United States Pharmacopeia-National Formulary (USP-NF), herein incorporated by reference.

The parenteral formulation can be any of the five general types of preparations identified by the USP-NF as suitable for parenteral administration:

(1) "Drug Injection:" a liquid preparation that is a drug substance (e.g., a conjugate of the invention), or a solution thereof;

(2) "Drug for Injection:" the drug substance (e.g., a conjugate of the invention) as a dry solid that will be combined with the appropriate sterile vehicle for parenteral administration as a drug injection;

(3) "Drug Injectable Emulsion:" a liquid preparation of the drug substance (e.g., a conjugate of the invention) that is dissolved or dispersed in a suitable emulsion medium;

(4) "Drug Injectable Suspension:" a liquid preparation of the drug substance (e.g., a conjugate of the invention) suspended in a suitable liquid medium; and (5) "Drug for Injectable Suspension:" the drug substance (e.g., a conjugate of the invention) as a dry solid that will be combined with the appropriate sterile vehicle for parenteral administration as a drug injectable suspension.

Exemplary formulations for parenteral administration include solutions of the conjugate prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in *Remington: The Science and Practice of Pharmacy,* $21^{st}$ Ed., Gennaro, Ed., Lippencott Williams & Wilkins (2005) and in The United States Pharmacopeia: The National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the conjugates. Other potentially useful parenteral delivery systems for conjugates include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the conjugate. Exemplary formulations for parenteral release of the conjugate include: aqueous solutions, powders for reconstitution, cosolvent solutions, oil/water emulsions, suspensions, oil-based solutions, liposomes, microspheres, and polymeric gels.

The following examples are meant to illustrate the invention. They are not meant to limit the invention in any way.

EXAMPLES

Preparation of Compounds

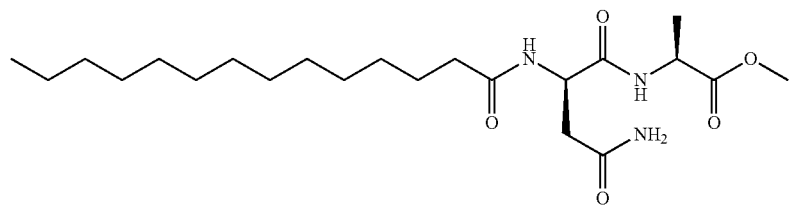 [SMILES: CCCCCCCCCCCCCC(=O)N[C@H](CC(N)=O)C(=O)N[C@@H](C)C(=O)OC]

Example 1: Methyl tetradecanoyl-D-asparaginyl-L-alaninate

Step 1:

Boc-D-asparagine (15.9 g, 69 mmol, 1.2 equiv.), HOBt (10.6 g, 63 mmol, 1.1 equiv.), and L alanine methyl ester hydrochloride (8 g, 57 mmol, 1 equiv.) were dissolved in anhydrous DMF (300 mL), followed by addition of triethylamine (17.4 mL, 126 mmol, 2.2 equiv.). The mixture was cooled to 0° C. with an ice bath and EDC·HCl (12 g, 63 mol, 1.1 equiv.) was added. The reaction mixture was stirred at 0° C. for 15 min, then the ice bath was removed, and the reaction was stirred at room temperature overnight. The mixture was diluted with ethyl acetate (1 L) and washed with saturated $NH_4Cl$ solution (1 L), saturated $NaHCO_3$ (1 L), deionized water (1 L), and brine (1 L). The organic layer was dried over anhydrous sodium sulfate, filtered, and concentrated by rotary evaporation to yield Boc-D-Asn-L-Ala-OMe as a white solid (6.6 g, 36%) which was used in the next step without any further purification. $^1$H NMR (400 MHz, DMSO-$d_6$) δ 8.04 (d, J=7.4 Hz, 1H), 7.23 (s, 1H), 6.94-6.74 (m, 2H), 4.31-4.18 (m, 2H), 3.60 (s, 3H), 2.45-2.24 (m, 2H), 1.36 (s, 9H), 1.24 (d, J=7.2 Hz, 3H). LCMS [M+H]$^+$ 318.1.

Step 2:

Boc-D-Asn-L-Ala-OMe (0.8 g, 2.5 mmol, 1 equiv.) was dissolved in THF (12 mL), followed by dropwise addition of 4M HCl in dioxane (6.3 mL, 25 mmol, 10 equiv.) under nitrogen. The reaction was stirred under nitrogen overnight, then solvent was removed in vacuo to yield the HCl salt of D-Asn-L-Ala-OMe as a white powder (0.6 g, 93%) which was used in the next step without any further purification. $^1$H NMR (400 MHz, DMSO-$d_6$) δ 8.89 (d, 0=7.1 Hz, 1H), 8.17 (s, 3H), 7.69 (s, 1H), 7.22 (s, 1H), 4.29 (p, J=7.2 Hz, 1H), 4.04 (s, 1H), 3.63 (s, 3H), 2.71 (dd, J=16.9, 4.8 Hz, 1H), 2.62 (dd, J=16.8, 7.9 Hz, 1H), 1.28 (d, J=7.2 Hz, 3H). LC/MS [M+H]$^+$ 218.2.

Step 3:

Tetradecanoic acid (270 mg, 1.2 mmol, 1.5 equiv.), HOBt (150 mg, 0.87 mmol, 1.1 equiv.) and EDC-HCl (230 mg, 1.2 mmol, 1.5 equiv.) were dissolved in anhydrous DMF (0.2M), followed by the addition of triethylamine (0.27 mL, 2.0 mmol, 2.5 equiv.). The reaction was stirred for 30 minutes at which time the HCl salt of D-Asn-L-Ala-OMe (200 mg, 0.79 mmol, 1 equiv.) was added in one portion. The reaction was stirred at room temperature overnight and then water was added to clarify the solution. Prior to injection onto reverse-phase C18 chromatography, additional DMSO was added and any insoluble were filtered out. Product was purified as a white solid (25 mg, 7.4%). LCMS [M−H]$^-$ 426.4. $^1$H NMR (400 MHz, DMSO-$d_6$) δ 8.03 (d, J=7.3 Hz, 1H), 7.90 (d, J=8.2 Hz, 1H), 7.23 (s, 1H), 6.82 (s, 1H), 4.56 (td, J=7.9, 6.0 Hz, 1H), 4.23 (p, J=7.2 Hz, 1H), 3.59 (s, 3H), 2.47-2.25 (m, 2H), 2.07 (t, J=7.4 Hz, 2H), 1.49-1.41 (m, 3H), 1.28-1.20 (m, 25H), 0.84 (t, J=6.8 Hz, 3H).

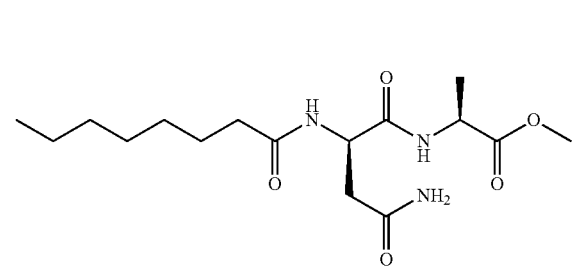 [SMILES: CCCCCCCC(=O)N[C@H](CC(N)=O)C(=O)N[C@@H](C)C(=O)OC]

Example 2: Methyl octanoyl-D-asparaginyl-L-alaninate

Step 1:

To a solution of (tert-butoxycarbonyl)-D-asparagine (998 mg, 4.30 mmol, 1.2 equiv.), HOBt (532 mg, 3.94 mmol, 1.1 equiv.), methyl L-alaninate·HCl (500 mg, 3.58 mmol, 1 equiv.), TEA (797 mg, 7.88 mmol, 1.10 mL, 2.2 equiv.) in DMF (5 mL) was added EDCl (755 mg, 3.94 mmol, 1.1 equiv.) at 0° C. The mixture was stirred at 25° C. for 12 hr. The reaction mixture was filtered and concentrated under reduced pressure and the residue was purified by prep-HPLC (column: Phenomenex luna C18 250*50 mm*10 urn; mobile phase: [water (0.1% TFA)-ACN]; B %: 5%-30%, 20 min) to give methyl (tert-butoxycarbonyl)-D-asparaginyl-L-alaninate (1 g, 88%) as a white solid.

Step 2:

To a solution of methyl (tert-butoxycarbonyl)-D-asparaginyl-L-alaninate (300 mg, 945 μmol) in EtOAc (3 mL) was added HCl/EtOAc (3 mL) (4M) at 25° C. The mixture was stirred at 25° C. for 2 hr. The reaction mixture was concentrated under reduced pressure to give methyl (tert-butoxycarbonyl)-D-asparaginyl-L-alaninate hydrochloride (100 mg, 394.19 μmol, 42%) as a yellow solid.

Step 3:

To a solution of methyl (tert-butoxycarbonyl)-D-asparaginyl-L-alaninate hydrochloride (100 mg, 394 μmol 1 equiv.), octanoic acid (68 mg, 473 μmol, 75 uL, 1.2 equiv.) and HOBt (59 mg, 434 μmol, 1.1 equiv.) in DMF (5 mL) was added TEA (88 mg, 867 μmol, 121 uL, 2.2 equiv.) at 25° C. The mixture was stirred at 25° C. for 5 min. The reaction mixture was cooled to 0° C. and EDCl (83 mg, 434 μmol, 1.1 equiv.) was added. The mixture was stirred at 0° C. for 15 min and was then warmed to 25° C. and stirred at 25° C. for 12 hr. The reaction mixture was filtered and concentrated under reduced pressure and the residue was purified by prep-HPLC (column: Nano-micro Kromasil C18 100*30 mm 5 um; mobile phase: [water (0.1% TFA)-ACN]; B %: 18%-48%, 10 min) to give the title compound (55 mg, 40%) as a white solid. LCMS: (M+H$^+$) 344.2 $^1$H NMR (400 MHz, DMSO-d$_6$) δ 8.0 (d, 1H), 7.9 (d, 1H), 7.2 (s 1H), 4.6 (q, 1H), 4.2 (m, 1H), 3.6 (s, 3H), 2.3 (dd, 2H), 2.1 (t, 2H), 2.0 (m, 2H), 1.4 (m, 11H), 0.83 (m, 3H).

Example 4: Methyl octanoyl-L-asparaginyl-L-alaninate

Step 1

To a mixture of (2S)-4-amino-2-(tert-butoxycarbonylamino)-4-oxo-butanoic acid (998 mg, 4.30 mmol, 1.2 equiv.), methyl (2S)-2-aminopropanoate (500 mg, 3.58 mmol, 1 equiv., HCl), HOBt (532 mg, 3.94 mmol, 1.1 equiv.) and TEA (797 mg, 7.88 mmol, 1.10 mL, 2.2 equiv.) in DMF (5 was added EDCl (755 mg, 3.94 mmol, 1.1 equiv.) at 0° C. The reaction mixture was stirred at 0° C. for 15 min and was then warmed to 25° C. for 12 hr. The reaction mixture was filtered and filtrate was concentrated under reduced pressure to give a residue which was purified by prep-HPLC (column: Phenomenex luna C18 250*50 mm*10 um; mobile phase: [water (0.1% TFA)-ACN]; B %: 10%-40%, 20 min). Methyl (2S)-2-[[(2S)-4-amino-2-(tert-butoxycarbonylamino)-4-oxo-butanoyl]amino] propanoate (750 mg, 66%) was obtained as a white solid.

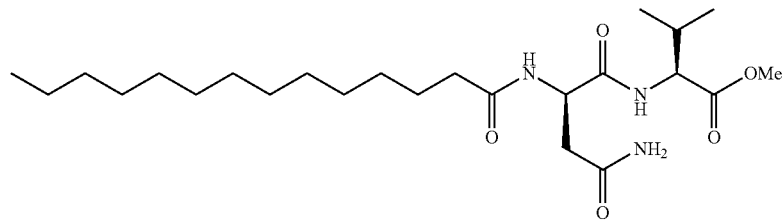 [SMILES: CCCCCCCCCCCCCC(=O)N[C@H](CC(N)=O)C(=O)N[C@H](C(=O)OC)C(C)C]

Example 3: Methyl tetradecanoyl-D-asparaginyl-L-valinate

To a solution of methyl (2S)-2-[[(2R)-2,4-diamino-4-oxo-butanoyl]amino]-3-methyl-butanoate hydrochloride (as synthesized in Example 6 Step 2, 230 mg, 816 μmol, 1 equiv.,) in DCM (5 mL) was added tetradecanoyl chloride (222 mg, 898 μmol, 1.1 equiv.). The reaction mixture was cooled to 0° C., and TEA (165 mg, 1.63 mmol, 227 uL, 2 equiv.) was added. The mixture was stirred at 25° C. for 12 h under N$_2$. The reaction mixture was concentrated under reduced pressure and the residue was purified by prep-HPLC (column: Waters Xbridge Prep OBD C18 150*30 5u; mobile phase: [water (0.1% TFA)-ACN]; B %: 60%-90%, 10 min). Methyl tetradecanoyl-D-asparaginyl-L-valinate (21 mg, 5.5%) was obtained as a white solid. LCMS [M+H]$^+$: 456.3 $^1$H NMR (400 MHz, DMSO-d6) δ 8.00 (d, J=8.1 Hz, 1H), 7.90 (d, J=8.5 Hz, 1H), 7.30 (s, 1H), 6.88 (s, 1H), 4.65 (q, J=7.5 Hz, 1H), 4.18 (dd, J=8.4, 6.0 Hz, 1H), 3.64 (s, 3H), 2.42-2.32 (m, 2H), 2.10 (t, J=7.4 Hz, 2H), 2.08-1.97 (m, 1H), 1.50-1.45 (m, 2H), 1.27-1.21 (m, 20H), 0.90-0.81 (m, 9H).

Step 2:

A mixture of methyl (2S)-2-[[(2S)-4-amino-2-(tert-butoxycarbonylamino)-4-oxo-butanoyl]amino]propanoate (700 mg, 2.21 mmol, 1 equiv.) in HCl/dioxane (3 M, 3.68 mL, 5 equiv.) was stirred at 25° C. for 1 hr. The reaction mixture was concentrated under reduced pressure to give a residue. Methyl (2S)-2-[[(2S)-2,4-diamino-4-oxo-butanoyl]amino]propanoate·HCl (400 mg, 71%) was obtained as a white solid and was used into the next step without further purification.

Step 3:

A mixture of methyl (2S)-2-[[(2S)-2,4-diamino-4-oxo-butanoyl]amino]propanoate·HCl (250 mg, 985 μmol, 1 equiv.,), octanoic acid (170 mg, 1.18 mmol, 187 uL, 1.2 equiv.), HOBt (146 mg, 1.08 mmol, 1.1 equiv.) and TEA (219 mg, 2.17 mmol, 302 uL, 2.2 equiv.) in DMF (5 mL) was cooled to 0° C. EDCl (208 mg, 1.08 mmol, 1.1 equiv.) was added to the mixture. The reaction mixture was stirred at 0° C. for 15 min and was then warmed to 25° C. for 12 hr. The reaction mixture was concentrated under reduced pressure and the residue was purified by prep-HPLC (column: Nano-micro Kromasil C18 100*30 mm 5 um; mobile phase: [water (0.1% TFA)-ACN]; B %: 23%-43%, 10 min). Methyl octanoyl-L-asparaginyl-L-alaninate (70 mg, 21%) was obtained as a white solid. LCMS: (M+H$^+$): 344.2 $^1$H NMR (400 MHz, DMSO-d$_6$) δ 8.1 (d, 1H), 7.9 (d, 1H), 7.2 (s, 1H), 6.8 (s, 1H), 4.5 (m, 1H), 4.2 (m, 1H), 3.3 (s, 3H), 2.4 (dd, 2H), 2.0 (t, 3H), 1.2 (m, 2H), 1.13 (m, 11H), 0.8 (t, 3H).

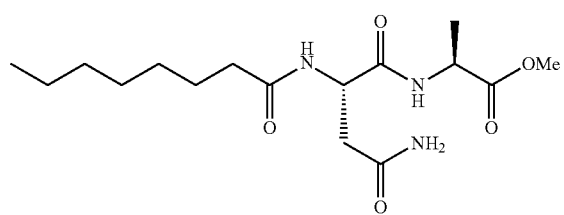 [SMILES: CCCCCCCC(=O)N[C@@H](CC(N)=O)C(=O)N[C@@H](C)C(=O)OC]

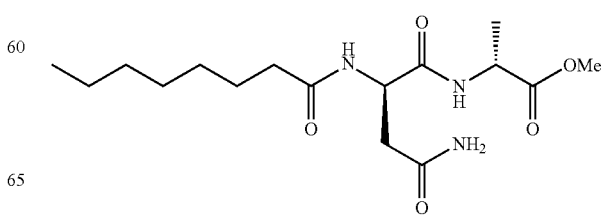

Example 5: Methyl octanoyl-D-asparaginyl-D-alaninate

Step 1:

A mixture of (2R)-4-amino-2-(tert-butoxycarbonylamino)-4-oxo-butanoic acid (998 mg, 4.30 mmol, 1.2 equiv.), methyl (2R)-2-aminopropanoate (500 mg, 3.58 mmol, 1 equiv., HCl), HOBt (532 mg, 3.94 mmol, 1.1 equiv.) and TEA (797 mg, 7.88 mmol, 1.10 mL, 2.2 equiv.) in DMF (5 mL) was cooled to 0° C. EDCl (755 mg, 3.94 mmol, 1.1 equiv.) was added and the reaction mixture was stirred at 0° C. for 15 min and was then warmed to 25° C. for 12 hr. The reaction mixture was filtered and concentrated under reduced pressure to give a residue which was purified by prep-HPLC (column: Phenomenex luna C18 250*50 mm*10 um; mobile phase: [water (0.1% TFA)-ACN]; B %: 5%-35%, 20 min). Methyl (2R)-2-[[(2R)-4-amino-2-(tert-butoxycarbonylamino)-4-oxo-butanoyl]amino] propanoate (890 mg, 78%) was obtained as a white solid.

Step 2:

A mixture of methyl (2R)-2-[[(2R)-4-amino-2-(tert-butoxycarbonylamino)-4-oxo-butanoyl]amino]propanoate (190 mg, 599 μmol) in HCl/dioxane (3 mL) was stirred at 20° C. for 1 hr. The reaction mixture was concentrated under reduced pressure to give methyl (2R)-2-[[(2R)-2,4-diamino-4-oxo-butanoyl]amino]propanoate·HCl (90 mg, 59%) as a white solid which was used without further purification.

Step 3:

A mixture of methyl (2R)-2-[[(2R)-2,4-diamino-4-oxo-butanoyl]amino]propanoate·HCl (90 mg, 355 umol, 1 equiv.), octanoic acid (61 mg, 423 μmol, 67 uL, 1.2 equiv.), HOBt (53 mg, 390 μmol, 1.1 equiv.) and TEA (79 mg, 781 μmol, 109 uL, 2.2 equiv.) in DMF (3 mL) was cooled to 0° C. EDCl (75 mg, 390 μmol, 1.1 equiv.) was added to the mixture and the reaction mixture was stirred at 0° C. for 15 min, and then stirred at 25° C. for 12 hr. The reaction mixture was filtered and filtrate was concentrated under reduced pressure to give a residue which was purified by prep-HPLC (column: Waters Xbridge Prep OBD C18 150*30 5u; mobile phase: [water (0.1% TFA)-ACN]; B %: 15%-75%, 10 min). Methyl octanoyl-D-asparaginyl-D-alaninate (25 mg, 20%) was obtained as a white solid. LCMS: (M+H$^+$): 344.1 $^1$H NMR (400 MHz, DMSO-d$_6$): 8.1 (d, 1H), 7.9 (d, 1H), 4.5 (m, 1H), 4.2 (m, 1H), 3.6 (s, 3H), 2.3 (dd, 2H), 2.0 (t, 2H), 1.2 (m, 2H), 1.2 (m, 11H), 0.87 (t, 3H).

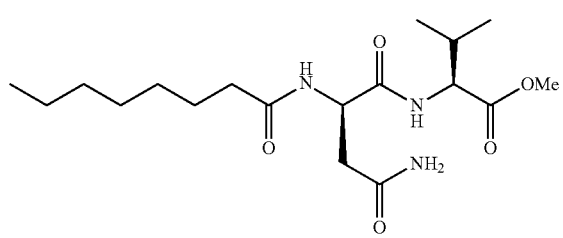 [SMILES: CCCCCCCC(=O)N[C@H](CC(N)=O)C(=O)N[C@H](C(=O)OC)C(C)C]

Example 6: Methyl octanoyl-D-asparaginyl-L-valinate

Step 1:

A mixture of (2R)-4-amino-2-(tert-butoxycarbonylamino)-4-oxo-butanoic acid (831 mg, 3.58 mmol, 1.2 equiv.), methyl (2S)-2-amino-3-methyl-butanoate (500 mg, 2.98 mmol, 1 equiv., HCl), HOBt (443 mg, 3.28 mmol, 1.1 equiv.) and TEA (664 mg, 6.56 mmol, 913 uL, 2.2 equiv.) in DMF (10 mL) was cooled to 0° C. EDCl (629 mg, 3.28 mmol, 1.1 equiv.) was added to the mixture. The reaction mixture was stirred at 0° C. for 15 min and was then warmed to 25° C. and stirred for 12 hr. The reaction mixture was filtered and filtrate was concentrated under reduced pressure to give a residue which was purified by prep-HPLC (column: Phenomenex luna C18 250*50 mm*10 um; mobile phase: [water (0.1% TFA)-ACN]; B %: 10%-40%, 20 min). Methyl (2S)-2-[[(2R)-4-amino-2-(tert-butoxycarbonylamino)-4-oxo-butanoyl]amino]-3-methyl-butanoate (800 mg, 78%) was obtained as a white solid.

Step 2:

A mixture of methyl (2S)-2-[[(2R)-4-amino-2-(tert-butoxycarbonylamino)-4-oxo-butanoyl]amino]-3-methyl-butanoate (500 mg, 1.45 mmol, 1 equiv.) in HCl/dioxane (3 M, 483 uL, 1 equiv.) was stirred at 25° C. for 1 hr. The reaction mixture was concentrated under reduced pressure to give methyl (2S)-2-[[(2R)-2,4-diamino-4-oxo-butanoyl]amino]-3-methyl-butanoate·HCl (300 mg, 74%) as a white solid. The product was used into the next step without further purification.

Step 3:

A mixture of methyl (2S)-2-[[(2R)-2,4-diamino-4-oxo-butanoyl]amino]-3-methyl-butanoate·HCl (250 mg, 887 μmol, 1 equiv.), octanoic acid (154 mg, 1.06 mmol, 169 uL, 1.2 equiv.), EDCl (187 mg, 976 μmol, 1.1 equiv.) and HOBt (132 mg, 976 μmol, 1.1 equiv.) in DMF (5 mL) was cooled to 0° C. and TEA (198 mg, 1.95 mmol, 272 uL, 2.2 equiv.) was added to mixture. The reaction mixture was stirred at 0° C. for 15 min and was then warmed to 25° C. and stirred for 12 hr. The reaction mixture was concentrated under reduced pressure to give a residue. The residue was washed with petroleum ether 3*5 mL. The solid residue was dried in vacuo. Methyl octanoyl-D-asparaginyl-L-valinate (20.8 mg, 6.3%) was obtained as a white solid. LCMS: (M+H$^+$): 372.2 $^1$H NMR (400 MHz, DMSO-d$_6$): 7.5 (s, 1H), 7.3 (s, 1H), 6.0 (s, 1H), 5.5 (s, 1H), 4.8 (s, 1H), 4.4 (s, 1H), 3.7 (s, 3H), 2.9 (dd, 2H), 2.2 (t, 2H), 2.1 (m, 1H) 1.2 (m, 8H), 0.9 (m, 9H).

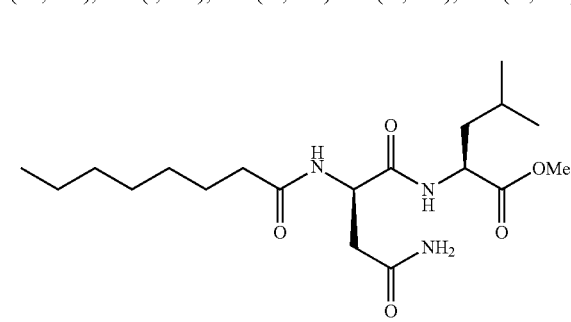

Example 7: Methyl octanoyl-D-asparaginyl-L-leucinate

Step 1:

A mixture of (2R)-4-amino-2-(tert-butoxycarbonylamino)-4-oxo-butanoic acid (767 mg, 3.30 mmol, 1.2 equiv.), methyl (2S)-2-amino-4-methyl-pentanoate·HCl (500 mg, 2.75 mmol, 1 equiv.), HOBt (409 mg, 3.03 mmol, 1.1 equiv.) and TEA (613 mg, 6.06 mmol, 8423 uL, 2.2 equiv.) in DMF (5 mL) was cooled to 0° C. EDCl (580 mg, 3.03 mmol, 1.1 equiv.) was added to the mixture. The reaction mixture was stirred at 0° C. for 15 min and at 25° C. for 12 hr. The reaction mixture was filtered and the filtrate was concentrated under reduced pressure. The residue was purified by prep-HPLC (column: Phenomenex luna C18 250*50 mm*10 um; mobile phase: [water (0.1% TFA)-ACN]; B %: 10%-40%, 20 min) to give methyl (2S)-2-[[(2R)-4-amino-2-(tert-butoxycarbonylamino)-4-oxo-butanoyl]amino]-4-methyl-pentanoate (680 mg, 69%) as a white solid.

Step 2:

A mixture of methyl (2S)-2-[[(2R)-4-amino-2-(tert-butoxycarbonylamino)-4-oxo-butanoyl] amino]-4-methyl-pentanoate (400 mg, 1.11 mmol, 1 equiv.) in HCl/dioxane (3 M, 5.56 mL, 15 equiv.) was stirred at 25° C. for 1 hr. The reaction mixture was concentrated under reduced pressure to give methyl (2S)-2-[[(2R)-2,4-diamino-4-oxo-butanoyl]amino]-4-methyl-pentanoate·HCl (260 mg, 79%) as a white solid. The product was used into the next step without further purification.

Step 3:

A mixture of methyl (2S)-2-[[(2R)-2,4-diamino-4-oxo-butanoyl]amino]-4-methyl-pentanoate·HCl (250 mg, 845 μmol, 1 equiv.), octanoic acid (134 mg, 930 μmol, 147 uL, 1.1 equiv.), HOBt (126 mg, 930 μmol, 1.1 equiv.) and TEA (188 mg, 1.86 mmol, 259 uL, 2.2 equiv.) in DMF (5 mL) was cooled to 0° C. EDCl (178 mg, 930 μmol, 1.1 equiv.) was added to the mixture. The reaction mixture was stirred at 0° C. for 15 min and at 25° C. for 12 hr. The reaction mixture was concentrated under reduced pressure and the residue was purified by prep-HPLC (column: Nano-micro Kromasil C18 100*30 mm 5 um; mobile phase: [water (0.1% TFA)-ACN]; B %: 35%-50%, 10 min). Methyl octanoyl-D-asparaginyl-L-leucinate (119 mg, 37%) was obtained as a white solid. LCMS: (M+H$^+$): 386.2 $^1$H NMR (400 MHz, DMSO-d$_6$): 8.0 (m, 1H), 7.9 (m, 1H), 7.2 (s, 1H) 6.8 (m, 1H), 4.5 (m, 1H), 4.2 (m, 1H), 3.5 (s, 3H), 2.4 (dd, 2H), 2.0 (m, 2H), 1.47 (m, 2H), 1.44 (m, 2H), 1.22 (m, 8H), 0.82 (m, 9H).

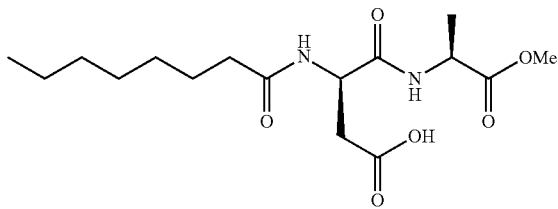 [SMILES: CCCCCCCC(=O)N[C@H](CC(=O)O)C(=O)N[C@@H](C)C(=O)OC]

Example 8: (R)-4-(((S)-1-methoxy-1-oxopropan-2-yl)amino)-3-octanamido-4-oxobutanoic acid Step 1:

A mixture of (2R)-4-benzyloxy-2-(tert-butoxycarbonylamino)-4-oxo-butanoic acid (1.39 g, 4.30 mmol, 1.2 equiv.), methyl (2S)-2-aminopropanoate hydrochloride (500 mg, 3.58 mmol, 1 equiv.), HOBt (532 mg, 3.94 mmol, 1.1 equiv.) and TEA (797 mg, 7.88 mmol, 1.10 mL, 2.2 equiv.) in DMF (10 mL) was cooled to 0° C. EDCl (755 mg, 3.94 mmol, 1.1 equiv.) was added to the mixture. The reaction mixture was stirred at 0° C. for 15 min and at 25° C. for 12 hr. The reaction mixture was filtered and the filtrate was concentrated under reduced pressure. The residue was purified by prep-HPLC (column: Phenomenex luna C18 250*50 mm*10 um; mobile phase: [water (0.1% TFA)-ACN]; B %: 25%-55%, 20 min). Benzyl (3R)-3-(tert-butoxycarbonylamino)-4-[[(1 S)-2-methoxy-1-methyl-2-oxo-ethyl] amino]-4-oxo-butanoate (1.2 g, 82%) was obtained as a yellow oil.

Step 2:

Benzyl (3R)-3-(tert-butoxycarbonylamino)-4-[[(1 S)-2-methoxy-1-methyl-2-oxo-ethyl]amino]-4-oxo-butanoate (1 g, 2.45 mmol, 1 equiv.) in HCl/dioxane (3 M, 10 mL, 12.25 equiv.) was stirred at 25° C. for 1 hr. The reaction mixture was concentrated under reduced pressure to give benzyl (3R)-3-amino-4-[[(1S)-2-methoxy-1-methyl-2-oxo-ethyl] amino]-4-oxo-butanoate·HCl (460 mg, 54%) as a white solid which was used into the next step without further purification.

Step 3:

A mixture of benzyl (3R)-3-amino-4-[[(1S)-2-methoxy-1-methyl-2-oxo-ethyl]amino]-4-oxo-butanoate·HCl (250 mg, 725 μmol, 1 equiv.), octanoic acid (125 mg, 870 μmol, 138 uL, 1.2 equiv.), HOBt (108 mg, 798 μmol, 1.1 equiv.) and TEA (161 mg, 1.60 mmol, 222 uL, 2.2 equiv.) in DMF (5 mL) was cooled to 0° C. EDCl (153 mg, 798 μmol, 1.1 equiv.) was added to the mixture. The reaction mixture was stirred at 0° C. for 15 min and at 25° C. for 12 hr. The reaction mixture was concentrated under reduced pressure and the residue was purified by prep-HPLC (column: Nano-micro Kromasil C18 100*30 mm 5 um; mobile phase: [water (0.1% TFA)-ACN]; B %: 40%-70%, 10 min). Benzyl (3R)-4-[[(1S)-2-methoxy-1-methyl-2-oxo-ethyl]amino]-3-(octanoylamino)-4-oxo-butanoate (123 mg, 39%) was obtained as a white solid.

Step 4:

To a solution of benzyl (3R)-4-[[(1S)-2-methoxy-1-methyl-2-oxo-ethyl]amino]-3-(octanoylamino)-4-oxo-butanoate (100 mg, 230 μmol, 1 equiv.) in THF (3 mL) was added Pd/C (10%, 0.03 g). The suspension was degassed and purged with H$_2$ 3 times. The mixture was stirred under H$_2$ with a pressure of 45 psi at 25° C. for 15 hr. The reaction mixture was filtered and concentrated under reduced pressure to give a residue. The residue was wished with petroleum ether 3*5 mL. The solid residue was dried in vacuo. (R)-4-(((S)-1-methoxy-1-oxopropan-2-yl)amino)-3-octanamido-4-oxobutanoic acid (100 mg, 95%) was obtained as a white solid. LCMS: (M+H$^+$): 345.2 $^1$H NMR (400 MHz, DMSO-d$_6$): 12.2 (s, 1H), 8.1 (d, 1H), 8.0 (d, 1H), 4.6 (m, 1H), 4.2 (m, 1H), 3.6 (s, 3H), 2.6 (dd, 2H), 2.1 (t, 2H), 1.24 (m, 2H), 1.2 (m, 11H), 0.85 (m, 3H).

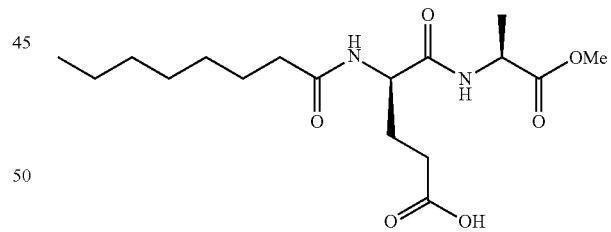

Example 9: (R)-5-(((S)-1-methoxy-1-oxopropan-2-yl)amino)-4-octanamido-5-oxopentanoic acid Step 1:

A mixture of (2R)-5-benzyloxy-2-(tert-butoxycarbonylamino)-5-oxo-pentanoic acid (1.45 g, 4.30 mmol, 1.2 equiv.), methyl (2S)-2-aminopropanoate·HCl (500 mg, 3.58 mmol, 1 equiv.), HOBt (532 mg, 3.94 mmol, 1.1 equiv.) and TEA (797 mg, 7.88 mmol, 1.10 mL, 2.2 equiv.) in DMF (5 mL) was cooled to 0° C. and EDCl (755 mg, 3.94 mmol, 1.1 equiv.) was added to the mixture. The reaction mixture was stirred at 0° C. for 15 min and at 25° C. for 12 hr. The reaction mixture was filtered and concentrated under reduced pressure to give a residue. The residue was purified by prep-HPLC (column: Phenomenex luna C18 250*50 mm*10 um; mobile phase: [water (0.1% TFA)-ACN]; B %: 10%-40%, 20 min). Benzyl (4R)-4-(tert-butoxycarbonylamino)-5-[[(1S)-2-methoxy-1-methyl-2-oxo-ethyl]amino]-5-oxo-pentanoate (650 mg, 43%) was obtained as a white solid.

Step 2:
A mixture of benzyl (4R)-4-(tert-butoxycarbonylamino)-5-[[(1S)-2-methoxy-1-methyl-2-oxo-ethyl]amino]-5-oxo-pentanoate (400 mg, 947 μmol, 1 equiv.) in HCl/dioxane (3 M, 3.16 mL, 10 equiv.) was stirred at 25° C. for 1 hr. The reaction mixture was concentrated under reduced pressure to give benzyl (4R)-4-amino-5-[[(1S)-2-methoxy-1-methyl-2-oxo-ethyl]amino]-5-oxo-pentanoate·HCl (240 mg, 71%) as a white solid.

Step 3:
A mixture of benzyl (4R)-4-amino-5-[[(1S)-2-methoxy-1-methyl-2-oxo-ethyl] amino]-5-oxo-pentanoate·HCl (240 mg, 669 μmol, 1 equiv.), octanoic acid (125 mg, 870 μmol, 138 uL, 1.3 equiv.), HOBt (99 mg, 736 μmol, 1.1 equiv.) and TEA (68 mg, 669 μmol, 93 uL, 1 equiv.) in DMF (5 mL) was cooled to 0° C. and EDCl (141 mg, 736 μmol, 1.1 equiv.) was added to the mixture. The reaction mixture was stirred at 0° C. for 15 min and at 25° C. for 12 hr. The reaction mixture was concentrated under reduced pressure to give a residue which was purified by prep-HPLC (column: Nano-micro Kromasil C18 100*30 mm 5 um; mobile phase: [water (0.1% TFA)-ACN]; B %: 40%-70%, 10 min). Benzyl (4R)-5-[[(1 S)-2-methoxy-1-methyl-2-oxo-ethyl]amino]-4-(octanoylamino)-5-oxo-pentanoate (175 mg, 58%) was obtained as a yellow solid.

Step 4:
To a solution of benzyl (4R)-5-[[(1S)-2-methoxy-1-methyl-2-oxo-ethyl]amino]-4-(octanoylamino)-5-oxo-pentanoate (150 mg, 334 μmol, 1 equiv.) in THF (3 mL) was added Pd/C (10%, 0.03 g). The mixture was stirred at 25° C. for 15 hr under $H_2$ at a pressure of 45 psi. The reaction mixture was filtered and concentrated under reduced pressure to give a residue which was purified by prep-HPLC (column: Waters Xbridge Prep OBD C18 150*30 mm*5 um; mobile phase: [water (0.1% TFA)-ACN]; B %: 20%-50%, 10 min). (R)-5-(((S)-1-methoxy-1-oxopropan-2-yl)amino)-4-octanamido-5-oxopentanoic acid (23 mg, 17%) was obtained as a white solid. LCMS: (M+H$^+$): 359.1 $^1$H NMR (400 MHz, DMSO-d$_6$): 8.2 (s, 1H), 7.9 (s, 1H), 4.2 (m, 2H), 3.6 (s, 3H), 2.1 (dd, 2H), 1.8 (m, 1H), 1.7 (m, 1H), 1.4 (m, 2H), 1.2 (m, 11H), 0.85 (m, 3H)

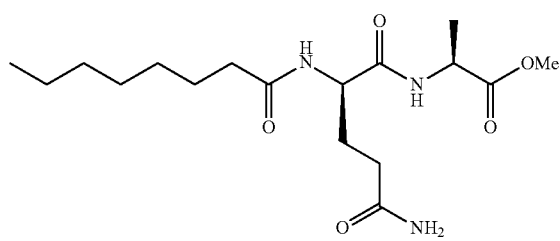 [SMILES: CCCCCCCC(=O)N[C@H](CCC(N)=O)C(=O)N[C@@H](C)C(=O)OC]

Example 10: Methyl octanoyl-D-glutaminyl-L-alaninate

Step 1:
A mixture of (2R)-5-amino-2-(tert-butoxycarbonylamino)-5-oxo-pentanoic acid (1.06 g, 4.30 mmol, 1.2 equiv.), methyl (2S)-2-aminopropanoate hydrochloride (500 mg, 3.58 mmol, 1 equiv.), HOBt (532 mg, 3.94 mmol, 1.1 equiv.) and TEA (797 mg, 7.88 mmol, 1.10 mL, 2.2 equiv.) in DMF (5 mL) was cooled to 0° C. and EDCl (755 mg, 3.94 mmol, 1.1 equiv.) was added to the mixture. The reaction mixture was stirred at 0° C. for 15 min and at 25° C. for 12 hr. The reaction mixture was filtered and concentrated under reduced pressure to give a residue which was purified by prep-HPLC (column: Phenomenex luna C18 250*50 mm*10 um; mobile phase: [water (0.1% TFA)-ACN]; B %: 10%-40%, 20 min). Methyl (2S)-2-[[(2R)-5-amino-2-(tert-butoxycarbonylamino)-5-oxo-pentanoyl]amino] propanoate (660 mg, 56%) was obtained as a white solid.

Step 2:
A mixture of methyl (2S)-2-[[(2R)-5-amino-2-(tert-butoxycarbonylamino)-5-oxo-pentanoyl]amino]propanoate (400 mg, 1.21 mmol, 1 equiv.) in HCl/dioxane (3 M, 4.02 mL, 10 equiv.) was stirred at 25° C. for 1 hr. The reaction mixture was concentrated under reduced pressure to give methyl (2S)-2-[[(2R)-2,5-diamino-5-oxo-pentanoyl]amino] propanoate·HCl (260 mg, 80%) as a white solid.

Step 3:
A mixture of methyl (2S)-2-[[(2R)-2,5-diamino-5-oxo-pentanoyl]amino]propanoate·HCl (250 mg, 934 μmol, 1 equiv.), octanoic acid (162 mg, 1.12 mmol, 178 uL, 1.2 equiv.), HOBt (139 mg, 1.03 mmol, 1.1 equiv.) and TEA (208 mg, 2.05 mmol, 286 uL, 2.2 equiv.) in DMF (5 mL) was cooled to 0° C. and EDCl (197 mg, 1.03 mmol, 1.1 equiv.) was added to the mixture. The reaction mixture was stirred at 0° C. for 15 min and at 25° C. for 12 hr. The reaction mixture was concentrated under reduced pressure to give a residue which was purified by prep-HPLC (column: Waters Xbridge Prep OBD C18 150*30 mm*5 um; mobile phase: [water (0.1% TFA)-ACN]; B %: 25%-85%, 10 min). Methyl octanoyl-D-glutaminyl-L-alaninate (33 mg, 10%) was obtained as a white solid. LCMS: (M+H$^+$): 358.2 $^1$H NMR (400 MHz, DMSO-d$_6$): 8.2 (d, 1H), 7.8 (d, 1H), 7.2 (s, 1H), 6.7 (s, 1H), 4.2 (m, 2H), 3.6 (s, 3H), 2.5 (dd, 2H), 2.1 (m, 1H), 2.05 (m, 1H), 1.4 (m, 1H), 1.2 (m, 11H), 0.83 (t, 3H).

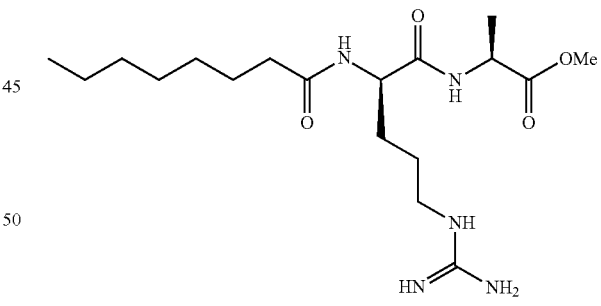

Example 11: Methyl octanoyl-D-arginyl-L-alaninate

Step 1:
A mixture of (2R)-2-(tert-butoxycarbonylamino)-5-guanidino-pentanoic acid (1.18 g, 4.30 mmol, 1.2 equiv.), methyl (2S)-2-aminopropanoate·HCl (500 mg, 3.58 mmol, 1 equiv.,), HOBt (532 mg, 3.94 mmol, 1.1 equiv.) and TEA (797 mg, 7.88 mmol, 1.10 mL, 2.2 equiv.) in DMF (5 mL) was cooled to 0° C. and EDCl (755 mg, 3.94 mmol, 1.1 equiv.) was added to the mixture. The reaction mixture was stirred at 0° C. for 15 min and was then warmed to 25° C. for 12 hr. The reaction mixture was filtered and concentrated under reduced pressure to give a residue which was purified by prep-HPLC (column: Luna C18 100*30 mm*5 um; mobile phase: [water (0.075% TFA)-ACN]; B %: 1%-30%, 14 min). Methyl (2S)-2-[[(2R)-2-(tert-butoxycarbonylamino)-5-guanidino-pentanoyl]amino]propanoate (880 mg, 68%) was obtained as a white solid.

Step 2:

A mixture of methyl (2S)-2-[[(2R)-2-(tert-butoxycarbonylamino)-5-guanidino-pentanoyl]amino]propanoate (600 mg, 1.67 mmol, 1 equiv.) in HCl/dioxane (3 M, 5.56 mL, 10 equiv.) was stirred at 25° C. for 1 hr. The reaction mixture was concentrated under reduced pressure to give methyl (2S)-2-[[(2R)-2-amino-5-guanidino-pentanoyl]amino] propanoate·HCl (420 mg, 85%) as a white solid.

Step 3:

A mixture of methyl (2S)-2-[[(2R)-2-amino-5-guanidino-pentanoyl]amino]propanoate·HCl (250 mg, 845 µmol, 1 equiv.), octanoic acid (146 mg, 1.01 mmol, 161 uL, 1.2 equiv.), HOBt (126 mg, 930 µmol, 1.1 equiv.) and TEA (188 mg, 1.86 mmol, 259 uL, 2.2 equiv.) in DMF (5 mL) was cooled to 0° C. and EDCl (178 mg, 930 µmol, 1.1 equiv.) was added to the mixture. The reaction mixture was stirred at 0° C. for 15 min and at 25° C. for 12 hr. The reaction mixture was concentrated under reduced pressure to give a residue which was purified by prep-HPLC (column: Waters Xbridge Prep OBD C18 150*30 mm*5 um; mobile phase: [water (0.1% TFA)-ACN]; B %: 15%-45%, 10 min). Methyl octanoyl-D-arginyl-L-alaninate trifluoroacetate salt (90 mg, 28%) was obtained as a white solid. LCMS: (M+H$^+$): 386.2 $^1$H NMR (400 MHz, DMSO-d$_6$): 8.3 (d, 1H), 7.9 (d, 1H), 7.5 (m, 1H), 6.9-7.2 (brm, 3H), 4.3 (m, 2H), 3.6 (s, 3H), 3.0 (m, 2H), 2.1 (m, 2H), 1.5 (m, 1H), 1.4 (m, 5H), 1.2 (M, 11H), 0.83 (t, 3H).

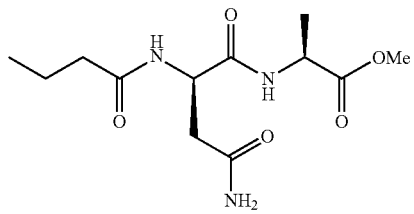 [SMILES: CCCC(=O)N[C@H](CC(N)=O)C(=O)N[C@@H](C)C(=O)OC]

Example 12: Methyl butyryl-D-asparaginyl-L-alaninate

Butanoic anhydride (0.1 mL, 0.6 mmol, 1.5 equiv.) was dissolved in anhydrous DMF (2 mL), followed by addition of triethylamine (0.14 mL, 1.0 mmol, 2.5 equiv.). The HCl salt of D-Asn-L-Ala-OMe (0.1 g, 0.4 mmol, 1 equiv.) was added and the reaction was stirred overnight. Product was purified on reverse phase chromatography following the general procedure shown in Example 1 Step 3 and lyophilized to afford a white solid (92 mg, 84%). LCMS (M+H), 286.1 $^1$H NMR (400 MHz, DMSO-d$_6$) δ 8.03 (d, J=7.3 Hz, 1H), 7.90 (d, J=8.2 Hz, 1H), 7.22 (s, 1H), 6.82 (s, 1H), 4.58 (td, J=8.0, 5.9 Hz, 1H), 4.24 (p, J=7.3 Hz, 1H), 3.59 (s, 3H), 2.46-2.26 (m, 2H), 2.07 (t, J=7.3 Hz, 2H), 1.49 (h, J=7.4 Hz, 2H), 1.24 (d, J=7.2 Hz, 3H), 0.83 (t, J=7.4 Hz, 3H).

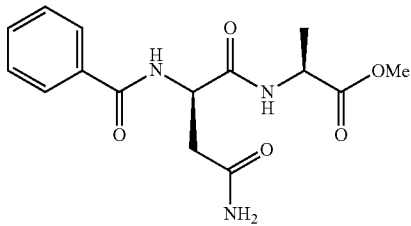 [SMILES: COC(=O)[C@H](C)NC(=O)[C@@H](CC(N)=O)NC(=O)c1ccccc1]

Example 13: Methyl benzoyl-D-asparaginyl-L-alaninate

Methyl benzoyl-D-asparaginyl-L-alaninate was synthesized following the general procedure for the N-acylated dipeptide shown in Example 1 Step 3 using benzoic acid (72 mg, 0.59 mmol, 1.5 equiv.), HOBt hydrate wetted with not less than 20 wt. % water (73 mg, 0.43 mmol, 1.1 equiv.), EDC-HCl (113 mg, 0.59 mmol, 1.5 equiv.), triethylamine (0.14 mL, 1.0 mmol, 2.5 equiv.), and the HCl salt of D-Asn-L-Ala-OMe (synthesized in Example 1 Step 2, 100 mg, 0.39 mmol, 1 equiv.). The product was purified as a white solid (93 mg, 55%). LCMS [M−H]$^−$ 320.2 $^1$H NMR (400 MHz, DMSO-d$_6$) δ 8.49 (d, J=8.0 Hz, 1H), 8.23 (d, J=7.3 Hz, 1H), 7.90-7.82 (m, 2H), 7.61-7.40 (m, 3H), 7.30 (s, 1H), 6.88 (s, 1H), 4.79 (td, J=8.0, 5.7 Hz, 1H), 4.26 (p, J=7.2 Hz, 1H), 3.58 (s, 3H), 2.65-2.52 (m, 2H), 1.25 (d, J=7.2 Hz, 3H).

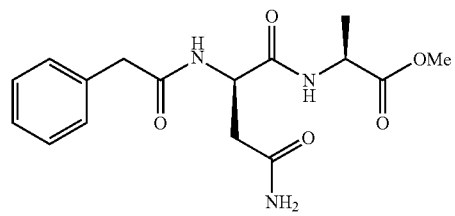 [SMILES: COC(=O)[C@H](C)NC(=O)[C@@H](CC(N)=O)NC(=O)Cc1ccccc1]

Example 14: Methyl (2-phenylacetyl)-D-asparaginyl-L-alaninate

Methyl (2-phenylacetyl)-D-asparaginyl-L-alaninate was synthesized following the general procedure for the N-acylated dipeptide shown in Example 1 Step 3 using phenylacetic acid (80.4 mg, 0.59 mmol, 1.5 equiv.), HOBt hydrate wetted with not less than 20 wt. % water (73 mg, 0.43 mmol, 1.1 equiv.), EDC-HCl (113 mg, 0.59 mmol, 1.5 equiv.), triethylamine (0.14 mL, 1.0 mmol, 2.5 equiv.), and the HCl salt of D-Asn-L-Ala-OMe (synthesized in Example 1 Step 2, 100 mg, 0.39 mmol, 1 equiv.). The product was purified as a white solid (17.9 mg, 13.5%). LCMS [M−H]$^−$ 334.1 $^1$H NMR (400 MHz, DMSO-d6) δ 8.22 (d, J=8.1 Hz, 1H), 8.09 (d, J=7.3 Hz, 1H), 7.30-7.20 (m, 5H), 7.24-7.15 (m, 1H), 6.85 (s, 1H), 4.57 (td, J=7.8, 6.0 Hz, 1H), 4.23 (p, J=7.2 Hz, 1H), 3.59 (s, 3H), 3.45 (s, 2H), 2.53-2.43 (m, 1H), 2.34 (dd, J=15.3, 7.7 Hz, 1H), 1.22 (d, J=7.2 Hz, 3H).

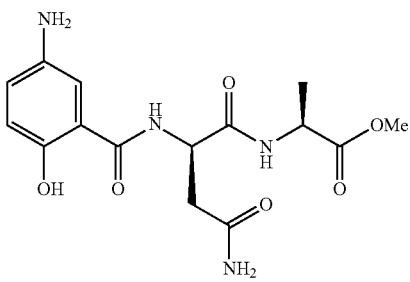 [SMILES: COC(=O)[C@H](C)NC(=O)[C@@H](CC(N)=O)NC(=O)c1cc(N)ccc1O]

Example 15: Methyl (5-amino-2-hydroxybenzoyl)-D-asparaginyl-L-alaninate

Methyl (5-amino-2-hydroxybenzoyl)-D-asparaginyl-L-alaninate was synthesized following the general procedure for the N-acylated dipeptide shown in Example 1 Step 3 using 5-aminosalicylic acid (90.5 mg, 0.59 mmol, 1 equiv.), HOBt hydrate wetted with not less than 20 wt. % water (99.7 mg, 0.59 mmol, 1 equiv.), EDC-HCl (113 mg, 0.59 mmol, 1.5 equiv.), triethylamine (0.16 mL, 1.2 mmol, 2 equiv.), and the HCl salt of D-Asn-L-Ala-OMe (synthesized in Example 1 Step 2, 150 mg, 0.59 mmol, 1 equiv.). The product was lyophilized with 2 eq of 1M HCl and purified as a HCl salt (10 mg, 4.4%). LCMS [M−H]⁻ 351.1 ¹H NMR (400 MHz, DMSO-d6) δ 11.85 (s, 1H), 9.88 (s, 3H), 9.03 (d, J=7.7 Hz, 1H), 8.36 (d, J=7.1 Hz, 1H), 7.85 (d, J=2.8 Hz, 1H), 7.40-7.31 (m, 2H), 7.05 (d, J=8.7 Hz, 1H), 6.88 (s, 1H), 4.80 (td, J=7.3, 5.7 Hz, 1H), 4.26 (p, J=7.2 Hz, 1H), 3.60 (s, 3H), 2.66-2.50 (m, 2H), 1.26 (d, J=7.2 Hz, 3H).

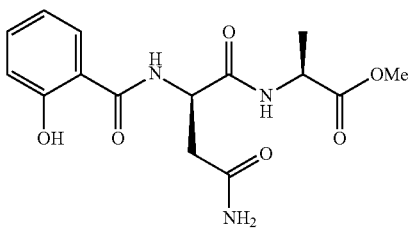 [SMILES: COC(=O)[C@H](C)NC(=O)[C@@H](CC(N)=O)NC(=O)c1ccccc1O]

Example 16: Methyl (2-hydroxybenzoyl)-D-asparaginyl-L-alaninate

Methyl (2-hydroxybenzoyl)-D-asparaginyl-L-alaninate was synthesized following the general procedure for the N-acylated dipeptide shown in Example 1 Step 3 using salicylic acid (138.1 mg, 0.59 mmol, 1.5 equiv.), HOBt hydrate wetted with not less than 20 wt. % water (73 mg, 0.43 mmol, 1.1 equiv.), EDC-HCl (113 mg, 0.59 mmol, 1.5 equiv.), triethylamine (0.14 mL, 1.0 mmol, 2.5 equiv.), and the HCl salt of D-Asn-L-Ala-OMe (synthesized in Example 1 Step 2, 100 mg, 0.39 mmol, 1 equiv.). The product was purified as a white solid (17 mg, 13%). LCMS [M−H]⁻ 336.1 ¹H NMR (400 MHz, DMSO-d6) δ 12.05 (s, 1H), 9.01 (s, 1H), 8.34 (d, J=7.2 Hz, 1H), 7.86 (dd, J=7.9, 1.7 Hz, 1H), 7.41-7.32 (m, 1H), 7.33 (s, 1H), 6.91-6.82 (m, 3H), 4.85-4.75 (m, 1H), 4.26 (p, J=7.2 Hz, 1H), 3.59 (s, 3H), 2.65-2.50 (m, 2H), 1.25 (d, J=7.2 Hz, 3H).

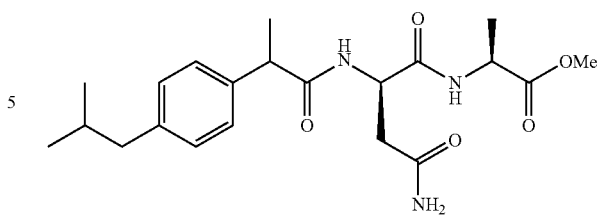

Example 17: Methyl (2-(4-isobutylphenyl)propanoyl)-D-asparaginyl-L-alaninate Methyl (2-(4-isobutylphenyl)propanoyl)-D-asparaginyl-L-alaninate was synthesized following the general procedure for the N-acylated dipeptide shown in Example 1 Step 3 using ibuprofen (122 mg, 0.59 mmol, 1.5 equiv.), HOBt hydrate wetted with not less than 20 wt. % water (73 mg, 0.43 mmol, 1.1 equiv.), EDC·HCl (113 mg, 0.59 mmol, 1.5 equiv.), triethylamine (0.14 mL, 1.0 mmol, 2.5 equiv.), and the HCl salt of D-Asn-L-Ala-OMe (synthesized in Example 1 Step 2, 100 mg, 0.39 mmol, 1 equiv.). The product, a mixture of diastereomers at the ibuprofen α-carbon, was purified as a white solid (118 mg, 74%). LCMS [M−H]⁻ 404.2 ¹H NMR (400 MHz, DMSO-d6) δ 8.14-8.02 (m, 1.5H), 7.76 (d, J=7.3 Hz, 0.5H), 7.25 (s, 0.5H), 7.24-7.15 (m, 2.5H), 7.07-7.01 (m, 2H), 6.85 (s, 0.5H), 6.79 (s, 0.5H), 4.61-4.48 (m, 1H), 4.25 (p, J=7.2 Hz, 0.5H), 4.17 (p, J=7.2 Hz, 0.5H), 3.69-3.60 (m, 1H), 3.61 (s, 1.5H), 3.54 (s, 1.5H), 2.49-2.42 (m, 1), 2.45-2.34 (m, 2H), 2.37-2.22 (m, 1H), 1.85-1.70 (m, 1H), 1.33-1.20 (m, 4.5H), 1.13 (d, J=7.2 Hz, 1.5H), 0.86-0.80 (m, 6H).

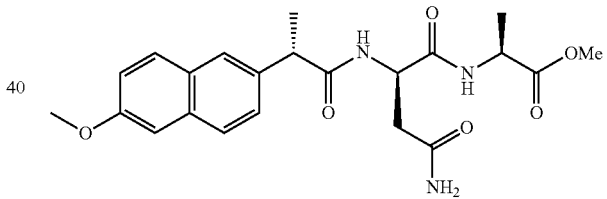

Example 18: Methyl ((S)-2-(6-methoxynaphthalen-2-yl)propanoyl)-D-asparaginyl-L-alaninate Methyl ((S)-2-(6-methoxynaphthalen-2-yl)propanoyl)-D-asparaginyl-L-alaninate was synthesized following the general procedure for the N-acylated dipeptide shown in Example 1 Step 3 using (S)-6-methoxy-α-methyl-2-naphthaleneacetic acid (140 mg, 0.59 mmol, 1.5 equiv.), HOBt hydrate wetted with not less than 20 wt. % water (73 mg, 0.43 mmol, 1.1 equiv.), EDC HCl (113 mg, 0.59 mmol, 1.5 equiv.), triethylamine (0.14 mL, 1.0 mmol, 2.5 equiv.), and the HCl salt of D-Asn-L-Ala-OMe (synthesized in Example 1 Step 2, 100 mg, 0.39 mmol, 1 equiv.). The product was isolated as a mixture of α-carbon diastereomers as a white solid (105 mg, 62%). LCMS [M−H]⁻ 428.2 ¹H NMR (400 MHz, DMSO-d₆) δ 8.25-8.04 (m, 2H), 7.85-7.66 (m, 3H), 7.47-7.37 (m, 1H), 7.31-7.16 (m, 2H), 7.11 (dd, J=8.9, 2.5 Hz, 1H), 6.86 (s, 0.5H), 6.78 (s, 0.5H), 4.64-4.51 (m, 1H), 4.26 (p, J=7.3 Hz, 0.5H), 4.15 (p, J=7.2 Hz, 0.5H), 3.86-3.83 (m, 3H), 3.83-3.76 (m, 1H), 3.61 (s, 1.5H), 3.49 (s, 1.5H), 2.44-2.22 (m, 2H), 1.43-1.34 (m, 3H), 1.24 (d, J=7.2 Hz, 1.5H), 1.08 (d, J=7.2 Hz, 1.5H).

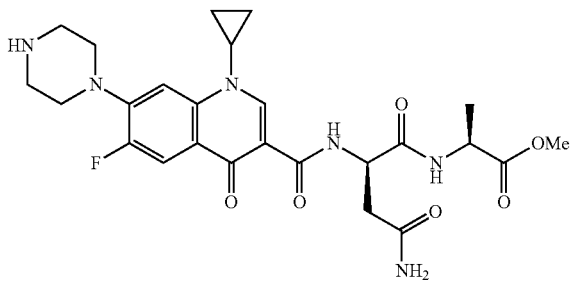 [SMILES: COC(=O)[C@H](C)NC(=O)[C@@H](CC(N)=O)NC(=O)c1cn(C2CC2)c2cc(N3CCNCC3)c(F)cc2c1=O]

Example 19: Methyl (1-cyclopropyl-6-fluoro-4-oxo-7-(piperazin-1-yl)-1,4-dihydroquinoline-3-carbonyl)-D-asparaginyl-L-alaninate Methyl (1-cyclopropyl-6-fluoro-4-oxo-7-(piperazin-1-yl)-1,4-dihydroquinoline-3-carbonyl)-D-asparaginyl-L-alaninate was synthesized following the general procedure for the N-acylated dipeptide shown in Example 1 Step 3 using 7-(4-tert-butoxycarbonylpiperazin-1-yl)-1-cyclopropyl-6-fluoro-4-oxo-quinoline-3-carboxylic acid (140 mg, 0.59 mmol, 1.5 equiv.), HOBt hydrate wetted with not less than 20 wt. % water (73 mg, 0.43 mmol, 1.1 equiv.), EDC HCl (113 mg, 0.59 mmol, 1.5 equiv.), triethylamine (0.14 mL, 1.0 mmol, 2.5 equiv.), and the HCl salt of D-Asn-L-Ala-OMe (synthesized in Example 1 Step 2, 100 mg, 0.39 mmol, 1 equiv.). The lyophilized boc-protected ciprofloxacin dipeptide was stirred in a solution of dichloromethane (1 mL) and trifluoroacetic acid (0.5 mL) until deprotection was complete as monitored by LCMS. Organic solvent was removed by rotary evaporation, and product was dissolved in water and acetonitrile, and then lyophilized to yield product as the trifluoroacetic acid salt (8 mg, 3%). LCMS [M+H]$^+$531.2 $^1$H NMR (400 MHz, DMSO-d6) δ 10.17 (d, J=7.9 Hz, 1H), 9.01 (s, 2H), 8.61 (s, 1H), 8.35 (d, J=7.1 Hz, 1H), 7.88 (d, J=13.2 Hz, 1H), 7.52 (d, J=7.4 Hz, 1H), 7.37 (d, J=2.5 Hz, 1H), 6.85 (d, J=2.4 Hz, 1H), 4.83 (q, J=7.1 Hz, 1H), 4.24 (p, J=7.2 Hz, 1H), 3.79-3.70 (m, 1H), 3.59 (s, 3H), 3.50-3.30 (m, 8H), 2.51 (d, J=6.8 Hz, 2H), 1.32-1.19 (m, 5H), 1.17-1.02 (m, 2H).

Example 20: Methyl (R)-4-(4-amino-4-oxo-2-tetradecanamidobutanamido)butanoate

Step 1:

A mixture of (2R)-4-amino-2-(tert-butoxycarbonylamino)-4-oxo-butanoic acid (1.81 g, 7.81 mmol, 1.2 equiv.), HOBt (968 mg, 7.16 mmol, 1.1 equiv.), TEA (1.45 g, 14.3 mmol, 1.99 mL, 2.2 equiv.) in DMF (10 mL) was cooled to 0° C. EDCl (1.37 g, 7.16 mmol, 1.1 equiv.) and methyl 4-aminobutanoate·HCl (1 g, 6.51 mmol, 1 equiv.) was added to the mixture. The reaction mixture was stirred at 0° C. for 15 min and was stirred at 25° C. for 12 hr. The reaction mixture was filtered and concentrated under reduced pressure to give a residue which was purified by prep-HPLC (column: Phenomenex luna C18 250*50 mm*10 um; mobile phase: [water (0.1% TFA)-ACN]; B %: 0%-32%, 20 min). Methyl 4-[[(2R)-4-amino-2-(tert-butoxycarbonylamino)-4-oxo-butanoyl] amino]butanoate (1.2 g, 56%) was obtained as a white solid.

Step 2:

A mixture of methyl 4-[[(2R)-4-amino-2-(tert-butoxycarbonylamino)-4-oxo-butanoyl]amino]butanoate (1 g, 3.02 mmol) in HCl/dioxane (2 M, 15.1 mL, 10 equiv.) was stirred at 25° C. for 1 hr under N$_2$ atmosphere. The reaction mixture was concentrated under reduced pressure to give methyl 4-[[(2R)-2,4-diamino-4-oxo-butanoyl]amino]butanoate·HCl (550 mg, 68%) as a yellow gum.

Step 3:

To a solution of methyl 4-[[(2R)-2,4-diamino-4-oxo-butanoyl]amino]butanoate·HCl (550 mg, 2.05 mmol, 1 equiv.) in DCM (5 mL) was added TEA (416 mg, 4.11 mmol, 572 uL, 2 equiv.). The reaction mixture was then cooled to 0° C. and tetradecanoyl chloride (558 mg, 2.26 mmol, 1.1 equiv.) was added. The mixture was stirred at 25° C. for 12 hr under N$_2$. The reaction mixture was concentrated under reduced pressure to give a residue which was purified by prep-HPLC (column: Waters Xbridge Prep OBD C18 150*30 mm 5 um; mobile phase: [water (0.1% TFA)-ACN]; B %: 55%-85%, 10 min). Methyl (R)-4-(4-amino-4-oxo-2-tetradecanamidobutanamido)butanoate (14.7 mg, 1.6%) was obtained as a white solid. LCMS: (M+H$^+$): 442.3 $^1$H NMR (400 MHz, DMSO-d$_6$) δ 7.8 (m, 1H), 7.7 (m, 1H), 7.2 (m, 1H), 6.8 (m, 1H), 4.4 (m, 1H) 3.5 (s, 3H), 3.0 (m, 2H), 2.4 (dd, 2H), 2.2 (m, 1H), 2.0 (m, 2H), 1.6 (m, 2H), 1.4 (m, 2H), 1.2 (m, 20H), 0.83 (t, 3H).

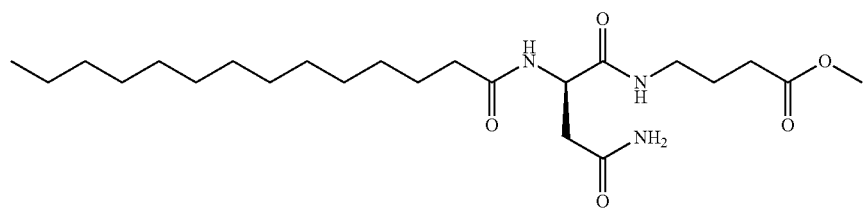 [SMILES: CCCCCCCCCCCCCC(=O)N[C@H](CC(N)=O)C(=O)NCCCC(=O)OC]

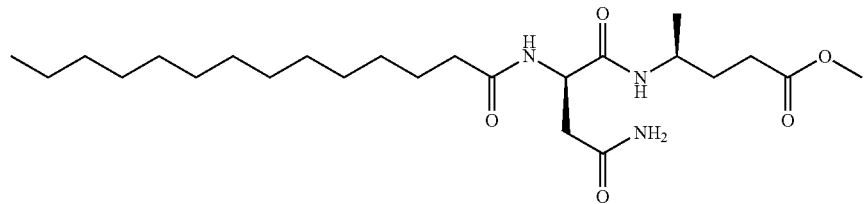 [SMILES: CCCCCCCCCCCCCC(=O)N[C@H](CC(N)=O)C(=O)N[C@@H](C)CCC(=O)OC]

Example 21: Methyl (S)-4-((R)-4-amino-4-oxo-2-tetradecanamidobutanamido)pentanoate Step 1:
To a mixture of tert-butyl N-[(1S)-1-methyl-2-oxo-ethyl] carbamate (5 g, 28.9 mmol, 1 equiv.) in toluene (50 mL) was added methyl (triphenylphosphoranylidene)acetate (9.65 g, 28.9 mmol, 1 equiv.) and then the mixture was stirred at 25° C. for 12 hr under $N_2$ atmosphere. The reaction mixture was concentrated under reduced pressure and the residue was purified by column chromatography ($SiO_2$, petroleum ether/ethyl acetate=10:1 to 4:1). Methyl (E,4S)-4-(tert-butoxycarbonylamino)pent-2-enoate (6 g, 91%) was obtained as a light yellow oil.

Step 2:
To a mixture of methyl (E,4S)-4-(tert-butoxycarbonylamino)pent-2-enoate (6 g, 26.2 mmol) in DCM (25 mL) was added TFA (5 mL), and the mixture was stirred at 25° C. for 2 hr. The reaction mixture was concentrated under reduced pressure to give methyl (E,4S)-4-aminopent-2-enic acid trifluoroacetate salt (4 g, 63%) as a light yellow oil. The product was used in the next step without further purification.

Step 3:
A mixture of methyl (E,4S)-4-aminopent-2-enoic acid trifluoroacetate salt (4 g, 16.5 mmol, 1 equiv.), HOBt (2.44 g, 18.1 mmol, 1.1 equiv.), TEA (3.66 g, 36.2 mmol, 5.04 mL, 2.2 equiv.) in DMF (10 mL) was cooled to 0° C. EDCl (3.47 g, 18.1 mmol, 1.1 equiv.) and (2R)-4-amino-2-(tert-butoxycarbonylamino)-4-oxo-butanoic acid (4.58 g, 19.7 mmol, 1.2 equiv.) was added to the mixture. The reaction mixture was stirred at 0° C. for 15 min and at 25° C. for 12 hr. The reaction mixture was diluted with $H_2O$ (25 mL) and extracted four times with EtOAc (10 mL). The combined organic layers were washed with brine (10 mL), dried over $Na_2SO_4$, filtered and concentrated under reduced pressure. The residue was purified by column chromatography ($SiO_2$, petroleum ether/ethyl acetate=1:1 to 0:1) to give methyl (E,4S)-4-[[(2R)-4-amino-2-(tert-butoxycarbonylamino)-4-oxo-butanoyl]amino] pent-2-enoate (5 g, 89%) as a white solid.

Step 4:
To a solution of methyl (E,4S)-4-[[(2R)-4-amino-2-(tert-butoxycarbonylamino)-4-oxo-butanoyl]amino]pent-2-enoate (5 g, 14.6 mmol) in MeOH (5 mL) was added Pd/C (10%, 0.4 g). The suspension was degassed and purged with $H_2$ three times. The mixture was stirred under $H_2$ at a pressure of 15 psi at 25° C. for 12 hr. The reaction mixture was filtered and concentrated under reduced pressure to give methyl(4S)-4-[[(2R)-4-amino-2-(tert-butoxycarbonylamino)-4-oxo-butanoyl]amino]pentanoate (4 g) as a white solid.

Step 5:
A mixture of methyl (4S)-4-[[(2R)-4-amino-2-(tert-butoxycarbonylamino)-4-oxo-butanoyl]amino]pentanoate (4 g, 11.6 mmol, 1 equiv.) in HCl/dioxane (2 M, 57.9 mL, 10 equiv.) was stirred at 25° C. for 1 hr. The reaction mixture was concentrated under reduced pressure. The residue was purified by prep-HPLC (column: Phenomenex luna c18 250 mm*100 mm*10 um; mobile phase: [water (0.1% TFA)-ACN]; B %: 5%-35%, 20 min) to give methyl (4S)-4-[[(2R)-2,4-diamino-4-oxo-butanoyl]amino]pentanoate (1 g, 31%) was obtained as a white solid.

Step 6:
To a solution of methyl (4S)-4-[[(2R)-2,4-diamino-4-oxo-butanoyl]amino]pentanoate (1 g, 3.55 mmol) in DCM (10 mL) was added TEA (718 mg, 7.10 mmol, 988 uL, 2 equiv.). The reaction mixture was cooled to 0° C. and tetradecanoyl chloride (964 mg, 3.90 mmol, 1.1 equiv.) was added. The mixture was stirred at 25° C. for 12 hr under $N_2$. The reaction mixture was concentrated under reduced pressure and the residue was purified by prep-HPLC (column: Phenomenex luna C18 250*50 mm*10 um; mobile phase: [water (0.1% TFA)-ACN]; B %: 50%-80%, 20 min). Methyl (S)-4-((R)-4-amino-4-oxo-2-tetradecanamidobutanamido) pentanoate (250 mg, 15%) was obtained as a white solid. LCMS: (M+H$^+$): 456.3 $^1$H NMR (400 MHz, DMSO-d$_6$) δ 7.8 (d, 1H), 7.4 (d, 1H), 7.2 (brs, 1H), 6.8 (brs, 1H), 4.4 (m, 1H), 3.7 (m, 1H), 3.6 (s, 3H), 2.4 (m, 1H), 2.2 (m, 3H), 2.0 (m, 1H), 1.4 (m, 1H), 1.2, m, 1H). 1.0 m, 20H), 0.87, (d, 3H), 0.84, (m, 3H).

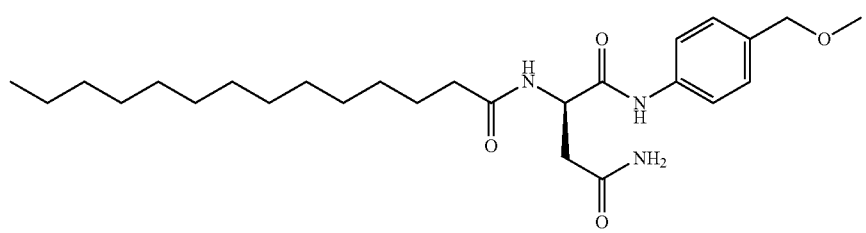 [SMILES: CCCCCCCCCCCCCC(=O)N[C@H](CC(N)=O)C(=O)Nc1ccc(COC)cc1]

Example 22: (R)—N1-(4-(methoxymethyl)phenyl)-2-tetradecanamidosuccinamide

Step 1:

A mixture of (2R)-4-amino-2-(tert-butoxycarbonylamino)-4-oxo-butanoic acid (1.02 g, 4.37 mmol, 1.2 equiv.), 4-(methoxymethyl)aniline (500 mg, 3.64 mmol, 1 equiv.) in EtOAc (5 mL) was cooled to 0° C. Propanephosphonic acid anhydride (1.74 g, 5.47 mmol, 1.63 mL, 1.5 equiv.) and DIPEA (942 mg, 7.29 mmol, 1.27 mL, 2 equiv.) was added to the mixture. The reaction mixture was stirred at 0° C. for 15 min and at 25° C. for 12 hr. The residue was purified by prep-HPLC (column: Phenomenex luna C18 250*50 mm*10 um; mobile phase: [water (0.1% TFA)-ACN]; B %: 10%-40%, 20 min). The residue was purified by prep-TLC (SiO$_2$, petroleum ether:ethyl acetate=0:1) to give tert-butyl N-[(1R)-3-amino-1-[[4-(methoxymethyl)phenyl]carbamoyl]-3-oxo-propyl]carbamate (80 mg, 6.3%) as a white solid.

Step 2:

A mixture of tert-butyl N-[(1R)-3-amino-1-[[4-(methoxymethyl)phenyl]carbamoyl]-3-oxo-propyl]carbamate (80 mg, 228 μmol, 1 equiv.) in HCl/dioxane (3M, 1.52 mL, 20 equiv.) was stirred at 25° C. for 1 hr under N$_2$ atmosphere. The reaction mixture was concentrated under reduced pressure to give the crude product (2R)-2-amino-N-[4-(methoxymethyl)phenyl]butanediamide hydrochloride (60 mg) as a white solid.

Step 3:

To a solution of (2R)-2-amino-N-[4-(methoxymethyl)phenyl]butanediamide hydrochloride (60 mg, 209 μmol, 1 equiv.) in DCM (5 mL) was added TEA (42 mg, 417 μmol, 58 uL, 2 equiv.). The reaction mixture was then cooled to 0° C. and tetradecanoyl chloride (57 mg, 229 μmol, 1.1 equiv.) was added. The mixture was stirred at 25° C. for 12 hr under N$_2$. The reaction mixture was concentrated under reduced pressure and the residue was purified by prep-HPLC (column: Waters Xbridge Prep OBD C18 150*30 mm 5 um; mobile phase: [water (0.1% TFA)-ACN]; B %: 55%-85%, 10 min) to give (R)—N1-(4-(methoxymethyl)phenyl)-2-tetradecanamidosuccinamide (6.1 mg, 5.9%) as a white solid. LCMS: (M+H$^+$): 462.3 $^1$H NMR (400 MHz, DMSO-d$_6$) δ 9.9 (s, 1H), 8.0 (m, 1H), 7.5 m, 2H), 7.3 (m, 1H), 7.2, (m, 2H), 6.8 (brs, 1H), 4.6 (m, 1H), 4.3 (s, 2H), 3.2 (s, 3H), 2.5, dd, 2H), 2.1 (m, 2H), 1.2 (m, 2H), 1.1 (brs, 20H), 0.84 (m, 3H).

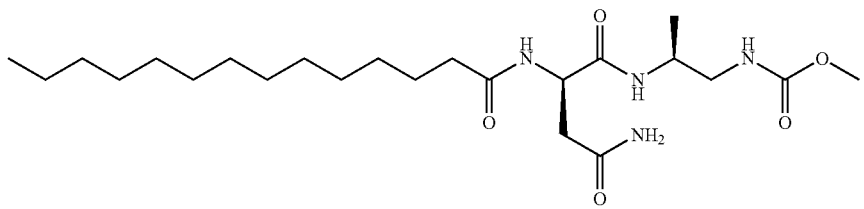 [SMILES: CCCCCCCCCCCCCC(=O)N[C@H](CC(N)=O)C(=O)N[C@@H](C)CNC(=O)OC]

Example 23: Methyl ((S)-2-((R)-4-amino-4-oxo-2-tetradecanamidobutanamido)propyl)carbamate Tetradecanoyl chloride (1.1 equiv.) is reacted with D-asparagine (1 equiv.) to synthesize tetradecanoyl-D-asparagine. The resulting tetradecanoyl-D-asparagine (1 equiv) is treated with EDCl (1.1 equiv), HOBt (1.1 equiv), and tert-butyl (S)-(2-aminopropyl)carbamate (1.1 equiv.), then deprotected with HCl in dioxane. The resulting amine (1 equiv.) is coupled with methyl chloroformate (1.1 equiv.) to yield the title compound. LCMS: (M+H+): 457.3 $^1$H NMR (400 MHz, DMSO-d6) δ 7.85 (d, J=7.6 Hz, 1H), 7.54 (dd, J=24.9, 8.3 Hz, 1H), 7.27-7.22 (m, 1H), 7.11-6.91 (m, 1H), 6.86-6.81 (m, 1H), 4.45-4.40 (m, 1H), 3.77-3.72 (m, 1H), 3.49 (s, 3H), 2.98-2.93 (m, 2H), 2.09-2.05 (m, 2H), 1.46-1.41 (m, 2H), 1.21 (s, 22H), 0.95 (d, J=6.6 Hz, 3H), 0.83 (t, J=6.4 Hz, 3H).

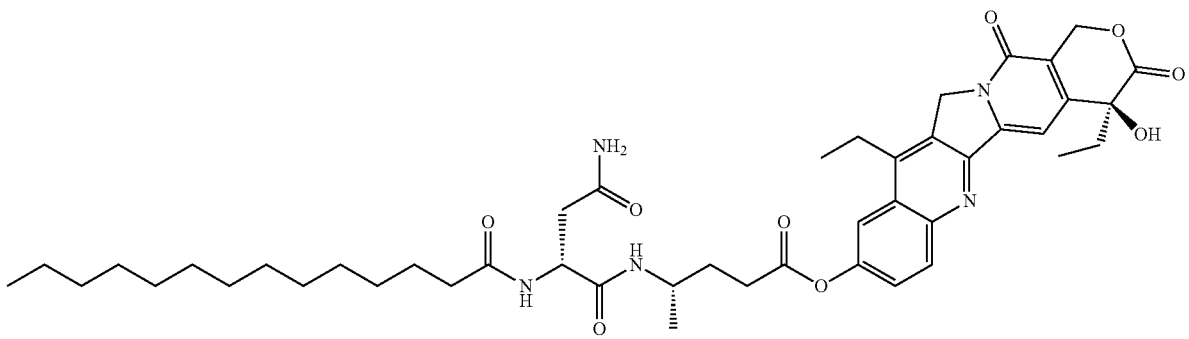 [SMILES: CCCCCCCCCCCCCC(=O)N[C@H](CC(N)=O)C(=O)N[C@@H](C)CCC(=O)Oc1ccc2nc3c(c(CC)c2c1)Cn1c-3cc2c(c1=O)COC(=O)[C@]2(O)CC]

Example 24: (S)-4,11-diethyl-4-hydroxy-3,14-dioxo-3,4,12,14-tetrahydro-1H-pyrano[3',4':6,7]indolizino[1,2-b]quinolin-9-yl (S)-4-((R)-4-amino-4-oxo-2-tetradecanamidobutanamido)pentanoate Compound (4S)-4-[[(2R)-4-amino-4-oxo-2-(tetradecanoylamino)butanoyl]amino]pentanoic acid was synthesized following the general procedure for the N-acylated dipeptide shown in Example 1, followed by treatment with HCl to form the carboxylate. To a solution of (4S)-4-[[(2R)-4-amino-4-oxo-2-(tetradecanoylamino)butanoyl]amino] pentanoic acid (20 mg, 45.29 µmol, 1 equiv.) and (21 S)-17,21-diethyl-10,21-dihydroxy-28-oxa-22,23-diazapentacyclohenicosa-2(10), 3(11), 4(12), 5(14), 13(16), 15(17), 18(22)-heptaene-19,20-dione (17.77 mg, 45.29 µmol, 1 eq) in DMF (5 mL) was added DMAP (2.77 mg, 22.64 µmol, 0.5 eq). The reaction mixture was then cooled to 0° C., and EDCl (9.55 mg, 49.82 µmol, 1.1 equiv.) was added. The mixture was stirred at 25° C. for 12 h under N2. LC-MS showed reactant was consumed completely and the desired m/z was detected. The reaction mixture was filtered and concentrated under reduced pressure to give a residue. The residue was purified by prep-HPLC. The title compound (2 mg, 2.45 µmol, 5.41% yield) was obtained as a yellow solid. LCMS: (M+H$^+$): 816.4 $^1$H NMR (400 MHz, DMSO-d6) δ 8.21 (d, J=9.1 Hz, 1H), 8.00 (d, J=2.5 Hz, 1H), 7.94 (d, J=7.9 Hz, 1H), 7.73-7.60 (m, 2H), 7.34 (s, 1H), 7.28 (s, 1H), 6.86 (s, 1H), 6.52 (s, 1H), 5.44 (s, 2H), 5.35 (s, 2H), 4.55-4.45 (m, 1H), 4.32-4.24 (m, 1H), 2.72-2.31 (m, 4H), 2.14-1.79 (m, 4H), 1.48-1.17 (m, 4H), 1.10 (d, J=6.5 Hz, 3H), 1.08 (s, 22H), 0.93-0.78 (m, 6H).

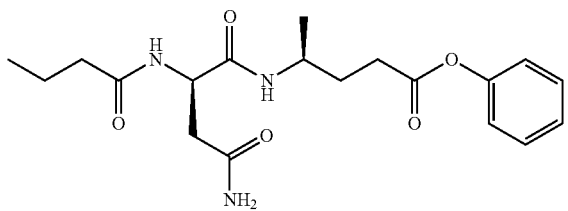 [SMILES: CCCC(=O)N[C@H](CC(N)=O)C(=O)N[C@@H](C)CCC(=O)Oc1ccccc1]

Example 25: Phenyl (S)-4-((R)-4-amino-2-butyramido-4-oxobutanamido)pentanoate Step 1:
To a mixture of (2R)-4-amino-2-(tert-butoxycarbonylamino)-4-oxo-butanoic acid (20 g, 86.12 mmol, 1 equiv.) in MeOH (200 mL) was added CS$_2$CO$_3$ (15.43 g, 47.37 mmol, 0.55 equiv.) in one portion at 25° C. under N$_2$. The mixture was stirred at 25° C. for 1 hour. The reaction mixture was concentrated under reduced pressure to give a residual. To a mixture of bromomethylbenzene (16.91 g, 98.87 mmol, 11.74 mL, 1.2 equiv.) in DMF (100 mL) was added the residual above in one portion at 25° C. under N$_2$. The mixture was stirred at 25° C. for 12 hours. TLC indicated reaction was completed and a new spot formed. The reaction mixture was filtered and then diluted with H$_2$O 50 mL and extracted with EtOAc 50 mL (10 mL*5). The combined organic layers were washed with brine 30 mL, dried over Na$_2$SO$_4$, filtered and concentrated under reduced pressure to give a residue. The residue was purified by column chromatography to give benzyl (2R)-4-amino-2-(tert-butoxycarbonylamino)-4-oxo-butanoate (25 g, 77.55 mmol, 94.13% yield) as a white solid.

Step 2:
To a solution of benzyl (2R)-4-amino-2-(tert-butoxycarbonylamino)-4-oxo-butanoate (20 g, 62.04 mmol, 1 equiv.) in HCl/EtOAc (200 mL, 4 M) was stirred at 25° C. for 2 hr. TLC indicated the reaction was completed. The reaction mixture was filtered and concentrated under reduced pressure to give benzyl (2R)-2,4-diamino-4-oxo-butanoate (16 g, crude, HCl) as a white solid.

Step 3:
To a mixture of benzyl (2R)-2,4-diamino-4-oxo-butanoate (4 g, 15.46 mmol, 1 equiv., HCl) in DCM (80 mL) was added TEA (4.69 g, 46.39 mmol, 6.46 mL, 3 equiv.) under N$_2$. The mixture was cooled to 0° C. and butanoyl chloride (1.81 g, 17.01 mmol, 1.78 mL, 1.1 equiv.) was dropped to the mixture at 0° C. and stirred for 2 hours at 25° C. TLC indicated reaction was completed and one new spot formed. The reaction mixture was filtered and concentrated under reduced pressure to remove DCM. The residue was diluted with H$_2$O 100 mL and EtOAc 100 mL. Then the mixture was washed with H$_2$O 150 mL (50 mL*3). The combined organic layers were dried over Na$_2$SO$_4$, filtered and concentrated under reduced pressure to give benzyl (2R)-4-amino-2-(butanoylamino)-4-oxo-butanoate (3.3 g, crude) as a white solid.

Step 4:
To a solution of benzyl (2R)-4-amino-2-(butanoylamino)-4-oxo-butanoate (3.3 g, 11.29 mmol, 1 equiv.) in THF (120 mL) was added Pd/C (1.5 g, 10% purity) under N$_2$ atmosphere. The suspension was degassed and purged with H$_2$ for 3 times. The mixture was stirred under H$_2$ (15 Psi) at 25° C. for 10 hr. TLC indicated benzyl (2R)-4-amino-2-(butanoylamino)-4-oxo-butanoate was consumed completely and one new spot formed. The reaction mixture was filtered and concentrated under reduced pressure to give (2R)-4-amino-2-(butanoylamino)-4-oxo-butanoic acid (2 g, crude) as a white solid.

Step 5:
To a mixture of (2R)-4-amino-2-(butanoylamino)-4-oxo-butanoic acid (1 g, 4.95 mmol, 1 equiv.), HOBt (735.06 mg, 5.44 mmol, 1.1 equiv.) and TEA (1.10 g, 10.88 mmol, 1.51 mL, 2.2 equiv.) in DMF (10 mL) was stirred at 0° C. under N$_2$. Then EDCl (1.04 g, 5.44 mmol, 1.1 equiv.) and methyl (E,4S)-4-aminopent-2-enoate (900.95 mg, 5.44 mmol, 1.1 equiv., HCl) was added to the mixture and stirred at 25° C. for 10 hr under N$_2$. LCMS showed the desired MS was detected. The reaction mixture was diluted with H$_2$O 15 mL and extracted with EtOAc (20 mL*4). The combined organic layers were washed with brine 10 mL, dried over Na$_2$SO$_4$, filtered and concentrated under reduced pressure to give a residue. The residue was purified by prep-HPLC to give methyl (E,4S)-4-[[(2R)-4-amino-2-(butanoylamino)-4-oxo-butanoyl]amino]pent-2-enoate (400 mg, 1.28 mmol, 25.81% yield) as a white solid.

Step 6:
To a mixture of methyl (E,4S)-4-[[(2R)-4-amino-2-(butanoylamino)-4-oxo-butanoyl]amino] pent-2-enoate (200 mg, 638.27 µmol, 1 equiv.) in THF (5 mL) and H$_2$O (5 mL) was added LiOH·H$_2$O (53.57 mg, 1.28 mmol, 2 equiv.) at 0° C. under N$_2$. The mixture was stirred at 25° C. for 5 hours. The reaction mixture was adjusted pH to 5~6 with 1 M HCl. LCMS showed desired compound was detected. The mixture was concentrated under reduced pressure to give a residue. The residue was purified by prep-HPLC to give (E,4S)-4-[[(2R)-4-amino-2-(butanoylamino)-4-oxo-butanoyl]amino]pent-2-enoic acid (50 mg, 167.04 µmol, 26.17% yield) as a white solid.

Step 7:

To a mixture of (E,4S)-4-[[(2R)-4-amino-2-(butanoylamino)-4-oxo-butanoyl]amino]pent-2-enoic acid (25 mg, 83.52 μmol, 1 equiv.) and phenol (11.79 mg, 125.28 μmol, 11.02 μL, 1.5 equiv.) in DMF (3 mL) was added DMAP (5.10 mg, 41.76 μmol, 0.5 equiv.) at 0° C. under N$_2$. EDCl (17.61 mg, 91.87 μmol, 1.1 equiv.) was added to the mixture and stirred at 25° C. for 10 hours. LCMS showed desired compound was detected. The reaction mixture was filtered and concentrated under reduced pressure to give a residue. The residue was purified by prep-HPLC to give phenyl (E,4S)-4-[[(2R)-4-amino-2-(butanoylamino)-4-oxo-butanoyl]amino]pent-2-enoate (5 mg, 13.32 μmol, 15.95% yield) as a yellow solid.

Step 8:

To a mixture of phenyl (E,4S)-4-[[(2R)-4-amino-2-(butanoylamino)-4-oxo-butanoyl]amino]pent-2-enoate (5 mg, 13.32 μmol, 1 equiv.) in THF (20 mL) was added Pd/C (20 mg, 10% purity) in one portion at 25° C. under H$_2$ (15 psi). The mixture was stirred at 25° C. for 5 hours. LCMS showed desired mass was detected. The reaction mixture was filtered and concentrated under reduced pressure to give a residue. The residue was purified by prep-HPLC to give (S)-phenyl 4-((R)-4-amino-2-butyramido-4-oxobutanamido)pentanoate (4.5 mg, 9.42 μmol, 70.71% yield, 79.99% purity) as a white solid. LCMS: (M+H$^+$) 378.2 $^1$H NMR (400 MHz, DMSO-d6) δ 7.95 (d, J=8.0 Hz, 1H), 7.62 (d, J=8.5 Hz, 1H), 7.39 (t, J=7.9 Hz, 2H), 7.28 (s, 1H), 7.23 (t, J=7.4 Hz, 1H), 7.12-7.05 (m, 2H), 6.86 (s, 1H), 4.47 (q, J=7.5 Hz, 1H), 3.85-3.80 (m, 1H), 2.59-2.28 (m, 2H), 2.05 (t, J=7.3 Hz, 2H), 1.80-1.60 (m, 2H), 1.54-1.41 (m, 2H), 1.04 (d, J=6.6 Hz, 3H), 0.81 (t, J=7.4 Hz, 3H).

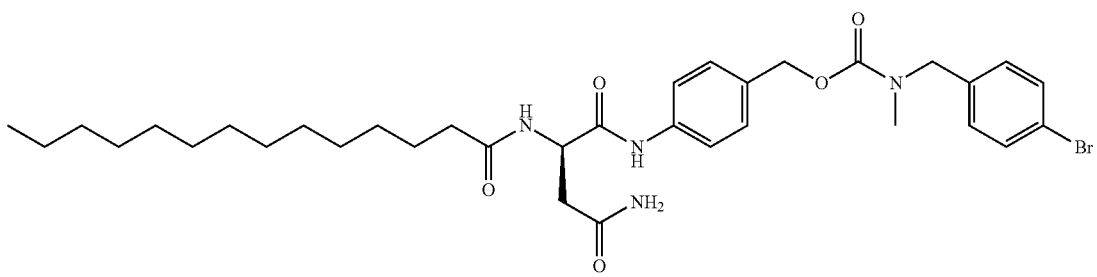 [SMILES: CCCCCCCCCCCCCC(=O)N[C@H](CC(N)=O)C(=O)Nc1ccc(COC(=O)N(C)Cc2ccc(Br)cc2)cc1]

Example 26: (R)-4-(4-amino-4-oxo-2-tetradecanamidobutanamido)benzyl (4-bromobenzyl)(methyl) carbamate Tetradecanoyl chloride (1.1 equiv.) is reacted with D-asparagine (1 equiv.) to synthesize tetradecanoyl-D-asparagine. The resulting tetradecanoyl-D-asparagine (1 equiv) is treated with EDCl (1.1 equiv), HOBt (1.1 equiv), and 4-aminobenzyl alcohol (1.1 equiv.). The resulting alcohol (1 equiv.) is reacted with 4,4'-dinitrophenyl carbonate (1.1 equiv.), then treated with 1-(4-bromophenyl)-N-methylmethanamine (1.1 equiv.) to yield the title compound.

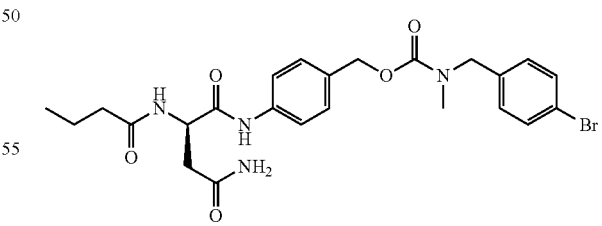

Example 27: (R)-4-(4-amino-2-butyramido-4-oxobutanamido)benzyl (4-bromobenzyl)(methyl) carbamate This compound may be synthesized according to the experimental procedure described for Example 26.

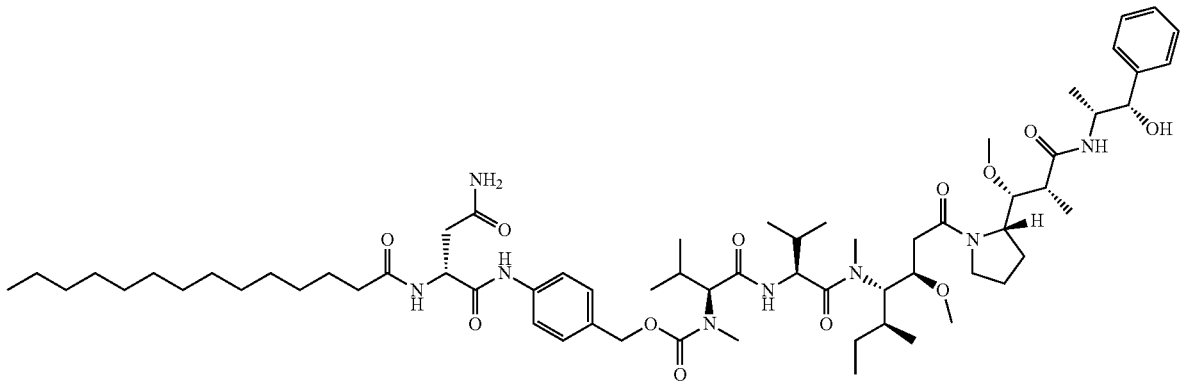 [SMILES: CCCCCCCCCCCCCC(=O)N[C@H](CC(N)=O)C(=O)Nc1ccc(COC(=O)N(C)[C@H](C(=O)N[C@H](C(=O)N(C)[C@@H]([C@@H](C)CC)[C@@H](CC(=O)N2CCC[C@H]2[C@H](OC)[C@@H](C)C(=O)N[C@H](C)[C@@H](O)c2ccccc2)OC)C(C)C)C(C)C)cc1]

Example 28: 4-((R)-4-amino-4-oxo-2-tetradecanamidobutanamido)benzyl ((S)-1-(((S)-1-(((3R,4S,5S)-1-((S)-2-((1R,2R)-3-(((1 S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl) (methyl)carbamate Tetradecanoyl chloride is reacted with D-asparagine, and the resulting tetradecanoyl-D-asparagine (1 equiv) is treated with EDCl (1.1 equiv), HOBt (1.1 equiv), and 4-aminobenzyl alcohol (1.1 equiv.). The resulting alcohol is treated with 4,4'-dinitrophenyl carbonate (1 equiv.). The resulting carbonate is treated with monomethyllauristatin E to afford the title compound,

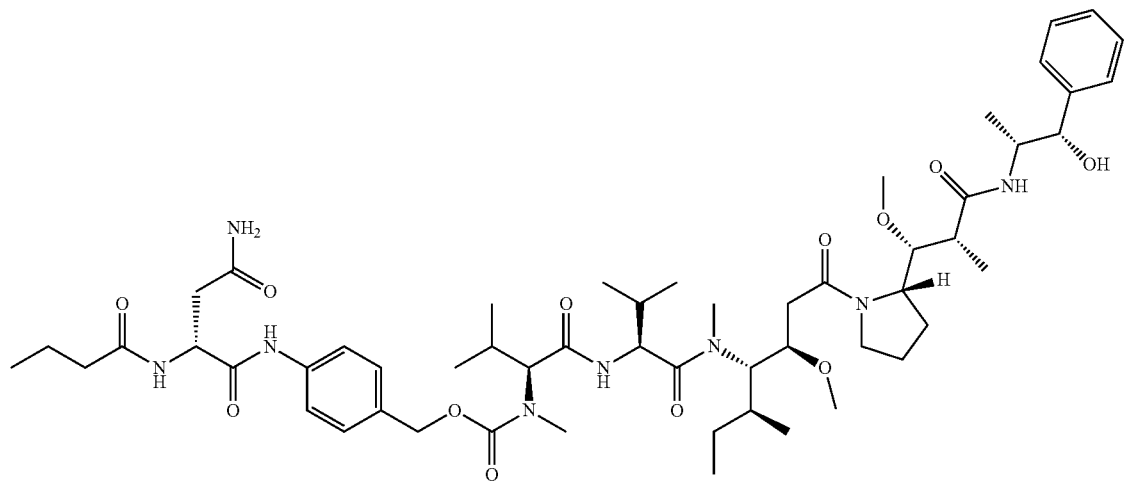 [SMILES: CCCC(=O)N[C@H](CC(N)=O)C(=O)Nc1ccc(COC(=O)N(C)[C@H](C(=O)N[C@H](C(=O)N(C)[C@@H]([C@@H](C)CC)[C@@H](CC(=O)N2CCC[C@H]2[C@H](OC)[C@@H](C)C(=O)N[C@H](C)[C@@H](O)c2ccccc2)OC)C(C)C)C(C)C)cc1]

Example 29: 4-((R)-4-amino-2-butyramido-4-oxobutanamido)benzyl ((S)-1-(((S)-1-(((3R,4S,5S)-1-((S)-2-((1R,2R)-3-(((1 S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl) (methyl)carbamate This compound may be synthesized according to the experimental procedure described for Example 28.

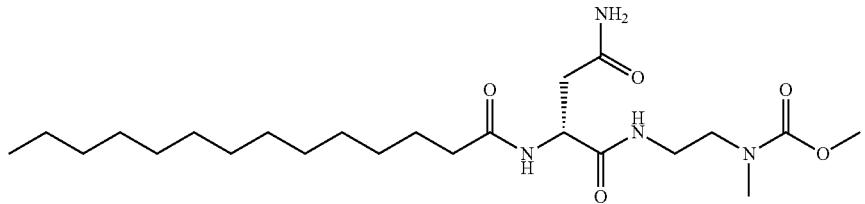 [SMILES: CCCCCCCCCCCCCC(=O)N[C@H](CC(N)=O)C(=O)NCCN(C)C(=O)OC]

Example 30: Methyl (R)-(2-(4-amino-4-oxo-2-tetradecanamidobutanamido)ethyl)(methyl)carbamate Step 1:

To a solution of (2R)-4-amino-4-oxo-2-(tetradecanoylamino)butanoic acid (100 mg, 292 μmol, 1 equiv.) and TEA (65 mg, 642 μmol, 89 μL, 2.2 equiv.) in DMF (3 mL) was added tert-butyl N-(2-aminoethyl)-N-methyl-carbamate (61 mg, 350 μmol, 63 μL, 1.2 equiv.) and HOBt (43 mg, 321 μmol, 1.1 equiv.). The reaction mixture was cooled to 0° C. and EDCl (62 mg, 321 μmol, 1.1 equiv.) was added. Then the mixture was stirred at 25° C. for 12 h under $N_2$. The reaction mixture was diluted with $H_2O$ (5 mL) and extracted four times with EtOAc (5 mL). The combined organic layers were washed with brine (5 mL), dried over $Na_2SO_4$, filtered and concentrated under reduced pressure to give tert-butyl N-[2-[[(2R)-4-amino-4-oxo-2-(tetradecanoylamino)butanoyl]amino]ethyl]-N-methyl-carbamate (80 mg) as a white solid which was used into the next step without further purification.

Step 2:

A mixture of tert-butyl N-[2-[[(2R)-4-amino-4-oxo-2-(tetradecanoylamino)butanoyl]amino]ethyl]-N-methyl-carbamate (80 mg, 160 μmol) in HCl/EtOAc (4 mL, 4M) was stirred at 25° C. for 1 hour. The reaction mixture was concentrated under reduced pressure to give (2R)—N-[2-(methylamino)ethyl]-2-(tetradecanoylamino)butanediamide hydrochloride (60 mg) as a white solid.

Step 3:

A mixture of (2R)—N-[2-(methylamino)ethyl]-2-(tetradecanoylamino)butanediamide hydrochloride (80 mg, 184 μmol, 1 equiv.) and TEA (41 mg, 405 μmol, 56 μL, 2.2 equiv.) in DCM (3 mL) was cooled to 0° C. and methyl carbonochloridate (17 mg, 184 μmol, 14 μL, 1 equiv.) was added. The mixture was warmed to 25° C. and was stirred for 12 h. The reaction mixture was filtered and concentrated under reduced pressure and the residue was purified by prep-TLC ($SiO_2$, DCM:MeOH=10:1) to give methyl (R)-(2-(4-amino-4-oxo-2-tetradecanamidobutanamido)ethyl)(methyl)carbamate (4.3 mg, 4.7%) as a white solid. LCMS: (M+H$^+$): 457.3 $^1$H NMR (400 MHz, DMSO-d6) δ 7.91-7.82 (m, 2H), 7.26 (s, 1H), 6.85 (s, 1H), 4.51-4.45 (m, 1H), 3.57 (s, 3H), 3.35-3.12 (m, 4H), 2.81 (s, 3H), 2.45-2.27 (m, 2H), 2.09 (t, J=7.5 Hz, 2H), 1.48-1.44 (m, 2H), 1.26-1.22 (m, 20H), 0.86 (t, J=6.6 Hz, 3H).

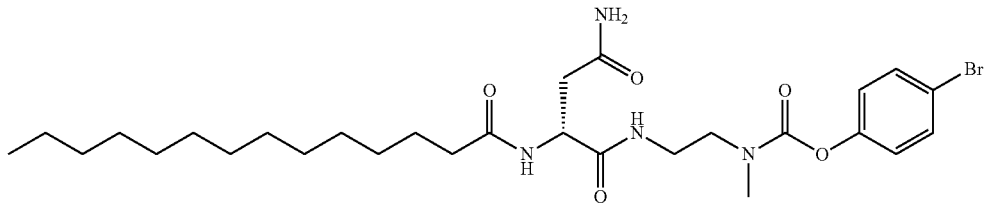 [SMILES: CCCCCCCCCCCCCC(=O)N[C@H](CC(N)=O)C(=O)NCCN(C)C(=O)Oc1ccc(Br)cc1]

Example 31: 4-bromophenyl (R)-(2-(4-amino-4-oxo-2-tetradecanamidobutanamido)ethyl)(methyl)carbamate Step 1:

To a solution of (2R)-4-amino-2-(tert-butoxycarbonylamino)-4-oxo-butanoic acid (10.0 g, 43 mmol, 1 equiv.) in MeOH (100 mL) was added $Cs_2CO_3$ (7.72 g, 23.7 mmol, 0.55 equiv.). The mixture was stirred at 25° C. for 2 h, then the MeOH (100 mL) was removed, and the residue was dissolved in DMF (50 mL). Benzyl bromide (11 g, 64.6 mmol, 7.67 mL, 1.5 equiv.) was added and the mixture was stirred at 25° C. for 12 h. The solvent was evaporated and the residue was purified by flash chromatography over silica gel (petroleum ether/ethyl acetate=10/1 to 0/1) to give benzyl (2R)-4-amino-2-(tert-butoxycarbonylamino)-4-oxo-butanoate (13.5 g, 77.8%) as a white solid.

Step 2:

To a mixture of benzyl (2R)-4-amino-2-(tert-butoxycarbonylamino)-4-oxo-butanoate (1.00 g, 3.10 mmol, 1 equiv.) in DCM (10 mL) was added TFA (3.54 g, 31.0 mmol, 2.30 mL, 10 equiv.) and the mixture was stirred at 25° C. for 0.5 h. The solvent was removed and the residue was dissolved in DCM (10 mL) and cooled to 0° C. TEA (1.26 g, 12.4 mmol, 1.73 mL, 4 equiv.) and DMAP (37.0 mg, 310 μmol, 0.1 equiv.) were added followed by tetradecanoyl chloride (919 mg, 3.72 mmol, 1.2 equiv.). The mixture was stirred at 25° C. for 11.5 h, then filtered and concentrated under reduced pressure. The residue was purified by column chromatography ($SiO_2$, petroleum ether/ethyl acetate=5/1 to 1:1) to give benzyl (2R)-4-amino-4-oxo-2-(tetradecanoylamino)butanoate (1.0 g, 52%) as white solid.

Step 3:

To a solution of benzyl (2R)-4-amino-4-oxo-2-(tetradecanoylamino)butanoate (1.00 g, 2.31 mmol, 1 equiv.) in EtOH (10 mL) was added 10% Pd/C (1 g) under $N_2$. The suspension was degassed under vacuum and purged with $H_2$ several times. The mixture was stirred under $H_2$ at a pressure of 15 psi at 25° C. for 12 hours. The reaction mixture was filtered and concentrated under reduced pressure to give (2R)-4-amino-4-oxo-2-(tetradecanoylamino)butanoic acid (0.3 g, 38%) as white solid.

Step 4:

A mixture of (2R)-4-amino-4-oxo-2-(tetradecanoylamino)butanoic acid (150 mg, 438 µmol, 1 equiv.), TEA (98 mg, 964 µmol, 134 µL, 2.2 equiv.) and HOBt (65 mg, 482 µmol, 1.1 equiv.) in DMF (3 mL) was stirred at 0° C. for 1 h. Then EDCl (92 mg, 482 µmol, 1.1 equiv.) and tert-butyl N-(2-aminoethyl)-N-methyl-carbamate (92 mg, 525 µmol, 93.9 µL, 1.2 equiv.) added and the mixture was stirred for 11 hours at 25° C. The mixture was partitioned between ethyl acetate (9 mL) and H$_2$O (9 mL). The organic phase was separated, filtered and concentrated under reduced pressure to give tert-butyl N-[2-[[(2R)-4-amino-4-oxo-2-(tetradecanoylamino)butanoyl]amino]ethyl]-N-methyl-carbamate (0.1 g, 41% yield) as white solid.

Step 5:

A mixture of tert-butyl N-[2-[[(2R)-4-amino-4-oxo-2-(tetradecanoylamino)butanoyl]amino] ethyl]-N-methyl-carbamate (0.05 g, 100 µmol, 1 equiv.) in HCl/dioxane (4 mL, 4M) was stirred at 25° C. for 30 min. The reaction mixture was filtered and concentrated under reduced pressure to give (2R)—N-[2-(methylamino)ethyl]-2-(tetradecanoylamino) butanediamide hydrochloride (0.05 g) as white solid which was used without additional purification.

Step 6:

To a mixture of triphosgene (3.43 g, 11.6 mmol, 0.4 equiv.) in THF (50 mL) was added 4-bromophenol (5 g, 28.9 mmol, 1 equiv.) and pyridine (2.29 g, 28.9 mmol, 2.33 mL, 1 equiv.) in one portion at 0° C. under N$_2$. Then the mixture stirred at 25° C. for 12 hours, then filtered and concentrated under reduced pressure. The residue was purified by column chromatography (SiO$_2$, petroleum ether/ethyl acetate=1:0) to give (4-bromophenyl) carbonochloridate (0.8 g, 12% yield) as white solid.

Step 7: To a mixture of (2R)—N-[2-(methylamino)ethyl]-2-(tetradecanoylamino)butanediamide hydrochloride (0.05 g, 115 µmol, 1 equiv.) and TEA (46.5 mg, 460 µmol, 64 µL, 4 equiv.) in DCM (5 mL) was added (4-bromophenyl) carbonochloridate (32.5 mg, 138 µmol, 19.7 µL, 1.2 equiv.) in one portion at 0° C. under N$_2$. Then the mixture was stirred at 25° C. for 12 hours. The mixture was filtered and concentrated under reduced pressure and the residue was purified by prep-HPLC (water (0.04% NH$_3$H$_2$O)-acetonitrile) to give (4-bromophenyl)N-[2-[[(2R)-4-amino-4-oxo-2-(tetradecanoylamino) butanoyl]amino]ethyl]-N-methyl-carbamate (0.003 g, 4% yield) as white solid.

LCMS: (M+H$^+$): 597.2 & 599.2

$^1$H NMR (400 MHz, Chloroform-d) δ 7.47 (d, 2H), 7.34-7.30 (m, 2H), 7.06 (d, 2H), 5.88-5.74 (m, 1H), 5.36 (d, 1H), 4.79-4.64 (m, 1H), 3.53 (s, 4H), 3.44 (s, 1H), 3.10 (s, 2H), 3.02 (s, 1H), 2.47 (dd, 1H), 2.24-2.16 (m, 1H), 2.10-2.02 (m, 1H), 1.27-1.23 (m, 22H), 0.88 (t, 3H).

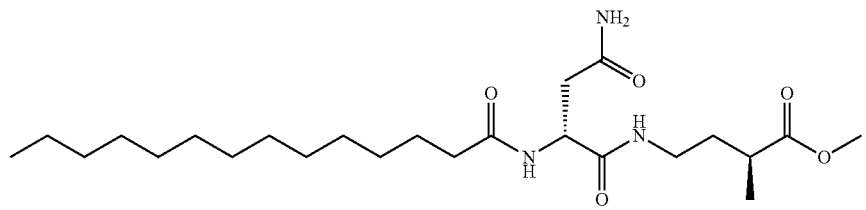 [SMILES: CCCCCCCCCCCCCC(=O)N[C@H](CC(N)=O)C(=O)NCC[C@H](C)C(=O)OC]

Example 32: Methyl (S)-4-((R)-4-amino-4-oxo-2-tetradecanamidobutanamido)-2-methylbutanoate Tetradecanoyl chloride (1.1 equiv.) is reacted with D-asparagine (1 equiv.) to synthesize tetradecanoyl-D-asparagine. The resulting tetradecanoyl-D-asparagine (1 equiv) is treated with EDCl (1.1 equiv), HOBt (1.1 equiv), and methyl (S)-4-amino-2-methylbutanoate (1.1 equiv.) to afford the title compound.

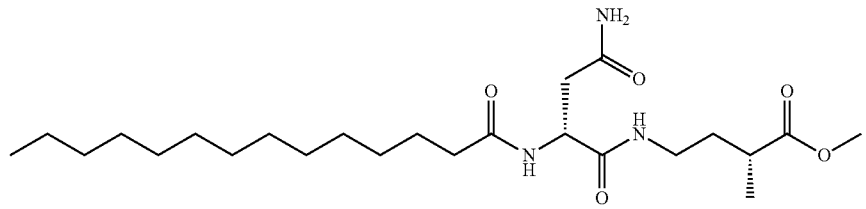 [SMILES: CCCCCCCCCCCCCC(=O)N[C@H](CC(N)=O)C(=O)NCC[C@@H](C)C(=O)OC]

Example 33: Methyl (R)-4-((R)-4-amino-4-oxo-2-tetradecanamidobutanamido)-2-methylbutanoate Compound (S)-(+)-4-benzyl-3-propionyl-2-oxazolidinone (1 equiv.) is reacted with methyl acrylate (1.1 equiv.), titanium(IV) isopropoxide, titanium (IV) chloride, and N,N-Diisopropylethylamine in dichloromethane to synthesize methyl (R)-5-((S)-4-benzyl-2-oxooxazolidin-3-yl)-4-methyl-5-oxopentanoate. The resulting compound (1 equiv.) is hydrolyzed with HCl in dioxane to yield (R)-5-((S)-4-benzyl-2-oxooxazolidin-3-yl)-4-methyl-5-oxopentanoic acid, which is then reacted with diphenylphosphoryl azide (1.1 equiv.), triethylamine (1.1 equiv.), and tert-butanol (1.5 equiv.) to afford tert-butyl ((R)-4-((S)-4-benzyl-2-oxooxazolidin-3-yl)-3-methyl-4-oxobutyl)carbamate. Hydrolysis of the resulting compound (1 equiv.) with LiOH—H$_2$O and H$_2$O$_2$ yields (R)-4-((tert-butoxycarbonyl)amino)-2-methylbutanoic acid, which is then methylated with SOCl$_2$ in methanol and deprotected with HCl in dioxane to afford methyl (R)-4-amino-2-methylbutanoate.

Tetradecanoyl chloride (1.1 equiv.) is reacted with D-asparagine (1 equiv.) to synthesize tetradecanoyl-D-asparagine. The resulting tetradecanoyl-D-asparagine (1 equiv) is treated with EDCl (1.1 equiv), HOBt (1.1 equiv), and methyl (R)-4-amino-2-methylbutanoate (1.1 equiv.) to afford the title compound.

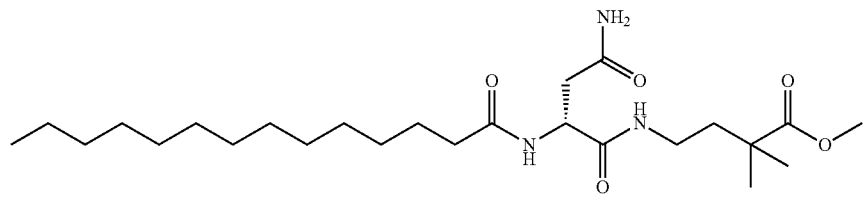 [SMILES: CCCCCCCCCCCCCC(=O)N[C@H](CC(N)=O)C(=O)NCCC(C)(C)C(=O)OC]

Example 34: Methyl (R)-4-(4-amino-4-oxo-2-tetradecanamidobutanamido)-2,2-dimethylbutanoate Step 1:

To a solution of tert-butyl 2-oxopyrrolidine-1-carboxylate (1.00 g, 5.40 mmol, 917 µL, 1 equiv.) in THF (10 mL) was added LiHMDS (1 M, 11.9 mL, 2.2 equiv.) at −60° C. The mixture was stirred at −60° C. for 0.5 hr. MeI (1.69 g, 11.9 mmol, 739 µL, 2.2 equiv.) was added at −60° C. The mixture was slow warmed to 25° C. and stirred for 12 hr. The reaction mixture was quenched with H₂O (15 mL) at 0° C. and extracted three times with ethyl acetate (10 mL). The combined organic layers were washed with brine (20 mL), dried over anhydrous sodium sulfate, filtered and concentrated under reduced pressure to give tert-butyl 3,3-dimethyl-2-oxo-pyrrolidine-1-carboxylate (1 g) as a yellow oil which was used without additional purification.

Step 2:

To a solution of tert-butyl 3,3-dimethyl-2-oxo-pyrrolidine-1-carboxylate (600 mg, 2.81 mmol, 917 µL, 1 equiv.) in THF (2 mL) and EtOH (2 mL) was added NaOH (576 mg, 14.4 mmol, 5.12 equiv.) in H₂O (1 mL) at 25° C. The mixture was stirred at 25° C. for 12 hr. The reaction mixture was concentrated under reduced pressure to give a residue which was taken up in H₂O (10 mL) and extracted with ethyl acetate (10 mL). The water layer was adjusted to pH=7 with HCl (1M) and extracted with ethyl acetate (10 mL). The combined organic layers were filtered and concentrated under reduced pressure to give 4-(tert-butoxycarbonylamino)-2,2-dimethyl-butanoic acid (280 mg, 43%) as a yellow oil.

Step 3:

To a solution of 4-(tert-butoxycarbonylamino)-2,2-dimethyl-butanoic acid (230 mg, 994 µmol, 1 equiv.) in DMF (2 mL) was added MeI (282 mg, 1.99 mmol, 124 µL, 2 equiv.) and K₂CO₃ (412 mg, 2.98 mmol, 3 equiv.) at 25° C. The mixture was stirred at 25° C. for 12 hr. The reaction mixture was diluted with H₂O (10 mL) and extracted three times with ethyl acetate (10 mL). The combined organic layers were washed with brine (10 mL), dried over anhydrous sodium sulfate, filtered and concentrated under reduced pressure to give methyl 4-(tert-butoxycarbonylamino)-2,2-dimethyl-butanoate (170 mg, 70%) as a yellow oil.

Step 4:

To a solution of methyl 4-(tert-butoxycarbonylamino)-2,2-dimethyl-butanoate (170 mg, 693 µmol, 1 equiv.) in MeOH (2.5 mL) was added HCl/MeOH (2.5 mL, 4 M) at 25° C. The mixture was stirred at 25° C. for 2 hr. The reaction mixture was concentrated under reduced pressure. The residue was washed with petroleum ether (10 mL) to give methyl 4-amino-2,2-dimethyl-butanoate hydrochloride (150 mg) as a red solid.

Step 5:

To a solution of methyl 4-amino-2,2-dimethyl-butanoate (100 mg, 689 µmol, 1 equiv.), (2R)-4-amino-4-oxo-2-(tetradecanoylamino)butanoic acid (283 mg, 826 µmol, 1.2 equiv.), HOBt (102 mg, 758 µmol, 1.1 equiv.) and TEA (153 mg, 1.52 mmol, 211 µL, 2.2 equiv.) in DMF (5 mL) was added EDCl (145 mg, 758 µmol, 1.1 equiv.) at 0° C. The mixture was stirred at 25° C. for 12 hr. The reaction mixture was filtered to give a filtrate. The filtrate was purified by prep-HPLC (column: Luna C18 100*30 5u; mobile phase: [water (0.1% TFA)-ACN]; B %: 55%-85%, 12 min) to give methyl4-[[(2R)-4-amino-4-oxo-2-(tetradecanoylamino)butanoyl]amino]-2,2-dimethyl-butanoate (50 mg, 14%) as a white solid.

LCMS: (M+H+): 470.3. ¹H NMR (400 MHz, Chloroform-d) δ 7.32 (d, 1H), 7.09 (t, 1H), 6.09 (s, 1H), 5.66 (s, 1H), 4.74-4.65 (m, 1H), 3.68 (s, 3H), 3.30-3.18 (m, 2H), 2.89 (dd, 1H), 2.47 (dd, 1H), 2.30-2.24 (m, 2H), 1.79-1.70 (m, 2H), 1.69-1.59 (m, 2H), 1.25 (m, 20H), 1.20 (s, 6H), 0.88 (t, 3H).

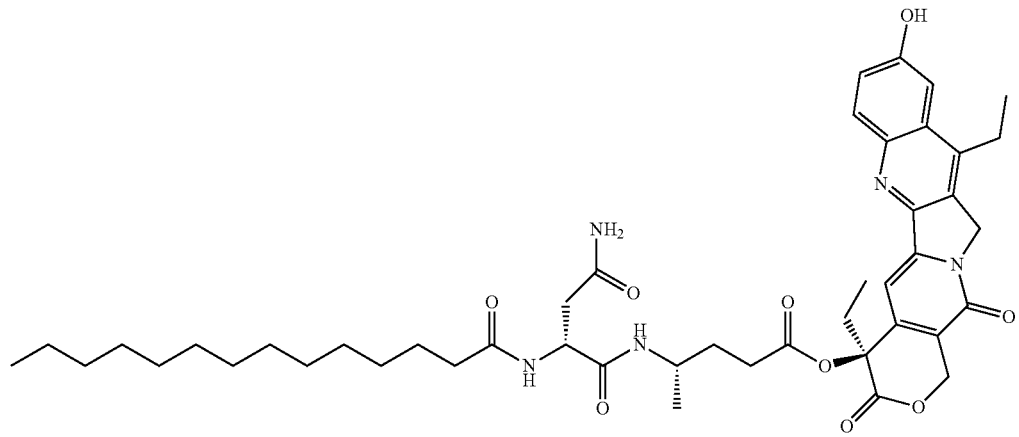 [SMILES: CCCCCCCCCCCCCC(=O)N[C@H](CC(N)=O)C(=O)N[C@@H](C)CCC(=O)O[C@]1(CC)C(=O)OCc2c1cc1n(c2=O)Cc2c-1nc1ccc(O)cc1c2CC]

Example 35: (S)-4,11-diethyl-9-hydroxy-3,14-dioxo-3,4,12,14-tetrahydro-1H-pyrano[3',4':6,7]indolizino[1,2-b]quinolin-4-yl (S)-4-((R)-4-amino-4-oxo-2-tetradecanamidobutanamido)pentanoate Steps 1-6:
Synthesized according to steps 1-6 of example 49.
Step 7:
To a solution of (S)-4,11-diethyl-9-hydroxy-3,14-dioxo-3,4,12,14-tetrahydro-1H-pyrano[3',4':6,7]indolizino[1,2-b]quinolin-4-yl (S)-4-aminopentanoate hydrochloride (50 mg, 102 µmol, 1 equiv.) in DMF (5 mL) was added HOBt (15 mg, 112 µmol, 1.1 equiv.), (2R)-4-amino-4-oxo-2-(tetradecanoylamino)butanoic acid (35 mg, 102 µmol, 1 equiv.), TEA (23 mg, 224 µmol, 31 µL, 2.2 equiv.) and EDCl (21 mg, 112 µmol, 1.1 equiv.) at 0° C. The mixture was stirred at 15° C. for 12 hr. The reaction mixture was filtered and purified by prep-HPLC (column: Welch Ultimate AQ-C18 150*30 mm*5 um; mobile phase: [water (0.1% TFA)-ACN]; B %: 55%-85%, 12 min) to yield (S)-4,11-diethyl-9-hydroxy-3,14-dioxo-3,4,12,14-tetrahydro-1H-pyrano[3',4':6,7]indoliz- ino[1,2-b]quinolin-4-yl (S)-4-((R)-4-amino-4-oxo-2-tetradecanamidobutanamido)pentanoate (14 mg, 16%) as a yellow solid. LCMS: (M+H+) 816.4

$^1$H NMR (400 MHz, Chloroform-d) δ 8.05 (d, 1H), 7.76 (d, 1H), 7.64-7.59 (m, 1H), 7.44-7.36 (m, 2H), 7.31 (s, 1H), 6.69-6.62 (m, 1H), 6.21 (s, 1H), 5.68 (d, 1H), 5.40 (d, 1H), 5.20-5.02 (m, 2H), 4.77 (s, 1H), 4.00 (s, 1H), 3.09-2.95 (m, 8H), 2.61-2.47 (m, 3H), 2.27 (dt, 3H), 2.14-2.06 (m, 1H), 1.90-1.86 (m, 1H), 1.34-1.19 (m, 19H), 1.09 (d, 3H), 0.94 (q, 3H), 0.87 (t, 3H).

Example 36: 4-(((((4-bromobenzyl)(methyl)carbamoyl)oxy)methyl)phenyl (R)-(2-(4-amino-2-octanamido-4-oxobutanamido)ethyl)(methyl)carbamate Tetradecanoyl chloride (1.1 equiv.) is reacted with D-asparagine (1 equiv.) to synthesize tetradecanoyl-D-asparagine. The resulting tetradecanoyl-D-asparagine (1 equiv) is treated with EDCl (1.1 equiv), HOBt (1.1 equiv), and tert-butyl (2-aminoethyl)(methyl)carbamate (1.1 equiv.), then deprotected with HCl in dioxane to generate the amine intermediate.

Compound (4-((tert-butyldimethylsilyl)oxy)phenyl) methanol (1 equiv.) is reacted with 4,4'-Dinitrophenyl carbonate (1.1 equiv.), followed by reaction with 1-(4-bromophenyl)-N-methylmethanamine. The resulting compound is deprotected with TBAF (1.1 equiv), then reacted with 4,4'-Dinitrophenyl carbonate (1 equiv.). The resulting compound (1.1 equiv.) is coupled with the amine intermediate (1 equiv.) to yield the title compound.

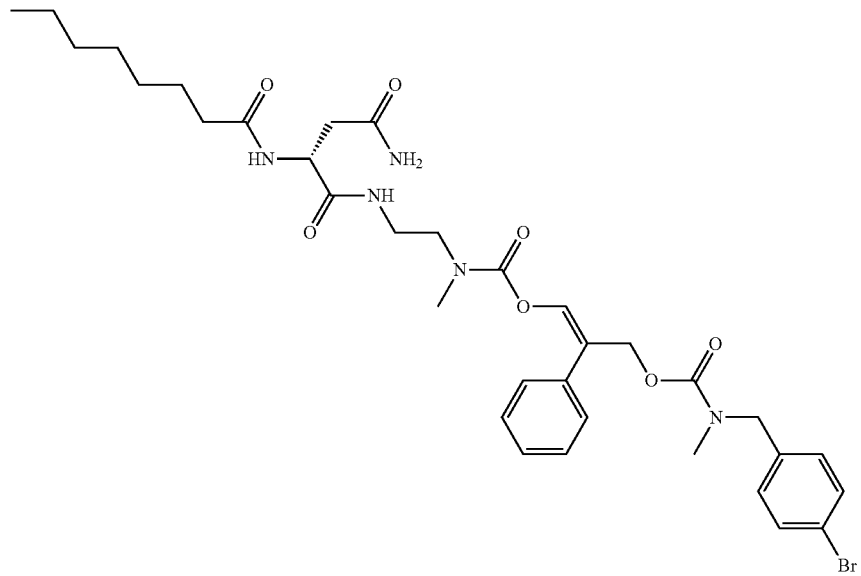 [SMILES: CCCCCCCC(=O)N[C@H](CC(N)=O)C(=O)NCCN(C)C(=O)O/C=C(/COC(=O)N(C)Cc1ccc(Br)cc1)c1ccccc1]

Example 37: (E)-3-(((4-bromobenzyl)(methyl)carbamoyl)oxy)-2-phenylprop-1-en-1-yl (R)-(2-(4-amino-2-octanamido-4-oxobutanamido)ethyl)(methyl)carbamate Tetradecanoyl chloride (1.1 equiv.) is reacted with D-asparagine (1 equiv.) to synthesize tetradecanoyl-D-asparagine. The resulting tetradecanoyl-D-asparagine (1 equiv) is treated with EDCl (1.1 equiv), HOBt (1.1 equiv), and tert-butyl (2-aminoethyl)(methyl)carbamate (1.1 equiv.), then deprotected with HCl in dioxane to generate the amine intermediate.

Compound 3-hydroxy-2-phenylpropanal (1 equiv.) is reacted with 4,4'-Dinitrophenyl carbonate (1.1 equiv.), followed by reaction with 1-(4-bromophenyl)-N-methylmethanamine. The resulting compound is reacted with triphosgene, and then the chloroformate (1.1 equiv.) is coupled with the amine intermediate (1 equiv.) to yield the title compound.

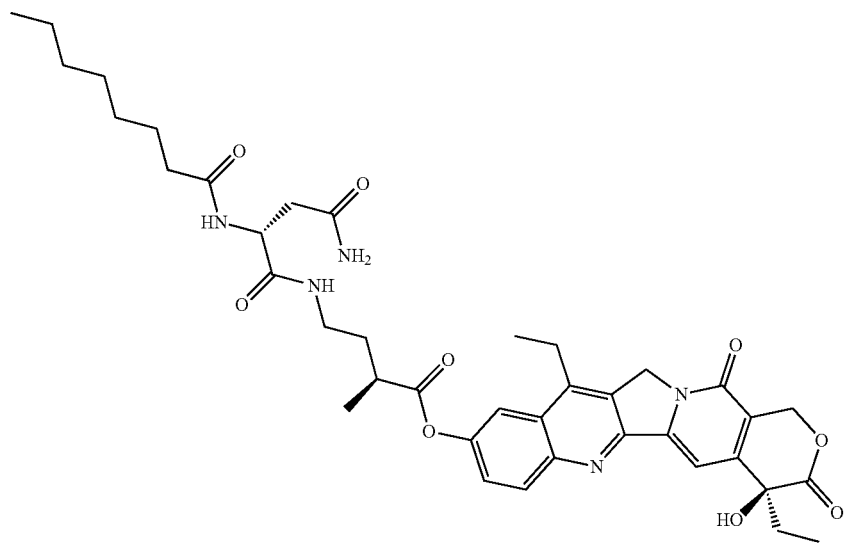 [SMILES: CCCCCCCC(=O)N[C@H](CC(N)=O)C(=O)NCC[C@H](C)C(=O)Oc1ccc2nc3c(c(CC)c2c1)Cn1c-3cc2c(c1=O)COC(=O)[C@]2(O)CC]

Example 38: (S)-4,11-diethyl-4-hydroxy-3,14-dioxo-3,4,12,14-tetrahydro-1H-pyrano[3',4':6,7]indolizino[1,2-b]quinolin-9-yl (S)-4-((R)-4-amino-2-octanamido-4-oxobutanamido)-2-methylbutanoate Compound (R)-(−)-4-Benzyl-3-propionyl-2-oxazolidinone (1 equiv.) is reacted with methyl acrylate (1.1 equiv.), titanium(IV) isopropoxide, titanium (IV) chloride, and N,N-Diisopropylethylamine in dichloromethane to synthesize methyl (S)-5-((R)-4-benzyl-2-oxooxazolidin-3-yl)-4-methyl-5-oxopentanoate. The resulting compound (1 equiv.) is hydrolyzed with HCl in dioxane to yield (S)-5-((R)-4-benzyl-2-oxooxazolidin-3-yl)-4-methyl-5-oxopentanoic acid, which is then reacted with diphenylphosphoryl azide (1.1 equiv.), triethylamine (1.1 equiv.), and tert-butanol (1.5 equiv.) to afford tert-butyl ((S)-4-((R)-4-benzyl-2-oxooxazolidin-3-yl)-3-methyl-4-oxobutyl)carbamate. Hydrolysis of the resulting compound (1 equiv.) with LiOH—$H_2O$ and $H_2O_2$ yields (S)-4-((tert-butoxycarbonyl)amino)-2-methylbutanoic acid, which is then methylated with $SOCl_2$ in methanol and deprotected with HCl in dioxane to afford methyl (S)-4-amino-2-methylbutanoate.

Octanoyl chloride (1.1 equiv.) is reacted with D-asparagine (1 equiv.) to synthesize octanoyl-D-asparagine. The resulting octanoyl-D-asparagine (1 equiv) is treated with EDCl (1.1 equiv), HOBt (1.1 equiv), and methyl (S)-4-amino-2-methylbutanoate (1.1 equiv.) to afford methyl (S)-4-((R)-4-amino-2-octanamido-4-oxobutanamido)-2-methylbutanoate.

Methyl (S)-4-((R)-4-amino-2-octanamido-4-oxobutanamido)-2-methylbutanoate (1 equiv.) is hydrolyzed under basic conditions (LiOH/2M in water/THF) to afford a free carboxylic acid. The resulting carboxylic acid is treated with DCC (1 equiv) and 7-Ethyl-10-hydroxy-camptothecin (1.1 equiv.) to afford the title compound.

Example 39: (S)-4,11-diethyl-4-hydroxy-3,14-dioxo-3,4,12,14-tetrahydro-1H-pyrano[3',4':6,7]indolizino[1,2-b]quinolin-9-yl (R)-4-((R)-4-amino-2-octanamido-4-oxobutanamido)-2-methylbutanoate Compound (S)-(−)-4-Benzyl-3-propionyl-2-oxazolidinone (1 equiv.) is reacted with methyl acrylate (1.1 equiv.), titanium(IV) isopropoxide, titanium (IV) chloride, and N,N-Diisopropylethylamine in dichloromethane to synthesize methyl (R)-5-((S)-4-benzyl-2-oxooxazolidin-3-yl)-4-methyl-5-oxopentanoate. The resulting compound (1 equiv.) is hydrolyzed with HCl in dioxane to yield (R)-5-((S)-4-benzyl-2-oxooxazolidin-3-yl)-4-methyl-5-oxopentanoic acid, which is then reacted with diphenylphosphoryl azide (1.1 equiv.), triethylamine (1.1 equiv.), and tert-butanol (1.5 equiv.) to afford tert-butyl ((R)-4-((S)-4-benzyl-2-oxooxazolidin-3-yl)-3-methyl-4-oxobutyl)carbamate. Hydrolysis of the resulting compound (1 equiv.) with LiOH—$H_2O$ and $H_2O_2$ yields (R)-4-((tert-butoxycarbonyl)amino)-2-methylbutanoic acid, which is then methylated with $SOCl_2$ in methanol and deprotected with HCl in dioxane to afford methyl (R)-4-amino-2-methylbutanoate.

Octanoyl chloride (1.1 equiv.) is reacted with D-asparagine (1 equiv.) to synthesize octanoyl-D-asparagine. The resulting octanoyl-D-asparagine (1 equiv) is treated with EDCl (1.1 equiv), HOBt (1.1 equiv), and methyl (R)-4-amino-2-methylbutanoate (1.1 equiv.) to afford methyl (R)-4-((R)-4-amino-2-octanamido-4-oxobutanamido)-2-methylbutanoate.

Methyl (R)-4-((R)-4-amino-2-octanamido-4-oxobutanamido)-2-methylbutanoate (1 equiv.) is hydrolyzed under basic conditions (LiOH/2M in water/THF) to afford a free carboxylic acid. The resulting carboxylic acid is treated with DCC (1 equiv) and 7-Ethyl-10-hydroxy-camptothecin (1. Equiv.) to afford the title compound.

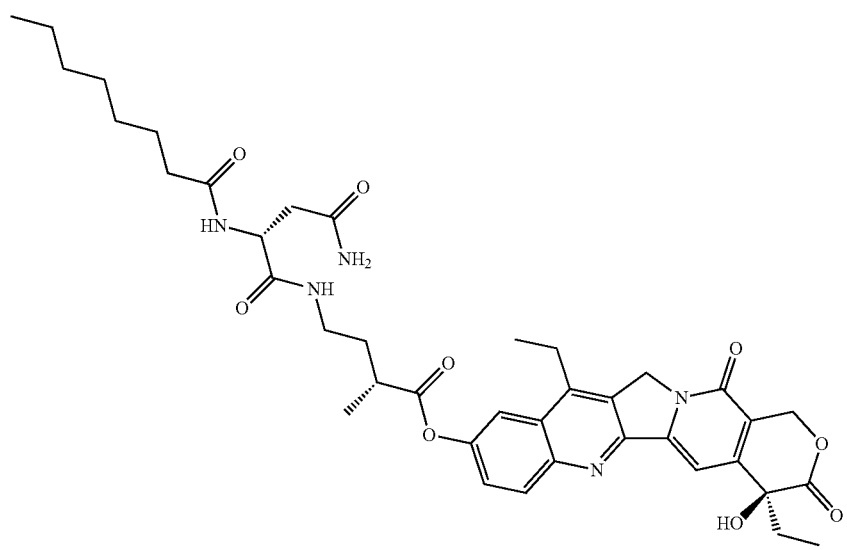 [SMILES: CCCCCCCC(=O)N[C@H](CC(N)=O)C(=O)NCC[C@@H](C)C(=O)Oc1ccc2nc3c(c(CC)c2c1)Cn1c-3cc2c(c1=O)COC(=O)[C@]2(O)CC]

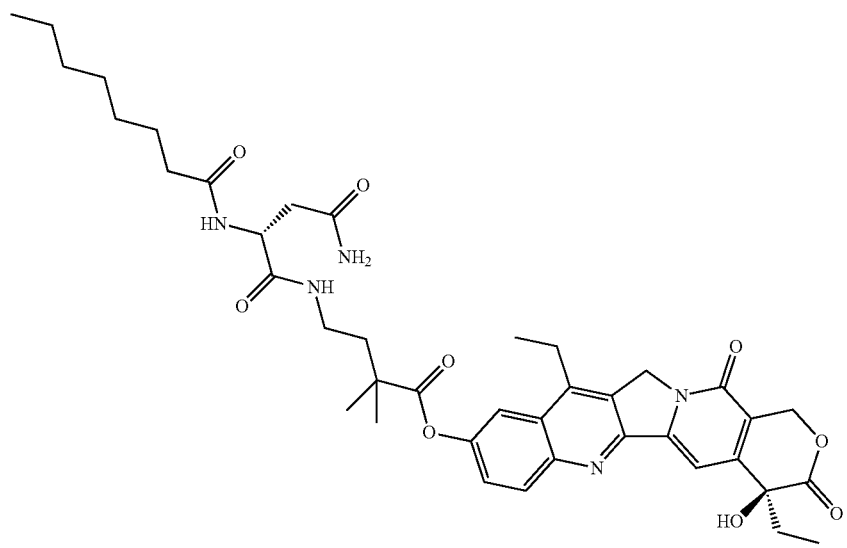 [SMILES: CCCCCCCC(=O)N[C@H](CC(N)=O)C(=O)NCCC(C)(C)C(=O)Oc1ccc2nc3c(c(CC)c2c1)Cn1c-3cc2c(c1=O)COC(=O)[C@]2(O)CC]

Example 40: (S)-4,11-diethyl-4-hydroxy-3,14-di-oxo-3,4,12,14-tetrahydro-1H-pyrano[3',4':6,7]indolizino[1,2-b]quinolin-9-yl 4-((R)-4-amino-2-octanamido-4-oxobutanamido)-2,2-dimethylbutanoate Step 1:
To a solution of tert-butyl 2-oxopyrrolidine-1-carboxylate (10 g, 54 mmol, 9.2 mL, 1 equiv.) in THF (60 mL) was added LiHMDS (1 M, 119 mL, 2.2 equiv.) at −60° C. The mixture was stirred at −60° C. for 0.5 hr. MeI (16.86 g, 118.8 mmol, 7.39 mL, 2.2 equiv.) was added at −60° C. The mixture was slowly warmed to 15° C. and stirred for 12 h. The reaction mixture was quenched by H₂O (100 mL) at 0° C. and extracted three times with ethyl acetate (200 mL). The combined organic layers were washed with brine (100 mL), dried over anhydrous sodium sulfate, filtered and concentrated under reduced pressure to give tert-butyl 3,3-dimethyl-2-oxo-pyrrolidine-1-carboxylate (12 g, crude) as a yellow oil.

Step 2:
To a solution of tert-butyl 3,3-dimethyl-2-oxo-pyrrolidine-1-carboxylate (12 g, 56 mmol, 920 µL, 1 equiv.) in THF (30 mL) and EtOH (30 mL) was added a solution of NaOH (11.25 g, 281 mmol, 5 equiv.) in H₂O (15 mL) at 15° C. The mixture was stirred at 15° C. for 12 h. The reaction mixture was concentrated under reduced pressure, diluted with H₂O (100 mL) and extracted with ethyl acetate (30 mL). The combined water layers were adjusted by HCl (1M) to pH=7 and concentrated under reduced pressure. The residue was washed with ethyl acetate (100 mL). The combined organic layers were filtered and concentrated under reduced pressure to give 4-(tert-butoxycarbonylamino)-2,2-dimethyl-butanoic acid (2.0 g, 15% yield) as a red oil.

Step 3:
To a mixture of (S)-4,11-diethyl-4,9-dihydroxy-1,12-dihydro-14H-pyrano[3',4':6,7]indolizino[1,2-b]quinoline-3,14 (4H)-dione (1 g, 2.55 mmol, 1 equiv.), 4-(tert-butoxycarbonylamino)-2,2-dimethyl-butanoic acid (707 mg, 3.06 mmol, 1.2 equiv.), HOBt (379 mg, 2.8 mmol, 1.1 equiv.) and TEA (570 mg, 5.6 mmol, 780 µL, 2.2 equiv.) in DMF (10 mL) was added EDCI (537 mg, 2.80 mmol, 1.1 equiv.) at 0° C. The mixture was stirred at 15° C. for 12 h. The solution was diluted with H₂O (40 mL) and extracted three times with ethyl acetate (50 mL). The combined organic layers were washed with brine (30 mL), dried over anhydrous sodium sulfate, filtered and concentrated under reduced. The residue was washed with petroleum ether (50 mL) and filtered to give (S)-4,11-diethyl-4-hydroxy-3,14-dioxo-3,4,12,14-tetrahydro-1H-pyrano[3',4':6,7]indolizino[1,2-b]quinolin-9-yl 4-((tert-butoxycarbonyl)amino)-2,2-dimethylbutanoate (600 mg, 39%) as a yellow solid.

Step 4:
A solution of (S)-4,11-diethyl-4-hydroxy-3,14-dioxo-3,4,12,14-tetrahydro-1H-pyrano[3',4':6,7]indolizino[1,2-b]quinolin-9-yl 4-((tert-butoxycarbonyl)amino)-2,2-dimethylbutanoate (600 mg, 991 µmol, 1 equiv.) in HCl/EtOAc (10 mL, 4M) was stirred at 15° C. for 2 h. The reaction mixture was concentrated under reduced pressure to give a residue. The residue was washed with ethyl acetate (60 mL) and filtered to give (S)-4,11-diethyl-4-hydroxy-3,14-dioxo-3,4,12,14-tetrahydro-1H-pyrano[3',4':6,7]indolizino[1,2-b]quinolin-9-yl 4-amino-2,2-dimethylbutanoate hydrochloride (300 mg, 46%) as a yellow solid.

Step 5:
A mixture of (S)-4,11-diethyl-4-hydroxy-3,14-dioxo-3,4,12,14-tetrahydro-1H-pyrano[3',4':6,7]indolizino[1,2-b]quinolin-9-yl 4-amino-2,2-dimethylbutanoate hydrochloride (50 mg, 92 µmol, 1 eq.), (2R)-2-(tert-butoxycarbonylamino)-4-oxo-4-(tritylamino)butanoic acid (53 mg, 111 µmol, 1.2 equiv.), DMAP (5.6 mg, 46 µmol, 0.5 equiv.), DCC (28.6 mg, 138 µmol, 27.99 µL, 1.5 equiv.) in DCM (3 mL) was stirred at 15° C. for 4 h. The reaction mixture was concentrated under ordinary pressure and the residue was purified by prep-HPLC (column: Luna C18 100*30 5u; mobile phase: [water (0.1% TFA)-ACN]; B %: 50%-75%, 12 min) to give (S)-4,11-diethyl-4-hydroxy-3,14-dioxo-3,4,12,14-tetrahydro-1H-pyrano[3',4':6,7]indolizino[1,2-b]quinolin-9-yl 4-((R)-2-((tert-butoxycarbonyl)amino)-4-oxo-4-(tritylamino)butanamido)-2,2-dimethylbutanoate trifluoroacetate (5 mg, 5% yield) as a yellow solid.

Step 6:
A mixture of (S)-4,11-diethyl-4-hydroxy-3,14-dioxo-3,4,12,14-tetrahydro-1H-pyrano[3',4':6,7]indolizino[1,2-b]quinolin-9-yl 4-((R)-2-((tert-butoxycarbonyl)amino)-4-oxo-4-(tritylamino)butanamido)-2,2-dimethylbutanoate trifluoroacetate (5 mg, 5 µmol, 1 equiv.) in TFA (0.5 mL) and DCM (2.5 mL) was stirred at 15° C. for 5 h. To the mixture was further added TFA (1 mL) and DCM (1 mL), and then the mixture was stirred at 15° C. for 12 h. The reaction mixture was concentrated under reduced pressure and the residue was washed with petroleum ether (10 mL) to give (S)-4,11-diethyl-4-hydroxy-3,14-dioxo-3,4,12,14-tetrahydro-1H-pyrano[3',4':6,7]indolizino[1,2-b]quinolin-9-yl 4-((R)-2,4-diamino-4-oxobutanamido)-2,2-dimethylbutanoate trifluoroacetate (5 mg) as a yellow solid.

Step 7:

To a solution of (S)-4,11-diethyl-4-hydroxy-3,14-dioxo-3,4,12,14-tetrahydro-1H-pyrano[3',4':6,7]indolizino[1,2-b]quinolin-9-yl 4-((R)-2,4-diamino-4-oxobutanamido)-2,2-dimethylbutanoate trifluoroacetate (5 mg, 6.8 μmol, 1 equiv.) in DCM (3 mL) was added octanoyl chloride (1.1 mg, 6.8 μmol, 1.16 μL, 1 equiv.) and TEA (690 ug, 6.81 μmol, 0.95 μL, 1 equiv.) at 0° C. The mixture was stirred at 0° C. for 1.5 h. The reaction mixture was concentrated under reduced pressure. The residue was purified by prep-HPLC (column: Luna C18 100*30 5u; mobile phase: [water (0.1% TFA)-ACN]; B %: 25%-55%, 12 min) to give (S)-4,11-diethyl-4-hydroxy-3,14-dioxo-3,4,12,14-tetrahydro-1H-pyrano[3',4':6,7]indolizino[1,2-b]quinolin-9-yl 4-((R)-4-amino-2-octanamido-4-oxobutanamido)-2,2-dimethylbutanoate-1/3 TFA (2 mg) as a white solid. LCMS: (M+H+): 746.4

$^1$H NMR (400 MHz, DMSO-d6) δ 8.20 (d, 1H), 8.06 (s, 1H), 7.90 (d, 1H), 7.83 (t, 1H), 7.65 (dd, 1H), 7.31 (s, 1H), 7.24 (s, 1H), 6.82 (s, 1H), 6.51 (s, 1H), 5.42 (s, 2H), 5.32 (s, 2H), 4.49 (q, 1H), 3.22-3.12 (m, 4H), 2.38-2.32 (m, 2H), 2.12-2.03 (m, 2H), 1.92-1.76 (m, 4H), 1.42 (dd, 2H), 1.34-1.31 (m, 6H), 1.27 (t, 3H), 1.25-1.15 (m, 8H), 0.93-0.77 (m, 6H).

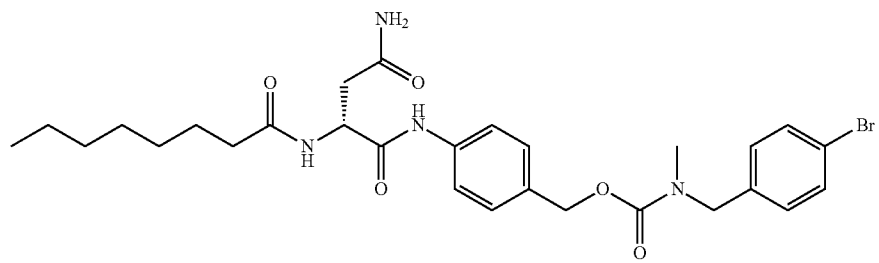 [SMILES: CCCCCCCC(=O)N[C@H](CC(N)=O)C(=O)Nc1ccc(COC(=O)N(C)Cc2ccc(Br)cc2)cc1]

Example 41: (R)-4-(4-amino-2-octanamido-4-oxobutanamido)benzyl (4-bromobenzyl)(methyl)carbamate This compound may be synthesized according to the experimental procedure described for Example 26.

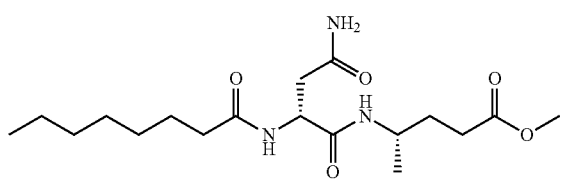 [SMILES: CCCCCCCC(=O)N[C@H](CC(N)=O)C(=O)N[C@@H](C)CCC(=O)OC]

Example 42: Methyl (S)-4-((R)-4-amino-2-octanamido-4-oxobutanamido)pentanoate

A mixture of methyl (4S)-4-[[(2R)-2,4-diamino-4-oxobutanoyl]amino]pentanoate hydrochloride (synthesized in Example 21 Step 5, 1 g, 3.55 mmol, 1 equiv.) and TEA (790 mg, 7.81 mmol, 1.09 mL, 2.2 equiv.) in DCM (20 mL) was cooled to 0° C. and octanoyl chloride (693 mg, 4.26 mmol, 727 μL, 1.2 equiv.) was added. Then the mixture was warmed to 25° C. and was stirred for 12 h. The reaction mixture was filtered and concentrated under reduced pressure. The residue was purified by prep-HPLC (column: Phenomenex luna C18 250*50 mm*10 um; mobile phase: [water (0.1% TFA)-ACN]; B %: 15%-45%, 20 min) to give methyl (S)-4-((R)-4-amino-2-octanamido-4-oxobutanamido)pentanoate (330 mg, 25%) as a white solid. LCMS (M+H+): 372.2 $^1$H NMR (400 MHz, DMSO-d6) δ 7.86 (d, J=8.0 Hz, 1H), 7.53 (d, J=8.5 Hz, 1H), 7.23 (s, 1H), 6.84 (s, 1H), 4.44 (q, J=7.2 Hz, 1H), 3.72-3.68 (m, 1H), 3.55 (s, 3H), 2.46-2.37 (m, 1H), 2.35-2.14 (m, 3H), 2.06 (t, J=7.4 Hz, 2H), 1.64-1.52 (m, 2H), 1.45-1.41 (m, 2H), 1.27-1.19 (m, 8H), 0.99 (d, J=6.6 Hz, 3H), 0.87-0.79 (m, 3H).

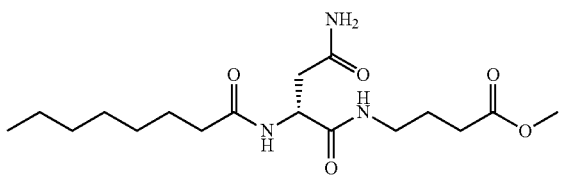 [SMILES: CCCCCCCC(=O)N[C@H](CC(N)=O)C(=O)NCCCC(=O)OC]

Example 43: Methyl (R)-4-(4-amino-2-octanamido-4-oxobutanamido)butanoate

Step 1:

A mixture of (2R)-4-amino-2-(tert-butoxycarbonylamino)-4-oxo-butanoic acid (500 mg, 2.15 mmol, 1 equiv.), HOBt (320 mg, 2.37 mmol, 1.1 equiv.), TEA (479 mg, 4.74 mmol, 659 μL, 2.2 equiv.) in DMF (5 mL) was cooled to 0° C. EDCl (454 mg, 2.37 mmol, 1.1 equiv.) and methyl 4-aminobutanoate (397 mg, 2.58 mmol, 1.2 equiv., HCl) was added. The reaction mixture was stirred at 0° C. for 15 min and was stirred at 25° C. for 12 h. The reaction mixture was filtered and concentrated under reduced pressure. The residue was purified by prep-HPLC (column: Phenomenex luna C18 250*50 mm*10 um; mobile phase: [water (0.1% TFA)-ACN]; B %: 5%-35%, 20 min) to give methyl 4-[[(2R)-4-amino-2-(tert-butoxycarbonylamino)-4-oxo-butanoyl]amino]butanoate (460 mg, 64%) as a white solid.

Step 2:

Methyl 4-[[(2R)-4-amino-2-(tert-butoxycarbonylamino)-4-oxo-butanoyl]amino]butanoate (460 mg, 1.39 mmol, 1 equiv.) in HCl-dioxane (2 M, 694 μL, 1 equiv.) was stirred at 25° C. for 1 h. The reaction mixture was concentrated under reduced pressure to give methyl 4-[[(2R)-2,4-diamino-4-oxo-butanoyl]amino]butanoate hydrochloride (420 mg) as a white solid which was used into the next step without further purification.

Step 3:

To a solution of methyl 4-[[(2R)-2,4-diamino-4-oxo-butanoyl]amino]butanoate hydrochloride (420 mg, 1.57 mmol, 1 equiv.) in DCM (5 mL) was added TEA (349 mg, 3.45 mmol, 480 μL, 2.2 equiv.). The reaction mixture was cooled to 0° C. and octanoyl chloride (306 mg, 1.88 mmol, 321 μL, 1.2 equiv.) was added. The mixture was stirred at 25° C. for 12 hr under $N_2$. The reaction mixture was concentrated under reduced pressure and the residue was purified by prep-HPLC (column: Luna C18 100*30 mm 5 um; mobile phase: [water (0.1% TFA)-ACN]; B %: 15%-40%, 12 min). Methyl (R)-4-(4-amino-2-octanamido-4-oxobutanamido) butanoate (254 mg, 45%) was obtained as a white solid. LCMS (M+H⁺): 358.2 ¹H NMR (400 MHz, DMSO-d6) δ 7.89 (d, J=8.1 Hz, 1H), 7.74 (t, J=5.8 Hz, 1H), 7.24 (s, 1H), 6.83 (s, 1H), 4.44 (q, J=7.3 Hz, 1H), 3.55 (s, 3H), 3.02 (q, J=6.5 Hz, 2H), 2.47-2.39 (m, 1H), 2.35-2.27 (m, 1H), 2.26 (t, J=7.5 Hz, 2H), 2.06 (t, J=7.5 Hz, 2H), 1.60 (p, J=7.0 Hz, 2H), 1.48-1.40 (m, 2H), 1.27-1.14 (m, 8H), 0.83 (t, J=6.6 Hz, 3H).

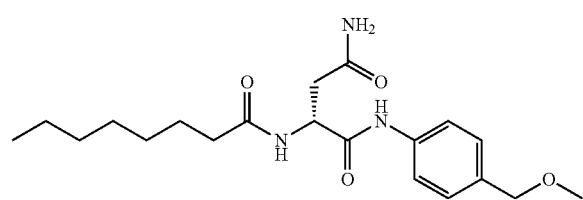 [SMILES: CCCCCCCC(=O)N[C@H](CC(N)=O)C(=O)Nc1ccc(COC)cc1]

Example 44: (R)—N1-(4-(methoxymethyl)phenyl)-2-octanamidosuccinamide

Step 1:

A mixture of (2R)-4-amino-2-(tert-butoxycarbonylamino)-4-oxo-butanoic acid (1.02 g, 4.37 mmol, 1.2 equiv.), 4-(methoxymethyl)aniline (500 mg, 3.64 mmol, 1 equiv.) in EtOAc (5 mL) was cooled to 0° C. Propanephosphonic acid anhydride (3.48 g, 5.47 mmol, 5.47 mL, 50% purity, 1.5 equiv.) and DIPEA (942.15 mg, 7.29 mmol, 1.27 mL, 2 equiv.) was added. The reaction mixture was stirred at 0° C. for 15 min and at 25° C. for 12 h. The reaction mixture was filtered and concentrated under reduced pressure and the residue was purified by prep-HPLC (column: Phenomenex luna C18 250*50 mm*10 um; mobile phase: [water (0.1% TFA)-ACN]; B %: 10%-35%, 20 min) to give tert-butyl N-[(1R)-3-amino-1-[[4-(methoxymethyl)phenyl] carbamoyl]-3-oxo-propyl]carbamate (210 mg, 16%) as a yellow solid.

Step 2:

Tert-butyl N-[(1R)-3-amino-1-[[4-(methoxymethyl)phenyl]carbamoyl]-3-oxo-propyl]carbamate (210 mg, 598 μmol, 1 equiv.) in HCl/dioxane (2 M, 299 μL, 1 equiv.) was stirred at 25° C. for 1 h. The reaction mixture was concentrated under reduced pressure to give (2R)-2-amino-N-[4-(methoxymethyl)phenyl]butanediamide hydrochloride (130 mg, 76%) as a white solid which was used into the next step without further purification.

Step 3:

To a solution of (2R)-2-amino-N-[4-(methoxymethyl)phenyl]butanediamide hydrochloride (210 mg, 730 μmol, 1 equiv.) in DCM (5 mL) was added TEA (162 mg, 1.61 mmol, 223 μL, 2.2 equiv.). The reaction mixture was then cooled to 0° C. and octanoyl chloride (142 mg, 876 μmol, 149 μL, 1.2 equiv.) was added. The mixture was stirred at 25° C. for 12 h under $N_2$. The reaction mixture was concentrated under reduced pressure and the residue was purified by prep-HPLC (column: Luna C18 100*30 mm 5 um; mobile phase: [water (0.1% TFA)-ACN]; B %: 20%-35%, 12 min). Compound (R)—N1-(4-(methoxymethyl) phenyl)-2-octanamidosuccinamide (130 mg, 40%) was obtained as a white solid. LCMS (M+H⁺): 378.2 ¹H NMR (400 MHz, Methanol-d4) δ 7.50 (d, J=7.7 Hz, 2H), 7.32 (d, J=7.9 Hz, 2H), 4.52-4.39 (m, 3H), 3.41 (s, 3H), 3.35-3.18 (m, 1H), 2.94-2.80 (m, 1H), 2.28 (t, J=7.3 Hz, 2H), 1.66-1.57 (m, 2H), 1.33-1.26 (m, 8H), 0.88 (t, J=6.9 Hz, 3H).

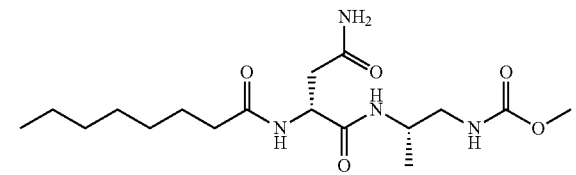 [SMILES: CCCCCCCC(=O)N[C@H](CC(N)=O)C(=O)N[C@@H](C)CNC(=O)OC]

Example 45: Methyl ((S)-2-((R)-4-amino-2-octanamido-4-oxobutanamido)propyl)carbamate Step 1:

A mixture of (2R)-4-amino-2-(octanoylamino)-4-oxo-butanoic acid (50 mg, 194 μmol, 1 equiv.), EDCl (41 mg, 213 μmol, 1.1 equiv.), tert-butyl N-[(2S)-2-aminopropyl]carbamate (41 mg, 232 μmol, 36 μL, 1.2 equiv.) in DMF (2 mL) was cooled to 0° C. HOBt (29 mg, 213 μmol, 1.1 equiv.) and TEA (43 mg, 426 μmol, 59 μL, 2.2 equiv.) was added to the mixture and the reaction mixture was stirred at 0° C. for 15 min and was stirred at 25° C. for 12 h. The reaction mixture was filtered and concentrated under reduced pressure and the residue was purified by prep-HPLC (column: Luna C18 100*30 mm 5 um; mobile phase: [water (0.1% TFA)-ACN]; B %: 25%-55%, 12 min) to give tert-butyl N-[(2S)-2-[[(2R)-4-amino-2-(octanoylamino)-4-oxo-butanoyl]amino]propyl] carbamate (40 mg, 50%) as a white solid.

Step 2:

A solution of tert-butyl N-[(2S)-2-[[(2R)-4-amino-2-(octanoylamino)-4-oxo-butanoyl]amino]propyl]carbamate (40 mg, 96 μmol, 1 equiv.) in HCl/dioxane (2 M, 8.00 mL, 166 equiv.) was stirred at 25° C. for 1 h. The reaction mixture was filtered and concentrated under reduced pressure to give (2R)—N-[(1S)-2-amino-1-methyl-ethyl]-2-(octanoylamino) butanediamide hydrochloride (20 mg, 59%) as a white solid which was used into the next step without further purification.

Step 3:

A mixture of (2R)—N-[(1S)-2-amino-1-methyl-ethyl]-2-(octanoylamino)butanediamide hydrochloride (15 mg, 43 μmol, 1 equiv.) and TEA (8.7 mg, 86 μmol, 11.9 μL, 2 equiv.) in DCM (2 mL) was cooled to 0° C. Methyl carbonochloridate (3.6 mg, 38 μmol, 2.98 μL, 0.9 equiv.) was added and the mixture was stirred at 25° C. for 12 h. The reaction mixture was filtered and concentrated under reduced pressure. The residue was purified by prep-HPLC (column: Luna C18 100*30 mm 5 um; mobile phase: [water (0.1% TFA)-ACN]; B %: 10%-45%, 12 min) to give methyl ((S)-2-((R)-4-amino-2-octanamido-4-oxobutanamido)propyl)carbamate (3.8 mg, 23%) as a white solid. LCMS (M+H⁺): 373.2 ¹H NMR (400 MHz, DMSO-d6) δ 7.88 (d, J=7.8 Hz, 1H), 7.64-7.51 (m, 1H), 7.28 (s, 1H), 7.06-7.00 (m, 1H), 6.87 (s, 1H), 4.48-4.43 (m, 1H), 3.81-3.73 (m, 1H), 3.54-3.49 (m, 3H), 3.02-2.93 (m, 2H), 2.46-2.29 (m, 2H), 2.14-2.06 (m, 2H), 1.49-1.45 (m, 2H), 1.26-1.22 (m, 8H), 0.97 (d, J=6.7 Hz, 3H), 0.90-0.82 (m, 3H).

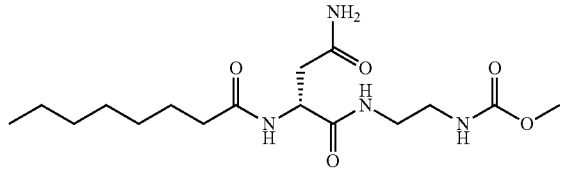 [SMILES: CCCCCCCC(=O)N[C@H](CC(N)=O)C(=O)NCCNC(=O)OC]

Example 46: Methyl (R)-(2-(4-amino-2-octanamido-4-oxobutanamido)ethyl)carbamate

Step 1:

A mixture of (2R)-4-amino-2-(tert-butoxycarbonylamino)-4-oxo-butanoic acid (1 g, 4.31 mmol, 1 equiv.) in HCl/dioxane (3 M, 14.4 mL, 10 equiv.) was stirred at 25° C. for 1 hr under $N_2$ atmosphere. The reaction mixture was filtered and filtrate was concentrated under reduced pressure to give (2R)-2,4-diamino-4-oxo-butanoic acid hydrochloride (650 mg, 90%) was obtained as a white solid and was used into the next step without further purification.

Step 2:

To a solution of (2R)-2,4-diamino-4-oxo-butanoic acid (10 g, 75.7 mmol, 1 equiv.) in DCM (10 mL) was added TEA (15.32 g, 151.4 mmol, 21.07 mL, 2 equiv.). The reaction mixture was then cooled to 0° C. and octanoyl chloride (18.47 g, 113.5 mmol, 19.38 mL, 1.5 equiv.) was added. The mixture was stirred at 25° C. for 12 hr under $N_2$. The reaction mixture was filtered and concentrated under reduced pressure and the residue was purified by prep-HPLC (column: Phenomenex luna C18 250 mm*100 mm*10 um; mobile phase: [water (0.1% TFA)-ACN]; B %: 15%-45%, 25 min) to give (2R)-4-amino-2-(octanoylamino)-4-oxo-butanoic acid (1 g, 5.1% yield) as a white solid.

Step 3:

A mixture of (2R)-4-amino-2-(octanoylamino)-4-oxo-butanoic acid (100 mg, 387 µmol, 1 equiv.), HOBt (58 mg, 426 µmol, 1.1 equiv.), TEA (86 mg, 852 µmol, 119 µL, 2.2 equiv.) in DMF (3 mL) was cooled to 0° C. EDCI (82 mg, 426 µmol, 1.1 equiv.) and tert-butyl N-(2-aminoethyl)carbamate (81 mg, 503 µmol, 79 µL, 1.3 equiv.) was added. The reaction mixture was stirred at 0° C. for 15 min and was then warmed to 25° C. for 12 hr. The reaction mixture was diluted with $H_2O$ (5 mL) and extracted four times with EtOAc (5 mL). The combined organic layers were washed with brine (10 mL), dried over $Na_2SO_4$, filtered and concentrated under reduced pressure to give a tert-butyl N-[2-[[(2R)-4-amino-2-(octanoylamino)-4-oxo-butanoyl]amino]ethyl]carbamate (60 mg, 39%) as a white solid.

Step 4:

A mixture of tert-butyl N-[2-[[(2R)-4-amino-2-(octanoylamino)-4-oxo-butanoyl]amino]ethyl]carbamate (60 mg, 150 µmol, 1 equiv.) in HCl/dioxane (3 M, 50 µL, 1 equiv.) was stirred at 25° C. for 1 hr under $N_2$ atmosphere. The reaction mixture was concentrated under reduced pressure to give (2R)—N-(2-aminoethyl)-2-(octanoylamino)butanediamide hydrochloride (30 mg, 59%) as a white solid.

Step 5:

A mixture of (2R)—N-(2-aminoethyl)-2-(octanoylamino)butanediamide hydrochloride (50 mg, 166 µmol, 1 equiv.) and TEA (34 mg, 333 µmol, 46 µL, 2 equiv.) in DCM (3 mL) was cooled to 0° C. Methyl carbonochloridate (24 mg, 250 µmol, 19 µL, 1.5 equiv.) was added into the mixture. Then the mixture was warmed to 25° C. and stirred for 12 hr. The reaction mixture was filtered and concentrated under reduced pressure. The residue was purified by prep-HPLC (column: Luna C18 100*30 mm 5 um; mobile phase: [water (0.1% TFA)-ACN]; B %: 20%-35%, 4 min) to give methyl (R)-(2-(4-amino-2-octanamido-4-oxobutanamido)ethyl)carbamate (9 mg, 13%) as a white solid. LCMS (M+H+): 359.2
$^1$H NMR (400 MHz, DMSO-d6) δ 7.89 (d, J=7.9 Hz, 1H), 7.83-7.77 (m, 1H), 7.25 (s, 1H), 7.07-7.03 (m, 1H), 6.85 (s, 1H), 4.44 (q, J=7.3 Hz, 1H), 3.49 (s, 3H), 3.13-2.95 (m, 4H), 2.48-2.40 (m, 1H), 2.31 (dd, J=15.1, 7.8 Hz, 1H), 2.07 (t, J=7.5 Hz, 2H), 1.48-1.40 (m, 2H), 1.28-1.16 (m, 8H), 0.87-0.80 (m, 3H).

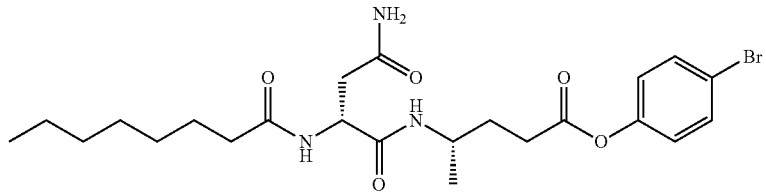 [SMILES: CCCCCCCC(=O)N[C@H](CC(N)=O)C(=O)N[C@@H](C)CCC(=O)Oc1ccc(Br)cc1]

Example 47: 4-bromophenyl (S)-4-((R)-4-amino-2-octanamido-4-oxobutanamido)pentanoate Step 1:

To a mixture of methyl (4S)-4-[[(2R)-4-amino-2-(octanoylamino)-4-oxo-butanoyl]amino]pentanoate (150 mg, 404 µmol, 1 equiv.) in MeOH (2 mL) and $H_2O$ (1 mL) was added LiOH·$H_2O$ (34 mg, 809 µmol, 2 equiv.), and the mixture was stirred at 25° C. for 5 hr under $N_2$. The reaction mixture was adjusted to pH4 with 2N HCl, and the solid product was collected by filtration to give (4S)-4-[[(2R)-4-amino-2-(octanoylamino)-4-oxo-butanoyl]amino]pentanoic acid (110 mg, 76%). LCMS: (M+H+) 358.2@1.255 min Step 2:

A mixture of (4S)-4-[[(2R)-4-amino-2-(octanoylamino)-4-oxo-butanoyl]amino]pentanoic acid (50 mg, 140 µmol, 1 equiv.), HOBt (21 mg, 154 µmol, 1.1 equiv.) and 4-bromophenol (29 mg, 168 µmol, 1.2 equiv.) in DMF (2 mL) was cooled to 0° C. EDCl (29.5 mg, 154 µmol, 1.1 equiv.) and TEA (31 mg, 308 µmol, 42.8 µL, 2.2 equiv.) were added and the mixture was stirred at 0° C. for 15 min and then at 25° C. for 12 hr. The mixture was filtered, concentrated under reduced pressure and the residue was purified by prep-HPLC (column: Luna C18 100*30 5u; mobile phase: [water (0.1% TFA)-ACN]; B %: 35%-60%, 12 min) to give (4-bromophenyl)(4S)-4-[[(2R)-4-amino-2-(octanoylamino)-4-oxo-butanoyl]amino]pentanoate (10 mg, 14%) as a white solid. LCMS: (M+H+) 514.1

$^1$H NMR (400 MHz, DMSO-d6) δ 7.88 (d, 1H), 7.58 (dd, 3H), 7.24 (s, 1H), 7.13-7.06 (m, 2H), 6.84 (s, 1H), 4.47 (q, 1H), 3.85-3.77 (m, 1H), 2.54 (dd, 1H), 2.44 (d, 1H), 2.32 (dd, 1H), 2.07 (t, 2H), 1.79-1.67 (m, 1H), 1.71-1.59 (m, 1H), 1.48-1.40 (m, 2H), 1.21 (s, 8H), 1.04 (d, 3H), 0.83 (q, 3H)

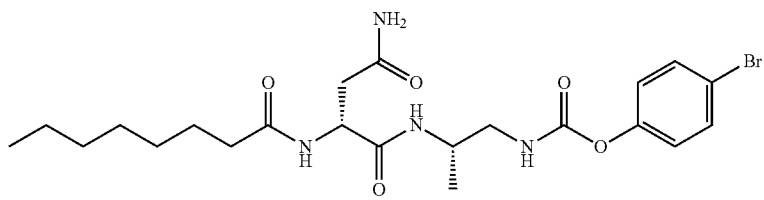 [SMILES: CCCCCCCC(=O)N[C@H](CC(N)=O)C(=O)N[C@@H](C)CNC(=O)Oc1ccc(Br)cc1]

Example 48: 4-bromophenyl ((S)-2-((R)-4-amino-2-octanamido-4-oxobutanamido)propyl)carbamate Step 1:

To a mixture of benzyl (2R)-4-amino-2-(tert-butoxycarbonylamino)-4-oxo-butanoate (3.00 g, 9.31 mmol, 1 equiv.) in DCM (30 mL) was added TFA (10.6 g, 93 mmol, 6.89 mL, 10 equiv.) and the mixture was stirred at 25° C. for 0.5 h. The solvent was evaporated and the residue was dissolved in DCM (30 mL) at 0° C. TEA (3.77 g, 37.2 mmol, 5.18 mL, 4 equiv.) and DMAP (114 mg, 931 μmol, 0.1 equiv.) were added followed by octanoyl chloride (1.82 g, 11.2 mmol, 1.91 mL, 1.2 equiv.). The mixture was stirred at 25° C. for 11.5 h, and then filtered and concentrated under reduced pressure. The residue was purified by column chromatography (SiO$_2$, petroleum ether/ethyl acetate, 5/1 to 1:1) to give benzyl (2R)-4-amino-2-(octanoylamino)-4-oxo-butanoate (1.9 g, 53%) as white solid.

Step 2:

To a solution of benzyl (2R)-4-amino-2-(octanoylamino)-4-oxo-butanoate (1.9 g, 5.45 mmol, 1 equiv.) in EtOH (20 mL) was added 10% Pd/C (1 g) under N$_2$. The suspension was degassed under vacuum and purged with H$_2$ several times. The mixture was stirred under H$_2$ at 25° C. at 15 psi for 2 hours. The reaction mixture was filtered and concentrated under reduced pressure to give (2R)-4-amino-2-(octanoylamino)-4-oxo-butanoic acid (1.3 g, 92% yield) as white solid.

Step 3:

A mixture of (2R)-4-amino-2-(octanoylamino)-4-oxo-butanoic acid (0.2 g, 774 μmol, 1 equiv.), HOBt (115 mg, 852 μmol, 1.1 equiv.) and TEA (172 mg, 1.70 mmol, 237 μL, 2.2 equiv.) in DMF (3 mL) was stirred at 0° C. for 1 h. EDCl (163 mg, 852 μmol, 1.1 equiv.) was added followed by tert-butyl N-[(2S)-2-aminopropyl]carbamate (162 mg, 929 μmol, 1.2 equiv.) and the mixture was stirred at 25° C. for 11 hours. The reaction mixture was partitioned between ethyl acetate (9 ml) and H$_2$O (9 ml). The organic phase was separated, filtered and concentrated under reduced pressure. The residue was purified by prep-TLC (SiO$_2$, DCM:MeOH, 10:1) to give tert-butyl N-[(2S)-2-[[(2R)-4-amino-2-(octanoylamino)-4-oxo-butanoyl]amino]propyl]carbamate (0.14 g, 39%) as white solid.

Step 4:

A mixture of tert-butyl N-[(2S)-2-[[(2R)-4-amino-2-(octanoylamino)-4-oxo-butanoyl] amino]propyl]carbamate (0.05 g, 121 μmol, 1 equiv.) in HCl/dioxane (3 mL, 4 M) was stirred at 25° C. for 0.5 h. The reaction mixture was filtered and concentrated under reduced pressure to give (2R)—N-[(1S)-2-amino-1-methyl-ethyl]-2-(octanoylamino)butanediamide hydrochloride as white solid.

Step 5:

To a mixture of (2R)—N-[(1S)-2-amino-1-methyl-ethyl]-2-(octanoylamino)butanediamide hydrochloride (0.05 g, 143 μmol, 1 equiv.) and TEA (29 mg, 285 μmol, 40 μL, 2 equiv.) in DCM (200 mL) was added (4-bromophenyl) carbonochloridate (40 mg, 171 μmol, 24 μL, 1.2 equiv.) in one portion at 0° C. under N$_2$. The mixture was stirred at 25° C. for 12 hours and was then filtered and concentrated under reduced pressure. The residue was purified by prep-HPLC ([water (0.1% TFA)-acetonitrile]) to give (4-bromophenyl) N-[(2S)-2-[[(2R)-4-amino-2-(octanoylamino)-4-oxo-butanoyl]amino]propyl]carbamate (2.4 mg, 3.3%) as white solid.

LCMS: (M+H$^+$): 513.1 & 515.1

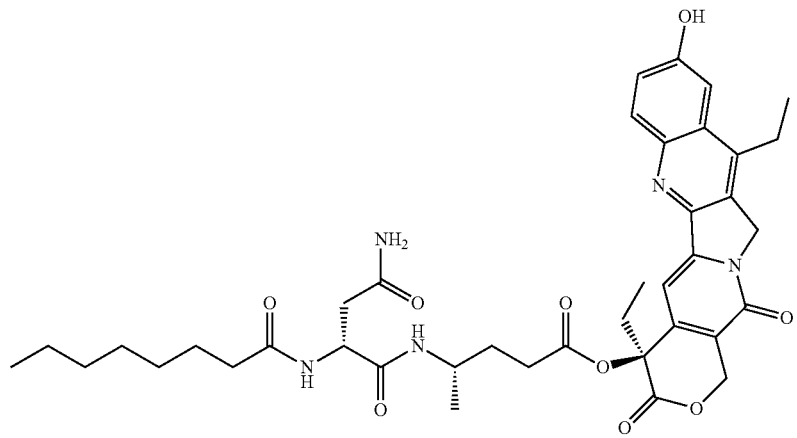 [SMILES: CCCCCCCC(=O)N[C@H](CC(N)=O)C(=O)N[C@@H](C)CCC(=O)O[C@]1(CC)C(=O)OCc2c1cc1n(c2=O)Cc2c-1nc1ccc(O)cc1c2CC]

Example 49: (S)-4,11-diethyl-9-hydroxy-3,14-di-oxo-3,4,12,14-tetrahydro-1H-pyrano[3',4':6,7]in-dolizino[1,2-b]quinolin-4-yl (S)-4-((R)-4-amino-2-octanamido-4-oxobutanamido)pentanoate Step 1:
To a solution of (S)-4,11-diethyl-4,9-dihydroxy-1,12-di-hydro-14H-pyrano[3',4':6,7]indolizino[1,2-b]quinoline-3,14 (4H)-dione (2.5 g, 6.37 mmol, 1 equiv.) in DCM (15 mL) was added Boc$_2$O (2.09 g, 9.56 mmol, 2.20 mL, 1.5 equiv.) and pyridine (1.01 g, 12.7 mmol, 1.03 mL, 2 equiv.) at 20° C. The mixture was stirred at 20° C. for 12 hr. The reaction mixture was concentrated under reduced pressure to give (S)-tert-butyl (4,11-diethyl-4-hydroxy-3,14-dioxo-3,4,12,14-tetrahydro-1H-pyrano[3',4':6,7]indolizino[1,2-b]quinolin-9-yl) carbonate (2.7 g, 86%) as a white solid.

Step 2:
To a solution of tert-butyl (S)-(1-oxopropan-2-yl)carbamate (4.0 g, 23 mmol, 1 equiv.) in toluene (20 mL) was added Methyl (triphenylphosphoranylidene)acetate (8.49 g, 25 mmol, 1.1 equiv.) at 0° C. The mixture was stirred at 20° C. for 12 hr. The reaction mixture was filtered and concentrated under reduced pressure. The residue was purified by column chromatography (SiO$_2$, petroleum ether/ethyl acetate=10:1 to 1:1) to give methyl (E,4S)-4-(tert-butoxycarbonylamino) pent-2-enoate (4.5 g, 85%) as a colourless oil.

Step 3:
To a solution of methyl (E,4S)-4-(tert-butoxycarbonylamino)pent-2-enoate (500 mg, 2.18 mmol, 1 equiv.) in THF (1 mL) and H$_2$O (1 mL) was added LiOH·H$_2$O (275 mg, 6.54 mmol, 3 equiv.) at 0° C. The mixture was stirred at 20° C. for 12 hr. The reaction mixture was diluted with H$_2$O (10 mL) and extracted with ethyl acetate 10 mL. The combined water layers were adjusted by HCl (1M, H$_2$O) to pH=3 and extracted with ethyl acetate (20 mL*3). The combined organic layers were washed with brine (20 mL), dried over anhydrous sodium sulfate, filtered and concentrated under reduced pressure to give (E,4S)-4-(tert-butoxycarbonylamino)pent-2-enoic acid (460 mg) as a white solid.

Step 4:
A mixture of (E,4S)-4-(tert-butoxycarbonylamino)pent-2-enoic acid (300 mg, 1.39 mmol, 1 equiv.), (S)-tert-butyl (4,11-diethyl-4-hydroxy-3,14-dioxo-3,4,12,14-tetrahydro-1H-pyrano[3',4':6,7]indolizino[1,2-b]quinolin-9-yl) carbonate (1.03 g, 2.09 mmol, 1.5 equiv.), DCC (431 mg, 2.09 mmol, 422.9 µL, 1.5 equiv.), DMAP (85.1 mg, 697 µmol, 0.5 equiv.) in DCM (3 mL) was stirred at 20° C. for 12 hr. The reaction mixture was filtered and concentrated under reduced pressure. The residue was purified by prep-HPLC (column: Phenomenex Luna C18 200*40 mm*10 um; mobile phase: [water (0.1% TFA)-ACN]; B %: 60%-80%, 10 min) to give (S)-9-((tert-butoxycarbonyl)oxy)-4,11-diethyl-3,14-dioxo-3,4,12,14-tetrahydro-1H-pyrano[3',4':6,7] indolizino[1,2-b]quinolin-4-yl (S,E)-4-((tert-butoxycarbonyl)amino)pent-2-enoate (450 mg, 47%) as a yellow solid.

Step 5:
To a solution of (S)-9-((tert-butoxycarbonyl)oxy)-4,11-diethyl-3,14-dioxo-3,4,12,14-tetrahydro-1H-pyrano[3',4':6, 7]indolizino[1,2-b]quinolin-4-yl (S,E)-4-((tert-butoxycarbonyl)amino)pent-2-enoate (450 mg, 652 µmol, 1 equiv.) in MeOH (10 mL) was added Pd/C (200 mg, 10% purity) at 20° C. The suspension was degassed and purged with H$_2$ three times. The mixture was stirred under H$_2$ (15 Psi) at 20° C. for 14 hr. The reaction mixture was filtered and concentrated under reduced pressure to give (S)-9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl (S)-4-((tert-butoxycarbonyl)amino)pentanoate (300 mg, 67%) as a yellow solid which was used without further purification.

Step 6:
To a solution of (S)-9-((tert-butoxycarbonyl)oxy)-4,11-diethyl-3,14-dioxo-3,4,12,14-tetrahydro-1H-pyrano[3',4':6, 7]indolizino[1,2-b]quinolin-4-yl (S)-4-((tert-butoxycarbonyl)amino)pentanoate (300 mg, 434 µmol, 1 equiv.) in HCl/EtOAc (5 mL, 4M) was stirred at 20° C. for 8 hr. The reaction mixture was concentrated under reduced pressure to give (S)-4,11-diethyl-9-hydroxy-3,14-dioxo-3,4,12,14-tetrahydro-1H-pyrano[3',4':6,7]indolizino[1,2-b]quinolin-4-yl (S)-4-aminopentanoate hydrochloride (100 mg, 44%) as a yellow solid which was without further purification.

Step 7:
To a solution of (S)-4,11-diethyl-9-hydroxy-3,14-dioxo-3,4,12,14-tetrahydro-1H-pyrano[3',4':6,7]indolizino[1,2-b] quinolin-4-yl (S)-4-aminopentanoate hydrochloride (50 mg, 102 µmol, 1 equiv.) in DMF (5 mL) was added HOBt (15.1 mg, 119 µmol, 1.1 equiv.), (2R)-4-amino-2-(octanoylamino)-4-oxo-butanoic acid (26.3 mg, 102 µmol, 1 equiv.), TEA (22.6 mg, 224 µmol, 31.2 µL, 2.2 equiv.) and EDCI (21.5 mg, 112 µmol, 1.1 equiv.) at 0° C. The mixture was stirred at 15° C. for 12 hr. The reaction mixture was filtered, concentrated, and purified by prep-HPLC (column: Nano-Micro UniSil 5-100 C18 ULTRA 100*250 mm 5 um; mobile phase: [water (0.1% TFA)-ACN]; B %: 38%-56%, 10 min) to give (S)-4,11-diethyl-9-hydroxy-3,14-dioxo-3,4,12,14-tetrahydro-1H-pyrano[3',4':6,7]indolizino[1,2-b]quinolin-4-yl (S)-4-((R)-4-amino-2-octanamido-4-oxobutanamido) pentanoate (24 mg, 30%) as a yellow solid. LCMS (M+H$^+$): 732.3. $^1$H NMR (400 MHz, DMSO-d6) δ 10.31 (s, 1H), 8.05-7.97 (m, 1H), 7.89 (dd, 1H), 7.62-7.55 (m, 1H), 7.42-7.36 (m, 2H), 7.28 (d, 1H), 6.96-6.93 (m, 1H), 6.85 (d, 1H), 5.45 (s, 2H), 5.28 (s, 2H), 4.58-4.41 (m, 1H), 3.87-3.70 (m, 1H), 3.13-3.02 (m, 2H), 2.67-2.63 (m, 2H), 2.39-2.28 (m, 2H), 2.16-2.01 (m, 4H), 1.66-1.55 (m, 2H), 1.46-1.41 (m, 2H), 1.27 (t, 3H), 1.24-1.11 (m, 8H), 1.00 (dd, 3H), 0.93-0.85 (m, 3H), 0.85-0.74 (m, 3H).

Example 50: Methyl (tridecylsulfonyl)-D-asparaginyl-L-alaninate

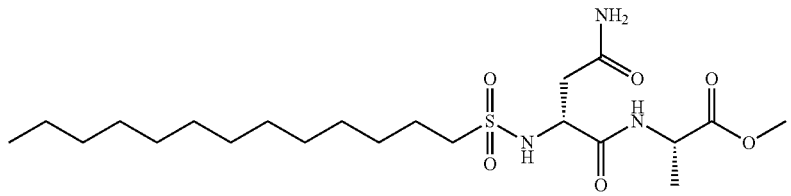 [SMILES: CCCCCCCCCCCCCS(=O)(=O)N[C@H](CC(N)=O)C(=O)N[C@@H](C)C(=O)OC]

Tridecane-1-sulfonyl chloride (1.5 equiv.) is dissolved in anhydrous DMF, followed by addition of triethylamine (2.5 equiv.). The HCl salt of D-Asn-L-Ala-OMe (synthesized in Example 1 step 2, 1 equiv.) is added until reaction is complete as monitored by LCMS. Product is purified by reverse phase chromatography and lyophilized to yield the title compound.

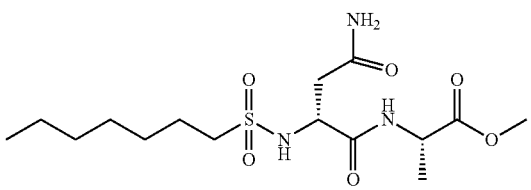 [SMILES: CCCCCCCS(=O)(=O)N[C@H](CC(N)=O)C(=O)N[C@@H](C)C(=O)OC]

Example 51: Methyl (heptylsulfonyl)-D-asparaginyl-L-alaninate

This compound may be synthesized with heptane-1-sulfonyl chloride according to the experimental procedure described for Example 50.

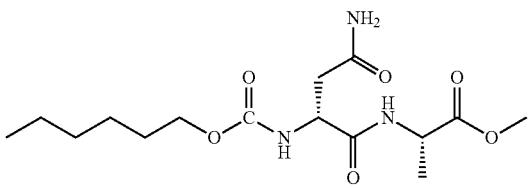 [SMILES: CCCCCCOC(=O)N[C@H](CC(N)=O)C(=O)N[C@@H](C)C(=O)OC]

Example 52: Methyl ((hexyloxy)carbonyl)-D-asparaginyl-L-alaninate

Hexyl chloroformate (0.035 g, 0.22 mmol, 1.1 equiv.) was dissolved in anhydrous DMF (1 mL), followed by addition of triethylamine (0.03 mL, 0.22 mmol, 1.1 equiv.). The HCl salt of D-Asn-L-Ala-OMe (synthesized in Example 1 Step 2, 0.05 g, 0.2 mmol 1 equiv.) was added and the reaction was stirred overnight. After adding water to clarify the solution, product was purified on reverse phase chromatography and lyophilized to afford a white solid (27.6 mg, 40%). LCMS (M–H)⁻, 344.2 ¹H NMR (400 MHz, DMSO-d6) δ 8.13 (d, J=7.3 Hz, 1H), 7.23 (s, 1H), 7.11 (d, J=8.4 Hz, 1H), 6.85 (s, 1H), 4.34-4.28 (m, 1H), 4.23 (p, J=7.2 Hz, 1H), 3.91 (t, J=6.6 Hz, 2H), 3.60 (s, 3H), 2.42 (dd, J=15.2, 5.2 Hz, 1H), 2.33 (dd, J=15.1, 8.5 Hz, 1H), 1.55-1.45 (m, 2H), 1.28-1.23 (m, 6H), 1.24 (d, J=7.2 Hz, 3H), 0.89-0.81 (m, 3H).

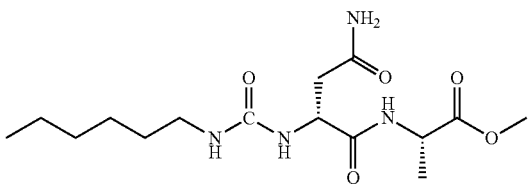 [SMILES: CCCCCCNC(=O)N[C@H](CC(N)=O)C(=O)N[C@@H](C)C(=O)OC]

Example 53: Methyl (hexylcarbamoyl)-D-asparaginyl-L-alaninate

Hexyl isocyanate (0.028 g, 0.22 mmol, 1.1 equiv.) was dissolved in anhydrous DMF (1 mL), followed by addition of triethylamine (0.03 mL, 0.22 mmol, 1.1 equiv.). The HCl salt of D-Asn-L-Ala-OMe (synthesized in Example 1 Step 2, 0.05 g, 0.2 mmol 1 equiv.) was added and the reaction was stirred overnight. After adding water to clarify the solution, product was purified on reverse phase chromatography and lyophilized to afford a white solid (36.2 mg, 53%). LCMS (M–H)⁻, 343.2 ¹H NMR (400 MHz, DMSO-d6) δ 8.09 (d, J=7.2 Hz, 1H), 7.28 (s, 1H), 6.83 (s, 1H), 6.18 (t, J=5.6 Hz, 1H), 6.04 (d, J=8.3 Hz, 1H), 4.39 (dt, J=8.4, 6.5 Hz, 1H), 4.23 (p, J=7.2 Hz, 1H), 3.60 (s, 3H), 3.01-2.88 (m, 2H), 2.42-2.29 (m, 2H), 1.32 (t, J=6.7 Hz, 2H), 1.30-1.18 (m, 9H), 0.88-0.80 (m, 3H).

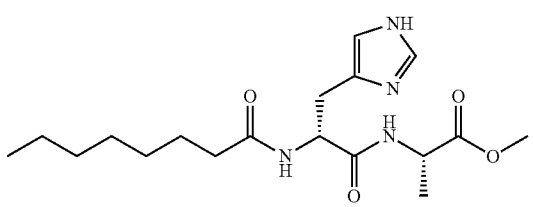 [SMILES: CCCCCCCC(=O)N[C@H](Cc1c[nH]cn1)C(=O)N[C@@H](C)C(=O)OC]

Example 54: Methyl octanoyl-D-histidyl-L-alaninate

Step 1:

To a solution of (2R)-2-(tert-butoxycarbonylamino)-3-(1H-imidazol-4-yl) propanoic acid (500 mg, 1.96 mmol, 1 equiv.) in DMF (5 mL) was added HOBt (318 mg, 2.35 mmol, 1.2 equiv.) and TEA (634 mg, 6.27 mmol, 872 μL, 3.2 equiv.). Then EDCl (451 mg, 2.35 mmol, 1.2 equiv.) and methyl (2S)-2-aminopropanoate hydrochloride (301 mg, 2.15 mmol, 1.1 equiv.) were added to the mixture at 0° C. The mixture was stirred at 25° C. for 12 h and was then diluted with H₂O (20 mL) and extracted three times with EtOAc (10 mL). The combined organic layer was washed three times with brine (20 mL), dried over Na₂SO₄, filtered and concentrated to give methyl (2S)-2-[[(2R)-2-(tert-butoxycarbonylamino)-3-(1H-imidazol-4-yl) propanoyl] amino]propanoate (300 mg) as colorless oil.

Step 2:

Methyl (2S)-2-[[(2R)-2-(tert-butoxycarbonylamino)-3-(1H-imidazol-4-yl) propanoyl] amino]propanoate (140 mg, 411 μmol, 1 equiv.) was dissolved in HCl/EtOAc (5 mL, 4M) and the mixture was stirred at 25° C. for 5 h. The mixture was concentrated to give methyl (2S)-2-[[(2R)-2-amino-3-(1H-imidazol-4-yl) propanoyl]amino]propanoate hydrochloride (150 mg) as white solid.

Step 3:

To a solution of methyl (2S)-2-[[(2R)-2-amino-3-(1H-imidazol-4-yl)propanoyl]amino]propanoate hydrochloride (90 mg, 325 μmol, 1 equiv.) in DCM (5 mL) was added TEA (132 mg, 1.30 mmol, 181 μL, 4 equiv.) and octanoyl chloride (58 mg, 358 μmol, 61 μL, 1.1 equiv.) at 0° C. The mixture was stirred at 25° C. for 12 h and then concentrated. The residue was purified by prep-HPLC (column: Luna C18 100*30 5u; mobile phase: [water (0.1% TFA)-acetonitrile]; B %: 10%-35%, 12 min) to give methyl (2S)-2-[[(2R)-3-(1H-imidazol-4-yl)-2-(octanoylamino) propanoyl]amino] propanoate trifluoroacetate (15 mg, 12%) as a white solid.

LCMS: (M+H⁺): 367.2

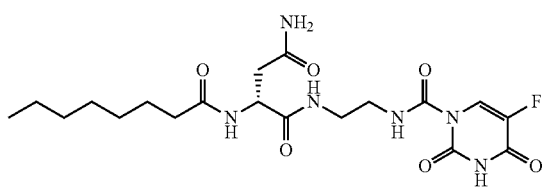 [SMILES: CCCCCCCC(=O)N[C@H](CC(N)=O)C(=O)NCCNC(=O)n1cc(F)c(=O)[nH]c1=O]

Example 55: (R)—N1-(2-(5-fluoro-2,4-dioxo-1,2,3,4-tetrahydropyrimidine-1-carboxamido)ethyl)-2-octanamidosuccinamide Step 1

A solution of 5-fluoro-1H-pyrimidine-2,4-dione (1.00 g, 7.69 mmol, 1 equiv.) in pyridine (15 mL) was added dropwise to a solution of bis(trichloromethyl) carbonate (1.14 g, 3.84 mmol, 0.5 equiv.) in THF (15 mL) at 0° C. The mixture was stirred at 0° C. for 2 h. The reaction mixture was filtered used in next step without further purification.

Step 2

A solution of (2R)—N-(2-aminoethyl)-2-(octanoylamino) butanediamide (100 mg, 333 μmol, 1 equiv.) in DMSO (1 mL) was added to 5-fluoro-2,4-dioxo-pyrimidine-1-carbonyl chloride (solution of step 1, ~0.256 M, in 30 mL of THF and pyridine, 23.07 equiv.). The mixture was stirred at 15° C. for 12 h. The reaction mixture was filtered and concentrated under reduced pressure. The residue was purified by prep-HPLC (column: Welch Ultimate AQ-C18 150*30 mm*5 um; mobile phase: [water (0.1% TFA)-ACN]; B %: 27%-57%, 12 min) to give (R)—N1-(2-(5-fluoro-2,4-dioxo-1,2,3,4-tetrahydropyrimidine-1-carboxamido)ethyl)-2-octanamidosuccinamide (25 mg, 16%) as a white solid. LCMS: (M+H$^+$): 457.3

$^1$H NMR (400 MHz, DMSO-d6) δ 12.27 (s, 1H), 9.13 (t, 1H), 8.39 (d, 1H), 7.91-7.84 (m, 2H), 7.23 (s, 1H), 6.82 (s, 1H), 4.52-4.42 (m, 1H), 3.26-3.14 (m, 2H), 2.47-2.42 (m, 1H), 2.39-2.28 (m, 1H), 2.12-2.04 (m, 2H), 1.45 (t, 2H), 1.32-1.16 (m, 10H), 0.90-0.82 (m, 3H).

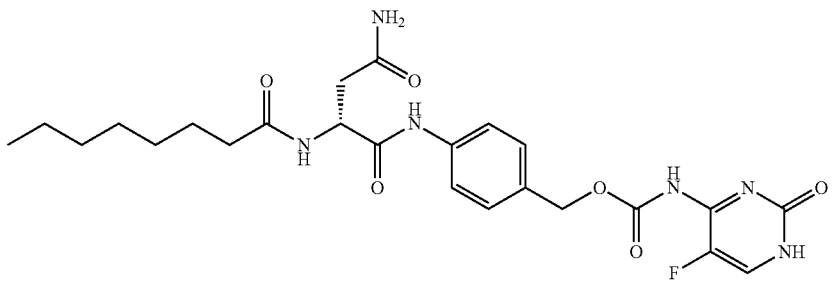 [SMILES: CCCCCCCC(=O)N[C@H](CC(N)=O)C(=O)Nc1ccc(COC(=O)Nc2nc(=O)[nH]cc2F)cc1]

Example 56: (R)-4-(4-amino-2-octanamido-4-oxobutanamido)benzyl (5-fluoro-2-oxo-1,2-dihydropyrimidin-4-yl)carbamate A mixture of octanoyl-D-asparagine (1 equiv), is treated with HOBt (1.1 equiv), and 4-aminobenzyl alcohol. The resulting alcohol is treated with 4,4'-Dinitrophenyl carbonate (1 equiv.). The resulting carbonate is treated with 4-amino-5-fluoropyrimidin-2(1H)-one (1 equiv) to afford the title compound.

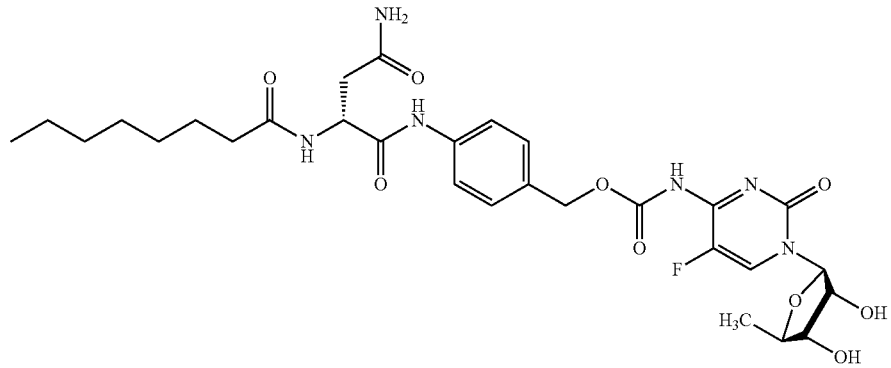

Example 57: 4-((R)-4-amino-2-octanamido-4-oxobutanamido)benzyl (1-((2R,5R)-3,4-dihydroxy-5-methyltetrahydrofuran-2-yl)-5-fluoro-2-oxo-1,2-dihydropyrimidin-4-yl)carbamate This compound may be synthesized according to the experimental procedure described for Example 56.

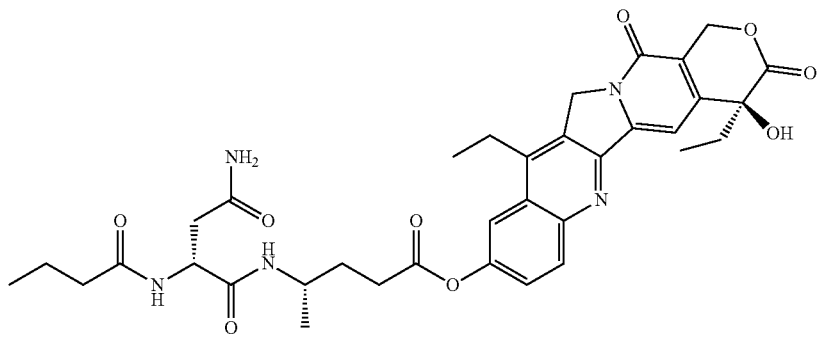 [SMILES: CCCC(=O)N[C@H](CC(N)=O)C(=O)N[C@@H](C)CCC(=O)Oc1ccc2nc3c(c(CC)c2c1)Cn1c-3cc2c(c1=O)COC(=O)[C@]2(O)CC]

Example 58: (S)-4,11-diethyl-4-hydroxy-3,14-dioxo-3,4,12,14-tetrahydro-1H-pyrano[3',4':6,7]indolizino[1,2-b]quinolin-9-yl (S)-4-((R)-4-amino-2-butyramido-4-oxobutanamido)pentanoate Step 1:
A mixture of (E,4S)-4-[[(2R)-4-amino-2-(butanoylamino)-4-oxo-butanoyl]amino]pent-2-enoic acid (87 mg, 290.66 μmol, 1 equiv.), (S)-4,11-diethyl-4,9-dihydroxy-1,12-dihydro-14H-pyrano[3',4':6,7]indolizino[1,2-b]quinoline-3,14(4H)-dione (91 mg, 233 μmol, 0.8 equiv.), EDCl (61 mg, 320 μmol, 1.1 equiv.) in DMF (5 mL) was degassed and purged with N$_2$ 3 times, and then the mixture was stirred at 0° C. under N$_2$ atmosphere. Then DMAP (18 mg, 145 μmol, 0.5 equiv.) in DMF (5 mL) was added and the mixture and stirred at 15° C. under N$_2$ atmosphere for 10 hours. EtOAc (10 mL) was added at 15° C., and H$_2$O (20 mL) and the mixture was extracted four times with EtOAc (20 mL). The combined organic phase was dried over Na$_2$SO$_4$, filtered and concentrated under reduced pressure to give (S)-4,11-diethyl-4-hydroxy-3,14-dioxo-3,4,12,14-tetrahydro-1H-pyrano[3',4':6,7]indolizino[1,2-b]quinolin-9-yl (S,E)-4-((R)-4-amino-2-butyramido-4-oxobutanamido)pent-2-enoate (100 mg, crude) as a yellow solid.

Step 2:
To a mixture of (S)-4,11-diethyl-4-hydroxy-3,14-dioxo-3,4,12,14-tetrahydro-1H-pyrano[3',4':6,7]indolizino[1,2-b]quinolin-9-yl (S,E)-4-((R)-4-amino-2-butyramido-4-oxobutanamido)pent-2-enoate (100 mg, 148 μmol, 1 equiv.) in THF (40 mL) was added Pd/C (0.1 g, 10% purity). The mixture was degassed and purged with H$_2$ 3 times, and then stirred at 15° C. for 2 hr under 15 psi H$_2$. The reaction mixture was filtered and concentrated under reduced pressure and the residue was purified by prep-TLC (SiO$_2$, DCM:MeOH=10:1) to give (S)-4,11-diethyl-4-hydroxy-3,14-dioxo-3,4,12,14-tetrahydro-1H-pyrano[3',4':6,7]indolizino[1,2-b]quinolin-9-yl (S)-4-((R)-4-amino-2-butyramido-4-oxobutanamido)pentanoate (27 mg, 22%) as a yellow solid.

LCMS: (M+H+) 676.2
$^1$H NMR (400 MHz, DMSO-d6) δ 8.21 (d, 1H), 8.05-7.94 (m, 2H), 7.74-7.61 (m, 2H), 7.34 (s, 1H), 7.31 (s, 1H), 6.89 (s, 1H), 6.55 (s, 1H), 5.45 (s, 2H), 5.35 (s, 2H), 4.60-4.46 (m, 1H), 3.95-3.89 (m, 1H), 3.19 (q, 2H), 2.72-2.64 (m, 2H), 2.42 (ddd, 2H), 2.14-2.05 (m, 2H), 1.98-1.64 (m, 4H), 1.58-1.43 (m, 2H), 1.30 (t, 3H), 1.10 (d, 3H), 0.93-0.79 (m, 6H).

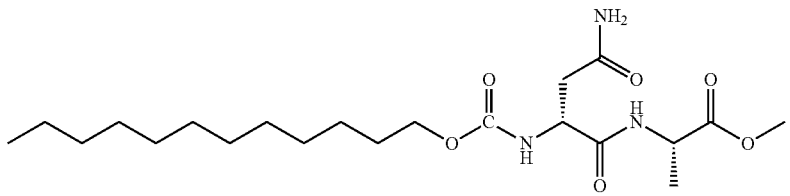 [SMILES: CCCCCCCCCCCCOC(=O)N[C@H](CC(N)=O)C(=O)N[C@@H](C)C(=O)OC]

Example 59: Methyl ((dodecyloxy)carbonyl)-D-asparaginyl-L-alaninate

Dodecyl chloroformate (0.054 g, 0.22 mmol, 1.1 equiv.) was dissolved in anhydrous DMF (1 mL), followed by addition of triethylamine (0.03 mL, 0.22 mmol, 1.1 equiv.). The HCl salt of D-Asn-L-Ala-OMe (synthesized in Example 1 Step 2, 0.05 g, 0.2 mmol 1 equiv.) was added and the reaction was stirred overnight. After adding water and DMSO to the solution and filtering out any insoluble material, the product was purified on reverse phase chromatography and lyophilized to afford a white solid (22.2 mg, 26%). LCMS (M−H)$^−$: 428.3 $^1$H NMR (400 MHz, DMSO-d6) δ 8.12 (d, J=7.3 Hz, 1H), 7.23 (s, 1H), 7.11 (d, J=8.3 Hz, 1H), 6.85 (s, 1H), 4.35-4.28 (m, 1H), 4.23 (p, J=7.2 Hz, 1H), 3.90 (t, J=6.4 Hz, 2H), 3.59 (s, 3H), 2.42 (dd, J=15.1, 5.2 Hz, 1H), 2.33 (dd, J=15.1, 8.5 Hz, 1H), 1.51 (t, J=6.9 Hz, 2H), 1.30-1.20 (m, 21H), 0.88-0.80 (m, 3H).

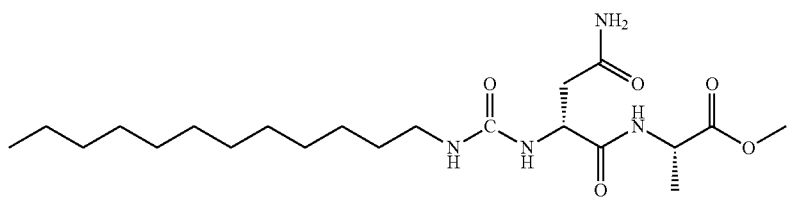 [SMILES: CCCCCCCCCCCCNC(=O)N[C@H](CC(N)=O)C(=O)N[C@@H](C)C(=O)OC]

Example 60: Methyl (dodecylcarbamoyl)-D-asparaginyl-L-alaninate

Dodecyl isocyanate (0.046 g, 0.22 mmol, 1.1 equiv.) was dissolved in anhydrous DMF (1 mL), followed by addition of triethylamine (0.03 mL, 0.22 mmol, 1.1 equiv.). The HCl salt of D-Asn-L-Ala-OMe (synthesized in Example 1 Step 2, 0.05 g, 0.2 mmol 1 equiv.) was added and the reaction was stirred overnight. After adding water and DMSO to the solution and filtering out any insoluble material, product was purified on reverse phase chromatography and lyophilized to afford a white solid (47.6 mg, 56%). LCMS (M−H)⁻, 427.3
$^1$H NMR (400 MHz, DMSO-d6) δ 8.08 (d, J=7.3 Hz, 1H), 7.28 (s, 1H), 6.82 (s, 1H), 6.17 (t, J=5.6 Hz, 1H), 6.04 (d, J=8.3 Hz, 1H), 4.39 (dt, J=8.3, 6.4 Hz, 1H), 4.23 (p, J=7.2 Hz, 1H), 3.60 (s, 3H), 3.00-2.87 (m, 2H), 2.41-2.30 (m, 2H), 1.32 (t, J=6.6 Hz, 2H), 1.26-1.19 (m, 21H), 0.88-0.80 (m, 3H).

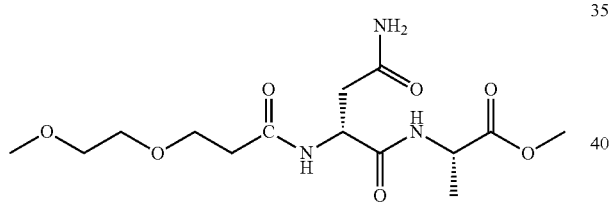

Example 61: Methyl (3-(2-methoxyethoxy)propanoyl)-D-asparaginyl-L-alaninate

To a solution of 3-(2-methoxyethoxy)propanoic acid (88 mg, 0.59 mmol, 1.5 equiv.), HOBt (1-Hydroxybenzotriazole hydrate wetted with not less than 20 wt. % water, 73 mg, 0.43 mmol, 1.1 equiv.), and EDC·HCl (113 mg, 0.59 mmol, 1.5 equiv.) in DMF (2 mL) was added triethylamine (0.14 mL, 1.0 mmol, 2.5 equiv.). After stirring for 5 minutes, D-Asn-L-Ala-OMe HCl salt (100 mg, 0.39 mmol, 1 equiv.) was added and the reaction was stirred at room temperature under N$_2$ overnight. The reaction was diluted with a small amount of water to dissolve the triethylamine salts, and then purified by preparative C18 column chromatography (10% MeCN in water to 100% MeCN) to yield the title compound as a white powder (46 mg, 34%).
LCMS (M+Na+): 370.4
$^1$H NMR (400 MHz, DMSO-d6) δ 8.01 (d, J=7.7 Hz, 2H), 7.24 (s, 1H), 6.83 (s, 1H), 4.62-4.52 (m, 1H), 4.23 (p, J=7.2 Hz, 1H), 3.60 (s, 3H), 3.57 (t, J=6.6 Hz, 2H), 3.49-3.37 (m, 4H), 3.21 (s, 3H), 2.46-2.25 (m, 4H), 1.23 (d, J=7.2 Hz, 3H).

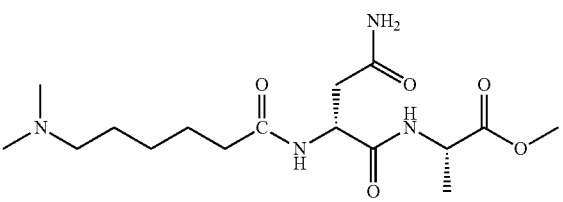

Example 62: Methyl (2S)-2-[(2R)-3-carbamoyl-2-[6-(dimethylamino)hexanamido]propanamido]propanoate The HCl salt of D-Asn-L-Ala-OMe (synthesized in Example 1 step 2, 1 equiv.) is treated with EDCl (1.1 equiv), HOBt (1.1 equiv), and 6-(dimethylamino)hexanoic acid (1.1 equiv.) to yield the title compound.

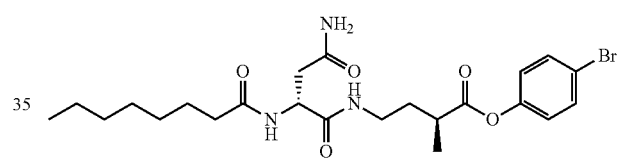

Example 63: 4-bromophenyl (S)-4-((R)-4-amino-2-octanamido-4-oxobutanamido)-2-methylbutanoate Compound (S)-4-((tert-butoxycarbonyl)amino)-2-methylbutanoic acid is reacted with EDCl (1.1 equiv), HOBt (1.1 equiv), and 4-bromophenol (1.1 equiv.), and deprotected with HCl in dioxane to yield 4-bromophenyl (S)-4-amino-2-methylbutanoate. Tetradecanoyl chloride (1.1 equiv.) is reacted with D-asparagine (1 equiv.) to synthesize tetradecanoyl-D-asparagine. The resulting tetradecanoyl-D-asparagine (1 equiv) is treated with EDCl (1.1 equiv), HOBt (1.1 equiv), and 4-bromophenyl (S)-4-amino-2-methylbutanoate (1.1 equiv.) to afford the title compound.

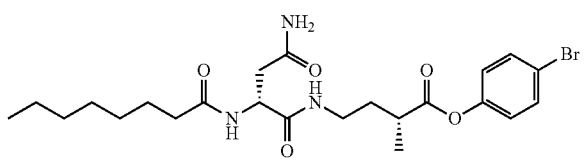 [SMILES: CCCCCCCC(=O)N[C@H](CC(N)=O)C(=O)NCC[C@@H](C)C(=O)Oc1ccc(Br)cc1]

Example 64: 4-bromophenyl (R)-4-((R)-4-amino-2-octanamido-4-oxobutanamido)-2-methylbutanoate This compound may be synthesized according to the experimental procedure described for Example 63.

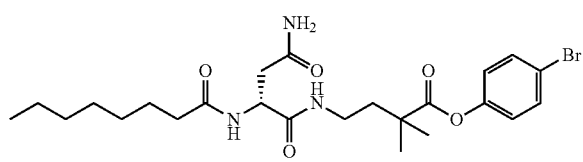 [SMILES: CCCCCCCC(=O)N[C@H](CC(N)=O)C(=O)NCCC(C)(C)C(=O)Oc1ccc(Br)cc1]

Example 65: 4-bromophenyl (R)-4-(4-amino-2-octanamido-4-oxobutanamido)-2,2-dimethylbutanoate This compound may be synthesized according to the experimental procedure described for Example 63.

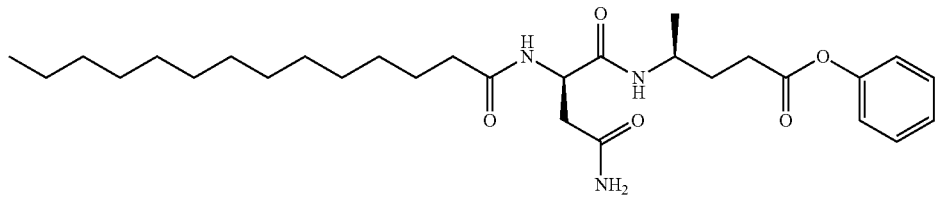 [SMILES: CCCCCCCCCCCCCC(=O)N[C@H](CC(N)=O)C(=O)N[C@@H](C)CCC(=O)Oc1ccccc1]

Example 66: phenyl (S)-4-((R)-4-amino-4-oxo-2-tetradecanamidobutanamido)pentanoate Step 1:

To a mixture of tert-butyl N-[(1S)-1-methyl-2-oxo-ethyl] carbamate (5 g, 28.9 mmol, 1 equiv.) in toluene (50 mL) was added methyl 2-(triphenyl-phosphanylidene) acetate (9.65 g, 28.9 mmol, 1 equiv.), and the mixture was stirred at 25° C. for 12 h under $N_2$ atmosphere. The reaction mixture was concentrated under reduced pressure and the residue was purified by column chromatography ($SiO_2$, petroleum ether/ethyl acetate=10:1 to 4:1) to give methyl (E,4S)-4-(tert-butoxycarbonylamino)pent-2-enoate (6 g, 91%) as a light yellow oil.

Step 2:

To a mixture of methyl (E,4S)-4-(tert-butoxycarbonylamino)pent-2-enoate (300 mg, 1.31 mmol) in DCM (2.5 mL) was added TFA (0.5 mL), and then the mixture was stirred at 25° C. for 1 h under $N_2$ atmosphere. The reaction mixture was concentrated under reduced pressure to give methyl (E,4S)-4-aminopent-2-enoate trifluoroacetate (200 mg, 63%) as a yellow oil. It was used into the next step without further purification.

Step 3:

A mixture of methyl (E,4S)-4-aminopent-2-enoate trifluoroacetate (200 mg, 1.21 mmol, 1 equiv.), HOBt (179 mg, 1.33 mmol, 1.1 equiv.), TEA (269 mg, 2.66 mmol, 370 μL, 2.2 equiv.) in DMF (10 mL) was cooled to 0° C. EDCl (255 mg, 1.33 mmol, 1.1 equiv.) and (2R)-4-amino-2-(tert-butoxycarbonylamino)-4-oxo-butanoic acid (337 mg, 1.45 mmol, 1.2 equiv.) was added to the mixture and the reaction mixture was stirred at 0° C. for 15 min and then warmed to 25° C. for 12 h. The reaction mixture was filtered and concentrated under reduced pressure. The residue was purified by prep-HPLC (column: Phenomenex luna C18 250*50 mm*10 um; mobile phase: [water (0.1% TFA)-ACN]; B %: 15%-45%, 20 min) to give methyl (E,4S)-4-[[(2R)-4-amino-2-(tert-butoxycarbonylamino)-4-oxo-butanoyl]amino] pent-2-enoate (350 mg, 84%) as a white solid.

Step 4:

A mixture of methyl (4S)-4-[[(2R)-4-amino-2-(tert-butoxycarbonylamino)-4-oxo-butanoyl]amino]pentanoate (80 mg, 232 μmol, 1 equiv.) in HCl/dioxane (2 M, 2.32 mL, 20 equiv.) was stirred at 25° C. for 1 h under $N_2$ atmosphere. The reaction mixture was concentrated under reduced pressure to give methyl (4S)-4-[[(2R)-2,4-diamino-4-oxo-butanoyl]amino]pentanoate hydrochloride (30 mg) as a white solid. It was used into the next step without further purification.

Step 5:

To a solution of methyl (4S)-4-[[(2R)-2,4-diamino-4-oxo-butanoyl]amino]pentanoate hydrochloride (30 mg, 106 μmol, 1 equiv.) in DCM (3 mL) was added TEA (22 mg, 213 μmol, 29.6 μL, 2 equiv.). The reaction mixture was then cooled to 0° C., and tetradecanoyl chloride (29 mg, 117 μmol, 1.1 equiv.) was added. The mixture was stirred at 25° C. for 12 h under $N_2$. The reaction mixture was concentrated under reduced pressure to give methyl (4S)-4-[[(2R)-4-amino-4-oxo-2-(tetradecanoylamino)butanoyl]amino]pentanoate as a white solid which was used without further purification.

Step 6:

To a mixture of methyl (4S)-4-[[(2R)-4-amino-4-oxo-2-(tetradecanoylamino)butanoyl]amino]pentanoate (195 mg, 428 μmol, 1 equiv.) in MeOH (3 mL) and $H_2O$ (1 mL) was added LiOH·$H_2O$ (36 mg, 856 μmol, 2 equiv.), and then the mixture was stirred at 25° C. for 5 h. To the reaction mixture was added 2N HCl to adjust pH4, and then filtered and the filtrate was concentrated under reduced pressure to give a residue. (4S)-4-[[(2R)-4-amino-4-oxo-2-(tetradecanoylamino)butanoyl] amino]pentanoic acid (150 mg, 79%) was obtained as a white solid. It was used into the next step without further purification.

Step 7:

To a solution of (4S)-4-[[(2R)-4-amino-4-oxo-2-(tetradecanoylamino)butanoyl]amino]pentanoic acid (120 mg, 271 μmol, 1 equiv.) and phenol (43 mg, 462 μmol, 40.6 μL, 1.7 equiv.) in DMF (2 mL) was added DMAP (16.6 mg, 136 μmol, 0.5 equiv.). The reaction mixture was then cooled to 0° C. and EDCl (57.3 mg, 299 μmol, 1.1 equiv.) was added. The mixture was stirred at 25° C. for 12 h under $N_2$. The reaction mixture was filtered and concentrated under reduced pressure. The residue was purified by prep-HPLC (column: Waters Xbridge Prep OBD C18 150*30 mm 5 um; mobile phase: [water (0.1% TFA)-ACN]; B %: 60%-90%, 10 min) to give phenyl (S)-4-((R)-4-amino-4-oxo-2-tetradecanamidobutanamido)pentanoate (35.6 mg, 19%) as a white solid. LCMS (M+H)$^+$518.3 $^1$H NMR (400 MHz, Methanol-d4) δ 7.44-7.35 (m, 2H), 7.29-7.20 (m, 1H), 7.18-7.07 (m, 2H), 4.67 (t, J=6.8 Hz, 1H), 4.06-4.01 (m, 1H), 2.71 (dd, J=15.4, 6.5 Hz, 1H), 2.69-2.58 (m, 3H), 2.27-2.19 (m, 2H), 2.02-1.89 (m, 1H), 1.87-1.74 (m, 1H), 1.65-1.55 (m, 2H), 1.32-1.25 (m, 20H), 1.21 (d, J=6.7 Hz, 3H), 0.92 (t, J=6.8 Hz, 3H).

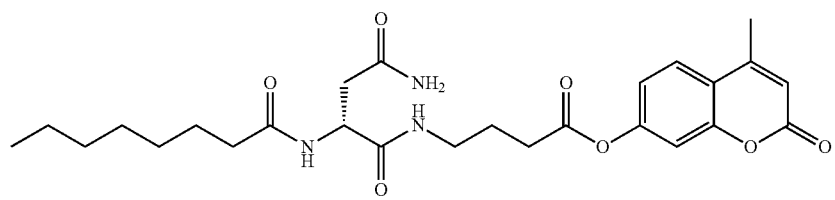 [SMILES: CCCCCCCC(=O)N[C@H](CC(N)=O)C(=O)NCCCC(=O)Oc1ccc2c(C)cc(=O)oc2c1]

Example 67: 4-methyl-2-oxo-2H-chromen-7-yl (R)-4-(4-amino-2-octanamido-4-oxobutanamido)butanoate Step 1:

A mixture of (2R)-4-amino-2-(octanoylamino)-4-oxo-butanoic acid (1000 mg, 3.87 mmol, 1.83 equiv.), methyl 4-aminobutanoate hydrochloride (324 mg, 2.11 mmol, 1 equiv.), EDCl (445 mg, 2.32 mmol, 1.1 equiv.), HOBt (314 mg, 2.32 mmol, 1.1 equiv.) and TEA (427 mg, 4.22 mmol, 588 µL, 2 equiv.) in DMF (10 mL) was stirred at 0° C. for 0.5 h and then at 25° C. for 9.5 hr under $N_2$ atmosphere. The reaction mixture was diluted with $H_2O$ (100 mL) and extracted twice with EtOAc (30 mL). The combined organic layers were washed with brine (20 mL), dried over $Na_2SO_4$, filtered and concentrated under reduced pressure to give methyl 4-[[(2R)-4-amino-2-(octanoylamino)-4-oxo-butanoyl]amino]butanoate (600 mg, crude) as a yellow solid which was used directly for next step.

Step 2:

To a mixture of methyl 4-[[(2R)-4-amino-2-(octanoy-lamino)-4-oxo-butanoyl]amino]butanoate (600 mg, 1.68 mmol, 1 equiv.) in THF (5 mL) and $H_2O$ (5 mL) was added LiOH·$H_2O$ (141 mg, 3.36 mmol, 2 equiv.) at 0° C. The mixture was stirred at 25° C. for 2 hr under $N_2$ atmosphere. The reaction mixture was acidified with 1N HCl to pH=4. The precipitate was collected by filtration and dried to give 4-[[(2R)-4-amino-2-(octanoylamino)-4-oxo-butanoyl] amino]butanoic acid (300 mg) as a white solid.

Step 3:

A mixture of 4-[[(2R)-4-amino-2-(octanoylamino)-4-oxo-butanoyl]amino]butanoic acid (300 mg, 874 µmol, 1 equiv.), 7-hydroxy-4-methyl-chromen-2-one (154 mg, 874 µmol, 1 equiv.), EDCl (184 mg, 961 µmol, 1.1 equiv.), DMAP (53 mg, 437 µmol, 0.5 equiv.) in DMF (5 mL) was stirred at 0° C. for 0.5 h, and then at 25° C. for 10 h under $N_2$ atmosphere. The mixture was purified by prep-HPLC (column: Nano-Micro UniSil 5-100 C18 ULTRA 100*250 mm 5 um; mobile phase: [water (0.1% TFA)-ACN]; B %: 33%-48%, 10 min) to give 4-methyl-2-oxo-2H-chromen-7-yl (R)-4-(4-amino-2-octanamido-4-oxobutanamido)butanoate (30 mg, 6.5%) as a white solid.

LCMS: (M+H$^+$) 502.3;

$^1$H NMR (400 MHz, DMSO-d6) δ 7.94 (d, 1H), 7.83 (t, 1H), 7.80 (d, 1H), 7.30-7.22 (m, 2H), 7.16 (dd, 1H), 6.83 (s, 1H), 6.37 (s, 1H), 4.46 (q, 1H), 3.12 (q, 2H), 2.58 (t, 2H), 2.41 (s, 3H), 2.45-2.30 (m, 2H), 2.06 (t, 2H), 1.72 (t, 2H), 1.43 (s, 2H), 1.36 (d, 1H), 1.18 (m, 8H), 0.80 (t, 3H).

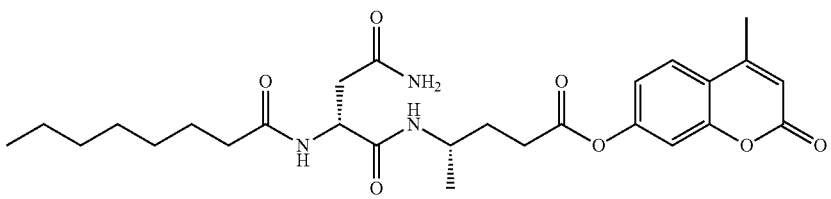 [SMILES: CCCCCCCC(=O)N[C@H](CC(N)=O)C(=O)N[C@@H](C)CCC(=O)Oc1ccc2c(C)cc(=O)oc2c1]

Example 68: 4-methyl-2-oxo-2H-chromen-7-yl (S)-4-((R)-4-amino-2-octanamido-4-oxobutanamido)pentanoate Step 1:

A mixture of (2R)-4-amino-2-(octanoylamino)-4-oxo-butanoic acid (1 g, 3.87 mmol, 1 equiv.), methyl (E,4S)-4-aminopent-2-enoate trifluoroacetate (941 mg, 3.87 mmol, 1 equiv.), EDCl (816 mg, 4.26 mmol, 1.1 equiv.), HOBt (575 mg, 4.26 mmol, 1.1 equiv.) and TEA (783 mg, 7.74 mmol, 1.08 mL, 2 equiv.) in DMF (15 mL) was degassed and purged with $N_2$ times at 0° C., and then the mixture was stirred at 20° C. for 10 hr under $N_2$ atmosphere. The reaction mixture was concentrated under reduced pressure to remove DMF. The residue was diluted with $H_2O$ (60 mL) and extracted three times with EtOAc (20 mL). The combined organic layers were washed with brine (20 mL), dried over $Na_2SO_4$, filtered and concentrated under reduced pressure. The residue was purified by column chromatography (SiO$_2$, ethyl acetate/methanol=10/1 to 1:1) to give methyl (E,4S)-4-[[(2R)-4-amino-2-(octanoylamino)-4-oxo-butanoyl]amino]pent-2-enoate (1.2 g, 84%) as a white solid.

Step 2:

A mixture of methyl (E,4S)-4-[[(2R)-4-amino-2-(oc-tanoylamino)-4-oxo-butanoyl]amino]pent-2-enoate (1.2 g, 3.25 mmol, 1 equiv.), 10% Pd/C (400 mg, 541 µmol) in MeOH (100 mL) was degassed and purged with $H_2$ for 3 times, and then the mixture was stirred at 20° C. for 10 hr under $H_2$ atmosphere at 15 psi. The reaction mixture was filtered and concentrated under reduced pressure to give methyl (4S)-4-[[(2R)-4-amino-2-(octanoylamino)-4-oxo-butanoyl]amino] pentanoate (800 mg) as a yellow solid.

Step 3:

To methyl (4S)-4-[[(2R)-4-amino-2-(octanoylamino)-4-oxo-butanoyl]amino]pentanoate (800 mg, 2.15 mmol, 1 equiv.) in THF (5 mL) and $H_2O$ (5 mL) was added LiOH·$H_2O$ (136 mg, 3.23 mmol, 1.5 equiv.) at 0° C., and then the mixture was stirred at 20° C. for 5 hr under $N_2$ atmosphere. The reaction mixture was acidified with aqueous HCl (1 M) to pH=4~5. The precipitate was collected by filtration and purified by prep-HPLC (column: Xbridge 150*30 mm*10 um; mobile phase: [water (0.1% TFA)-ACN]; B %: 10%-40%, 10 min) to give (4S)-4-[[(2R)-4-amino-2-(octanoylamino)-4-oxo-butanoyl]amino]pentanoic acid (400 mg, 52%) as a white solid.

Step 4:

To a mixture of (4S)-4-[[(2R)-4-amino-2-(octanoylamino)-4-oxo-butanoyl]amino]pentanoic acid (300 mg, 839 µmol, 1 equiv.), 7-hydroxy-4-methyl-chromen-2-one (148 mg, 839 µmol, 1 equiv.), EDCl (177 mg, 923 µmol, 1.1 equiv.) in DMF (10 mL) was added DMAP (51 mg, 420 µmol, 0.5 equiv.) at 20° C. and then the mixture was stirred at 20° C. for 10 hr under N$_2$ atmosphere. The mixture was purified by prep-HPLC (column: Welch Ultimate AQ-C18 150*30 mm*5 um; mobile phase: [water (0.1% TFA)-ACN]; B %: 32%-62%, 12 min) to give 4-methyl-2-oxo-2H-chromen-7-yl (S)-4-((R)-4-amino-2-octanamido-4-oxobutanamido)pentanoate (70 mg, 16%) as a white solid. LCMS: (M+H$^+$) 516.3

$^1$H NMR (400 MHz, DMSO-d6) δ 7.79 (d, 1H), 7.67 (d, 1H), 7.34 (d, 1H), 7.20 (d, 1H), 7.15 (dd, 1H), 7.07 (s, 1H), 6.63 (s, 1H), 6.33 (s, 1H), 4.49 (q, 1H), 3.87 (m, 1H), 2.64-2.56 (m, 2H), 2.43 (s, 3H), 2.10 (t, 2H), 1.89-1.66 (m, 2H), 1.48 (m, 2H), 1.23 (d, 10H), 1.09 (d, 3H), 0.88-0.78 (m, 3H).

Example 69: 4-methyl-2-oxo-2H-chromen-7-yl (R)-(2-(4-amino-2-octanamido-4-oxobutanamido)ethyl)carbamate Step 1:

A mixture of (2R)-4-amino-2-(octanoylamino)-4-oxo-butanoic acid (500 mg, 1.94 mmol, 1.1 equiv.), HOBt (262 mg, 1.94 mmol, 1.1 equiv.), TEA (392 mg, 3.87 mmol, 539 µL, 2.2 equiv.) and EDCl (371 mg, 1.94 mmol, 1.1 equiv.) in DMF (5 mL) was stirred at 0° C. under N$_2$ atmosphere. Then tert-butyl N-(2-aminoethyl)carbamate (282 mg, 1.76 mmol, 276 µL, 1 equiv.) was added at 0° C. and the mixture was stirred at 15° C. for 10 hours under N$_2$ atmosphere. The reaction mixture was diluted with H$_2$O (20 mL) and extracted three times with EtOAc (20 mL). The combined organic layers were dried over Na$_2$SO$_4$, filtered and concentrated under reduced pressure to give tert-butyl N-[2-[[(2R)-4-amino-2-(octanoylamino)-4-oxo-butanoyl]amino]ethyl]carbamate (0.66 g) as a yellow solid.

Step 2:

A mixture of tert-butyl N-[2-[[(2R)-4-amino-2-(octanoylamino)-4-oxo-butanoyl]amino]ethyl]carbamate (660 mg, 1.65 mmol) in HCl/EtOAc (100 mL, 4M) was stirred at 15° C. for 2 hr under N$_2$ atmosphere. The reaction mixture was concentrated under reduced pressure. The residue was triturated with EtOAc (40 mL) at 15° C. for 30 min. The mixture was filtered, and the filter cake was dried under reduced pressure to give (2R)—N-(2-aminoethyl)-2-(octanoylamino)butanediamide hydrochloride (440 mg) as a yellow solid.

Step 3:

A mixture of bis(trichloromethyl) carbonate (100 mg, 337 µmol, 0.33 equiv.) in DCM (8 mL) was slowly added to 7-hydroxy-4-methyl-chromen-2-one (180 mg, 1.02 mmol, 1 equiv.) and DIPEA (132 mg, 1.02 mmol, 178 µL, 1 equiv.) in THF (8 mL). The mixture was stirred at 0° C. for 2 hr under N$_2$ atmosphere. Compound (4-methyl-2-oxo-chromen-7-yl) carbonochloridate (115 mg, 481 µmol, 47.1% yield) was obtained as a white liquid. The crude product (4-methyl-2-oxo-chromen-7-yl) carbonochloridate (115 mg, 47%) was used into the next step without further purification.

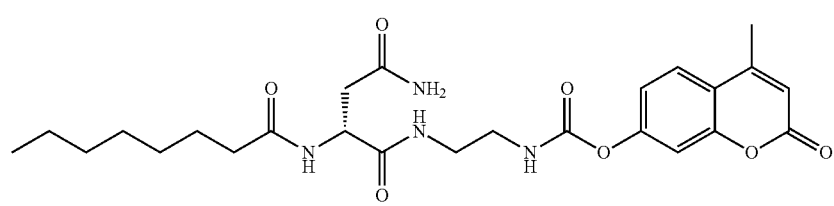 [SMILES: CCCCCCCC(=O)N[C@H](CC(N)=O)C(=O)NCCNC(=O)Oc1ccc2c(C)cc(=O)oc2c1]

Step 4:

To a mixture of (2R)—N-(2-aminoethyl)-2-(octanoylamino)butanediamide hydrochloride (114 mg, 338 µmol, 1 equiv.) and DIPEA (87.5 mg, 677 µmol, 118 µL, 2 equiv.) in DMF (5 mL) was added (4-methyl-2-oxo-chromen-7-yl) carbonochloridate (81 mg, 338 µmol, 1 equiv.) at 15° C., and then the mixture was stirred at 15° C. for 10 hr under N$_2$ atmosphere. The reaction mixture was filtered and the filter cake was purified by prep-HPLC (column: Welch Ultimate AQ-C18 150*30 mm*5 um; mobile phase: [water (0.1% TFA)-ACN]; B %: 30%-60%, 12 min) to give 4-methyl-2-oxo-2H-chromen-7-yl (R)-(2-(4-amino-2-octanamido-4-oxobutanamido)ethyl)carbamate (20 mg, 95%) as a white solid. LCMS: (M+H$^+$) 503.4. $^1$H NMR (400 MHz, DMSO-d6) δ 7.92 (d, 1H), 7.86 (d, 1H), 7.78 (d, 1H), 7.27 (s, 1H), 7.23 (d, 1H), 7.17 (dd, 1H), 6.86 (s, 1H), 6.36 (d, 1H), 4.49 (td, 1H), 3.25-3.08 (m, 4H), 2.43 (d, 3H), 2.41-2.33 (m, 2H), 2.08 (t, 2H), 1.46 (d, 2H), 1.26-1.17 (m, 8H), 0.84 (t, 3H).

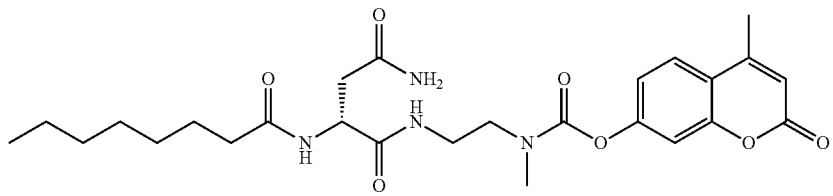 [SMILES: CCCCCCCC(=O)N[C@H](CC(N)=O)C(=O)NCCN(C)C(=O)Oc1ccc2c(C)cc(=O)oc2c1]

Example 70: 4-methyl-2-oxo-2H-chromen-7-yl (R)-(2-(4-amino-2-octanamido-4-oxobutanamido)ethyl)(methyl)carbamate Step 1:

A mixture of (2R)-4-amino-2-(octanoylamino)-4-oxo-butanoic acid (500 mg, 1.94 mmol, 1.1 equiv.), HOBt (262 mg, 1.94 mmol, 1.1 equiv.), EDCl (371 mg, 1.94 mmol, 1.1 equiv.) and TEA (392 mg, 3.87 mmol, 539 μL, 2.2 equiv.) in DMF (5 mL) was degassed and purged with $N_2$ 3 times. tert-Butyl N-(2-aminoethyl)-N-methyl-carbamate (307 mg, 1.76 mmol, 314 μL, 1 equiv.) was added to the mixture at 0° C. under $N_2$ and the mixture was stirred at 15° C. for 10 hr under $N_2$ atmosphere. The reaction mixture was diluted with $H_2O$ (20 mL) and extracted three times with EtOAc (20 mL). The combined organic layers were dried over $Na_2SO_4$, filtered and concentrated under reduced pressure to give tert-butyl N-[2-[[(2R)-4-amino-2-(octanoylamino)-4-oxo-butanoyl]amino]ethyl]-N-methyl-carbamate (0.66 g) as a yellow solid.

Step 2:

A mixture of tert-butyl N-[2-[[(2R)-4-amino-2-(octanoylamino)-4-oxo-butanoyl]amino]ethyl]-N-methyl-carbamate (660 mg, 1.59 mmol, 1 equiv.) in HCl/EtOAc (100 mL, 4 M) was stirred at 15° C. for 2 hr under $N_2$ atmosphere. The reaction mixture was concentrated under reduced pressure and the residue was triturated with EtOAc 40 mL at 15° C. for 30 min. The solid product was collected by filtration and dried to give (2R)—N-[2-(methylamino)ethyl]-2-(octanoylamino)butanediamide hydrochloride (460 mg) as a yellow solid.

Step 3:

A mixture of (2R)—N-[2-(methylamino)ethyl]-2-(octanoylamino)butanediamide hydrochloride (100 mg, 285 μmol, 1 equiv.) and DIPEA (55 mg, 427 μmol, 74.4 μL, 1.5 equiv.) in DMF (5 mL) was added (4-methyl-2-oxo-chromen-7-yl) carbonochloridate (68 mg, 284 μmol, 1 equiv.) at 15° C., and then the mixture was stirred at 15° C. for 10 hr under $N_2$ atmosphere. The reaction mixture was filtered and concentrated under reduced pressure. The residue was purified by prep-HPLC (column: Phenomenex Luna C18 200*40 mm*10 um; mobile phase: [water (0.1% TFA)-ACN]; B %: 30%-50%, 10 min) to give 4-methyl-2-oxo-2H-chromen-7-yl (R)-(2-(4-amino-2-octanamido-4-oxobutanamido)ethyl)(methyl)carbamate (6 mg, 4%) as a white solid.

LCMS: (M+H+) 517.3

$^1$H NMR (400 MHz, Methanol-d4) δ 7.79 (dd, 1H), 7.28-7.17 (m, 2H), 6.31 (s, 1H), 4.69 (q, 1H), 3.62-3.41 (m, 4H), 3.09 (d, 3H), 2.75-2.56 (m, 2H), 2.48 (d, 3H), 2.17 (dt, 2H), 1.58-1.50 (m, 2H), 1.26 (d, 8H), 0.87 (td, 3H).

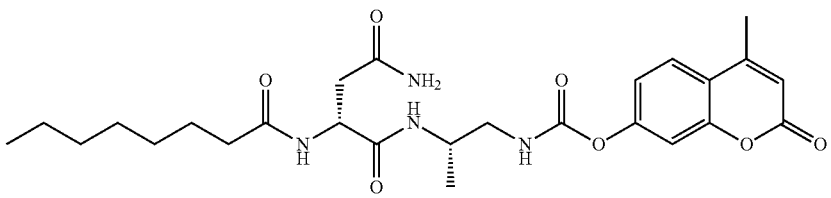 [SMILES: CCCCCCCC(=O)N[C@H](CC(N)=O)C(=O)N[C@@H](C)CNC(=O)Oc1ccc2c(C)cc(=O)oc2c1]

Example 71: 4-methyl-2-oxo-2H-chromen-7-yl ((S)-2-((R)-4-amino-2-octanamido-4-oxobutanamido)propyl)carbamate Step 1:

To a mixture of (2R)-4-amino-2-(octanoylamino)-4-oxo-butanoic acid (500 mg, 1.94 mmol, 1.1 equiv.) in DMF (5 mL) was added HOBt (262 mg, 1.94 mmol, 1.1 equiv.), TEA (392 mg, 3.87 mmol, 539 μL, 2.2 equiv.) and EDCl (371 mg, 1.94 mmol, 1.1 equiv.) in one portion at 0° C. under $N_2$. Then tert-butyl N-[(2S)-2-aminopropyl]carbamate (307 mg, 1.76 mmol, 1 equiv.) was added and the mixture was stirred at 15° C. for 10 hours under $N_2$. The reaction mixture was diluted with $H_2O$ (20 mL) and extracted five times with EtOAc (20 mL). The combined organic layers were washed with brine (20 mL), dried over $Na_2SO_4$, filtered and concentrated under reduced pressure to give tert-butyl N-[(2S)-2-[[(2R)-4-amino-2-(octanoylamino)-4-oxo-butanoyl]amino]propyl]carbamate (620 mg, crude) as a white solid.

Step 2:

A mixture of tert-butyl N-[(2S)-2-[[(2R)-4-amino-2-(octanoylamino)-4-oxo-butanoyl]amino]propyl]carbamate (620 mg, 1.50 mmol, 1 equiv.) in 4 M HCl/EtOAc (100 mL) was stirred at 15° C. for 2 hr under $N_2$ atmosphere. The reaction mixture was concentrated under reduced pressure. The residue was triturated in EtOAc (40 mL) at 15° C. for 30 min. The solid material was collected by filtration and dried to give (2R)—N-[(1S)-2-amino-1-methyl-ethyl]-2-(octanoylamino)butanediamide hydrochloride (480 mg).

Step 3:

To bis(trichloromethyl) carbonate (56 mg, 189 μmol, 0.33 equiv.) in DCM (5 mL) was slowly added 7-hydroxy-4-methyl-chromen-2-one (101 mg, 570 μmol, 1 equiv.) and DIPEA (74 mg, 570 μmol, 100 μL, 1 equiv.) in THF (5 mL) at 0° C. and the mixture was stirred at 15° C. for 2 hr under $N_2$ atmosphere. The solution of (4-methyl-2-oxo-chromen- 7-yl) carbonochloridate was (10 mL, 0.056 M in DCM and THF). was used into the next step without further purification.

Step 4:

To a mixture of (2R)—N-[(1S)-2-amino-1-methyl-ethyl]-2-(octanoylamino)butanediamide hydrochloride (200 mg, 570 µmol, 1 equiv.) and DIPEA (147 mg, 1.14 mmol, 199 µL, 2 equiv.) in DMF (5 mL) was added the solution of (4-methyl-2-oxo-chromen-7-yl) carbonochloridate (570 µmol, 10 mL, 1 equiv.) at 15° C., and then the mixture was stirred at 15° C. for 10 hr under N₂ atmosphere. The reaction mixture was filtered to give a liquid, which was purified by prep-HPLC (column: Xbridge 150*30 mm*10 um; mobile phase: [water (0.1% TFA)-ACN]; B %: 25%-55%, 10 min). (4-Methyl-2-oxo-chromen-7-yl)N-[(2S)-2-[[(2R)-4-amino-2-(octanoylamino)-4-oxo-butanoyl]amino]propyl]carbamate (10 mg, 2.7% yield) was obtained as a white solid.

LCMS: (M+H$^+$) 517.3

$^1$H NMR (400 MHz, DMSO-d6) δ 7.89 (d, 1H), 7.82-7.72 (m, 1H), 7.68-7.58 (m, 1H), 7.28 (s, 1H), 7.22 (d, 1H), 7.15 (d, 1H), 6.87 (s, 1H), 6.35 (s, 1H), 4.44 (d, 1H), 3.89 (s, 1H), 3.12 (s, 2H), 2.42 (s, 3H), 2.36 (d, 2H), 2.03 (t, 2H), 1.43-1.39 (m, 2H), 1.24-1.12 (m, 10H), 1.03 (d, 3H), 0.81 (q, 3H)

chromen-7-yl) 4-amino-2,2-dimethyl-butanoate hydrochloride (350 mg, 70%) as a white solid.

Step 3:

A mixture of (4-methyl-2-oxo-chromen-7-yl) 4-amino-2,2-dimethyl-butanoate hydrochloride (50 mg, 150 µmol, 1 equiv.), (2R)-2-(tert-butoxycarbonylamino)-4-oxo-4-(tritylamino)butanoic acid (87 mg, 180 µmol, 1.2 equiv.), DCC (48 mg, 230 µmol, 47 µL, 1.5 equiv.), DMAP (9.4 mg, 77 µmol, 0.5 equiv.) in DCM (5 mL) was stirred at 15° C. for 2 hr under N₂ atmosphere. The reaction mixture was concentrated and purified by prep-HPLC (column: Luna C18 100*30 5u; mobile phase: [water (0.1% TFA)-ACN]; B %: 55%-75%, 12 min). Then the product was further purified by prep-TLC (SiO₂, petroleum ether/ethyl acetate=1:1) to give (4-methyl-2-oxo-chromen-7-yl) 4-[[(2R)-2-(tert-butoxycarbonylamino)-4-oxo-4-(tritylamino)butanoyl]amino]-2,2-dimethyl-butanoate (7 mg, 6%) as a white solid.

Step 4:

A mixture of (4-methyl-2-oxo-chromen-7-yl) 4-[[(2R)-2-(tert-butoxycarbonylamino)-4-oxo-4-(tritylamino)butanoyl]

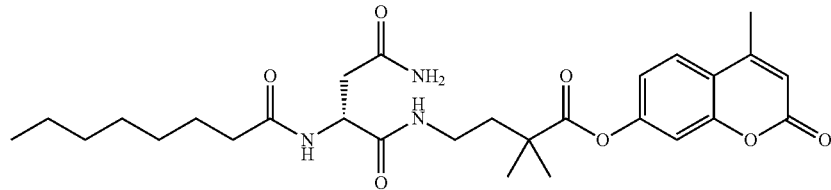 [SMILES: CCCCCCCC(=O)N[C@H](CC(N)=O)C(=O)NCCC(C)(C)C(=O)Oc1ccc2c(C)cc(=O)oc2c1]

Example 72A: 4-methyl-2-oxo-2H-chromen-7-yl (R)-4-(4-amino-2-octanamido-4-oxobutanamido)-2,2-dimethylbutanoate Step 1:

To a mixture of 7-hydroxy-4-methyl-chromen-2-one (500 mg, 2.84 mmol, 1 equiv.), 4-(tert-butoxycarbonylamino)-2,2-dimethyl-butanoic acid (788 mg, 3.41 mmol, 1.2 equiv.), HOBt (422 mg, 3.12 mmol, 1.1 equiv.), TEA (632 mg, 6.24 mmol, 869 µL, 2.2 equiv.) in DMF (5 mL) was added EDCl (599 mg, 3.12 mmol, 1.1 equiv.) at 0° C. The mixture was stirred at 15° C. for 12 hr. The reaction mixture was diluted with H₂O (20 mL) and extracted three times with ethyl acetate (20 mL). The combined organic layers were washed with brine (20 mL), dried over anhydrous sodium sulfate, filtered and the filtrate was concentrated under reduced pressure The residue was purified by prep-TLC (SiO₂, petroleum ether/ethyl acetate=1:1) To give (4-methyl-2-oxo-chromen-7-yl) 4-(tert-butoxycarbonylamino)-2,2-dimethyl-butanoate (600 mg, 54%) as a white solid.

Step 2:

A mixture of (4-methyl-2-oxo-chromen-7-yl) 4-(tert-butoxycarbonylamino)-2,2-dimethyl-butanoate (600 mg, 1.54 mmol, 1 equiv.) in HCl/EtOAc (10 mL, 4 M) was stirred at 15° C. for 3 hr. The reaction mixture was concentrated under reduced pressure. The residue was washed twice with ethyl acetate (30 mL), and filtered to give (4-methyl-2-oxoamino]-2,2-dimethyl-butanoate (7 mg, 9 µmol, 1 equiv.) in TFA (0.25 mL) and DCM (1 mL) was stirred at 15° C. for 1 hr. To the mixture was added TFA (1 mL) and DCM (4 mL) and the mixture was stirred at 15° C. for 12 h. The reaction mixture was concentrated under to give (4-methyl-2-oxo-chromen-7-yl) 4-[[(2R)-2,4-diamino-4-oxo-butanoyl]amino]-2,2-dimethyl-butanoate trifluoroacetate (4 mg) as a white solid.

Step 5:

To a solution of (4-methyl-2-oxo-chromen-7-yl) 4-[[(2R)-2,4-diamino-4-oxo-butanoyl]amino]-2,2-dimethyl-butanoate trifluoroacetate (4.0 mg, 7.7 µmol, 1 equiv.) in DCM (3 mL) was added TEA (780 ug, 7.7 µmol, 1.08 µL, 1 equiv.) and octanoyl chloride (1.3 mg, 7.7 µmol, 1.3 µL, 1 equiv.) at 0° C. The mixture was stirred at 0° C. for 2 hr. The reaction mixture was concentrated and the residue was purified by prep-HPLC (column: Luna C18 100*30 5u; mobile phase: [water (0.1% TFA)-ACN]; B %: 40%-55%, 12 min) to give 4-methyl-2-oxo-2H-chromen-7-yl (R)-4-(4-amino-2-octanamido-4-oxobutanamido)-2,2-dimethylbutanoate (2.0 mg, 46%) as a white solid.

LCMS: (M+H$^+$): 530.3

$^1$H NMR (400 MHz, DMSO-d6) δ 7.91 (d, 1H), 7.82 (dd, 2H), 7.30 (d, 1H), 7.24 (s, 1H), 7.19 (dd, 1H), 6.83 (s, 1H), 6.39 (s, 1H), 4.48 (q, 1H), 3.10 (dt, 2H), 2.43 (s, 3H), 2.37-2.27 (m, 2H), 2.07 (t, 2H), 1.80-1.72 (m, 2H), 1.45 (q, 2H), 1.28 (s, 6H), 1.20 (m, 8H), 0.82 (t, 3H).

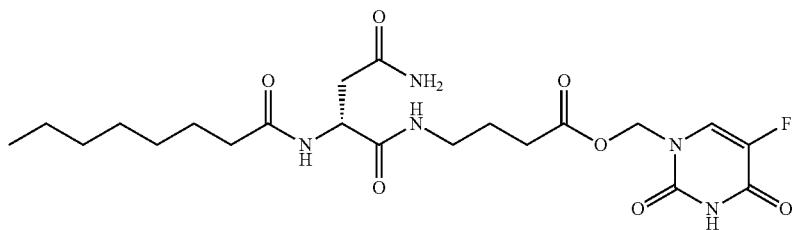 [SMILES: CCCCCCCC(=O)N[C@H](CC(N)=O)C(=O)NCCCC(=O)OCn1cc(F)c(=O)[nH]c1=O]

Example 72B: (5-fluoro-2,4-dioxo-3,4-dihydropyrimidin-1(2H)-yl)methyl (R)-4-(4-amino-2-octanamido-4-oxobutanamido)butanoate Step 1:
To a solution of (2R)-4-amino-2-(octanoylamino)-4-oxo-butanoic acid (5.00 g, 19.4 mmol, 1.1 equiv.) in DMF (40 mL) was added HOBt (2.6 g, 19 mmol, 1.1 equiv.), EDCl (3.71 g, 19.4 mmol, 1.1 equiv.), methyl 4-aminobutanoate (2.70 g, 17.6 mmol, 1 equiv., HCl) and TEA (3.92 g, 38.7 mmol, 5.39 mL, 2.2 equiv.) at 0° C. The mixture was stirred at 15° C. for 12 hr. The reaction mixture was quenched by addition H$_2$O (100 mL), ethyl acetate (100 mL), and filtered. The filter cake was dried to give methyl 4-[[(2R)-4-amino-2-(octanoylamino)-4-oxo-butanoyl]amino]butanoate (4.2 g, 67%) as a white solid.

Step 2:
To a solution of methyl 4-[[(2R)-4-amino-2-(octanoylamino)-4-oxo-butanoyl]amino]butanoate (2.20 g, 6.15 mmol, 1 equiv.) in H$_2$O (20 mL) and THF (20 mL) was added LiOH·H$_2$O (517 mg, 12.3 mmol, 2 equiv.) in H$_2$O (5 mL) at 0° C. The mixture was stirred at 0° C. for 2 hr. The reaction mixture was washed with ethyl acetate (30 mL). The combined water layers were acidified with 1N HCl to pH=4. The solid product was collected by filtration, and washed with H$_2$O (10 mL) and petroleum ether (10 mL) to give 4-[[(2R)-4-amino-2-(octanoylamino)-4-oxo-butanoyl] amino]butanoic acid (1.3 g, 62%) as a white solid. LCMS: (M+H+): 344.2 @ 1.112 min Step 3:
A mixture of 5-fluoro-1H-pyrimidine-2,4-dione (260 mg, 2.00 mmol, 1 equiv.) in methanal solution (1 mL, 37% in H$_2$O) was stirred at 60° C. for 2 hr under N$_2$ atmosphere. The reaction mixture was concentrated under reduced pressure to give 5-fluoro-1-(hydroxymethyl)pyrimidine-2,4-dione (300 mg) as a colorless oil.

Step 4:
To a solution of 4-[[(2R)-4-amino-2-(octanoylamino)-4-oxo-butanoyl]amino]butanoic acid (300 mg, 874 µmol, 1 equiv.) in DMF (5 mL) was added HOBt (130 mg, 961 µmol, 1.1 equiv.), EDCl (184 mg, 961 µmol, 1.1 equiv.), 5-fluoro-1-(hydroxymethyl)pyrimidine-2,4-dione (180 mg, 1.12 mmol, 1.29 equiv.) and TEA (194 mg, 1.92 mmol, 268 µL, 2.2 equiv.) at 0° C. The mixture was stirred at 15° C. for 12 hr. The reaction mixture was diluted with DMSO (5 mL) and purified by prep-HPLC (column: Waters Xbridge BEH C18 100*30 mm*10 um; mobile phase: [water (0.1% TFA)-ACN]; B %: 10%-40%, 10 min) to give (5-fluoro-2,4-dioxo-3,4-dihydropyrimidin-1 (2H)-yl)methyl (R)-4-(4-amino-2-octanamido-4-oxobutanamido)butanoate (10 mg, 2.3%) as a white solid. LCMS: (M+H+): 486.2 $^1$H NMR (400 MHz, Methanol-d4) δ 7.93 (d, 1H), 5.64 (s, 2H), 4.64 (t, 1H), 3.23 (q, 1H), 2.73-2.55 (m, 2H), 2.41 (t, 2H), 2.23 (t, 2H), 1.79 (m, 2H), 1.63- 1.56 (m, 2H), 1.31 (s, 8H), 0.93-0.86 (m, 3H).

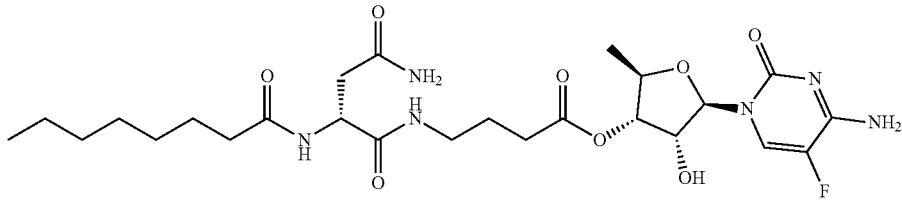 [SMILES: CCCCCCCC(=O)N[C@H](CC(N)=O)C(=O)NCCCC(=O)O[C@H]1[C@@H](O)[C@H](n2cc(F)c(N)nc2=O)O[C@@H]1C]

Example 73: (2R,3S,4R,5R)-5-(4-amino-5-fluoro-2-oxopyrimidin-1(2H)-yl)-4-hydroxy-2-methyltetrahydrofuran-3-yl 4-((R)-4-amino-2-octanamido-4-oxobutanamido)butanoate To a stirred solution of 4-[[(2R)-4-amino-2-(octanoylamino)-4-oxo-butanoyl]amino]butanoic acid (500 mg, 1.46 mmol, 1 equiv.) (as prepared in Steps 1-2 of Example 72) in DMF (5 mL) was added HOBt (216 mg, 1.60 mmol, 1.1 equiv.), EDCl (307 mg, 1.60 mmol, 1.1 equiv.), 4-amino-1-[(2R,3R,4S,5R)-3,4-dihydroxy-5-methyl-tetrahydrofuran-2-yl]-5-fluoro-pyrimidin-2-one (393 mg, 1.60 mmol, 1.1 equiv.) and TEA (324 mg, 3.20 mmol, 446 µL, 2.2 equiv.) at 0° C. The mixture was stirred at 15° C. for 12 hr. The reaction mixture was diluted with DMSO (5 mL) and purified by prep-HPLC (column: Xbridge 150*30 mm*10 um; mobile phase: [water (0.04% NH3H2O)-ACN]; B %: 10%-40%, 10 min. The product was further purified by prep-HPLC (column: Xbridge 150*30 mm*10 um; mobile phase: [water (0.1% TFA)-ACN]; B %: 10%-40%, 10 min) to give (2R,3S,4R,5R)-5-(4-amino-5-fluoro-2-oxopyrimidin-1(2H)-yl)-4-hydroxy-2-methyltetrahydrofuran-3-yl 4-((R)-4-amino-2-octanamido-4-oxobutanamido)butanoate (2 mg, 3%) as a white solid. LCMS: (M+H+): 571.3 $^1$H NMR (400 MHz, Methanol-d4) δ 7.87 (d, 1H), 5.86-5.81 (m, 1H), 4.81 (t, 1H), 4.66 (t, 1H), 4.41 (t, 1H), 4.21 (m, 1H), 3.26 (m, 2H), 2.66 (qd, 2H), 2.46 (m, 2H), 2.23 (m, 2H), 1.83 (q, 2H), 1.62-1.57 (m, 2H), 1.42 (d, 3H), 1.31 (s, 10H), 0.89 (t, 3H).

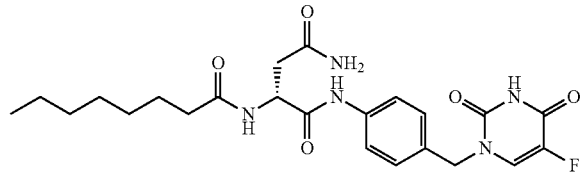 [SMILES: CCCCCCCC(=O)N[C@H](CC(N)=O)C(=O)Nc1ccc(Cn2cc(F)c(=O)[nH]c2=O)cc1]

mixture was concentrated and the residue was purified by prep-HPLC (column: Waters Xbridge BEH C18 100*30 mm*10 um; mobile phase: [water (0.1% TFA)-ACN]; B %: 20%-50%, 10 min) to give (2R)—N-[4-[(5-fluoro-2,4-dioxo-pyrimidin-1-yl)methyl]phenyl]-2-(octanoylamino)butanediamide (8 mg, 1.2%) as a white solid. LCMS: (M+H$^+$): 476.2 $^1$H NMR (400 MHz, DMSO-d6) δ 11.82 (d, 1H), 9.97 (s, 1H), 8.16 (d, 1H), 8.07 (d, 1H), 7.55 (d, 2H), 7.29 (s, 1H), 7.24 (d, 2H), 6.88 (s, 1H), 4.73 (m, 3H), 2.08 (m, 2H), 1.45 (m, 2H), 1.20 (m, 10H), 0.81 (t, 3H).

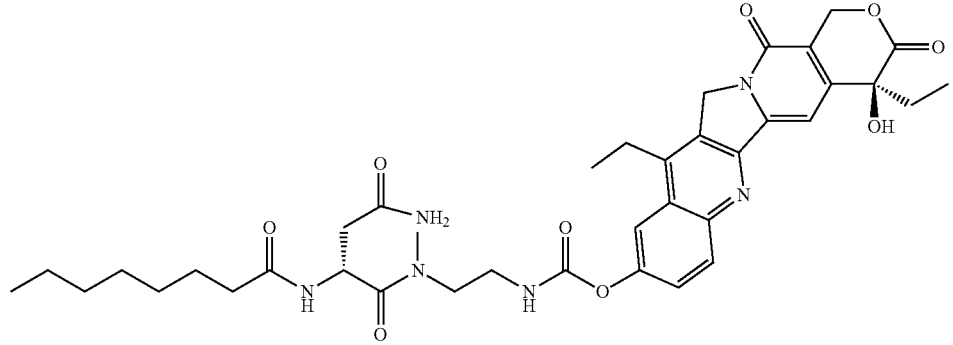 [SMILES: CCCCCCCC(=O)N[C@H](CC(N)=O)C(=O)N(C)CCNC(=O)Oc1ccc2nc3c(c(CC)c2c1)Cn1c-3cc2c(c1=O)COC(=O)[C@]2(O)CC]

Example 74: (R)—N1-(4-((5-fluoro-2,4-dioxo-3,4-dihydropyrimidin-1(2H)-yl)methyl)phenyl)-2-octanamidosuccinamide Step 1:

A mixture of 1-[(4-aminophenyl)methyl]-5-fluoro-pyrimidine-2,4-dione (430 mg, 1.83 mmol, 1 equiv.), (2R)-2-(tert-butoxycarbonylamino)-4-oxo-4-(tritylamino)butanoic acid (1.04 g, 2.19 mmol, 1.2 equiv.), DCC (566 mg, 2.74 mmol, 555 μL, 1.5 equiv.) and DMAP (112 mg, 914 μmol, 0.5 equiv.) in DCM (10 mL) was stirred at 15° C. for 2 hr under N$_2$ atmosphere. The reaction mixture was diluted with H$_2$O (20 mL) and extracted three times with ethyl acetate (30 mL). The combined organic layers were dried over anhydrous sodium sulfate, filtered and concentrated under reduced pressure. The residue was purified by prep-TLC (SiO$_2$, petroleum ether/ethyl acetate=0:1) to give tert-butyl N-[(1R)-1-[[4-[(5-fluoro-2,4-dioxo-pyrimidin-1-yl)methyl]phenyl]carbamoyl]-3-oxo-3-(tritylamino)propyl]carbamate (400 mg, 32%) as a white solid.

Step 2:

A mixture of tert-butyl N-[(1R)-1-[[4-[(5-fluoro-2,4-dioxo-pyrimidin-1-yl)methyl]phenyl] carbamoyl]-3-oxo-3-(tritylamino)propyl]carbamate (400 mg, 578 μmol, 1 equiv.) in DCM (8 mL) and TFA (2 mL) was stirred at 15° C. for 12 hr under N$_2$ atmosphere. Additional TFA (2 mL) was added and the mixture was stirred at 15° C. for 3 h. The mixture was concentrated under reduced pressure to give (2R)-2-amino-N-[4-[(5-fluoro-2,4-dioxo-pyrimidin-1-yl)methyl]phenyl]butanediamide trifluoroacetate (500 mg, crude) as a yellow solid.

Step 3:

To a solution of (2R)-2-amino-N-[4-[(5-fluoro-2,4-dioxo-pyrimidin-1-yl)methyl]phenyl]butanediamide trifluoroacetate (500 mg, 1.43 mmol, 1 equiv.) in DCM (10 mL) was added TEA (145 mg, 1.43 mmol, 199 μL, 1 equiv.) and octanoyl chloride (233 mg, 1.43 mmol, 244 μL, 1 equiv.) at 0° C. The mixture was stirred at 0° C. for 1 hr. The reaction

Example 75: (S)-4,11-diethyl-4-hydroxy-3,14-dioxo-3,4,12,14-tetrahydro-1H-pyrano[3',4':6,7]indolizino[1,2-b]quinolin-9-yl (2-((R)-4-amino-N-methyl-2-octanamido-4-oxobutanamido)ethyl) carbamate Step 1: To a stirred solution of N2-(((9H-fluoren-9-yl)methoxy)carbonyl)-N$_4$-trityl-D-asparagine (1.00 g, 1 equiv., 1.68 mmol), HATU (765 mg, 1.2 equiv., 2.01 mmol), 3H-[1,2,3]triazolo[4,5-b]pyridin-3-ol (274 mg, 1.2 equiv., 2.01 mmol) in 30 mL DMF under nitrogen, tert-butyl (2-(methylamino)ethyl)carbamate (584 mg, 2 equiv., 3.35 mmol) was added dropwise and the resulting solution was stirred for 5 minutes at room temperature DIEA (650 mg, 0.88 mL, 3 equiv., 5.03 mmol) was added and solution was stirred for 90 minutes at room temperature. Reaction was concentrated by rotary evaporation and residue was purified by reverse phase flash chromatography (0-100% acetonitrile/water with 0.1% TFA). Fractions were concentrated to (9H-fluoren-9-yl)methyl (R)-(7,13,13-trimethyl-3,6,11-trioxo-1,1,1-triphenyl-12-oxa-2,7,10-triazatetradecan-5-yl)carbamate (0.852 g, 66.3%) a white solid.

Step 2: tert-butyl (R)-(2-(2-((((9H-fluoren-9-yl)methoxy)carbonyl)amino)-N-methyl-4-oxo-4-(tritylamino)butanamido)ethyl)carbamate (0.852 g, 1 equiv., 1.13 mmol) was dissolved in 20 mL 2% DBU, 2% Piperidine, 96% DMF. Reaction was stirred at room temperature for 10 minutes, concentrated and residue was purified by reverse phase flash chromatography (0-100% acetonitrile/water with 0.1% TFA. Fractions were concentrated to tert-butyl (R)-(2-(2-amino-N-methyl-4-oxo-4-(tritylamino)butanamido)ethyl)carbamate, Trifluoracetate (770 mg, 89.9%) as a white solid.

Step 3: To a stirred solution of tert-butyl (R)-(2-(2-amino-N-methyl-4-oxo-4-(tritylamino)butanamido)ethyl)carbamate (380 mg, 1 equiv., 590 μmol) in 8 mL DMF at room temperature, octanoic anhydride (350 μL, 2 equiv.) was added followed by DIEA (310 μL, 3 equiv.). Reaction was stirred for 1 hour then was concentrated by rotary evaporation. Residue was purified by reverse phase chromatography (0-100% acetonitrile in water w/0.1% TFA). Fractions were concentrated to yield tert-butyl (R)-(2-(N-methyl-2-octanamido-4-oxo-4-(tritylamino)butanamido)ethyl)carbamate (340 mg, 85.8%) as a white solid.

Step 4: tert-butyl (R)-(2-(N-methyl-2-octanamido-4-oxo-4-(tritylamino)butanamido)ethyl)carbamate (310 mg, 1 equiv., 472 µmol) was dissolved in 4 mL 2.5% treithylsilane/2.5% water/5% DCM/95% trifluoroacetic acid and stirred at room temperature under nitrogen for 1 hour. Reaction was concentrated and residue was purified by reverse phase flash chromatography (10-95% acetonitrile in water with 0.1% TFA buffer). Fractions were combined and concentrated to yield (R)—N1-(2-aminoethyl)-N$_1$-methyl-2-octanamidosuccinamide (160 mg, 77.5%) as a white crystalline solid.

Step 5: Synthesized according to step 5 of Example 76.

Step 6: (S)-4,11-diethyl-4-hydroxy-3,14-dioxo-3,4,12,14-tetrahydro-1H-pyrano[3',4':6,7]indolizino[1,2-b]quinolin-9-yl (4-nitrophenyl) carbonate (71 mg, 1 equiv., 0.13 mmol) was dissolved in 3 mL anhydrous DMF and stirred under nitrogen at room temperature. A solution (R)—N1-(2-aminoethyl)-N1-methyl-2-octanamidosuccinamide trifluoroacetate (71 mg, 1.3 equiv., 0.17 mmol) in 2 mL DMF was added followed by N,N-dimethylpyridin-4-amine (37 mg, 2 equiv., 0.30 mmol). Reaction was stirred at room temperature for 30 minutes, concentrated, and residue was purified by reverse phase prep HPLC (0-95% acetonitrile in water w/0.1% TFA). Fractions were concentrated to yield (S)-4,11-diethyl-4-hydroxy-3,14-dioxo-3,4,12,14-tetrahydro-1H-pyrano[3',4':6,7]indolizino[1,2-b]quinolin-9-yl (2-((R)-4-amino-N-methyl-2-octanamido-4-oxobutanamido)ethyl)carbamate (52 mg, 56%) as a yellow solid.
LCMS: (M+H+): 733.3
$^1$H NMR (400 MHz, DMSO-d6) δ 8.14 (dd, 1H), 8.07-7.98 (m, 1H), 7.93 (dd, 1H), 7.76 (t, 1H), 7.63 (dd, 1H), 7.30 (s, 2H), 6.82 (s, 1H), 5.42 (s, 2H), 5.31 (s, 2H), 5.15-4.91 (m, 1H), 3.70-3.46 (m, 2H), 3.41-3.28 (m, 1H), 3.19 (m, HH), 2.95 (d, 3H) 2.61 (m, 1H), 2.25 (m, 1H), 2.11-1.94 (m, 2H), 1.94-1.73 (m, 2H), 1.41 (m, 2H), 1.28 (t, 3H), 1.17 (m, 8H), 0.86 (t, 3H), 0.79 (t, 3H).

ethyl)(methyl)carbamate (0.29 g, 0.30 mL, 2 equiv., 1.7 mmol) was added dropwise and the resulting solution was stirred for 5 minutes at room temperature. DIEA (0.32 g, 0.44 mL, 3 equiv., 2.5 mmol) was added and solution was stirred for 90 minutes at room temperature. Reaction was concentrated by rotary evaporation and residue was purified by reverse phase flash chromatography (0-100% acetonitrile/water with 0.1% TFA). Fractions were concentrated to yield tert-butyl (R)-(2-(2-((((9H-fluoren-9-yl)methoxy)carbonyl)amino)-4-oxo-4-(tritylamino)butanamido)ethyl)(methyl)carbamate (600 mg, 95%) as a white glassy solid.

Step 2: tert-butyl (R)-(2-(2-((((9H-fluoren-9-yl)methoxy)carbonyl)amino)-4-oxo-4-(tritylamino)butanamido)ethyl)(methyl)carbamate (600 mg, 1 equiv., 797 µmol) was dissolved in 20 mL 2% DBU, 2% Piperidine, 96% DMF. Reaction was stirred at room temperature for 10 minutes, concentrated and residue was purified by reverse phase flash chromatography (0-100% acetonitrile/water with 0.1% TFA. Fractions were concentrated to yield tert-butyl (R)-(2-(2-amino-4-oxo-4-(tritylamino)butanamido)ethyl)(methyl)carbamate (347 mg, 82.1%) as a white solid.

Step 3: To a stirred solution of tert-butyl (R)-(2-(2-amino-4-oxo-4-(tritylamino)butanamido)ethyl)(methyl)carbamate (347 mg, 1 equiv., 654 µmol) in 9 mL DMF under nitrogen at room temperature, octanoic anhydride (265 mg, 291 µL, 1.5 equiv., 981 µmol) was added followed by DIEA (338 mg, 457 µL, 4 equiv., 2.62 mmol). Reaction was stirred for 1 hour then was concentrated by rotary evaporation. Residue was purified by reverse phase chromatography (0-100% acetonitrile in water w/0.1% TFA). Fractions were concentrated to yield tert-butyl (R)-methyl(2-(2-octanamido-4-oxo-4-(tritylamino)butanamido)ethyl)carbamate (257 mg, 59.8%) as a white solid.

Step 4: tert-butyl (R)-methyl(2-(2-octanamido-4-oxo-4-(tritylamino)butanamido)ethyl)carbamate (257 mg, 1 equiv., 391 µmol) was dissolved in 4 mL 2.5% treithylsilane/2.5% water/5% DCM/95% trifluoroacetic acid and stirred at room temperature under nitrogen for 1 hour. Reaction was concentrated and residue was purified by reverse phase flash chromatography (10-95% acetonitrile in water with 0.1%

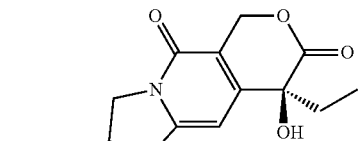

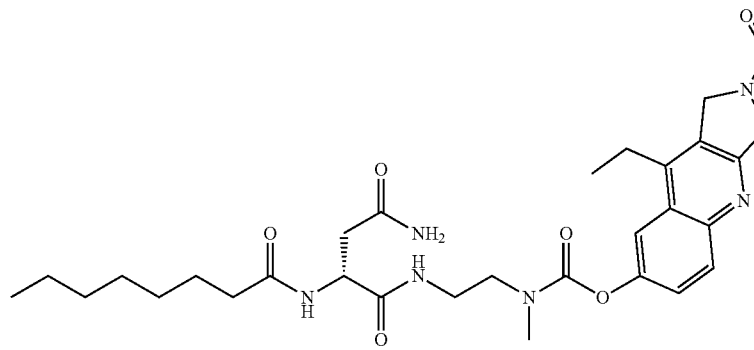

Example 76: (S)-4,11-diethyl-4-hydroxy-3,14-dioxo-3,4,12,14-tetrahydro-1H-pyrano[3',4':6,7]indolizino[1,2-b]quinolin-9-yl (2-((R)-4-amino-2-octanamido-4-oxobutanamido)ethyl)(methyl)carbamate Step 1: To a stirred solution of N2-(((9H-fluoren-9-yl)methoxy)carbonyl)-N$_4$-trityl-D-asparagine (0.50 g, 1 equiv., 0.84 mmol), HATU (0.38 g, 1.2 equiv., 1.0 mmol), 3H-[1,2,3]triazolo[4,5-b]pyridin-3-ol (0.14 g, 1.2 equiv., 1.0 mmol) in 30 mL DMF under nitrogen, tert-butyl (2-amino- TFA buffer). Fractions were combined and concentrated to yield (R)—N1-(2-(methylamino)ethyl)-2-octanamidosuccinamide, trifluoracetate (150 mg, 89.7%) as a white crystalline solid.

Step 5: DIEA (40 µL, 1.5 equiv., 0.23 mmol) was added drop-wise to a stirred dispersion of SN-38 (60 mg, 1 equiv., 0.15 mmol) and 4-nitrophenyl carbonochloridate (37 mg, 1.2 equiv., 0.18 mmol) in THF (5 mL) at 0° C. under nitrogen. The reaction was stirred for 2 hours. Solution was concentrated to yield (S)-4,11-diethyl-4-hydroxy-3,14-dioxo-3,4,12,14-tetrahydro-1H-pyrano[3',4':6,7]indolizino[1,2-b]quinolin-9-yl (4-nitrophenyl) carbonate as a crude light yellow residue.

Step 6: (S)-4,11-diethyl-4-hydroxy-3,14-dioxo-3,4,12,14-tetrahydro-1H-pyrano[3',4':6,7]indolizino[1,2-b]quinolin-9-yl (4-nitrophenyl) carbonate (85 mg, 1 equiv., 0.15 mmol) was dissolved in 3 mL anhydrous DMF and stirred under nitrogen at room temperature. A solution of (R)—N$_1$-(2-(methylamino)ethyl)-2-octanamidosuccinamide, Trifluoracetate (72 mg, 1.1 equiv., 0.17 mmol) in 2 mL DMF was added followed by N,N-dimethylpyridin-4-amine (37 mg, 2 equiv., 0.30 mmol). Reaction was stirred at room temperature for 30 minutes, concentrated, and residue was purified by reverse phase prep HPLC (0-95% acetonitrile in water w/0.1% TFA). Fractions were concentrated to yield (S)-4,11-diethyl-4-hydroxy-3,14-dioxo-3,4,12,14-tetrahydro-1H-pyrano[3',4':6,7]indolizino[1,2-b]quinolin-9-yl (2-((R)-4-amino-2-octanamido-4-oxobutanamido)ethyl)(methyl)carbamate (0.052 g, 47%) as a yellow solid. LCMS: (M+H+): 733.2 $^1$H NMR (400 MHz, DMSO-d6) δ 8.17 (d, 1H), 8.06-7.83 (m, 3H), 7.69 (dd, 1H), 7.33 (s, 1H), 7.25 (s, 1H), 6.84 (d, 1H), 6.50 (s, 1H), 5.44 (s, 2H), 5.34 (s, 2H), 4.61-4.49 (m, 1H), 3.55-3.48 (m, 2H), 3.35-3.28 (m, 2H), 3.19 (q, 2H), 3.04 (d, 3H), 2.54-2.51 (m, 1H), 2.37 (dd, 1H), 2.12-1.98 (m, 2H), 1.95-1.79 (m, 2H), 1.50-1.35 (m, 2H), 1.30 (t, 3H), 1.26-1.05 (m, 8H), 0.88 (t, 3H), 0.85-0.77 (m, 3H)

(R)-(2-(2-(3-hexylureido)-4-oxo-4-(tritylamino)butanamido)ethyl)(methyl)carbamate (310 mg, 67.6%) as a white solid.

Step 4: tert-butyl (R)-(2-(2-(3-hexylureido)-4-oxo-4-(tritylamino)butanamido)ethyl)(methyl)carbamate (310 mg, 1 equiv., 471 μmol) was dissolved in 4 mL 2.5% treithylsilane/2.5% water/5% DCM/95% trifluoroacetic acid and stirred at room temperature under nitrogen for 1 hour. Reaction was concentrated and residue was purified by reverse phase flash chromatography (10-95% acetonitrile in water with 0.1% TFA buffer). Fractions were combined and concentrated to yield (R)-2-(3-hexylureido)-N$_1$-(2-(methylamino)ethyl)succinamide, Trifluoracetate (171 mg, 84.7%)

Step 5: DIEA (40 μL, 1.5 equiv., 0.23 mmol) was added drop-wise to a stirred dispersion of SN-38 (60 mg, 1 equiv., 0.15 mmol) and 4-nitrophenyl carbonochloridate (37 mg, 1.2 equiv., 0.18 mmol) in THF (5 mL) at 0° C. under nitrogen. The reaction was stirred for 2 hours. Solution was concentrated to yield (S)-4,11-diethyl-4-hydroxy-3,14-dioxo-3,4,12,14-tetrahydro-1H-pyrano[3',4':6,7]indolizino[1,2-b]quinolin-9-yl (4-nitrophenyl) carbonate as a crude light yellow residue.

Step 6: (S)-4,11-diethyl-4-hydroxy-3,14-dioxo-3,4,12,14-tetrahydro-1H-pyrano[3',4':6,7]indolizino[1,2-b]quinolin-9-yl (4-nitrophenyl) carbonate (85 mg, 1 equiv., 0.15 mmol) was dissolved in 3 mL anhydrous DMF and stirred under nitrogen at room temperature. A solution of (R)-2-(3-hexylureido)-N$_1$-(2-(methylamino)ethyl)succinamide, Trifluoracetate (72 mg, 1.1 equiv., 0.17 mmol) in 2 mL DMF was

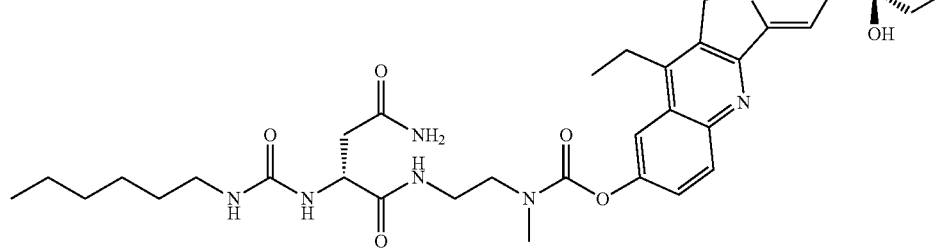

Example 77: (S)-4,11-diethyl-4-hydroxy-3,14-dioxo-3,4,12,14-tetrahydro-1H-pyrano[3',4':6,7]indolizino[1,2-b]quinolin-9-yl (2-((R)-4-amino-2-(3-hexylureido)-4-oxobutanamido)ethyl)(methyl)carbamate Step 1-2: Followed the steps described in Example 76.

Step 3: To a stirred solution of tert-butyl (R)-(2-(2-amino-4-oxo-4-(tritylamino)butanamido)ethyl)(methyl)carbamate (0.370 g, 1 equiv., 697 μmol) and 1-isocyanatohexane (97.5 mg, 112 μL, 1.1 equiv., 767 μmol) in 5 mL anhydrous DMF under N$_2$, triethylamine (106 mg, 146 μL, 1.5 equiv., 1.05 mmol) was added dropwise. The resulting solution was stirred for 18 hours, concentrated, and the residue was purified by reverse phase flash chromatography (10-100% acetonitrile in water with 0.1% TFA) to yield tert-butyl added followed by N,N-dimethylpyridin-4-amine (37 mg, 2 equiv., 0.30 mmol). Reaction was stirred at room temperature for 30 minutes, concentrated, and residue was purified by reverse phase prep HPLC (0-95% acetonitrile in water w/0.1% TFA) to yield (S)-4,11-diethyl-4-hydroxy-3,14-dioxo-3,4,12,14-tetrahydro-1H-pyrano[3',4':6,7]indolizino[1,2-b]quinolin-9-yl (2-((R)-4-amino-2-(3-hexylureido)-4-oxobutanamido)ethyl)(methyl)carbamate (26 mg, 23%) as a yellow solid. LCMS: (M+H+): 734.2 $^1$H NMR (400 MHz, DMSO-d6) δ 8.15 (d, 1H), 8.05-7.88 (m, 2H), 7.67 (dd, 1H), 7.31 (s, 1H), 7.30 (s, 1H), 6.83 (d, 1H), 6.49 (s, 1H), 6.17 (q, 1H), 6.06 (t, 1H), 5.42 (s, 2H), 5.32 (s, 2H), 4.43-4.32 (m, 1H), 3.58-3.45 (m, 2H), 3.36-3.24 (m, 2H), 3.18 (q, 2H), 3.03 (d, 3H), 2.93 (d, 2H), 2.43-2.35 (m, 2H), 1.93-1.77 (m, 2H), 1.36-1.13 (m, 11H), 0.86 (t, 3H), 0.81 (td, 3H).

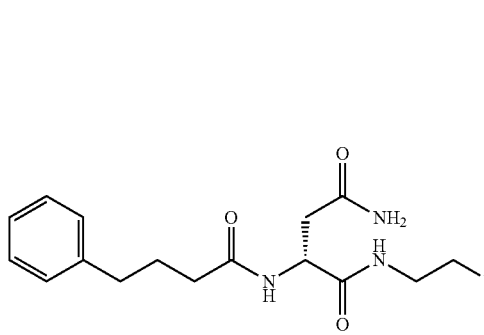

Example 78: (S)-4,11-diethyl-4-hydroxy-3,14-dioxo-3,4,12,14-tetrahydro-1H-pyrano[3',4':6,7]indolizino[1,2-b]quinolin-9-yl (2-((R)-4-amino-4-oxo-2-(4-phenylbutanamido)butanamido)ethyl)(methyl)carbamate Step 1-2: Followed the steps described in Example 76.

Step 3: To a stirred solution of 4-phenylbutanoic acid (80 mg, 1 equiv., 0.49 mmol), HATU (0.20 g, 1.1 equiv., 0.54 mmol), and 3H-[1,2,3]triazolo[4,5-b]pyridin-3-ol (73 mg, 1.1 equiv., 0.54 mmol) in 10 mL anhydrous DMF under nitrogen, tert-butyl (R)-(2-(2-amino-4-oxo-4-(tritylamino)butanamido)ethyl)(methyl)carbamate (0.34 g, 1.3 equiv., 0.63 mmol) was added. The solution was stirred for 5 minutes. DIEA (0.19 g, 0.26 mL, 3 equiv., 1.5 mmol) was added and the reaction was stirred for 1 hour then concentrated by rotary evaporation. The residue was purified by reverse phase flash chromatography (0-100% Acetonitrile in water w/0.1% TFA) to yield tert-butyl (R)-methyl(2-(4-oxo-2-(4-phenylbutanamido)-4-(tritylamino)butanamido)ethyl)carbamate (290 mg, 88%) as a white solid.

Step 4: tert-butyl (R)-methyl(2-(4-oxo-2-(4-phenylbutanamido)-4-(tritylamino)butanamido)ethyl)carbamate (290 mg, 1 equiv., 428 µmol) was dissolved in 4 mL 2.5% treithylsilane/2.5% water/5% DCM/95% trifluoroacetic acid and stirred at room temperature under nitrogen for 1 hour. Reaction was concentrated and residue was purified by reverse phase flash chromatography (10-95% acetonitrile in water with 0.1% TFA buffer). Fractions were combined and concentrated to yield (R)—N1-(2-(methylamino)ethyl)-2-(4-phenylbutanamido)succinamide, Trifluoracetate (100 mg, 52.2%) as a solid.

Step 5: DIEA (17 mg, 23 µL, 1.5 equiv., 0.13 mmol) was added drop-wise to a stirred dispersion of SN-38 (34 mg, 1 equiv., 87 µmol) and 4-nitrophenyl carbonochloridate (21 mg, 1.2 equiv., 0.10 mmol) in THF (3 mL) at 0° C. under nitrogen. The reaction was stirred for 2 hours. Solution was concentrated to yield (S)-4,11-diethyl-4-hydroxy-3,14-dioxo-3,4,12,14-tetrahydro-1H-pyrano[3',4':6,7]indolizino[1,2-b]quinolin-9-yl (4-nitrophenyl) carbonate as a crude white residue.

Step 6: (S)-4,11-diethyl-4-hydroxy-3,14-dioxo-3,4,12,14-tetrahydro-1H-pyrano[3',4':6,7]indolizino[1,2-b]quinolin-9-yl (4-nitrophenyl) carbonate (45 mg, 1 equiv., 81 µmol) was dissolved in 3 mL anhydrous DMF and stirred under nitrogen at room temperature. A solution of (R)—N₁-(2-(methylamino)ethyl)-2-(4-phenylbutanamido)succinamide, Trifluoracetate (40 mg, 1.1 equiv., 89 µmol) in 2 mL DMF was added followed by N,N-dimethylpyridin-4-amine (20 mg, 2 equiv., 0.16 mmol). Reaction was stirred at room temperature for 30 minutes, concentrated, and residue was purified by reverse phase prep HPLC (0-95% acetonitrile in water w/0.1% TFA) to yield (S)-4,11-diethyl-4-hydroxy-3,14-dioxo-3,4,12,14-tetrahydro-1H-pyrano[3',4':6,7]indolizino[1,2-b]quinolin-9-yl (2-((R)-4-amino-4-oxo-2-(4-phenylbutanamido)butanamido)ethyl)(methyl)carbamate (19 mg, 31%) LCMS: (M+H+): 753.2

$^1$H NMR (400 MHz, DMSO-d6) δ 8.15 (d, 1H), 8.05-7.89 (m, 3H), 7.67 (dd, 1H), 7.31 (s, 1H), 7.27-7.17 (m, 3H), 7.12 (dd, 3H), 6.83 (s, 1H), 6.48 (s, 1H), 5.42 (s, 2H), 5.31 (d, 2H), 4.67-4.37 (m, 1H), 3.52-3.45 (m, 2H), 3.45-3.25 (m, 2H), 3.17 (q, 2H), 3.02 (d, 3H), 2.54-2.50 (m, 2H), 2.47-2.43 (m, 1H), 2.36 (dd, 1H), 2.13-2.03 (m, 2H), 1.86 (hept, 2H), 1.79-1.64 (m, 2H), 1.28 (t, 3H), 0.86 (t, 3H).

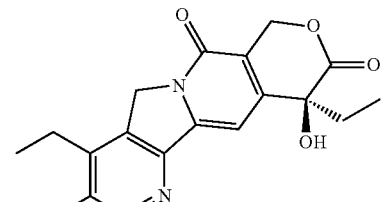

Example 79: (S)-4,11-diethyl-9-hydroxy-3,14-dioxo-3,4,12,14-tetrahydro-1H-pyrano[3',4':6,7]indolizino[1,2-b]quinolin-4-yl (2-((R)-4-amino-2-octanamido-4-oxobutanamido)ethyl)(methyl)carbamate Step 1-4: Followed the steps described in Example 76.

Step 5: To a stirred suspension of Boc-anhydride (65 mg, 69 µL, 1.3 equiv., 0.30 mmol) and (S)-4,11-diethyl-4,9-dihydroxy-1,12-dihydro-14H-pyrano[3',4':6,7]indolizino[1,2-b]quinoline-3,14(4H)-dione (90 mg, 1 equiv., 0.23 mmol) in 5 mL anhydrous DCM under nitrogen, pyridine (0.54 g, 0.56 mL, 30 equiv., 6.9 mmol) was added dropwise. Reaction was stirred for 18 hours at room temperature then diluted with 10 mL DCM. Organic layer was washed with 1M HCl (10 mL×2) and saturated NaCl (10 mL). Organic layer was dried over MgSO₄, filtered and concentrated to yield (S)-tert-butyl (4,11-diethyl-4-hydroxy-3,14-dioxo-3,4,12,14-tetrahydro-1H-pyrano[3',4':6,7]indolizino[1,2-b]quinolin-9-yl) carbonate as a crude residue.

Step 6: To a stirred solution of (S)-tert-butyl (4,11-diethyl-3,14-dioxo-3,4,12,14-tetrahydro-1H-pyrano[3',4':6,7]indolizino[1,2-b]quinoline-4,9-diyl) (4-nitrophenyl) bis(carbonate) (130 mg, 1.1 equiv., 0.19 mmol) in 2 mL DMF under nitrogen, a solution of (R)—N1-(2-(methylamino)ethyl)-2-octanamidosuccinamide trifluoracetate (75 mg, 1 equiv., 0.18 mmol) in 2 mL DMF was added followed by triethylamine (53 mg, 73 μL, 3 equiv., 0.53 mmol). Reaction was stirred at room temperature for 45 minutes, concentrated and purified by reverse phase prep chromatography (10-100% acetonitrile in water w/0.1% TFA). Fractions were concentrated to yield (S)-9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl (2-((R)-4-amino-2-octanamido-4-oxobutanamido)ethyl)(methyl)carbamate (0.052 g, 36%)

Step 7: To a solution of (S)-9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl (2-((R)-4-amino-2-octanamido-4-oxobutanamido)ethyl)(methyl)carbamate (50 mg, 1 equiv., 60 μmol) in 2 mL anhydrous dichloromethane, 2 mL trifluoroacetic acid was added. Reaction was stirred for 30 mins, concentrated, and purified by reverse phase prep HPLC (0-90% acetonitrile in water with 0.1% TFA) to yield (S)-4,11-diethyl-9-hydroxy-3,14-dioxo-3,4,12,14-tetrahydro-1H-pyrano[3',4':6,7]indolizino[1,2-b]quinolin-4-yl (2-((R)-4-amino-2-octanamido-4-oxobutanamido)ethyl) (methyl)carbamate (14 mg, 32%) LCMS: (M+H+): 733.5

¹H NMR (400 MHz, DMSO-d6) δ 10.27 (s, 1H), 8.01 (dd, 1H), 7.99-7.70 (m, 2H), 7.42-7.35 (m, 2H), 7.20 (d, 1H), 6.94 (d, 1H), 6.79 (d, 1H), 5.41 (d, 2H), 5.26 (d, 2H), 4.49 (dq, 1H), 3.46-3.26 (m, 2H), 3.22-2.96 (m, 5H), 2.76 (s, 2H), 2.52-2.22 (m, 2H), 2.11 (p, 3H), 2.03 (t, 1H), 1.51-1.35 (m, 2H), 1.27 (t, 3H), 1.24-1.11 (m, 8H), 0.97-0.86 (m, 3H), 0.86-0.74 (m, 3H).

Example 80: (5-fluoro-2,4-dioxo-3,4-dihydropyrimidin-1 (2H)-yl)methyl (R)-(2-(4-amino-2-octanamido-4-oxobutanamido)ethyl)(methyl)carbamate Synthesized according to the experimental procedure described for Example 72 to give (5-fluoro-2,4-dioxo-3,4-dihydropyrimidin-1(2H)-yl)methyl (R)-(2-(4-amino-2-octanamido-4-oxobutanamido)ethyl)(methyl)carbamate as a white solid (50 mg). LCMS: (M+H+): 501.1. 1H NMR (400 MHz, DMSO-d6) δ 11.94 (t, 1H), 8.09 (d, 1H), 7.88 (m, 2H), 7.25 (s, 1H), 6.84 (s, 1H), 5.53 (s, 2H), 4.48 (m, 1H), 3.22 (m, 4H), 2.82 (s, 3H), 2.37-2.28 (m, 2H), 2.09 (t, 2H), 1.47 (m, 2H), 1.24 (m, 8H), 0.86 (t, 3H).

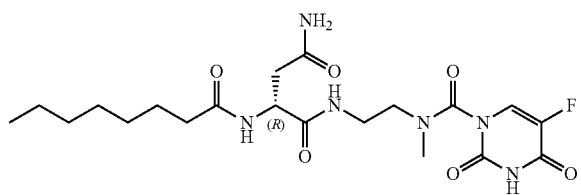

Example 81: (R)—N1-(2-(5-fluoro-N-methyl-2,4-dioxo-1,2,3,4-tetrahydropyrimidine-1-carboxamido) ethyl)-2-octanamidosuccinamide Synthesized according to the experimental procedure described for Example 55 to give (R)—N₁-(2-(5-fluoro-N-methyl-2,4-dioxo-1,2,3,4-tetrahydropyrimidine-1-carboxamido)ethyl)-2-octanamidosuccinamide as a white solid (30 mg). LCMS: (M+H+): 471.1. 1H NMR (400 MHz, DMSO-d6) δ 12.03 (s, 1H), 8.05 (d, 1H), 7.90 (m, 2H), 7.75 (m, 1H), 7.27 (s, 1H), 6.83 (s, 1H), 4.48 (q, 1H), 3.22-3.18 (m, 2H) 2.94 (d, 3H), 2.30-2.39 (m, 2H), 2.12 (m, 2H), 1.51-1.38 (m, 3H), 1.26-1.21 (m, 8H), 0.89- 0.81 (m, 3H).

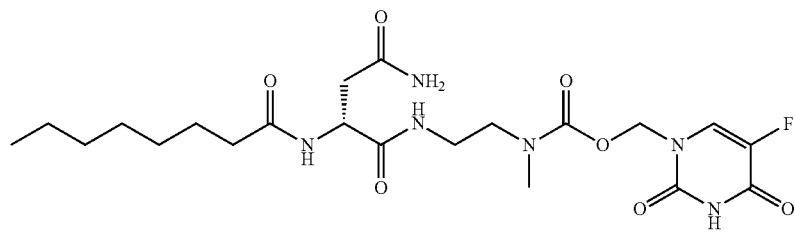

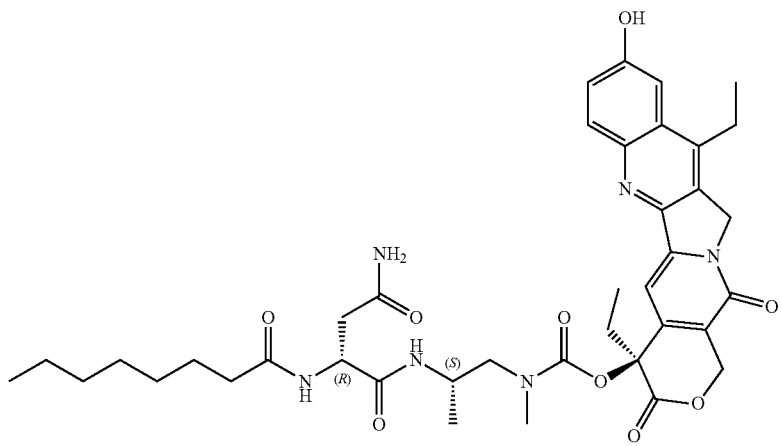

Example 82: (S)-4,11-diethyl-9-hydroxy-3,14-dioxo-3,4,12,14-tetrahydro-1H-pyrano[3',4':6,7]indolizino[1,2-b]quinolin-4-yl ((S)-2-((R)-4-amino-2-octanamido-4-oxobutanamido)propyl)(methyl)carbamate This compound may be synthesized according to the experimental procedure described for Example 79.

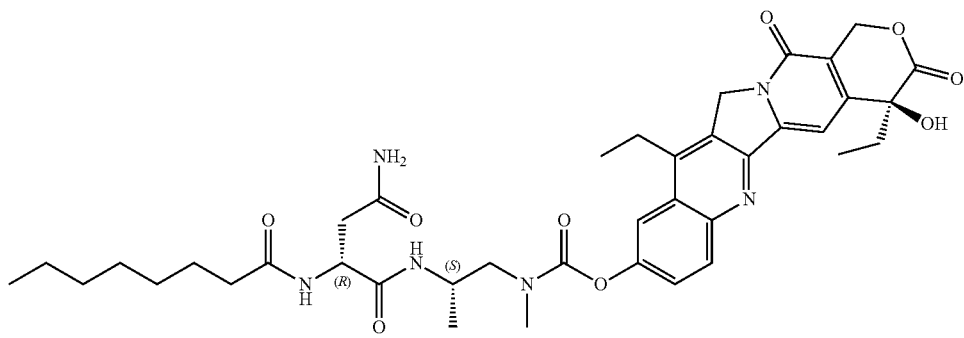

Example 83: (S)-4,11-diethyl-4-hydroxy-3,14-dioxo-3,4,12,14-tetrahydro-1H-pyrano[3',4':6,7]indolizino[1,2-b]quinolin-9-yl ((S)-2-((R)-4-amino-2-octanamido-4-oxobutanamido)propyl)(methyl)carbamate This compound may be synthesized according to the experimental procedure described for Example 76.

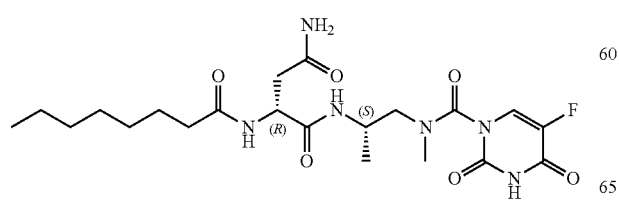

Example 84: (R)—N1-((S)-1-(5-fluoro-N-methyl-2,
4-dioxo-1,2,3,4-tetrahydropyrimidine-1-carbox-
amido)propan-2-yl)-2-octanamidosuccinamide This compound may be synthesized according to the experimental procedure described for Example 74.

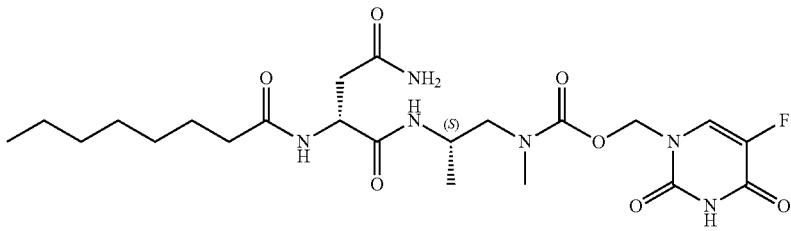

Example 85: (5-fluoro-2,4-dioxo-3,4-dihydropyrimi-
din-1 (2H)-yl)methyl ((S)-2-((R)-4-amino-2-octana-
mido-4-oxobutanamido)propyl)(methyl)carbamate This compound may be synthesized according to the experimental procedure described for Example 72.

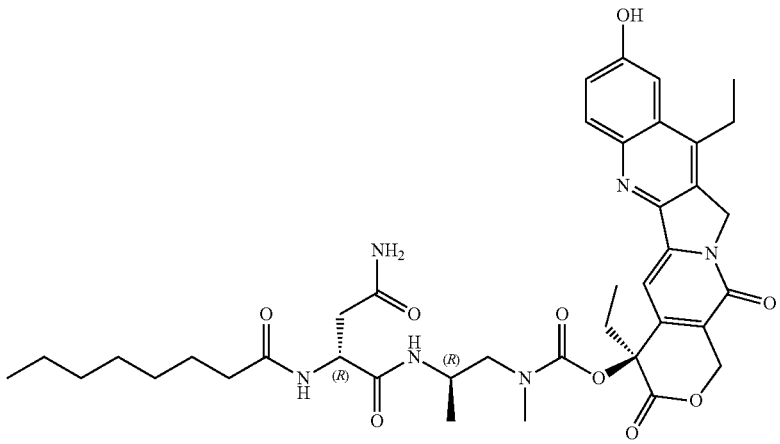

Example 86: (S)-4,11-diethyl-9-hydroxy-3,14-di-
oxo-3,4,12,14-tetrahydro-1H-pyrano[3',4':6,7]in-
dolizino[1,2-b]quinolin-4-yl ((R)-2-((R)-4-amino-2-
octanamido-4-oxobutanamido)propyl)(methyl)
carbamate This compound may be synthesized according to the experimental procedure described for Example 79.

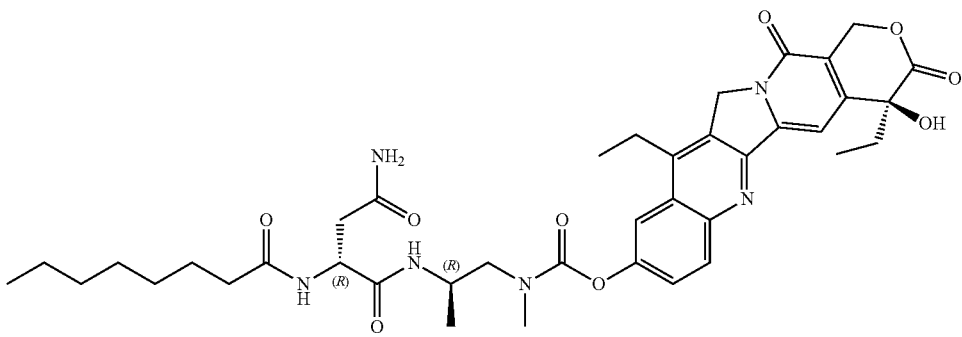

Example 87: (S)-4,11-diethyl-4-hydroxy-3,14-dioxo-3,4,12,14-tetrahydro-1H-pyrano[3',4':6,7]indolizino[1,2-b]quinolin-9-yl ((R)-2-((R)-4-amino-2-octanamido-4-oxobutanamido)propyl)(methyl)carbamate This compound may be synthesized according to the experimental procedure described for Example 76.

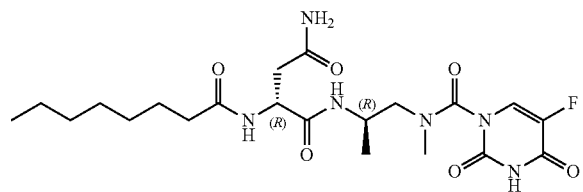

Example 88: (R)—N1-((R)-1-(5-fluoro-N-methyl-2,4-dioxo-1,2,3,4-tetrahydropyrimidine-1-carboxamido)propan-2-yl)-2-octanamidosuccinamide This compound may be synthesized according to the experimental procedure described for Example 74.

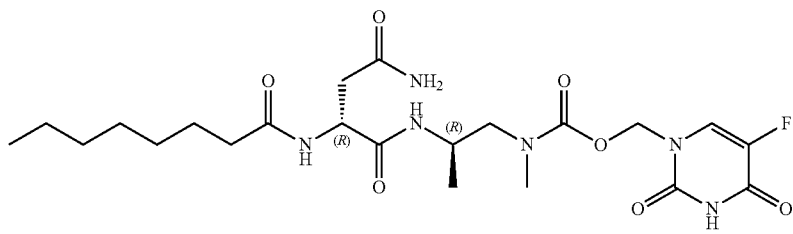

Example 89: (5-fluoro-2,4-dioxo-3,4-dihydropyrimidin-1 (2H)-yl)methyl ((R)-2-((R)-4-amino-2-octanamido-4-oxobutanamido)propyl)(methyl)carbamate This compound may be synthesized according to the experimental procedure described for Example 72.

Biological Assays

The examples below describe assays for assessing the activity and susceptibility to cleavage of exemplary conjugates of the invention.

Example 90: In Vitro Stability of Conjugates

Assay 1. Stability of conjugates in Simulated Gastric Fluid (SGF). This assay was used to assess the stability of a conjugate in a stomach. Medium was prepared by dissolving 2 g of sodium chloride in 0.6 L in ultrapure water (MilliQ®, Millipore Sigma, Darmstadt, Germany). The pH was adjusted to 1.6 with 1N hydrochloric acid, and the volume was then adjusted to 1 L with purified water. 60 mg FaSSIF powder (Biorelevant™, London, UK) were dissolved in 500 mL buffer (above). Pepsin was added (0.1 mg/mL) (Millipore Sigma, Darmstadt, Germany), and the solution was stirred. The resulting SGF media were used fresh for each experiment. Test compounds were dissolved in DMSO stock to 1 mM. An aliquot of the DMSO stock solution was removed and diluted in the SGF Media in 15 mL falcon tubes to generate a total compound concentration of 1 µM. A 1 mL aliquot was immediately removed and diluted once with 1 volume of acetonitrile for T0 timepoint. The mixture was sealed and mixed at 37° C. in an incubator. Aliquots (1 mL) were removed at regular intervals and immediately quenched by the addition of 1 volume of acetonitrile. The resulting samples were analyzed by LC/MS to determine degradation rates in SGF.

Assay 2. Stability of conjugates in Simulated Intestinal Fluid (SIF). This assay was used to assess the stability of a conjugate in a small intestine. Phosphate buffer was prepared by dissolving 0.42 g of sodium hydroxide pellets and 3.95 g of monobasic sodium phosphate monohydrate and 6.19 g of sodium chloride in ultrapure water (MilliQ®, Millipore Sigma, Darmstadt, Germany). The pH was adjusted to 6.7 using aq. HCl and aq. NaOH, as necessary, and the solution was diluted with ultrapure water to produce 1 L of the pH 6.7 buffer. 112 mg FaSSIF powder (Biorelevant™, London, UK) was dissolved in 50 mL of the pH 6.7 buffer. 2 to 3 mL of the resulting solution were then added to 500 mg pancreatin (Millipore Sigma, Darmstadt, Germany). The resulting mixture was agitated by finger tapping the vessel containing the mixture until milky suspension formed. At this time, the remainder of the 50 mL FaSSiF/pH 6.7 buffer solution was added. The resulting suspension was flipped upside down 10 times to produce SIF, which was used fresh. Test compounds were dissolved in DMSO stock to 1 mM. An aliquot of the DMSO stock solution was removed and diluted in the SIF media in 15 mL falcon tubes to produce a mixture with a tested compound concentration of 1 µM. A 1 mL aliquot was immediately removed and diluted once with 1 volume of acetonitrile for T0 timepoint. The mixture was sealed and agitated at 37° C. in an incubator. Aliquots (1 mL) were removed at regular intervals and immediately quenched by the addition of 1 volume of acetonitrile. The resulting samples were analyzed by LC/MS to determine degradation rates Assay 3 In vitro Colonic Material Stability Assay. This assay was used to assess the stability of an acylated active agent in a large intestine. All experiments were performed in an anaerobic chamber containing 90% nitrogen, 5% hydrogen and 5% carbon dioxide. Colonic material was resuspended as a slurry (15% w/v final concentration) in pre-reduced, anaerobically sterilized dilution blanks (Anaerobe Systems AS-908). The colonic material was then inoculated into 96 well plates containing YCFAC media (Anaerobe Systems AS-680) or other suitable media (6.7 µL slurry into 1 mL total media). Compounds or groups of compounds were added to each individual well to reach a final analyte concentration of 1 or 10 µM, and the material was mixed by pipetting. Sample was removed after set timepoints (0, 120, 240, 480, 1440, 2880 minutes after initiation of the assay), quenched with acetonitrile containing internal standard, and analyzed by LC/MS. Results are shown in Table 2.

TABLE 2

| Example # | Assay 1 (SGF) (% Remaining @ 1 hours) | Assay 2 (SIF) (% @ Remaining 4 hours) | Assay 3 (% Remaining at 24 h) |
|---|---|---|---|
| 1 | C | A | A |
| 2 | C | A | C |
| 3 | C | C | B |
| 4 | C | A | A |
| 5 | C | C | C |
| 6 | C | A | B |
| 7 | C | A | A |
| 8 |   |   | B |
| 9 | C | B | B |
| 10 | C | C | C |
| 11 | C | A | C |
| 12 |   | C | A |
| 13 |   |   | C |
| 14 | C | A | C |
| 16 | C | A | B |
| 17 | C | A | C |
| 18 | C | A | C |
| 19 |   |   | A |
| 20 | C | B | A |
| 21 | C | C | B |
| 22 | C | C | A |
| 25 | C |   | B |
| 34 | C |   | C |
| 35 | C | C |   |
| 40 |   |   | B |
| 42 |   |   | C |
| 43 | B | B | B |
| 45 |   |   | B |
| 47 | C | A | A |
| 49 | C | C | C |
| 52 |   |   | B |
| 55 | C | A | A |
| 58 | C | A | A |
| 59 |   |   | C |
| 60 |   |   | C |
| 61 | C | B | C |
| 66 | C | B | A |
| 67 | C | A |   |
| 69 | C | A | A |
| 70 | C | C | C |

In Table 2, A: <25% of the tested compound remaining; B: 25-75% of the tested compound remaining; and C: >75% of the tested compound remaining.

Table 2 shows that, for example, compounds 12, 20, 21, 22, and 66 can be selectively delivered to the colon.

Example 91: Isolation of Enzymes for Biochemical Assays

A soluble domain of the protein of interest was identified and cloned into an appropriate vector suitable for heterologous expression as a fusion protein in a host such as E. coli. Similarly, a soluble variant that was catalytically inactive was constructed by mutating an amino acid critical to the enzymatic activity.

The protein and the catalytically inactive variant were expressed in a suitable expression host. The cells were lysed, the lysates were clarified, and the protein was incubated with an appropriate resin to enable purification. After isolation, the tag may optionally be removed, and a second, orthogonal chromatographic step used to isolate the untagged version of the protein.

Example 92: Isolation of ClbP for Biochemical Assays

This example is representative of the method described in Example 91 the soluble peptidase domain (amino acids 38 to 375) of ClbP or the catalytically inert mutant S95A was cloned into pET28a using previously defined boundaries as a starting point (Brotherton, J. Am. Chem. Soc., 135:3359-3362, 2013).

WT ClbP or S95A ClbP was isolated as an N-terminally tagged $HiS_6$-SUMO1-fusion protein from pET28b using E. coli BL21(DE3)RIPL to express the protein. The cells were lysed in 30 mM Tris pH 8.0, 300 mM NaCl, 10% (v/v) glycerol, benzonase (Sigma-Millipore), lysozyme, B-per (ThermoFisher), and Y-per (ThermoFisher). The lysate was clarified via centrifugation (13,000 g, 20 min), and the supernatant was incubated with HiBond Ni-NTA agarose (5 mL). The resin was subsequently washed with wash buffer (30 mM Tris pH 7.5, 250 mM NaCl, 10 mM imidazole, 3% (v/v) glycerol, and 2 mM TCEP). The resin was incubated at 30° C. for 1 h with 1.4 mg ULP1 protease. The resin was then washed with an additional fraction of wash buffer. Centrifuge filtration was used to concentrate the protein, and the concentrated protein was subsequently applied to a 16/600 Superdex 200 size exclusion column with an isocratic elution of 25 mM HEPES, 25 mM Tris pH 7.4, 325 mM NaCl, 10 mM KCl and 3% (v/v) glycerol at a flow rate of X mL/min. The fractions containing the protein were determined by SDS-PAGE, combined, and concentrated by centrifuge filtration. 3 mM TCEP was added to the concentrated protein, which was then aliquoted, flash frozen in liquid $N_2$, and stored at −80° C.

Example 93: Isolation of Other Bacterial Enzymes for Biochemical Assays

Following the principles laid out in Examples A and B, other bacterial enzymes may be cloned, expressed, and isolated for biochemical assays. These include soluble versions of the D-alanyl-D-alanine carboxypeptidase (gene WP_002531210.1) and β-N-acetylglucosaminidase (gene WP_041444232.1) from P. acnes strain KPA171202, protease (gene NP_224809.1) and cinnamoyl esterase (gene NP_224360.1) from C. pneumoniae CWL029, penicillin-insensitive murein endopeptidase (gene NP_456924.1) and endoglucanase (gene NP_458303.1) from S. enterica ssp. enterica serovar Typhi strain CT18, D-alanyl-D-alanine carboxypeptidase (gene WP_041372295.1) and cellulase (WP_012317297.1) from M. radiotolerans JCM 2831, and D-alanyl-D-alanine carboxypeptidase (gene NP_220066.1) and Cinnamoyl esterase (gene NP_219652.1) from C. trachomatis D/UW-3/CX. In each case, a soluble, catalytically inactive version of the protein will likewise be cloned, expressed, and isolated.

Example 94: Assay with Purified Proteins

To assess the activity of the purified enzyme, the purified protein or its catalytically inactive variant is incubated with compound. As a control, the compound is also incubated with buffer alone. After a designated interval, the reaction is stopped by addition of organic solvent. LCMS analysis is used to determine the relative amounts of starting material and product in the reactions with the active enzyme, the inert enzyme, and the no-enzyme control.

Example 95: Assay with Purified ClbP Protein

This example is representative of the method described in Example D, ClbP was incubated with test compounds in an in vitro assay. In a typical assay, 0, 1, or 20 μM purified WT or S95A ClbP was incubated with 100 or 500 μM compound in reaction buffer (50 mM Tris-HCl pH 7.5, 37.5 mM NaCl) at room temperature for 24 h. The total volume of this reaction was 150 µL.

After 24 h, 2 volumes of acetonitrile (300 µL) were added to the reaction to quench the solution.

The reaction was centrifuged (4,000 g, 15 min), and then the supernatant was analyzed by LCMS. 5 µL of the supernatant was injected onto an Acquity UPLC BEH C18 1.7 µm 2.1×100 column. Buffer A was 0.1% (v/v) formic acid in water and buffer B was 0.1% (v/v) formic acid in acetonitrile. The flow rate was 0.5 mL/min. The initial % B was 10, which was held for 30 s then ramped up to 90% B over 3 min, held at 90% B for 1 min, ramped down to 10% B over 15 s, and then held at 10% B for 15 s. The UV-Vis spectrum from 210-400 nm was monitored with 3.6 nm resolution. Positive and negative mode ESI were monitored from 100-1000 m/z with a 20 V cone voltage at 5 Hz sampling frequency in centroid collection.

The relative starting material remaining in the WT ClbP reaction was determined by LCMS and then compared to the residual starting material in the no-enzyme and catalytically inert enzyme (S95A ClbP) reactions. In an ideal case, the amount of residual starting material in the WT ClbP reaction was <25% of the amount in the S95A ClbP and no-enzyme conditions. In an acceptable case, the amount of residual starting material in the WT ClbP reaction was 25-75% of the amount in the S95A ClbP and no-enzyme conditions. In a non-preferred case, the amount of residual starting material in the WT ClbP reaction was >75% of the amount in the S95A ClbP and no-enzyme conditions.

Formation of the anticipated product was likewise quantified by LCMS analysis and confirmed by coelution with an external product standard. In an ideal case, the amount of product formed in the WT ClbP reaction corresponded to >75% of the theoretical maximum. In an acceptable case, the amount of product formed in the WT ClbP reaction corresponded to 25-75% of the theoretical maximum. In a non-preferred case, the amount of product formed in the WT ClbP reaction corresponded to <25% of the theoretical maximum. The results are shown in Table 3 below.

TABLE 3

| Example # | Status | Concentration of compound |
|---|---|---|
| 1 | – | 500 µM |
| 2 | ++ | 100 µM |
| 4 | – | 500 µM |
| 5 | ++ | 100 µM |
| 6 | ++ | 100 µM |
| 7 | ++ | 100 µM |
| 8 | – | 500 µM |
| 9 | – | 100 µM |
| 10 | – | 500 µM |
| 11 | – | 500 µM |
| 12 | ++ | 100 µM |
| 13 | ++ | 100 µM |
| 18 | ++ | 100 µM |
| 20 | – | 100 µM |
| 21 | + | 100 µM |
| 22 | + | 100 µM |

In Table 3, status: "–" indicates >75% compound remaining in the 20 µM WT ClbP reaction relative to the no-enzyme control, "+" indicates between 25-75% compound remaining in the 20 µM WT ClbP reaction relative to the no-enzyme control, and "++" indicates <25% compound remaining in the 20 µM WT ClbP reaction relative to the control.

Example 96: Assay with Other Bacterial Enzymes

Following the principles laid out in Examples D and E, active and inactive versions of the proteins listed in Example C may be assayed for their activity to react with suitably designed compounds.

Example 97: Cell-Based Assay with Bacterial Enzymes with an LCMS Readout

A vector may be designed to express an enzyme in its native form or a catalytically inactive version. The vector may be transformed into a heterologous host, for example an E. coli expression strain. Alternatively, the naturally-occurring strain encoding one of the enzymes identified in Example 93 may be procured, and a closely-related strain lacking the enzyme identified will be used as a negative control. In the case of ClbP, a strain natively encoding ClbP such as E. coli CFT073 ATCC 700928 or E. coli Nissle 1917 may be used. E. coli BL21(DE3) does not encode ClbP and therefore may be used as a negative control.

The heterologous host (containing the wild-type enzyme, a catalytically inert version, or the empty vector) or the native strain may be grown to a desirable level.

Compound may be added to the bacterial growth or uninoculated medium. The mixture may be incubated for a designated period of time.

After incubation, the mixture may be rendered compatible with LCMS analysis via addition of organic solvent or lyophilization followed by dissolution in organic solvent. The amount of residual starting material and the product may be quantified by LCMS analysis.

Example 98: Cell-Based Assay with ClbP with an LCMS

This example is representative of the methods described in Example 97. ClbP was tested for its ability to activate compounds. Various test compounds were incubated with E. coli natively expressing full-length WT ClbP (E. coli CFT073 ATCC 700928 and/or E. coli Nissle 1917) or, as a negative control, an E. coli strain that does not encode ClbP (E. coli BL21(DE3)). Each of these three strains was struck out onto an appropriate solid media such as LB agar or BHI agar. The bacteria were then grown aerobically overnight at 37° C.

A single colony was isolated from the plate and inoculated into 10 mL LB. The liquid cultures were grown overnight aerobically at 37° C. with rocking on a nutator.

The saturated E. coli cultures were transferred into a biosafety cabinet. 5 µL of each culture was inoculated into fresh LB broth (200 µL total, 1:40 (v/v) dilution of the overnight culture), and the tested compound was added to a final concentration of 10 µM. To establish the native stability of the compound in media alone, the compound was also added to uninoculated media at a final concentration of 10 µM. Each compound was tested in duplicate with each strain or the media-alone incubation. The plate was sealed and incubated aerobically on a nutator at 37° C. for 20 h.

After 20 h, the reactions were stopped by addition of 200 µL acetonitrile. The contents of each well were mixed, and then the plate was centrifuged (4,000 rpm, 10 min). The plate was diluted serially to a final dilution of 1:100 first with Acetonitrile (10× dilution) and then with (4:1) Mobile Phase A-20 mM ammonium formate+water:Mobile Phase B-Isopropanol:Methanol:Water (4:4:2)+20 mM ammonium formate (10× dilution).

The amount of each remaining parent compound in each incubation was quantified by LC-MS analysis, with multiple-reaction monitoring targeting transitions specific to each parent compound.

The amount of compound present in the media-alone condition was normalized to 100%. The amount of parent compound present in the reaction with the ClbP-encoding *E. coli* (*E. coli* CFT073 ATCC 700928 and/or *E. coli* Nissle 1917) was compared to the amount present in the media-alone and expressed as a percent. Likewise, the amount of parent compound present in the reaction with the negative control *E. coli* BL21(DE3) was compared to the amount present in the media-alone and expressed as a percent.

In an ideal case, the amount of residual starting material in the reaction(s) with ClbP-encoding *E. coli* was <25% of the amount in the *E. coli* BL21(DE3) and media-alone conditions. In an acceptable case, the amount of residual starting material in the reaction(s) with ClbP-encoding *E. coli* was 25-75% of the amount in the *E. coli* BL21(DE3) and media-alone conditions. In a non-preferred case, the amount of residual starting material in the reaction(s) with ClbP-encoding *E. coli* was >75% of the amount in the *E. coli* BL21(DE3) and media-alone conditions. The results are summarized in Table 4.

TABLE 4

| Compound | % Remaining in ClbP Negative Relative to Media-Only | % Remaining in ClbP Positve Relative to Media-Only |
| --- | --- | --- |
| 5 | − | ++ |
| 2 | + | ++ |
| 4 | ++ | ++ |
| 6 | + | ++ |
| 7 | + | + |
| 8 | + | − |
| 10 | + | + |
| 11 | − | + |
| 1 | + | + |
| 18 | + | + |
| 9 | − | + |
| 13 | + | ++ |
| 20 | − | + |
| 12 | + | − |
| 21 | − | + |
| 22 | − | − |
| 66 | ++ | + |
| 3 | + | + |
| 14 | − | + |
| 17 | + | + |
| 16 | + | + |
| 19 | − | + |
| 42 | − | − |
| 24 | − | + |
| 60 | + | + |
| 59 | ++ | ++ |
| 52 | ++ | ++ |
| 46 | − | ++ |
| 30 | − | + |
| 43 | − | − |
| 44 | − | − |
| 35 | − | + |
| 49 | + | ++ |
| 53 | − | ++ |
| 45 | − | + |
| 23 | − | + |
| 31 | − | − |
| 48 | + | + |
| 54 | + | + |
| 47 | − | − |
| 34 | − | + |
| 25 | − | + |
| 70 | − | + |
| 61 | − | + |
| 58 | + | ++ |
| 40 | − | + |
| 72A | + | + |
| 72B | − | ++ |

In Table 4, status: "−" indicates >75% compound remaining in the 20 μM WT ClbP reaction relative to the no-enzyme control, "+" indicates between 25-75% compound remaining in the 20 μM WT ClbP reaction relative to the no-enzyme control, and "++" indicates <25% compound remaining in the 20 μM WT ClbP reaction relative to the control.

Compounds 5, 13, 46, 35, 53, 70, and 72B exhibited particularly favorable difference between the ClbP Positive and ClbP Negative release profiles.

Example 99: Cell-Based Assay with Other Bacterial Enzymes with an LCMS Readout Following the principles in Examples 97 and 98, active and inactive versions of the proteins listed in Example 93 may be assayed for their ability to react with suitably-designed compounds in a cell-based assay.

Example 100: Cell-Based Assay of Bacterial Enzymes with Mammalian CT26.CL25 Mouse Colorectal Carcinoma Viability Readout To assess the ability of bacterial enzymes to transform compounds into cytotoxins, steps 1-3 of Example 98 may be followed.

After incubation, the supernatants may be filtered to remove all bacteria. The supernatants may then be applied to a mammalian cell line, and the resulting cell viability may be assessed after an appropriate incubation period, e.g., using a CellTiter-Glo kit (Promega).

Example 101: Cell-Based Assay of ClbP with Caco-2 Viability Readout

This example is representative of the methods described in Example 100.

Bacteria-free media was incubated with the indicated test compound. ((R)—N1-(2-(methylamino)ethyl)-2-octanamidosuccinamide, a recognition element-linker conjugate lacking a payload, was serially diluted 1:1000 in DMSO and 1:10000 in medium+10% FBS to give a final concentration of 10 nM. Compound 35, Compound 76, Compound 77, Compound 78, Compound 79, and SN-38 were serially diluted 1:1000 in DMSO and 1:1000 in medium to give a final concentration of 10 nM, and then the bacteria-free supernatants were tested for their ability to kill mammalian cells. As an additional control, the test compound will also be incubated with bacteria-free media. The above steps can also be performed in the presence of *E. coli* (CFT073 ATCC 700928, Nissle 1917, or BL21 (DE3)) to effect cleavage of the conjugates of the application.

On Day 1, CT26.CL25 cells (15,000 cells/well) were seeded in triplicate into a 24 well plate and incubated overnight in 100 μL of complete medium. The reactions (bacteria or media blank) was pelleted by centrifugation, and then the supernatant was passed through a 0.2 μm sterile filter to remove residual bacteria.

On Day 2, 300 μL of a 10 nM solution of each compound in media were applied to separate wells of CT26.CL25 cells as prepared on Day 1. The cells were incubated at 37° C. for 72 h. After this point, viability was assessed using a Cell-Titer-Glo kit.

Binning of the compounds was achieved by measuring cell growth or arrest (e.g. remaining cells are >90% viable, >80% viable, >70% viable, >60% viable, >50% viable, >40% viable, >30% viable, >20% viable, or >10% viable). The results are shown in Table 5.

TABLE 5

| Compound | Bacteria-free media (Luminescence, average of three runs) |
| --- | --- |
| DMSO | 313127 |
| ((R)-N1-(2-(methylamino)ethyl)-2-octanamidosuccinamide | 278313 |
| Compound 76 | 282345 |
| Compound 77 | 345334 |
| Compound 79 | 288245 |
| Compound 35 | 380490 |
| Compound 78 | 317645 |
| SN-38 | 121387 |

Example 102: Cell-Based Assay of Other Bacterial Enzymes with CT26.CL25 Viability Readout Following the principles of Examples 100 and 101, the enzymes listed in Example 93 may be assessed for their ability to generate cytotoxins that can reduce the viability of mammalian cells.

Example 103: Compound Kinetics by Bacterial Enzyme Activation in the Presence of Fecal Matter Fecal samples may be assayed for the presence of a specific gene of interest by using primers specific for that gene to amplify it by PCR. Samples that do not yield a significant signal may be used as the source material for ex vivo incubations in subsequent steps.

A heterologous host containing an expression vector with the gene of interest (wild-type or catalytically inert) may be grown to a desirable level. Alternatively, the native strain containing the wild-type gene or a closely related strain lacking the gene may be grown to a desirable level.

The fecal sample may be amended with the heterologous host (expressing either the wild-type or catalytically inert protein). Alternatively, the fecal sample may be amended at varying levels with the native strain or the closely-related strain lacking its activity.

Compound stability may be assessed by LCMS analysis of the supernatants after predetermined time intervals. Compound stability may also be assessed by the ability of the filtered supernatant to reduce the viability of mammalian cells.

Example 104: Compound Kinetics by ClbP Activation in the Presence of Fecal Matter This example is representative of the methods described in Example 103. Fecal samples were subjected to metagenomic whole-genome shotgun sequencing followed by querying the dataset for the presence of the clbP gene or by attempting to amplify the gene with primers specific for it by qPCR. Samples that gave a signal below the detection limit were used in subsequent steps. The fecal sample was resuspended as a 15% (w/v) slurry in Anaerobic Phosphate Buffer Saline.

Following steps 1 and 2 as detailed in Example 98, E. coli CFT073 ATCC 700928, E. coli Nissle 1917, or E. coli BL21(DE3) were grown in liquid culture.

In an anaerobic chamber, the E. coli strains were added to the fecal samples obtained in step 1 at a dilution level calculated to represent 0, 1, 10, 50, 90, 99, or 100% of all organisms present in PRAS dilution blank on a 200 µL volume. The test compound (10 µM final concentration) was added to the mixture. The test compound was also added to a bacteria-free media control under similar conditions. The plate was sealed and incubated at 37° C. for 20 h. Under similar conditions, a standard curve of both the starting material and the payload compound was made in bacteria-free media.

After 20 h, an aliquot was tested for breakdown and release of a payload by LCMS by diluting serially to a final dilution of 1:100 first with Acetonitrile (10× dilution) and then with (1:1) Mobile Phase A-0.1% Formic Acid in Water:Mobile Phase B-0.1% Formic acid in Acetonitrile (1 OX dilution), with absolute quantification compared to the external standard curve. In an ideal case, the amount of payload released in the reaction(s) with ClbP-encoding E. coli was >75% of the theoretical maximum, and none was released in the E. coli BL21(DE3) and media-alone conditions. In an acceptable case, the amount of payload released in the reaction(s) with ClbP-encoding E. coli was 25-75% of the theoretical maximum, and <25% of the theoretical maximum was released in the E. coli BL21(DE3) and media-alone conditions. In a non-preferred case, the amount of payload released in the reactions(s) with ClbP-encoding E. coli was <25% of the theoretical maximum, and >25% of the theoretical maximum was released in the E. coli BL21 (DE3) and media-alone conditions.

Alternatively, the compounds may be tested for efficacy by adding the supernatant to the assay described in Example 100.

TABLE 6

| Compound | % payload released in ClbP negative (BL21 DE3) at 1:1 ratio of E. coli to fecal bacteria | % payload released in ClbP positive (Nissle 1917) at 1:1 ratio of E. coli to fecal bacteria | Payload (4-MU = fluorophore, 5-FU = fluorouracil, SN-38 = active of irinotecan) |
| --- | --- | --- | --- |
| 70 | 1.9 | 25.1 | 4-MU |
| 72B | 5.4 | 41.1 | 5-FU |
| 35 | 0.6 | 0.9 | SN-38 |
| 76 | 0 | 25 | SN-38 |
| 77 | 0 | 0 | SN-38 |
| 78 | 0 | 0 | SN-38 |
| 79 | 0 | 0 | SN-38 |

Example 105: Compound Kinetics by Other Bacterial Enzymes in the Presence of Fecal Matter Following the principles of Examples 103 and 104, the genes listed in Example 93 may be tested in a similar manner.

Example 106: Compound Efficacy in Preclinical Mouse Model

The following periclinal model is generally recognized as suitable model for studying inflammation associated colorectal cancer (De Robertis, J. Carcinog. 2011, 10, 1-22 The AOM/DSS murine model for the study of colon carcinogenesis: From pathways to diagnosis and therapy studies). Germ-free or antibiotic-treated mice may be mono-colonized with wildtype E. coli that express ClbP or E. coli mutants lacking or expressing a catalytically inactive version of the protein. Bacterial colonization may be determined by collection, homogenization, and plating of fecal pellets for determination of bacterial colony forming units at various timepoints throughout the experiment. After colonization is established, mice treated intraperitoneally with the carcinogen azoxymethane (AOM) may be followed one week later by a 7-day course of dextran sodium sulfate (DSS) administered in the drinking water. In control mice that have not been colonized by bacteria, tumors are predicted to form 12 weeks post AOM treatment (weeks post AOM). Mice may be treated with the compounds of interest orally intravenously or subcutaneously, at various time points prior to or upon tumor manifestation (ranging from 5 to 11 weeks post AOM) and with differing durations of treatment. Earlier time points of compound intervention may define pre-cancer and aide in determining the potential for inhibiting the progression to carcinoma. Later time points of intervention may determine the ability of the compounds to treat an established cancerous phenotype.

All mice may be sacrificed between 18 and 20 weeks post AOM treatment. Colons may be collected and monitored macroscopically for overall length. The therapeutic efficacy of the compound may be determined by measuring its effect on the frequency and size of tumors. Colon tissue may then be fixed and embedded after which histological examination will determine the effect of the compound on various markers of tumorigenesis. Inflammation, tumor invasion, and levels of dysplasia may be scored. Markers of cellular proliferation (i.e. Ki67) and DNA damage (i.e. H2AX) may be assessed. Involvement of the Wnt/Apc/B-catenin pathway, as well as K-Ras and c-Myc activation may be monitored. To assess the effect of compounds in prevention of tumor formation in cases where bacterial proliferation and increasing inflation markers is established, the following markers of inflammation, including cytokines (IL6, IL17, IL18, IL23, IL1b, IL12, TNFα), COX-2, TGF-beta, and iNOS may be monitored. For example, the therapeutically effective compound may alter the levels of the above markers by at least 10%, at least 20%, at least 30%, at least 40%, at least 50%, at least 100%, lower than the untreated cohort. To determine the effect of the compound on overall survival, mice may be mono-colonized with bacteria, treated with AOM/DSS and therapeutic compound as previously described. The health of each mouse may be scored (based on movement, grooming, hunching) and body weight may be measured at regular intervals. Mice may be euthanized upon meeting predetermined criteria based on extreme declines in health score and weight.

Example 107: Orthotopic Rectal Cancer Model in Mice

An orthotopic rectal cancer model that mimics human rectal cancers will be also used. Antibiotic-treated Balb/C mice may be mono-colonized with wildtype E. coli that express ClbP or E. coli mutants lacking or expressing a catalytically inactive version of the protein. Bacterial colonization may be determined by collection, homogenization, and plating of fecal pellets for determination of bacterial colony forming units at various timepoints throughout the experiment. After colonization is established, A mouse colon carcinoma cell line CT26-Luc-2A-GFP cells will be injected under the mucosa of the distal rectum of the Balb/C mice. A 30G needle on a 50 ul Hamilton syringe will be carefully inserted into the distal posterior rectal submucosa, 1-2 mm above the anal canal. Tumor cells will be slowly injected into the rectal submucosa with 1e06 tumor cells in a volume of 50 uL of SF RPMI-1640: 20% GFR Matrigel™. Animals will be monitored as they recover from anesthesia and will be observed for ~1 hr after injection. To follow tumor development in the mouse and to quantitate the response. Tumor burden will be measured twice each week (2×/week) via whole body imaging (ventral) at 12 minutes following i.p. injection of 0.2 mL RediJect D-Luciferin Bioluminescent Substrate (PerkinElmer #770504), by Lumina Series III in-life imaging system (IVIS; PerkinElmer) and total radiance flux (TRF; photons/second (ph/s)) recorded. Mice may be treated with the compounds of interest orally intravenously or subcutaneously, at various time points prior to or upon tumor manifestation and with differing durations of treatment. Earlier time points of compound intervention may define pre-cancer and aide in determining the potential for inhibiting the progression to carcinoma. Later time points of intervention may determine the ability of the compounds to treat an established cancerous phenotype. All mice may be sacrificed when they reach the humane endpoint. Colons may be collected and monitored macroscopically for overall length. The therapeutic efficacy of the compound may be determined by measuring its effect on the frequency and size of primary and secondary tumors. Colon tissue may then be fixed and embedded after which histological examination will determine the effect of the compound on various markers of tumorigenesis. Inflammation, tumor invasion, and levels of dysplasia may be scored. Markers of cellular proliferation (i.e. Ki67) and DNA damage (i.e. H2AX) may be assessed. Involvement of the Wnt/Apc/B-catenin pathway, as well as K-Ras and c-Myc activation may be monitored. To assess the effect of compounds in prevention of tumor formation in cases where bacterial proliferation and increasing inflation markers is established, the following markers of inflammation, including cytokines (IL6, IL17, IL18, IL23, IL1b, IL12, TNF-α, COX-2, TGF-β, and iNOS may be monitored. For example, the therapeutically effective compound may alter the levels of the above markers by at least 10%, at least 20%, at least 30%, at least 40%, at least 50%, at least 100%, lower than the untreated cohort.

Example 109: Evaluation of Anti-Infective Conjugates on K. pneumoniae Viability in Culture Step 1: A strain of K. pneumoniae encoding the pks pathoegenicity island (preferably a clinical isolate belonging to the hypervirulent clonal-group 23 such as strain K. pneumoniae subsp. SGH10, see Lam, Nat. Commun., 2018, 9, 2703 Population genomics of hypervirulent Klebsiella pneumoniae clonal-group 23 reveals early emergence and rapid global dissemination) may be obtained.

Step 2: The strain may be grown on a suitable solid growth medium such as nutrient agar (ATCC Medium 3). A single colony may be selected and inoculated into 5 mL nutrient broth and grown to mid-log phase at 37° C.

Step 3: An aliquot may be withdrawn to confirm the expression of the gene clbP via reverse transcriptase polymerase chain reaction or the production of the protein ClbP via Western blotting. To the remaining bacterial culture, compound (e.g., 0 or 10 μM) may be added, and the mixture may be incubated at 37° C. for 2 h.

Step 4: The effectiveness of the compound may be evaluated by monitoring the optical density at 600 nm and by plating to enumerate the colony forming units compared to the no-compound control. To evaluate the residual starting material and the product, an aliquot may be withdrawn and analyzed by LCMS, for example, as in step 3 of Example 95.

Example 108: Evaluation of Anti-Infective Conjugates on *K. pneumoniae* in a Pyogenic Hepatic Abscess Mouse Model The following preclinical model has been used to mimic human pyogenic hepatic abscesses (Chung, Infect. Immun., 2011, 79, 2234-2240 Role of T Lymphocytes in Liver Abscess Formation by *Bacteroides fragilis* in Mice). C57BL/6 mice (4 to 6 weeks, male) may be obtained. Mice may be anesthetized, shaved, and disinfected. An anterior midline incision may be made through the abdominal wall and peritoneum of the mouse. A bacterial inoculum prepared at a 0.1 mL volume by following steps 1-2 of Example 107 may be injected into the hepatic portal vein. The bacterial inoculum may include a virulent strain of *K. pneumoniae* or *K. pneumoniae* lacking the clbP gene (or in which it may have been genetically deleted). The abdominal wall may then be closed with sutures.

The mice may be treated with the compounds of interest orally, intravenously, or subcutaneously, at various time points prior to or upon bacterial infection and with different durations of treatment. Stool may be collected periodically from the mice and cultured to assess whether *K. pneumoniae* has infiltrated the gastrointestinal tract of the mice. All mice may be sacrificed between 1 and 3 weeks after bacterial infection. To examine liver abscess formation, liver sections may be removed from the mice. The livers may be examined histopathologically to assess metrics including but not limited to the number of abscesses and the size of the abscesses. *K. pneumoniae* may be cultured from the liver sections to evaluate the efficacy of the compound in clearing the bacterial infection. Additionally, other organs may be removed from the mice at the time of sacrifice and used to culture *K. pneumoniae* and determine if the bacterium has metastasized.

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A conjugate or pharmaceutically acceptable salt thereof, wherein the conjugate or pharmaceutically acceptable salt thereof comprises the following structure:

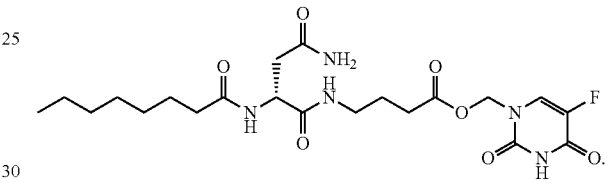

2. A pharmaceutical composition comprising the conjugate of claim 1 or pharmaceutically acceptable salt thereof and a pharmaceutically acceptable excipient.

* * * * *